(12) United States Patent
Nugent et al.

(10) Patent No.: US 9,677,993 B2
(45) Date of Patent: Jun. 13, 2017

(54) SYSTEMS AND METHODS FOR SAMPLE USE MAXIMIZATION

(71) Applicant: Theranos, Inc., Palo Alto, CA (US)

(72) Inventors: Anthony Nugent, Palo Alto, CA (US); Daniel Young, Palo Alto, CA (US); Elizabeth A. Holmes, Palo Alto, CA (US); Michael Siegel, Palo Alto, CA (US); Ryan Wistort, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 0 days.

(21) Appl. No.: 14/789,967

(22) Filed: Jul. 1, 2015

(65) Prior Publication Data

US 2016/0047834 A1 Feb. 18, 2016

Related U.S. Application Data

(60) Continuation of application No. 14/562,066, filed on Dec. 5, 2014, now Pat. No. 9,464,981, which is a
(Continued)

(51) Int. Cl.
*G01N 21/00* (2006.01)
*G01N 33/569* (2006.01)
(Continued)

(52) U.S. Cl.
CPC .......... *G01N 21/00* (2013.01); *B04B 5/0421* (2013.01); *C12Q 1/42* (2013.01); *C12Q 1/48* (2013.01);
(Continued)

(58) Field of Classification Search
CPC ............. G01N 35/1097; G01N 1/4077; G01N 2035/1039; C30B 29/58; C30B 7/00;
(Continued)

(56) References Cited

U.S. PATENT DOCUMENTS 2,398,234 A 4/1946 Long
3,640,434 A 2/1972 Walker
(Continued)

FOREIGN PATENT DOCUMENTS

CN 1526074 A 9/2004
CN 101010579 A 8/2007
(Continued)

OTHER PUBLICATIONS

Notice of Allowance issued for U.S. Appl. No. 13/916,553 on Dec. 20, 2013.
(Continued)

*Primary Examiner* — Kara E Geisel
*Assistant Examiner* — Maurice Smith

(57) ABSTRACT

The present invention provides systems, devices, and methods for point-of-care and/or distributed testing services. The methods and devices of the invention are directed toward automatic detection of analytes in a bodily fluid. The components of the device can be modified to allow for more flexible and robust use with the disclosed methods for a variety of medical, laboratory, and other applications. The systems, devices, and methods of the present invention can allow for effective use of samples by improved sample preparation and analysis.

23 Claims, 74 Drawing Sheets

Related U.S. Application Data division of application No. 13/355,458, filed on Jan. 20, 2012, now abandoned.

(60) Provisional application No. 61/435,250, filed on Jan. 21, 2011.

(51) Int. Cl.

| | |
|---|---|
| *B04B 5/04* | (2006.01) |
| *G01N 33/543* | (2006.01) |
| *G01N 21/03* | (2006.01) |
| *G01N 21/51* | (2006.01) |
| *C12Q 1/42* | (2006.01) |
| *C12Q 1/48* | (2006.01) |
| *C12Q 1/68* | (2006.01) |
| *G01N 21/59* | (2006.01) |
| *G01N 33/573* | (2006.01) |
| *G01N 33/74* | (2006.01) |
| *G01N 33/80* | (2006.01) |
| *G06T 3/40* | (2006.01) |
| *G06T 7/00* | (2017.01) |
| *H04N 5/232* | (2006.01) |
| *C12Q 1/52* | (2006.01) |
| *G01N 1/40* | (2006.01) |
| *G01N 33/53* | (2006.01) |
| *G01N 33/82* | (2006.01) |
| *G01N 33/92* | (2006.01) |
| *G01N 35/10* | (2006.01) |
| *B01L 3/02* | (2006.01) |
| *G06F 19/00* | (2011.01) |
| *G01N 35/00* | (2006.01) |

(52) U.S. Cl.
CPC ............ *C12Q 1/52* (2013.01); *C12Q 1/6806* (2013.01); *C12Q 1/6809* (2013.01); *C12Q 1/689* (2013.01); *G01N 1/4077* (2013.01); *G01N 21/0303* (2013.01); *G01N 21/51* (2013.01); *G01N 21/59* (2013.01); *G01N 33/5308* (2013.01); *G01N 33/54326* (2013.01); *G01N 33/54393* (2013.01); *G01N 33/56972* (2013.01); *G01N 33/56983* (2013.01); *G01N 33/573* (2013.01); *G01N 33/74* (2013.01); *G01N 33/743* (2013.01); *G01N 33/80* (2013.01); *G01N 33/82* (2013.01); *G01N 33/92* (2013.01); *G01N 35/10* (2013.01); *G06T 3/4084* (2013.01); *G06T 7/0002* (2013.01); *G06T 7/0012* (2013.01); *H04N 5/23222* (2013.01); *B01L 3/0275* (2013.01); *B01L 2300/168* (2013.01); *C12Q 2600/158* (2013.01); *G01N 2001/4083* (2013.01); *G01N 2035/00495* (2013.01); *G01N 2333/575* (2013.01); *G01N 2333/62* (2013.01); *G01N 2333/91188* (2013.01); *G01N 2333/96463* (2013.01); *G06F 19/703* (2013.01); *G06T 2207/30004* (2013.01); *G06T 2207/30168* (2013.01)

(58) Field of Classification Search
CPC . B01L 3/02; B04B 5/00; B04B 5/0421; B04B 3/00
USPC ............ 356/244–246, 440, 433; 435/7.92, 2
See application file for complete search history.

(56) References Cited

U.S. PATENT DOCUMENTS

| | | | |
|---|---|---|---|
| 3,696,971 A | 10/1972 | Maclin | |
| 3,722,789 A * | 3/1973 | Kennedy | B04B 5/0421 494/1 |
| 3,766,381 A | 10/1973 | Watson | |
| 3,865,495 A | 2/1975 | Sanz et al. | |
| 3,953,172 A * | 4/1976 | Shapiro | B04B 5/0421 422/72 |
| 4,010,893 A | 3/1977 | Smith et al. | |
| 4,157,781 A | 6/1979 | Maruyama | |
| 4,250,830 A * | 2/1981 | Leif | B04B 5/0407 422/72 |
| 4,270,921 A | 6/1981 | Graas | |
| 4,276,258 A | 6/1981 | Ginsberg et al. | |
| 4,327,595 A | 5/1982 | Schultz | |
| 4,362,698 A | 12/1982 | Boosalis et al. | |
| 4,437,586 A | 3/1984 | Columbus | |
| 4,486,315 A * | 12/1984 | Teipel | B01D 11/0288 210/518 |
| 4,488,814 A | 12/1984 | Johnson | |
| 4,545,497 A | 10/1985 | Martha | |
| 4,554,839 A | 11/1985 | Hewett et al. | |
| 4,593,837 A | 6/1986 | Jakubowicz et al. | |
| 4,683,195 A | 7/1987 | Mullis et al. | |
| 4,744,955 A | 5/1988 | Shapiro | |
| 4,756,884 A | 7/1988 | Hillman et al. | |
| 4,784,834 A | 11/1988 | Hirschmann | |
| 4,810,096 A | 3/1989 | Russell et al. | |
| 4,816,567 A | 3/1989 | Cabilly et al. | |
| 4,822,331 A | 4/1989 | Taylor | |
| 4,830,832 A | 5/1989 | Arpagaus et al. | |
| 4,925,629 A | 5/1990 | Schramm | |
| 4,927,545 A | 5/1990 | Roginski | |
| 4,933,291 A | 6/1990 | Daiss et al. | |
| 4,962,041 A | 10/1990 | Roginski | |
| 4,967,604 A | 11/1990 | Arpagaus et al. | |
| 5,005,981 A | 4/1991 | Schulte et al. | |
| 5,055,263 A | 10/1991 | Meltzer | |
| 5,061,449 A | 10/1991 | Torti et al. | |
| 5,072,382 A | 12/1991 | Kamentsky | |
| 5,089,229 A | 2/1992 | Heidt et al. | |
| 5,112,574 A | 5/1992 | Horton | |
| 5,130,238 A | 7/1992 | Malek et al. | |
| 5,171,534 A | 12/1992 | Smith et al. | |
| 5,186,162 A | 2/1993 | Talish et al. | |
| 5,230,864 A | 7/1993 | Columbus | |
| 5,270,163 A | 12/1993 | Gold et al. | |
| 5,270,184 A | 12/1993 | Walker et al. | |
| 5,273,905 A | 12/1993 | Muller et al. | |
| 5,281,395 A | 1/1994 | Markart et al. | |
| 5,292,658 A | 3/1994 | Cormier et al. | |
| 5,310,652 A | 5/1994 | Gelfand et al. | |
| 5,320,808 A | 6/1994 | Holen et al. | |
| 5,322,770 A | 6/1994 | Gelfand | |
| 5,324,481 A | 6/1994 | Dunn et al. | |
| 5,380,487 A | 1/1995 | Choperena et al. | |
| 5,393,903 A | 2/1995 | Gratzel et al. | |
| 5,399,491 A | 3/1995 | Kacian et al. | |
| 5,416,879 A | 5/1995 | Liu | |
| 5,418,155 A | 5/1995 | Cormier et al. | |
| 5,443,790 A | 8/1995 | Coeurveille et al. | |
| 5,455,166 A | 10/1995 | Walker | |
| 5,456,652 A * | 10/1995 | Eberle | B04B 5/0421 494/20 |
| 5,475,096 A | 12/1995 | Gold et al. | |
| 5,480,784 A | 1/1996 | Kacian et al. | |
| 5,483,799 A | 1/1996 | Dalto | |
| 5,507,410 A | 4/1996 | Clark et al. | |
| 5,527,257 A | 6/1996 | Piramoon | |
| 5,527,670 A | 6/1996 | Stanley | |
| 5,530,101 A | 6/1996 | Queen et al. | |
| 5,545,540 A | 8/1996 | Mian | |
| 5,578,269 A | 11/1996 | Yaremko et al. | |
| 5,578,270 A | 11/1996 | Reichler et al. | |
| 5,580,529 A | 12/1996 | Devaughn et al. | |
| 5,585,089 A | 12/1996 | Queen et al. | |
| 5,602,647 A | 2/1997 | Xu et al. | |
| 5,628,890 A | 5/1997 | Carter et al. | |
| 5,670,375 A | 9/1997 | Seaton et al. | |
| 5,683,888 A | 11/1997 | Campbell | |
| 5,693,233 A | 12/1997 | Schembri | |
| 5,693,761 A | 12/1997 | Queen et al. | |
| 5,693,762 A | 12/1997 | Queen et al. | |

(56) References Cited

U.S. PATENT DOCUMENTS

| | | |
|---|---|---|
| 5,741,411 A | 4/1998 | Yeung et al. |
| 5,741,668 A | 4/1998 | Ward et al. |
| 5,758,443 A | 6/1998 | Pedrazzini |
| 5,772,962 A | 6/1998 | Uchida et al. |
| 5,777,079 A | 7/1998 | Tsien et al. |
| 5,779,981 A | 7/1998 | Danssaert et al. |
| 5,804,387 A | 9/1998 | Cormack et al. |
| 5,807,523 A | 9/1998 | Watts et al. |
| 5,821,337 A | 10/1998 | Carter et al. |
| 5,844,686 A | 12/1998 | Treptow et al. |
| 5,854,033 A | 12/1998 | Lizardi |
| 5,859,205 A | 1/1999 | Adair et al. |
| 5,874,304 A | 2/1999 | Zolotukhin et al. |
| 5,876,995 A | 3/1999 | Bryan |
| 5,902,549 A | 5/1999 | Mimura et al. |
| 5,906,795 A | 5/1999 | Nakashima et al. |
| 5,915,284 A | 6/1999 | Meltzer et al. |
| 5,925,558 A | 7/1999 | Tsien et al. |
| 5,939,291 A | 8/1999 | Loewy et al. |
| 5,961,451 A | 10/1999 | Reber et al. |
| 5,980,830 A | 11/1999 | Savage et al. |
| 5,993,417 A | 11/1999 | Yerfino et al. |
| 6,013,528 A | 1/2000 | Jacobs et al. |
| 6,030,582 A | 2/2000 | Levy |
| 6,033,850 A | 3/2000 | Purvis |
| 6,042,909 A | 3/2000 | Dunleavy et al. |
| 6,054,297 A | 4/2000 | Carter et al. |
| 6,056,661 A | 5/2000 | Schmidt |
| 6,060,022 A | 5/2000 | Pang et al. |
| 6,063,341 A | 5/2000 | Fassbind et al. |
| 6,074,616 A | 6/2000 | Buechler et al. |
| 6,091,490 A | 7/2000 | Stellman et al. |
| 6,114,122 A | 9/2000 | Besemer et al. |
| 6,115,545 A | 9/2000 | Mellquist |
| 6,121,054 A | 9/2000 | Lebl |
| 6,143,252 A | 11/2000 | Haxo, Jr. et al. |
| 6,159,368 A | 12/2000 | Moring et al. |
| 6,168,914 B1 | 1/2001 | Campbell et al. |
| 6,180,370 B1 | 1/2001 | Queen et al. |
| 6,191,852 B1 | 2/2001 | Paffhausen et al. |
| 6,197,572 B1 | 3/2001 | Schneebeli |
| 6,210,891 B1 | 4/2001 | Nyren et al. |
| 6,235,534 B1 | 5/2001 | Brookes et al. |
| 6,244,119 B1 | 6/2001 | Theran |
| 6,251,639 B1 | 6/2001 | Kurn |
| 6,277,605 B1 | 8/2001 | Wijnhoven et al. |
| 6,290,907 B1 | 9/2001 | Takahashi et al. |
| 6,291,249 B1 | 9/2001 | Mahant et al. |
| 6,294,331 B1 | 9/2001 | Ried et al. |
| 6,309,828 B1 | 10/2001 | Schleifer et al. |
| 6,333,157 B1 | 12/2001 | Miller-Jones et al. |
| 6,341,490 B1 | 1/2002 | Jones |
| 6,348,176 B1 | 2/2002 | Hammer et al. |
| 6,372,185 B1 | 4/2002 | Shumate et al. |
| 6,375,028 B1 | 4/2002 | Smith |
| 6,379,929 B1 | 4/2002 | Burns et al. |
| 6,407,213 B1 | 6/2002 | Carter et al. |
| 6,410,278 B1 | 6/2002 | Notomi et al. |
| 6,420,143 B1 | 7/2002 | Kopf-Sill |
| 6,440,725 B1 | 8/2002 | Pourahmadi et al. |
| 6,468,474 B2 | 10/2002 | Bachand et al. |
| 6,477,394 B2 | 11/2002 | Rice et al. |
| 6,484,897 B1 | 11/2002 | Crawley |
| 6,491,666 B1 | 12/2002 | Santini et al. |
| 6,506,611 B2 | 1/2003 | Bienert et al. |
| 6,509,193 B1 | 1/2003 | Tajima |
| 6,517,475 B1 | 2/2003 | Brown et al. |
| 6,565,813 B1 | 5/2003 | Garyantes |
| 6,583,879 B1 | 6/2003 | Berg et al. |
| 6,589,789 B1 | 7/2003 | Hubert et al. |
| 6,599,476 B1 | 7/2003 | Watson et al. |
| 6,605,213 B1 | 8/2003 | Smith |
| 6,627,160 B2 | 9/2003 | Wanner |
| 6,663,003 B2 | 12/2003 | Johnson et al. |
| 6,689,615 B1 | 2/2004 | Murto et al. |
| 6,732,598 B2 | 5/2004 | Schoeppe |
| 6,748,337 B2 | 6/2004 | Wardlaw et al. |
| 6,752,965 B2 | 6/2004 | Levy |
| 6,780,645 B2 | 8/2004 | Hayter et al. |
| 6,805,842 B1 | 10/2004 | Bodner et al. |
| 6,825,921 B1 | 11/2004 | Modlin et al. |
| 6,833,246 B2 | 12/2004 | Balasubramanian |
| 6,858,185 B1 | 2/2005 | Kopf-Sill et al. |
| 6,859,830 B1 | 2/2005 | Ronneburg et al. |
| 6,899,848 B1 | 5/2005 | Chen et al. |
| 6,905,816 B2 | 6/2005 | Jacobs et al. |
| 6,917,726 B2 | 7/2005 | Levene et al. |
| 6,946,251 B2 | 9/2005 | Kurn |
| 6,947,582 B1 | 9/2005 | Vilsmeier et al. |
| 6,949,377 B2 | 9/2005 | Ho |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,109,293 B2 | 9/2006 | Hwang et al. |
| 7,170,050 B2 | 1/2007 | Turner et al. |
| 7,172,897 B2 | 2/2007 | Blackburn et al. |
| 7,185,551 B2 | 3/2007 | Schwartz |
| 7,272,252 B2 | 9/2007 | De La Torre-Bueno et al. |
| 7,276,158 B1 | 10/2007 | Shukla et al. |
| 7,358,098 B2 | 4/2008 | Noda et al. |
| 7,361,466 B2 | 4/2008 | Korlach et al. |
| 7,394,363 B1 | 7/2008 | Ghahramani |
| 7,416,844 B2 | 8/2008 | Korlach et al. |
| 7,422,554 B2 | 9/2008 | Moscone et al. |
| 7,429,652 B2 | 9/2008 | Wang et al. |
| 7,438,857 B2 | 10/2008 | Massaro |
| 7,481,787 B2 | 1/2009 | Gable et al. |
| 7,494,791 B2 | 2/2009 | Goel |
| 7,548,034 B2 | 6/2009 | Takahashi et al. |
| 7,581,660 B2 | 9/2009 | Nay et al. |
| 7,587,201 B2 | 9/2009 | Ohara |
| 7,609,654 B2 | 10/2009 | Lubeck et al. |
| 7,632,462 B2 | 12/2009 | Holtlund et al. |
| 7,635,594 B2 | 12/2009 | Holmes et al. |
| 7,650,395 B2 | 1/2010 | Johnson et al. |
| 7,662,343 B2 | 2/2010 | Mathus et al. |
| 7,691,332 B2 | 4/2010 | Kacian et al. |
| 7,702,524 B1 | 4/2010 | Whibbs et al. |
| 7,711,800 B2 | 5/2010 | Gavrilescu et al. |
| 7,744,821 B2 | 6/2010 | Eberle |
| 7,771,926 B2 | 8/2010 | Petyt et al. |
| 7,824,612 B2 | 11/2010 | Fuisz et al. |
| 7,824,890 B2 | 11/2010 | Hoser et al. |
| 7,923,256 B2 | 4/2011 | Widrig Opalsky et al. |
| 7,925,069 B2 | 4/2011 | Ortyn et al. |
| 7,955,867 B2 | 6/2011 | Park |
| 7,978,665 B1 | 7/2011 | Jaynes et al. |
| 8,008,066 B2 | 8/2011 | Lair et al. |
| 8,030,080 B2 | 10/2011 | Spence et al. |
| 8,088,593 B2 * | 1/2012 | Burd .................. B01J 19/0046 435/7.92 |
| 8,133,671 B2 | 3/2012 | Williams et al. |
| 8,158,430 B1 | 4/2012 | Roy et al. |
| 8,211,386 B2 | 7/2012 | Talmer et al. |
| 8,309,035 B2 | 11/2012 | Chen et al. |
| 8,309,317 B2 | 11/2012 | Chen et al. |
| 8,323,564 B2 | 12/2012 | Padmanabhan et al. |
| 8,380,541 B1 | 2/2013 | Holmes |
| 8,383,421 B2 | 2/2013 | Yanagida et al. |
| 8,387,811 B2 | 3/2013 | Livingston et al. |
| 8,392,585 B1 | 3/2013 | Balwani |
| 8,435,738 B2 | 5/2013 | Holmes |
| 8,475,739 B2 | 7/2013 | Holmes et al. |
| 8,588,807 B2 | 11/2013 | Kumar |
| 8,877,507 B2 | 11/2014 | Xia et al. |
| 8,883,518 B2 | 11/2014 | Roy et al. |
| 9,121,801 B2 | 9/2015 | Clark et al. |
| 9,128,015 B2 | 9/2015 | Holmes et al. |
| 9,131,884 B2 | 9/2015 | Holmes et al. |
| 9,168,523 B2 | 10/2015 | Ludowise et al. |
| 2001/0019845 A1 | 9/2001 | Bienert et al. |
| 2001/0048899 A1 | 12/2001 | Marouiss et al. |
| 2002/0039723 A1 | 4/2002 | Fox et al. |
| 2002/0052761 A1 | 5/2002 | Fey et al. |

(56) References Cited

U.S. PATENT DOCUMENTS

| | | |
|---|---|---|
| 2002/0059030 A1 | 5/2002 | Otworth et al. |
| 2002/0065457 A1 | 5/2002 | Kuth |
| 2002/0085952 A1 | 7/2002 | Ellingboe et al. |
| 2002/0087101 A1 | 7/2002 | Barrick et al. |
| 2002/0108857 A1 | 8/2002 | Paschetto et al. |
| 2002/0110496 A1 | 8/2002 | Samsoondar |
| 2002/0114739 A1 | 8/2002 | Weigl et al. |
| 2002/0120183 A1 | 8/2002 | Abraham-Fuchs et al. |
| 2002/0120187 A1 | 8/2002 | Eiffert et al. |
| 2002/0127708 A1 | 9/2002 | Kluttz et al. |
| 2002/0130100 A1 | 9/2002 | Smith |
| 2002/0139936 A1 | 10/2002 | Dumas |
| 2002/0141904 A1 | 10/2002 | Rosen et al. |
| 2002/0149772 A1 | 10/2002 | Halg |
| 2002/0155599 A1 | 10/2002 | Vellinger et al. |
| 2002/0155616 A1 | 10/2002 | Hiramatsu et al. |
| 2002/0156365 A1 | 10/2002 | Tsekos |
| 2002/0160353 A1 | 10/2002 | Sundaram et al. |
| 2002/0161606 A1 | 10/2002 | Bennett et al. |
| 2002/0164770 A1 | 11/2002 | Hoffmann |
| 2002/0168784 A1 | 11/2002 | Sundrehagen et al. |
| 2002/0176801 A1 | 11/2002 | Giebeler et al. |
| 2002/0187074 A1 | 12/2002 | O'Connor et al. |
| 2003/0012699 A1 | 1/2003 | Moore et al. |
| 2003/0049865 A1 | 3/2003 | Santini et al. |
| 2003/0052074 A1 | 3/2003 | Chang et al. |
| 2003/0064386 A1 | 4/2003 | Karaki et al. |
| 2003/0077207 A1 | 4/2003 | Tyndorf et al. |
| 2003/0100822 A1 | 5/2003 | Lew et al. |
| 2003/0127609 A1 | 7/2003 | El-Hage et al. |
| 2003/0138140 A1 | 7/2003 | Marcelpoil et al. |
| 2003/0170705 A1 | 9/2003 | Schulman et al. |
| 2003/0175164 A1 | 9/2003 | Micklash et al. |
| 2003/0175993 A1 | 9/2003 | Toranto et al. |
| 2003/0207463 A1 | 11/2003 | Iheme et al. |
| 2003/0208113 A1 | 11/2003 | Mault et al. |
| 2003/0211618 A1 | 11/2003 | Patel |
| 2003/0224457 A1 | 12/2003 | Hurt et al. |
| 2004/0005699 A1 | 1/2004 | Roos et al. |
| 2004/0014202 A1 | 1/2004 | King et al. |
| 2004/0020310 A1 | 2/2004 | Escal |
| 2004/0022677 A1 | 2/2004 | Wohlstadter et al. |
| 2004/0029266 A1 | 2/2004 | Barbera-Guillem |
| 2004/0044560 A1 | 3/2004 | Giglio et al. |
| 2004/0055361 A1 | 3/2004 | Schneider et al. |
| 2004/0058378 A1 | 3/2004 | Kong et al. |
| 2004/0086872 A1 | 5/2004 | Childers et al. |
| 2004/0096959 A1 | 5/2004 | Stiene et al. |
| 2004/0099628 A1 | 5/2004 | Casterlin |
| 2004/0109793 A1 | 6/2004 | Mcneely et al. |
| 2004/0115720 A1 | 6/2004 | McWilliams et al. |
| 2004/0120848 A1 | 6/2004 | Teodorczyk |
| 2004/0127252 A1 | 7/2004 | Tsunomoto et al. |
| 2004/0134750 A1 | 7/2004 | Luoma |
| 2004/0161368 A1 | 8/2004 | Holtlund et al. |
| 2004/0166027 A1 | 8/2004 | Wilmer et al. |
| 2004/0228766 A1 | 11/2004 | Witty et al. |
| 2004/0230400 A1 | 11/2004 | Tomasso et al. |
| 2004/0241043 A1 | 12/2004 | Sattler |
| 2004/0241048 A1 | 12/2004 | Shin et al. |
| 2005/0010098 A1 | 1/2005 | Frigstad et al. |
| 2005/0036907 A1 | 2/2005 | Shoji |
| 2005/0074873 A1 | 4/2005 | Shanler et al. |
| 2005/0100937 A1 | 5/2005 | Holmes |
| 2005/0106713 A1 | 5/2005 | Phan et al. |
| 2005/0125258 A1 | 6/2005 | Yellin et al. |
| 2005/0147559 A1 | 7/2005 | Von Alten |
| 2005/0152900 A1 | 7/2005 | Najib et al. |
| 2005/0159982 A1 | 7/2005 | Showalter et al. |
| 2005/0164204 A1 | 7/2005 | Reed |
| 2005/0176940 A1 | 8/2005 | King |
| 2005/0180892 A1 | 8/2005 | Davies et al. |
| 2005/0220668 A1 | 10/2005 | Coville |
| 2005/0225751 A1 | 10/2005 | Sandell et al. |
| 2005/0227370 A1 | 10/2005 | Ramel et al. |
| 2005/0231723 A1 | 10/2005 | Blasenheim et al. |
| 2005/0236317 A1 | 10/2005 | DeSilets et al. |
| 2006/0019274 A1 | 1/2006 | Goel |
| 2006/0024841 A1 | 2/2006 | Yao et al. |
| 2006/0026040 A1 | 2/2006 | Reeves et al. |
| 2006/0034732 A1 | 2/2006 | Bargh et al. |
| 2006/0057599 A1 | 3/2006 | Dzenitis et al. |
| 2006/0062697 A1 | 3/2006 | Eberle |
| 2006/0062852 A1 | 3/2006 | Holmes |
| 2006/0073538 A1 | 4/2006 | Konrad |
| 2006/0074063 A1 | 4/2006 | Fernandez-Pol |
| 2006/0083660 A1 | 4/2006 | Schorno et al. |
| 2006/0095429 A1 | 5/2006 | Abhyankar et al. |
| 2006/0110725 A1 | 5/2006 | Lee et al. |
| 2006/0115384 A1 | 6/2006 | Wohleb |
| 2006/0121491 A1 | 6/2006 | Wolber et al. |
| 2006/0121502 A1 | 6/2006 | Cain et al. |
| 2006/0160170 A1 | 7/2006 | Giordano |
| 2006/0182738 A1 | 8/2006 | Holmes |
| 2006/0183217 A1 | 8/2006 | Yanagida et al. |
| 2006/0210435 A1 | 9/2006 | Alavie et al. |
| 2006/0223178 A1 | 10/2006 | Barber et al. |
| 2006/0263263 A1 | 11/2006 | Shimizu |
| 2006/0263871 A1 | 11/2006 | Kluttz et al. |
| 2006/0264780 A1 | 11/2006 | Holmes et al. |
| 2006/0264783 A1 | 11/2006 | Holmes et al. |
| 2006/0275861 A1 | 12/2006 | Angros et al. |
| 2006/0292039 A1 | 12/2006 | Iida |
| 2007/0004577 A1 | 1/2007 | Lederer |
| 2007/0035819 A1 | 2/2007 | Bahatt et al. |
| 2007/0048188 A1 | 3/2007 | Bigus |
| 2007/0055538 A1 | 3/2007 | Burton |
| 2007/0059196 A1 | 3/2007 | Brister et al. |
| 2007/0073113 A1 | 3/2007 | Squilla et al. |
| 2007/0077173 A1 | 4/2007 | Melet |
| 2007/0109294 A1 | 5/2007 | Gotman et al. |
| 2007/0118399 A1 | 5/2007 | Avinash et al. |
| 2007/0125677 A1 | 6/2007 | Oronsky et al. |
| 2007/0134128 A1 | 6/2007 | Korlach |
| 2007/0146873 A1 | 6/2007 | Ortyn et al. |
| 2007/0149874 A1 | 6/2007 | Say et al. |
| 2007/0154922 A1 | 7/2007 | Collier et al. |
| 2007/0177778 A1 | 8/2007 | Massaro |
| 2007/0192138 A1 | 8/2007 | Saito et al. |
| 2007/0202538 A1 | 8/2007 | Glezer et al. |
| 2007/0207161 A1 | 9/2007 | Ralph |
| 2007/0207450 A1 | 9/2007 | Rodgers et al. |
| 2007/0224084 A1 | 9/2007 | Holmes et al. |
| 2007/0264629 A1 | 11/2007 | Holmes et al. |
| 2007/0269345 A1 | 11/2007 | Schilffarth et al. |
| 2007/0295113 A1 | 12/2007 | Londo et al. |
| 2008/0001735 A1 | 1/2008 | Tran |
| 2008/0003649 A1 | 1/2008 | Maltezos et al. |
| 2008/0019878 A1 | 1/2008 | Trump |
| 2008/0032416 A1 | 2/2008 | Park et al. |
| 2008/0038771 A1 | 2/2008 | Taylor et al. |
| 2008/0065420 A1 | 3/2008 | Tirinato et al. |
| 2008/0118988 A1 | 5/2008 | Johnson et al. |
| 2008/0144005 A1 | 6/2008 | Guiney et al. |
| 2008/0153096 A1 | 6/2008 | Witty et al. |
| 2008/0166753 A1 | 7/2008 | Storey et al. |
| 2008/0179301 A1 | 7/2008 | Garty et al. |
| 2008/0198379 A1 | 8/2008 | Coker et al. |
| 2008/0206751 A1 | 8/2008 | Squirrell et al. |
| 2008/0228107 A1 | 9/2008 | Reddy |
| 2008/0253933 A1 | 10/2008 | Redfern |
| 2008/0261210 A1 | 10/2008 | Frantzen et al. |
| 2008/0299652 A1 | 12/2008 | Owen et al. |
| 2009/0004754 A1 | 1/2009 | Oldenburg |
| 2009/0043607 A1 | 2/2009 | Nemoto et al. |
| 2009/0057259 A1 | 3/2009 | Johnson et al. |
| 2009/0059218 A1 | 3/2009 | Harner et al. |
| 2009/0081648 A1 | 3/2009 | Wangh |
| 2009/0088336 A1 | 4/2009 | Burd et al. |
| 2009/0093970 A1 | 4/2009 | Lewy et al. |
| 2009/0094361 A1 | 4/2009 | Srinivasan |
| 2009/0098594 A1 | 4/2009 | Fantl et al. |
| 2009/0104079 A1 | 4/2009 | O'Connell et al. |
| 2009/0117009 A1 | 5/2009 | Cote |

(56) References Cited

U.S. PATENT DOCUMENTS

| | | |
|---|---|---|
| 2009/0124284 A1 | 5/2009 | Scherzer et al. |
| 2009/0143235 A1 | 6/2009 | Drmanac et al. |
| 2009/0148941 A1 | 6/2009 | Florez et al. |
| 2009/0181463 A1 | 7/2009 | Chen |
| 2009/0203085 A1 | 8/2009 | Kurn et al. |
| 2009/0204435 A1 | 8/2009 | Gale |
| 2009/0208966 A1 | 8/2009 | Kacian et al. |
| 2009/0215157 A1 | 8/2009 | Jung et al. |
| 2009/0246782 A1 | 10/2009 | Kelso et al. |
| 2009/0274348 A1 | 11/2009 | Jakubowicz et al. |
| 2009/0274587 A1 | 11/2009 | Butz et al. |
| 2009/0298075 A1 | 12/2009 | Travers et al. |
| 2009/0298129 A1 | 12/2009 | Spence et al. |
| 2009/0305392 A1 | 12/2009 | Alfredsson et al. |
| 2009/0318775 A1 | 12/2009 | Michelson et al. |
| 2010/0009364 A1 | 1/2010 | Fantl et al. |
| 2010/0009456 A1 | 1/2010 | Prins et al. |
| 2010/0009460 A1 | 1/2010 | Clark et al. |
| 2010/0015634 A1 | 1/2010 | VanDine et al. |
| 2010/0034706 A1 | 2/2010 | Mathus et al. |
| 2010/0047128 A1 | 2/2010 | Mototsu et al. |
| 2010/0047790 A1 | 2/2010 | Southern et al. |
| 2010/0081144 A1 | 4/2010 | Holmes et al. |
| 2010/0081894 A1 | 4/2010 | Zdeblick et al. |
| 2010/0082781 A1 | 4/2010 | Lubeck et al. |
| 2010/0111773 A1 | 5/2010 | Pantelidis |
| 2010/0121156 A1 | 5/2010 | Yoo |
| 2010/0124746 A1 | 5/2010 | Liew |
| 2010/0132487 A1 | 6/2010 | Haack et al. |
| 2010/0151472 A1 | 6/2010 | Nolan et al. |
| 2010/0152885 A1 | 6/2010 | Regan et al. |
| 2010/0174181 A1 | 7/2010 | Nemoto |
| 2010/0184093 A1 | 7/2010 | Donovan et al. |
| 2010/0215644 A1 | 8/2010 | Fantl et al. |
| 2010/0240544 A1 | 9/2010 | Liu et al. |
| 2010/0246416 A1 | 9/2010 | Sinha et al. |
| 2010/0256470 A1 | 10/2010 | Miller |
| 2010/0262432 A1 | 10/2010 | Benja-Athon |
| 2010/0291588 A1 | 11/2010 | Mcdevitt et al. |
| 2010/0294950 A1 | 11/2010 | Kitamura et al. |
| 2011/0003392 A1 | 1/2011 | Stayton et al. |
| 2011/0003699 A1 | 1/2011 | Yoder et al. |
| 2011/0007261 A1 | 1/2011 | Abbott et al. |
| 2011/0008825 A1 | 1/2011 | Ingber et al. |
| 2011/0093249 A1 | 4/2011 | Holmes et al. |
| 2011/0116385 A1 | 5/2011 | Turlington et al. |
| 2011/0124128 A1 | 5/2011 | Oosterbroek et al. |
| 2011/0129931 A1 | 6/2011 | Reboud et al. |
| 2011/0130740 A1 | 6/2011 | Levy |
| 2011/0143947 A1 | 6/2011 | Chamberlin et al. |
| 2011/0183433 A1 | 7/2011 | Motadel et al. |
| 2011/0189785 A1 | 8/2011 | Gutmann et al. |
| 2011/0201121 A1 | 8/2011 | Kaartinen |
| 2011/0207617 A1 | 8/2011 | Faham et al. |
| 2011/0213564 A1 | 9/2011 | Henke |
| 2011/0213579 A1 | 9/2011 | Henke |
| 2011/0213619 A1 | 9/2011 | Henke |
| 2011/0218428 A1 | 9/2011 | Westmoreland et al. |
| 2011/0233148 A1 | 9/2011 | Antonchuk et al. |
| 2011/0256025 A1 | 10/2011 | Mabuchi et al. |
| 2011/0287447 A1 | 11/2011 | Norderhaug et al. |
| 2012/0053068 A1 | 3/2012 | Remacle et al. |
| 2012/0059664 A1 | 3/2012 | Georgiev et al. |
| 2012/0141339 A1 | 6/2012 | Sattler et al. |
| 2012/0142043 A1 | 6/2012 | Koyata et al. |
| 2012/0149035 A1 | 6/2012 | Burd et al. |
| 2012/0171759 A1 | 7/2012 | Williams et al. |
| 2012/0178091 A1 | 7/2012 | Glezer et al. |
| 2012/0206587 A1 | 8/2012 | Oz et al. |
| 2012/0224179 A1 | 9/2012 | Page |
| 2012/0291872 A1 | 11/2012 | Brady et al. |
| 2012/0309636 A1 | 12/2012 | Gibbons et al. |
| 2013/0074614 A1 | 3/2013 | Holmes et al. |
| 2013/0078149 A1 | 3/2013 | Holmes et al. |
| 2013/0078624 A1 | 3/2013 | Holmes et al. |
| 2013/0078625 A1 | 3/2013 | Holmes et al. |
| 2013/0079599 A1 | 3/2013 | Holmes et al. |
| 2013/0080071 A1 | 3/2013 | Holmes |
| 2013/0243794 A1 | 9/2013 | Hauser |
| 2013/0244898 A1 | 9/2013 | Burd et al. |
| 2013/0252320 A1 | 9/2013 | Burd et al. |
| 2013/0274139 A1 | 10/2013 | Burd et al. |
| 2014/0045170 A1 | 2/2014 | Patel et al. |
| 2014/0057255 A1 | 2/2014 | Holmes |
| 2014/0057770 A1 | 2/2014 | Holmes et al. |
| 2014/0073043 A1 | 3/2014 | Holmes |
| 2014/0081665 A1 | 3/2014 | Holmes |
| 2014/0170678 A1 | 6/2014 | Kasdan et al. |
| 2014/0170688 A1 | 6/2014 | Matje et al. |
| 2014/0170691 A1 | 6/2014 | Ingber et al. |
| 2014/0170735 A1 | 6/2014 | Holmes |
| 2014/0186238 A1 | 7/2014 | Holmes et al. |
| 2014/0229955 A1 | 8/2014 | Holmes et al. |
| 2014/0234949 A1 | 8/2014 | Wasson et al. |
| 2014/0272938 A1 | 9/2014 | Loo et al. |
| 2014/0287955 A1 | 9/2014 | Wende et al. |
| 2014/0295439 A1 | 10/2014 | Patel |
| 2014/0295440 A1 | 10/2014 | Belhocine et al. |
| 2014/0295447 A1 | 10/2014 | Hayashizaki et al. |
| 2014/0296089 A1 | 10/2014 | Holmes et al. |
| 2014/0308661 A1 | 10/2014 | Holmes et al. |
| 2014/0335505 A1 | 11/2014 | Holmes |
| 2014/0335506 A1 | 11/2014 | Burd et al. |
| 2014/0342371 A1 | 11/2014 | Holmes |
| 2015/0072338 A1 | 3/2015 | Holmes |
| 2015/0072362 A1 | 3/2015 | Lui et al. |
| 2015/0072889 A1 | 3/2015 | Lui et al. |
| 2015/0185234 A1 | 7/2015 | Gibbons et al. |
| 2015/0198588 A1 | 7/2015 | Burd et al. |
| 2015/0338428 A1 | 11/2015 | Holmes et al. |
| 2015/0368717 A1 | 12/2015 | Holmes et al. |
| 2016/0003823 A1 | 1/2016 | Holmes |
| 2016/0006928 A1 | 1/2016 | Gibbons et al. |
| 2016/0011215 A1 | 1/2016 | Holmes |
| 2016/0011225 A1 | 1/2016 | Holmes |
| 2016/0025760 A1 | 1/2016 | Holmes |
| 2016/0025763 A1 | 1/2016 | Holmes |
| 2016/0032361 A1 | 2/2016 | Holmes et al. |
| 2016/0033544 A1 | 2/2016 | Holmes et al. |
| 2016/0054343 A1 | 2/2016 | Holmes |
| 2016/0069919 A1 | 3/2016 | Holmes |
| 2016/0069920 A1 | 3/2016 | Holmes |
| 2016/0069921 A1 | 3/2016 | Holmes |
| 2016/0070884 A1 | 3/2016 | Lui et al. |
| 2016/0077015 A1 | 3/2016 | Holmes et al. |
| 2016/0084863 A1 | 3/2016 | Holmes et al. |
| 2016/0103123 A1 | 4/2016 | Holmes |
| 2016/0266108 A1 | 9/2016 | Burd |
| 2016/0266158 A1 | 9/2016 | Burd |
| 2016/0266163 A1 | 9/2016 | Burd |
| 2016/0320381 A1 | 11/2016 | Holmes |
| 2016/0370396 A1 | 12/2016 | Wasson |
| 2016/0377640 A1 | 12/2016 | Balwani |

FOREIGN PATENT DOCUMENTS

| | | |
|---|---|---|
| CN | 101031362 A | 9/2007 |
| CN | 101128738 A | 2/2008 |
| EP | 0410645 A2 | 1/1991 |
| EP | 684315 A1 | 11/1995 |
| EP | 0684315 A1 | 11/1995 |
| EP | 0488761 B1 | 1/1998 |
| EP | 0871034 A2 | 10/1998 |
| EP | 1054250 A1 | 11/2000 |
| EP | 1498067 A | 1/2005 |
| EP | 1722235 A | 11/2006 |
| EP | 0828222 B1 | 3/2010 |
| EP | 2259070 A2 | 12/2010 |
| EP | 2298931 B1 | 8/2013 |
| FR | 2498331 A | 7/1982 |
| JP | 61202142 A | 9/1986 |
| JP | S61254833 A | 11/1986 |
| JP | S6382359 A | 4/1988 |
| JP | S6420453 A | 1/1989 |

(56) References Cited

FOREIGN PATENT DOCUMENTS

| | | |
|---|---|---|
| JP | H03181853 A | 8/1991 |
| JP | 07027700 | 1/1995 |
| JP | H07304799 A | 11/1995 |
| JP | 8122336 | 5/1996 |
| JP | H08211071 | 8/1996 |
| JP | 2000258341 A | 9/2000 |
| JP | 2001255272 A | 9/2001 |
| JP | 2002538440 A | 11/2002 |
| JP | 2003329696 A | 11/2003 |
| JP | 2004101381 A | 4/2004 |
| JP | 2005010179 A | 1/2005 |
| JP | 2005130855 A | 5/2005 |
| JP | 2005291954 A | 10/2005 |
| JP | 2007017354 A | 1/2007 |
| JP | 2007178328 A | 7/2007 |
| JP | 2007187677 A | 7/2007 |
| JP | 2008064701 A | 3/2008 |
| JP | 2010175342 A | 8/2010 |
| JP | 2011174746 A | 9/2011 |
| RU | 2147123 C1 | 3/2000 |
| RU | 2179887 C1 | 2/2002 |
| RU | 2237426 C2 | 10/2004 |
| TW | 265262 B | 12/1995 |
| WO | 9013668 A1 | 11/1990 |
| WO | 9215673 A1 | 9/1992 |
| WO | 9507463 A | 3/1995 |
| WO | 9508774 A2 | 3/1995 |
| WO | 9603637 A1 | 2/1996 |
| WO | 9735171 A1 | 9/1997 |
| WO | 9814605 A1 | 4/1998 |
| WO | 9826277 A2 | 6/1998 |
| WO | 9904043 A1 | 1/1999 |
| WO | 9949019 A2 | 9/1999 |
| WO | 0049176 A1 | 8/2000 |
| WO | 0244703 A2 | 6/2002 |
| WO | 02064038 A | 8/2002 |
| WO | 2004055198 A2 | 7/2004 |
| WO | 2004059312 A1 | 7/2004 |
| WO | 2004112602 A1 | 12/2004 |
| WO | 2005025413 A2 | 3/2005 |
| WO | 2005065157 A2 | 7/2005 |
| WO | 2005065538 A2 | 7/2005 |
| WO | 2005072145 A2 | 8/2005 |
| WO | 2005121780 A2 | 12/2005 |
| WO | 2006090154 A | 8/2006 |
| WO | 2006120656 A1 | 11/2006 |
| WO | 2006121510 A2 | 11/2006 |
| WO | 2007002579 A | 1/2007 |
| WO | 2008050254 A1 | 5/2008 |
| WO | 2008115632 A2 | 9/2008 |
| WO | 2009046227 A1 | 4/2009 |
| WO | 2009130309 A1 | 10/2009 |
| WO | 2011106315 A1 | 9/2011 |
| WO | 2011106512 A | 9/2011 |
| WO | 2012012779 A2 | 1/2012 |
| WO | 2012040641 A | 3/2012 |
| WO | 2012069925 A1 | 5/2012 |
| WO | 2010090857 | 6/2012 |
| WO | 2012100235 A | 7/2012 |
| WO | 2013043203 A | 3/2013 |
| WO | 2013052318 A1 | 4/2013 |
| WO | 2013148866 A1 | 10/2013 |
| WO | 2014127379 A1 | 8/2014 |
| WO | 2015035256 A2 | 3/2015 |

OTHER PUBLICATIONS

Nwakanma, et al. Quantitative detection of plasmodium falciparum NDA in saliva, blood, and urine. Journal of Infectious Diseases (2009) 199 1567-1574.

Obryadina A.P. et al, "Avidnost antitel v diagnostike infektsionnykh zabolevaniy" Laboratornaya diagnostika infektsionnykh zabolevaniy, 2007, No. 4, p. 3-7.

O'Connor, et al. Humanization of an antibody against human protein C and calcium-dependence involving framework residues. Protein Eng. 1998; 11(4):321-8.

Office Action dated Jan. 11, 2012 for U.S. Appl. No. 13/244,951.
Office Action dated Jan. 13, 2015 for U.S. Appl. No. 13/647,325.
Office Action dated Jan. 14, 2014 for U.S. Appl. No. 13/893,258.
Office Action dated Jan. 19, 2011 for U.S. Appl. No. 12/244,723.
Office Action dated Jan. 19, 2012 for U.S. Appl. No. 13/244,956.
Office Action dated Jan. 23, 2013 for U.S. Appl. No. 13/355,458.
Office Action dated Jan. 24, 2012 for Application No. MX/a/2010/003578.
Office Action dated Jan. 27, 2012 for U.S. Appl. No. 13/244,946.
Office Action dated Jan. 29, 2015 for U.S. Appl. No. 13/893,258.
Office Action dated Jan. 29, 2015 for U.S. Appl. No. 14/479,241.
Office Action dated Jan. 3, 2012 for Application No. SG201002319-0.
Office Action dated Jan. 9, 2015 for U.S. Appl. No. 14/157,343.
Office Action dated Oct. 17, 2011 for Application No. MX/a/2010/003578.
Office Action dated Oct. 25, 2012 for Application No. SG201002319-0.
Office Action dated Nov. 12, 2014 for U.S. Appl. No. 14/479,245.
Office Action dated Nov. 15, 2012 for Application No. JP2010-528139.
Office Action dated Nov. 6, 2012 for U.S. Appl. No. 13/244,954.
Office Action dated Nov. 6, 2013 for U.S. Appl. No. 13/916,553.
Office Action dated Feb. 12, 2015 for U.S. Appl. No. 14/479,190.
Office Action dated Feb. 15, 2012 for U.S. Appl. No. 13/244,952.
Office Action dated Feb. 20, 2014 for U.S. Appl. No. 13/764,642.
Office Action dated Feb. 24, 2012 for U.S. Appl. No. 13/244,954.
Office Action dated Mar. 1, 2012 for U.S. Appl. No. 13/244,953.
Office Action dated Mar. 12, 2012 for Application No. IL204877.
Office Action dated Mar. 12, 2012 for U.S. Appl. No. 13/244,947.
Office Action dated Mar. 21, 2012 for U.S. Appl. No. 13/244,950.
Office Action dated Mar. 22, 2012 for U.S. Appl. No. 13/244,949.
Office Action dated Mar. 25, 2014 for U.S. Appl. No. 13/889,674.
Office Action dated Mar. 26, 2012 for U.S. Appl. No. 13/244,836.
Office Action dated Apr. 17, 2012 for U.S. Appl. No. 13/244,952.
Office Action dated Apr. 20, 2015 for U.S. Appl. No. 13/769,779.
Office Action dated Apr. 22, 2015 for U.S. Appl. No. 13/244,956.
Office Action dated Apr. 29, 2015 for U.S. Appl. No. 13/769,820.
Office Action dated Apr. 3, 2015 for U.S. Appl. No. 14/479,245.
Office Action dated Apr. 6, 2015 for U.S. Appl. No. 13/244,950.
Office Action dated Jun. 12, 2015 for U.S. Appl. No. 13/326,023.
Office Action dated Jun. 18, 2012 for U.S. Appl. No. 13/244,951.
Office Action dated Jun. 19, 2015 for U.S. Appl. No. 14/183,500.
Office Action dated Jun. 20, 2012 for U.S. Appl. No. 13/244,946.
Office Action dated Jun. 21, 2011 for Application No. NZ584963.
Office Action dated Jun. 22, 2012 for Application No. EP 8836072.2.
Office Action dated Jun. 29, 2012 for Application No. CN 200880118646.2.
Office Action dated Jun. 9, 2010 for U.S. Appl. No. 12/244,723.
Office Action dated Jul. 13, 2012 for U.S. Appl. No. 13/244,836.
Office Action dated Jul. 13, 2012 for U.S. Appl. No. 13/244,956.
Office Action dated Jul. 18, 2013 for U.S. Appl. No. 13/893,258.
Zhao, et al. Phylogenetic distribution and genetic mapping of a (GGC)n microsatellite from rice (*Oryza sativa* L.). Plant Mol Biol. Feb. 1993;21(4):607-14.
Zietkiewicz, et al. Genome fingerprinting by simple sequence repeat (SSR)-anchored polymerase chain reaction amplification. Genomics. Mar. 15, 1994;20(2):176-83.
Zimmerman O et al. C-reactive protein serum levels as an early predictor of outcome in patients with pandemic H1N1 influenza A virus infection. BMC Infect Dis. Oct. 4, 2010;10:288.
Niiemz, et al. Nucleic acid testing for tuberculosis at the point-of-care in high-burden countries. Expert Rev Mol Diagn. Sep. 2012; 12(7): 687-701.
Notice of Allowance dated Nov. 12, 2015 for U.S. Appl. No. 13/769,779.
Notice of Allowance dated Nov. 20, 2015 for U.S. Appl. No. 13/244,956.
Office Action dated Jan. 5, 2016 for U.S. Appl. No. 14/831,734.

(56) References Cited

OTHER PUBLICATIONS

Office Action dated Nov. 12, 2015 for U.S. Appl. No. 14/562,066.
Office Action dated Nov. 19, 2015 for U.S. Appl. No. 14/604,194.
Office Action dated Nov. 24, 2015 for U.S. Appl. No. 14/831,838.
Office Action dated Nov. 4, 2015 for U.S. Appl. No. 13/933,035.
Office Action dated Dec. 15, 2015 for U.S. Appl. No. 14/848,775.
Office Action dated Dec. 17, 2015 for U.S. Appl. No. 14/860,149.
Office Action dated Dec. 18, 2015 for U.S. Appl. No. 14/860,048.
Office Action dated Dec. 18, 2015 for U.S. Appl. No. 14/872,919.
Office Action dated Dec. 3, 2015 for U.S. Appl. No. 14/848,032.
Office Action dated Dec. 4, 2015 for U.S. Appl. No. 14/670,200.
Office Action dated Dec. 7, 2015 for U.S. Appl. No. 14/859,064.
Van Ierssel, et al., Flow cytometric detectopm of endothelial microparticles (EMP): Effects of centrifugation and storage alter with the phenotype studied, Thrombosis Research 125 (2010) 332-339.
Abbott. FDA Clears Abbott's i-STAT 1 Wireless Point of Care Testing System. Press release dated Mar. 29, 2011.
Abbott. Procedure Manual for the i-STAT System. Rev. dated Jul. 12, 2004.
ABBOTT. Testing Cartridges for the i-STAT System. Rev. B. Jun. 2009. Available at http://www.abbottpointofcare.com/PDFs/17845_CrtrdgeBrochure_M1.pdf. Accessed Sep. 13, 2011.
Advisory Action dated Sep. 25, 2015 for U.S. Appl. No. 14/479,241.
Anders et al., Am Journal Med Hyg 87(1), 2012, pp. 165-170.
AppliedBiosystems StepOne Real-Time PCR System Manual, Rev. 2010.
B. Rodriguez-Sanchez et al. Improved Diagnosis for Nine Viral Diseases Considered as Notifiable by the World Organization for Animal Health. Transbound Emerg Dis. Aug. 2008; 55(5-6): 215-25.
Botstein, et al. Construction of a genetic linkage map in man using restriction fragment length polymorphisms. Am J Hum Genet. May 1980;32(3):314-31.
Bruggemann, et al. Production of human antibody repertoires in transgenic mice. Curr Opin Biotechnol. 1997; 8 (4):455-458.
Carter, et al. Humanization of an anti-p185HER2 antibody for human cancer therapy. Proc. Natl. Acad. Sci. USA. 1992;89(10):4285-9.
Chantreuil J. et al. "Artial chaotic tachycardia during a respiratory tract infection due to NL63 coronavirus". Arch Pediatr, Mar. 2013; 20(3):pp. 278-281, abstract.
Dapat I.C. et al. Genetic characterization of human influenza viruses in the pandemic (2009-2010) and post-pandemic (2010-2011) periods in Japan. PLoS One, 2012; 7(6):e36455.
Di Serio, et al. Integration between the tele-cardiology unit and the central laboratory: methodological and clinical evaluation of point-of-care testing cardiac marker in the ambulance. Clin Chem Lab Med. 2006;44(6):768-73.
Diamandis. Theranos phenomenon: promises and fallacies. Clin Chem Lab Med. Jun. 2015;53(7):989-93.
ebm Industries, Inc. Motor Design, Quality and Performance are Critical to Reliable Operation of Fans and Blowers. pp. 15-17. emb Industries, Inc. 1995, 1996, 1997, 1999.
European search report and opinion dated Sep. 18, 2013 for Application No. 13178059.5.
European search report dated Aug. 31, 2010 for Application No. 8836072.2.
Gibbons, et al. Patient-side immunoassay system with a single-use cartridge for measuring analytes in blood. Clin Chem. Sep. 1989;35(9):1869-73.
Gill, et al. Nucleic acid isothermal amplification technologies: a review. Nucleosides, Nucleotides and Nucleic Acids. Mar. 2008; 27(3):224-43.
Godolphin et al. Automated blood-sample handling in the clinical laboratory. Clinical Chemistry (1990) 36 1551-1555.
Griffiths, et al. Strategies for selection of antibodies by phage display. Curr Opin Biotechnol. Feb. 1998;9(1):102-8.
Guatelli, et al. Isothermal, in vitro amplification of nucleic acids by a multienzyme reaction modeled after retroviral replication. Proc. Natl. Acad. Sci. USA. 1990;87:1874-1878.
Health Buddy device. Available at http://www.3hc.org/images/2009 %20images/health-buddy-appliance.gif. Accessed Aug. 26, 2011.
Health Buddy Health Management Programs. Available at http://www.bosch-telehealth.com/content/language1/img_zoom/health_buddy_system.gif. Accessed Aug. 26, 2011.
Hung et al. Effect of clinical and virological parameters on the level of neutralizing antibody against pandemic influenza A virus H1N1 2009. Clin Infect Dis. Aug. 1, 2010;51(3):274-9.
International Search Report and Written Opinion dated Jan. 16, 2014 for Application No. PCT/US2013/061485.
International search report and written opinion dated Jan. 18, 2012 for PCT/US2011/053189.
International search report and written opinion dated Jan. 20, 2012 for PCT/US2011/053188.
International search report and written opinion dated Nov. 5, 2012 for PCT/US2012/057093.
International search report and written opinion dated Feb. 6, 2013 for PCT/US2012/057155.
International Search Report and Written Opinion dated Jun. 19, 2014 for PCT/US2014/016997.
International search report and written opinion dated Aug. 3, 2012 for PCT/US2012/022130.
International search report and written opinion dated Sep. 16, 2008 for PCT/US2007/009878.
International search report dated Dec. 5, 2008 for PCT Application No. U52008/78636.
Jones, et al. Replacing the complementarity-determining regions in a human antibody with those from a mouse. Nature. 1986;321:522-525.
Kautner et al., Journal of Pediatrics, 1997, 131, pp. 516-524.
Khan, et al. Detection of influenza virus neuraminidase-specific antibodies by an enzyme-linked immunosorbent assay. J Clin Microbiol. Jul. 1982;16(1): 115-22.
Kimura Y et al. Tail variation of the folding primer effects the SmartAmp2 process differently. Biochem Biophys Res Commun. Jun. 12, 2009;383(4):455-9.
Kwok, et al. Increasing the information content of STS-based genome maps: identifying polymorphisms in mapped STSs. Genomics. Jan. 1, 1996;31(1):123-6.
Landgren. Molecular mechanics of nucleic acid sequence amplification. Trends Genet. Jun. 1993;9(6):199-204.
Lee, et al. Nucleic Acid Amplication Technologies. 1997. (Textbook).
Li, Peng. (2012) Microfluidics for IVD: In Pursuit of the Holy Grail. J Bioengineer & Biomedical Sci S8:e001.
Little, et al. Of mice and men: hybridoma and recombinant antibodies. Immunol Today. Aug. 2000;21(8):364-70.
Lizardi, et al. Exponential amplification of recombinant-RNA hybridization probes. BioTechnol. 1988; 6:1197-1202.
Lounsbury et al., Lab Chip, 2013, 13, pp. 1384-1393.
Luk F.O. et al. A case of dengue maculopathy with spontaneous recovery. Case Rep Ophthalmol, Jun. 8, 2013;4(2):pp. 28-33.
Notice of Allowance dated Dec. 15, 2014 for U.S. Appl. No. 14/339,946.
Notice of Allowance dated May 29, 2015 for U.S. Appl. No. 14/480,960.
Notice of Allowance dated May 6, 2015 for U.S. Appl. No. 13/893,258.
Notice of Allowance dated Aug. 11, 2014 for U.S. Appl. No. 13/244,954.
Office Action dated Jul. 24, 2012 for U.S. Appl. No. 13/244,947.
Office Action dated Jul. 28, 2014 for U.S. Appl. No. 13/244,949.
Office Action dated Jul. 7, 2014 for U.S. Appl. No. 13/769,779.
Office Action dated Jul. 8, 2014 for U.S. Appl. No. 13/355,458.
Office Action dated Jul. 8, 2014 for U.S. Appl. No. 14/157,343.
Office Action dated Jul. 8, 2015 for U.S. Appl. No. 14/479,241.
Office Action dated Aug. 1, 2012 for U.S. Appl. No. 13/244,949.
Office Action dated Aug. 16, 2012 for U.S. Appl. No. 13/244,950.
Office Action dated Aug. 16, 2012 for U.S. Appl. No. 13/244,953.
Office Action dated Aug. 22, 2014 for U.S. Appl. No. 13/244,950.

(56) References Cited

OTHER PUBLICATIONS

Office Action dated Sep. 18, 2014 for U.S. Appl. No. 14/339,946.
Office Action dated Sep. 24, 2015 for U.S. Appl. No. 14/479,245.
Office Action dated Sep. 26, 2013 for U.S. Appl. No. 13/889,674.
Office Action dated Sep. 8, 2014 for U.S. Appl. No. 13/244,956.
Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05.
Papautsky, et al. Micromachined pipette arrays. IEEE Trans Biomed Eng. Jun. 2000;47(6):812-9.
Plebani. Evaluating and using innovative technologies: a lesson from Theranos? Clin Chem Lab Med. Jun. 2015;53 (7):961-2.
Queen, et al. A humanized antibody that binds to the interleukin 2 receptor. Proc. Natl. Acad. Sci. USA. 1989; 86 (24):10029-33.
Ray, et al. Distinct hemagglutinin and neuraminidase epitopes involved in antigenic variation of recent human parainfluenza virus type 2 isolates. Virus Res. Jun. 1992;24(1):107-13.
Resch-Genger, Ute, et al., "Quantum dots versus organic dyes as fluorescent labels," Sep. 2008, Nature Methods, 5, pp. 763-775.
Restriction Requirement dated Aug. 1, 2013 for U.S. Appl. No. 13/916,553.
Restriction Requirement dated Aug. 26, 2013 for U.S. Appl. No. 13/916,533.
Riechmann, et al. Reshaping human antibodies for therapy. Nature. Mar. 24, 1988;332(6162):323-7.
Roskos et al. Simple System for Isothermal DNA Amplification Coupled to Lateral Flow Detection. PLOS One. Jul. 26, 2013;8(7):e69335. Print 2013.
Rouzic. Contamination-pipetting: relative efficiency of filter tips compared to Microman(R) postitive displacement pipette. Nature Methods (2006) 3 iii-iv.
Sahni et al. Reverse transcription loop-mediated isothermal amplification (RT-LAMP) for diagnosis of dengue. Med J Armed Forces India. Jul. 2013; 69(3):246-53. doi: 10.1016/j.mjafi.2012.07.017. Epub Dec. 1, 2012.
Sakas. Trends in Medical Imaging from 2D to 3D. Computers and Graphics. 2002;26:577-587.
Singapore combined search report/examination dated Jan. 3, 2012 for Application No. 201002319.
Tautz. Hypervariability of simple sequences as a general source for polymorphic DNA markers. Nucleic Acids Res. Aug. 25, 1989;17(16):6463-71.
Thermo Scientific: Thermo Scientific Heraeus Labofuge 400 and 400 R Centrifuges Great value and performance for everyday use in the lab, Jan. 1, 2008.
Tholouli, Eleni, et al., "Imaging of multiple mRNA targets using quantum dot based in situ hybridization and spectral deconvolution in clinical biopsies," Jul. 31, 2006, Biochemical and Biophysical Research Communications, 348, pp. 628-636.
U.S. Appl. No. 14/604,194, filed Jan. 23, 2015.
U.S. Appl. No. 13/896,171, filed May 16, 2013. Inventors: Holmes, et al.
U.S. Appl. No. 14/050,235, filed Oct. 9, 2013. Inventors: Holmes, et al.
U.S. Appl. No. 60/997,460, filed Oct. 2, 2007.
U.S. Appl. No. 61/435,250, filed Jan. 21, 2011. Inventors: Gibbons et al.
U.S. Appl. No. 61/766,113, filed Feb. 18, 2013.
U.S. Appl. No. 61/766,119, filed Feb. 18, 2013.
U.S. Appl. No. 61/805,923, filed Mar. 27, 2013.
Verhoeyen, et al. Reshaping human antibodies: grafting an antilysozyme activity. Science. 1988;239:1534-1536.
Von Lode, P. Point-of-care immunotesting: approaching the analytical performance of central laboratory methods. Clin Biochem. Jul. 2005;38(7):591-606.
Vos, et al. AFLP: a new technique for DNA fingerprinting. Nucleic Acids Res. Nov. 11, 1995;23(21):4407-14.
Voudoukis et al., 2011, Med Sci Monit, 17(4), pp, 185-188.
Wang Y. et al. "Methicillin resistant *Staphyloccus aureus* infection: a case report and literature review". Zhonghua Jie He Hu Xi Za Zhi, Sep. 2009; 32(9):pp. 665-659, abstract.
Weber, et al. Abundant class of human DNA polymorphisms which can be typed using the polymerase chain reaction. Am J Hum Genet. Mar. 1989;44(3):388-96.
Wikipedia. Electric motor. Available at http://en.wikipedia.org/wiki/Electric_motor. Accessed May 22, 2012.
Wikipedia. Outrunner. Available at http://en.wikipedia.org/wiki/Outrunner. Accessed May 22, 2012.
Williams, et al. DNA polymorphisms amplified by arbitrary primers are useful as genetic markers. Nucleic Acids Res. Nov. 25, 1990;18(22):6531-5.
World Health Organization (WHO) Guide to Field Operations, Oct. 2006, pp. 1-80.
Written Opinion and International Search Report dated Dec. 18, 2014 for PCT/US2014/054424.
Dinca et al. Fast and accurate temperature control of a PCT microsystem with a disposable reactor, J. Micromech. Microeng. 19 (2009).
Dzenitis, Presentation of Autonomous Pathogen Detection System, Lawrence Livermore National Laboratory, Aug. 21, 2006, Washington, DC, UCRL-PRES-22311.
Ma et al. Study of ELISA Technique, Nature and Science, 4(2), 2006, Ma, ELISA Technique.
Notice of Allowance dated Jun. 22, 2016 for U.S. Appl. No. 13/326,023.
Notice of Allowance dated Jun. 6, 2016 for U.S. Appl. No. 14/479,245.
Notice of Allowance dated Jun. 6, 2016 for U.S. Appl. No. 14/562,066.
Office Action dated U.S. Appl. No. 14/183,500 dated Jun. 16, 2016 for U.S. Appl. No. 14/183,500.
Office Action dated Jun. 10, 2016 for U.S. Appl. No. 14/839,749.
Office Action dated Jun. 10, 2016 for U.S. Appl. No. 14/855,303.
Office Action dated Jun. 10, 2016 for U.S. Appl. No. 14/859,064.
Office Action dated Jun. 17, 2016 for U.S. Appl. No. 14/872,919.
Office Action dated Jun. 24, 2016 for U.S. Appl. No. 14/860,048.
Office Acton dated Jun. 9, 2016 for U.S. Appl. No. 13/933,035.
Schembri, et al. Centrifugation and capillarity integrated ino a multiple analyte whole blood analyser, Jounal of Automatic Chemistry, vol. 17, No. 3 (May-Jun. 1995), pp. 99-104.
Advisory Action dated Apr. 29, 2016 for U.S. Appl. No. 14/183,500.
Office Action dated May 10, 2016 for U.S. Appl. No. 14/793,625.
Office Action dated May 12, 2016 for U.S. Appl. No. 13/769,820.
Office Action dated May 13, 2016 for U.S. Appl. No. 14/857,224.
Office Action dated May 19, 2016 for U.S. Appl. No. 14/831,734.
Office Action dated May 6, 2016 for U.S. Appl. No. 14/857,407.
Advisory Action dated Aug. 19, 2016 for U.S. Appl. No. 14/839,749.
Advisory Action dated Aug. 19, 2016 for U.S. Appl. No. 14/855,303.
Advisory Action dated Aug. 3, 2016 for U.S. Appl. No. 14/857,407.
Advisory Action dated Aug. 8, 2016 for U.S. Appl. No. 14/857,224.
Notice of Allowance dated Jul. 19, 2016 for U.S. Appl. No. 15/007,585.
Notice of Allowance dated Aug. 22, 2016 for U.S. Appl. No. 13/244,949.
Notice of Allowance dated Aug. 22, 2016 for U.S. Appl. No. 14/479,241.
Dffice Action dated Jun. 30, 2016 for U.S. Appl. No. 14/872,718.
Dffice Action dated Jul. 1, 2016 for U.S. Appl. No. 14/848,775.
Office Action dated Jul. 1, 2016 for U.S. Appl. No. 14/860,149.
Office Action dated Jul. 14, 2016 for U.S. Appl. No. 14/829,572.
Office Action dated Jul. 14, 2016 for U.S. Appl. No. 14/848,032.
Office Action dated Jul. 8, 2016 for U.S. Appl. No. 14/918,090.
Office Action dated Aug. 15, 2016 for U.S. Appl. No. 14/183,503.
Office Action dated Aug. 15, 2016 for U.S. Appl. No. 14/789,920.
Office Action dated Aug. 18, 2016 for U.S. Appl. No. 14/831,838.
Office Action dated Aug. 24, 2016 for U.S. Appl. No. 14/848,084.
Office Action dated Aug. 25, 2016 for U.S. Appl. No. 14/872,995.
Office Action dated Aug. 26, 2016 for U.S. Appl. No. 14/789,930.
Office Action dated Aug. 8, 2016 for U.S. Appl. No. 13/244,950.

(56) References Cited

OTHER PUBLICATIONS

Webb et al. Vascular endothelial growth factor (VEGF) is released from platelets during blood clotting: implications for measurement of circulating VEGF levels in clinical disease, Clinical Science (1998) 94,395-404 (printed in Great Britain).
510(k) Substantial Equivalence Determination Decision Summary dated Jul. 16, 2015 for "Theranos Herpes Simplex Virus-1 (HSV-1) IgG Assay".
510(k) Substantial Equivalence Determination issued for "Theranos Herpes Simplex Virus-1 IgG Assay" by the FDA on Jul. 7, 2015.
Allain, Charles C. et al. Enzymatic determination of total serum cholesterol. Clinical Chemistry (1974) 20 470-475.
Chin et al. Low-Cost Microdevices for Point-of-Care Testing. Biological and Medical Physics, Biomedical Engineering pp. 3-21. Oct. 12, 2012.
Drosten et al. Rapid detection and quantification of RNA of Ebola and Marburg viruses, Lassa virus, Crimean-Congo hemorrhagic fever virus, Rift Valley fever virus, dengue virus, and yellow fever virus by real-time reverse transcription-PCR, J Clin Microbiol, Jul. 2002, 40(7), 2323-2330.
Examiner's Answer to Appeal Brief dated Feb. 26, 2016 for U.S. Appl. No. 14/157,343.
Fuller K. Centers for Medicare and Medicaid Services (CMS). Condition Level Deficiencies Notice—Immediate Jeopardy. Notice to Theranos, Inc. director Dr. Sunil Dhawan. Jan. 25, 2016. https://cdn2.vox-cdn.com/uploads/chorus_asset/file/5969923/Theranos_Inc_Cover_Letter_01-25-2016.0.pdf.
Havlickova M et al. Influenza virus detection in clinical specimens. Abstract. Acta Virol. Sep. 1990;34(5):449-56.
Jannetto et al. Real-Time Detection of Influenza A, Influenza B, and Respiratory Syncytial Virus A and B in Respiratory Specimens by Use of Nanoparticle Probes. J Clin Microbiol. Nov. 2010;48(11):3997-4002. Epub Sep. 8, 2010.
Loria K. More skeptical than ever: Experts respond to the government's warning letter to Theranos. Jan. 28, 2016. Tech Insider. http://www.techinsider/io/how-bad-the-cms-letter-to-theranos-really-is-2016-1.
Mahony et al. Molecular diagnosis of respiratory virus infections. Crit Rev Clin Lab Sci. Sep.-Dec. 2011;48(5-6):217-49.
Martin, David H. et al. Use of multiple acid amplification tests to define the infected-patient "gold standard" in clinical trials of new diagnostic tests for Chlamydia trachomatis infections. J. Clinical Microbiology (2004) 42 4749-4758.
Metzgar D. et al. Single assay for simultaneous detection and differential identification of human and avian influenza virus types, subtypes, and emergent variants. PLoS One. Feb. 3, 2010;5(2):e8995.
Notice of Allowance dated Jan. 12, 2016 for U.S. Appl. No. 14/670,200.
Notice of Allowance dated Jan. 14, 2016 for U.S. Appl. No. 13/326,023.
Notice of Allowance dated Feb. 5, 2016 for U.S. Appl. No. 13/244,949.
Office Action dated Jan. 11, 2016 for U.S. Appl. No. 14/829,572.
Office Action dated Jan. 12, 2016 for U.S. Appl. No. 14/857,224.
Office Action dated Jan. 13, 2016 for U.S. Appl. No. 14/857,407.
Office Action dated Jan. 21, 2016 for U.S. Appl. No. 14/183,503.
Office Action dated Feb. 23, 2016 for U.S. Appl. No. 14/183,500.
Office Action dated Feb. 24, 2016 for U.S. Appl. No. 14/479,245.
Office Action dated Feb. 24, 2016 for U.S. Appl. No. 14/848,084.
Office Action dated Feb. 29, 2016 for U.S. Appl. No. 13/244,950.
Office Action dated Feb. 4, 2016 for U.S. Appl. No. 13/769,820.
Office Action dated Feb. 4, 2016 for U.S. Appl. No. 14/839,749.
Office Action dated Feb. 8, 2016 for U.S. Appl. No. 14/855,303.
Office Action dated Mar. 22, 2016 for U.S. Appl. No. 14/918,090.
Office Action dated Mar. 8, 2016 for U.S. Appl. No. 14/604,194.
Office Action dated Apr. 18, 2016 for U.S. Appl. No. 14/479,241.
Office Action dated Apr. 7, 2016 for U.S. Appl. No. 15/007,585.
Pacaniello. Detection of antigens or antibodies by ELISA, Jul. 16, 2010, published by Virology Blog. Downloaded by USPTO Examiner on Jan. 5, 2016 from http://www.virology.ws/2010/07/16/detection-of-antigens-or-antibodies-by-elisa/.
Preliminary Amendment date Jan. 26, 2016 for U.S. Appl. No. 15/006,349.
Preliminary Amendment dated Jan. 19, 2016 for U.S. Appl. No. 14/928,087.
Preliminary Amendment dated Jan. 25, 2016 for U.S. Appl. No. 15/005,897.
Preliminary Amendment dated Dec. 10, 2015 for U.S. Appl. No. 14/965,665.
Preliminary Amendment dated Dec. 10, 2015 for U.S. Appl. No. 14/965,725.
Ramsey L. Theranos has a week to respond to the searing report about its business. Business Insider. Feb. 5, 2016. http://www.businessinsider.com/theranos-response-to-cms-2016-2.
Rappleye E. Theranos gets extension to fix issues following CMS investigation. Becker's Hospital Review. Feb. 8, 2016. http://www.beckershospitalreview.com/hospital-management-adminstration/theranos-gets-extension-to-fix-issues-following-cms-investigation.html.
Teles, Fernando S. R. R. Biosensors and rapid diagnostic tests on the frontier between analytical and clinical chemistry for biomolecular diagnosis of dengue disease: A review. Analytical Chimica Acta (2011) 687 28-42.
Advisory Action dated Sep. 15, 2016 for U.S. Appl. No. 14/918,090.
Notice of Allowance dated Oct. 3, 2016 for U.S. Appl. No. 13/769,820.
Notice of Allowance dated Sep. 28, 2016 for U.S. Appl. No. 14/831,734.
Office Action dated Sep. 13, 2016 for U.S. Appl. No. 14/965,725.
Office Action dated Sep. 19, 2016 for U.S. Appl. No. 14/839,749.
Office Action dated Sep. 19, 2016 for U.S. Appl. No. 14/855,303.
Office Action dated Sep. 2, 2016 for U.S. Appl. No. 14/857,224.
Office Action dated Sep. 7, 2016 for U.S. Appl. No. 14/857,407.
Office Action dated Sep. 9, 2016 for U.S. Appl. No. 15/160,491.
Preliminary Amendment dated Aug. 5, 2016 for U.S. Appl. No. 15/159,501.
Notice of Allowance dated Dec. 2, 2016 for U.S. Appl. No. 15/007,585.
Notice of Allowance dated Dec. 9, 2016 for U.S. Appl. No. 13/933,035.
Office Action dated Jan. 3, 2017 for U.S. Appl. No. 15/160,578.
Office Action dated Oct. 20, 2016 for U.S. Appl. No. 14/848,032.
Office Action dated Oct. 26, 2016 for U.S. Appl. No. 14/793,625.
Office Action dated Oct. 31, 2016 for U.S. Appl. No. 14/918,090.
Office Action dated Nov. 17, 2016 for U.S. Appl. No. 14/965,665.
Office Action dated Nov. 18, 2016 for U.S. Appl. No. 15/005,897.
Office Action dated Nov. 21, 2016 for U.S. Appl. No. 14/183,503.
Office Action dated Nov. 18, 2016 for U.S. Appl. No. 14/604,194.
Office Action dated Dec. 15, 2016 for U.S. Appl. No. 14/183,500.
Office Action dated Dec. 28, 2016 for U.S. Appl. No. 14/872,718.
Office Action dated Dec. 29, 2016 for U.S. Appl. No. 15/041,421.
Office Action dated Dec. 30, 2016 for U.S. Appl. No. 14/848,084.
Notice of Allowance dated Jan. 13, 2017 for U.S. Appl. No. 14/872,919.
Notice of Allowance dated Nov. 5, 2017 for U.S. Appl. No. 14/859,064.
Office Action dated Feb. 9, 2017 for U.S. Appl. No. 14/831,838.
Office Action dated Mar. 2, 2017 for U.S. Appl. No. 14/918,090.
Office Action dated Mar. 22, 2017 for U.S. Appl. No. 15/160,491.
Office Action dated Mar. 29, 2017 for U.S. Appl. No. 14/789,904.
Office Action dated Apr. 7, 2017 for U.S. Appl. No. 14/860,048.
Office Action dated Apr. 7, 2017 for U.S. Appl. No. 14/860,149.
Craw et al. Isothermal nucleic acid amplification technologies for point-of-care diagnostics: a critical review, Lab on a Chip, vol. 12, No. 14, Jul. 1, 2012.
Horton et al. Engineering hybrid genes without the use of restriction enzymes: gene splicing byoverlap extension. Gene, Elsevier, Amsterdam, NL, vol. 77, No. 1, Apr. 15, 1989, pp. 61-68.

\* cited by examiner

SECTION E-E

A: Negative

B: Positive

D: Positive

Control: OK

Centrifugation Vessel        Extraction Tip

Key:

| Symbol | Condition | ESR (mm/hour maximum) |
|---|---|---|
| Squares | Hashimoto thyroiditis | 8.3 |
| Circles | Systemic lupus erythematosus | 1.8 |
| Triangles | Rheumatoid arthritis | 3.3 |

Distribution of Pixel Intensities

Sample 1 – non-agglutinated (no virus, no antibody)

Sample 2 – non agglutinated (virus plus antibody)

Sample 3 – agglutinated (virus, no antibody)

SEQUENCE LISTING

<160> NUMBER OF SEQ ID NOS: 2

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tttttttttt tttttttttt tttttttttt tttttttttt ttttggttg gtgtggttgg          60

<210> SEQ ID NO 2
<211> LENGTH: 60
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 2
tttttttttt tttttttttt tttttttttt ttacaggggt gtggggacag gggtgtgggg      60
```

SYSTEMS AND METHODS FOR SAMPLE USE MAXIMIZATION

CROSS-REFERENCE

This application claims priority to U.S. Provisional Patent Application Ser. No. 61/435,250, filed Jan. 21, 2011, which application is entirely incorporated herein by reference.

The instant application contains a Sequence Listing which has been submitted in ASCII format via EFS-Web and is hereby incorporated by reference in its entirety. The ASCII copy, created on Nov. 3, 2015, is titled "733.204_SeqListing" and is 908 bytes in size.

BACKGROUND OF THE INVENTION

The discovery of a vast number of disease biomarkers, new therapies and the establishment of miniaturized medical systems have opened up new avenues for the prediction, diagnosis and monitoring of treatment of diseases in a point-of-care or other distributed test settings. Point-of-care systems can rapidly deliver test results to medical personnel, other medical professionals and patients. Early diagnosis of a disease or disease progression and monitoring of therapy are often critical for treatment of deadly conditions such as certain cancers and infectious diseases.

Diagnosis and treatment of diseases can take advantage of multiplexed biomarker measurements, which provide additional knowledge of the condition of a patient. For example, when monitoring the effects of a drug, three or more biomarkers can be measured in parallel. Typically, microtiter plates and other similar apparatuses have been used to perform multiplexed separation-based assays. A microtiter plate (for example, a 384 well microtiter plate) can perform a large number of assays in parallel.

In a Point-of-Care (POC) device, the number of assays that can be performed in parallel is often limited by the size of the device and the volume of the sample to be analyzed. In many POC devices, the number assays performed is about 1 to 10. A POC device capable of performing multiplexed assays on a small sample would be desirable.

A shortcoming of many multiplexed POC assay devices is the high cost of manufacturing the components of the device. If the device is disposable, the cost of the components can make the manufacturing of a POC device impractical. Further, for multiplexed POC devices that incorporate all of the necessary reagents onboard of the device, if any one of those reagents exhibit instability, an entire manufactured lot of devices may have to be discarded even if all the other reagents are still usable.

When a customer is interested in customizing a POC device to a particular set of analytes, manufacturers of multiplexed POC assay systems are often confronted with the need to mix and match the assays and reagents of the device. A multiplexed POC assay suitable to each customer can be very expensive, difficult to calibrate, and difficult to maintain quality control.

POC methods have proven to be very valuable in monitoring disease and therapy (for example, blood glucose systems in diabetes therapy, Prothrombin Time measurement in anticoagulant therapy using Warfarin). By measuring multiple markers, it is believed that complex diseases (such as cancer) for which multi-drug therapies are required can be better monitored and controlled.

There exists the need to use multiple sources of information for monitoring the health status or disease condition of individuals as well as treatments of various diseases. Especially important is the measurement of concentrations of several selected analytes (biomarkers, antibodies, gene expression levels, metabolites, therapeutic drug concentrations and the like) over time. To make this process convenient and maximally effective, technologies that enable measurement of any and all needed analytes (of whatever types) using a small blood sample (blood drop obtained by finger-stick) or other suitable sample are particularly valuable. Such technology will ideally be operable by non-technically trained users in distributed test settings, e.g., homes, clinics, doctor's offices, pharmacies, and retail shops. The present invention addresses these issues and allows for one to be able to make such measurements routinely in patient's home or other non-laboratory setting.

There also exists the need to make the greatest use of available samples, particularly in the instance where samples (e.g., blood samples) are limited by sample size. Blood samples are used for the great majority of medical/clinical tests. Blood cells have to be separated from plasma (or serum) prior to most types of analysis since the presence of cells would compromise the assay chemistries. For example, glucose and cholesterol are often measured by color-forming chemistries which would be interfered with by the presence of formed elements, especially red cells, or hemoglobin (from lysed red cells).

Distributed test systems ideally require a small blood sample obtained by fingerstick methods. Such samples may be as small as 20 microliters (uL) (one drop) or less. Larger volume samples (say up to 200 uL) usually cannot be taken by fingerstick methods without repeated, inconvenient ("milking") of fingers. Alternatively venous samples of several milliliters (mL) can be taken but this requires a medically trained phlebotomist.

It is usually very difficult to perform more than a single assay using small blood sample with 20 uL or less. This is especially so when the blood sample has to be filtered to remove cells and the recovery of usable plasma from such small volumes is inefficient. Typically only about 5 uL or less of plasma can be recovered. Samples as large as 200 uL can be efficiently separated by automated POC systems (Abaxis, Biosite etc.) but this cannot be done routinely unless a technician is available to draw the sample.

SUMMARY OF THE INVENTION

In view of the limitations of current methods, there is a pressing need for improved methods of automatically separating plasma and/or other materials from blood cells. There is also a need for improved accuracy of these measurements on analyte concentration. In measurements of biomarkers and other components of blood for the purposes of monitoring therapy and diagnosis, it is important that the correct volume of sample be used. In a laboratory setting, this is achieved by utilizing complex automated instruments and skilled professional staff members. In contrast in "point-of-care" settings such as homes, retail pharmacies and shops, and the like, the methods and equipment used must enable non-technically trained people reliably to obtain and process samples.

The present invention addresses the aforementioned needs and provides related advantages.

In some embodiments, the present invention relates to point-of-care and/or point-of-service devices. In some embodiments, the present invention relates to systems, devices, user interfaces, and methods for assaying samples using a point-of-care and/or point-of-service device.

In one aspect, the devices and methods disclosed herein are designed to identify the sample type (blood versus plasma and etc.) to measure the volume of sample early enough in the assay procedure to ensure an appropriate sample is used is an intended assay. In another aspect, the present invention also allows for one to be able to correct for significant volume errors that occur in performing an assay.

In yet another aspect, this invention allows for simultaneous measurements on several analytes of different types with high accuracy.

An aspect of the invention may be directed to an automated system for separating one or more components in a biological fluid. The automated system may comprise a pipette tip or closed tube adapted to engage with an aspirator wherein said pipette tip or tube comprises two opposing ends, at least one of which is closed or sealable; and a centrifuge configured to receive said sealed pipette tip or closed tube to effect said separating of one or more components in a biological fluid. In an embodiment, the one or more components are selected from the group consisting of blood plasma, blood serum, blood cells, and particulates. In another embodiment, when the pipette tip is engaged with the aspirator to effect a draw of the biological fluid. In another embodiment, the pipette tip has an open end that forms an airtight seal with the aspirator. In another embodiment, the system further comprises an imaging device; and at least one other pipette tip dimensioned to allow dispensing of a liquid into the pipette tip or tube of (a) or to allow the aspiration of a liquid from the pipette tip or tube of (a). In another embodiment, the pipette tip or closed tube is oriented vertically when the centrifuge is at rest. In another embodiment, the pipette tip or closed tube is oriented horizontally when the centrifuge is spinning at a predetermined rotational velocity.

Another aspect of the invention may be a method for isolating components in a sample comprising one or more of the following steps: loading a sample into a pipette tip or a tube comprising two opposing ends, at least one of which is sealable or sealed; sealing the pipette tip on the at least one end of the pipette tip; centrifuging the sealed pipette tip, thereby forming an interfacial region that separates the sample into a supernatant and a pellet; imaging the centrifuged pipette tip to determine the location of the interfacial region; and automatically aspirating the supernatant based on the location of the interfacial region. In an embodiment, the method further comprises determining the location of the supernatant by said imaging step and automatically aspirating the supernatant based on the location of the supernatant. In another embodiment, the determination occurs with the aid of a processor, and said processor provides instructions to an aspirating device which performs the automated aspiration step. In another embodiment, the imaging occurs by use of a camera that is configured to capture the image of the side profile of the pipette tip or the tube. In another embodiment, the supernatant includes one or more of the following: blood plasma or blood serum. In another embodiment, the pellet includes one or more of the following: blood cells or particulates.

A computer-assisted method for characterizing an analyte suspected to be present in a sample may be provided in accordance with an additional aspect of the invention. The computer-assisted method may comprise obtaining a digital image of the sample, wherein the digital image comprises at least a two-dimensional array of pixels, and wherein each pixel comprises a plurality of intensity values, each of which corresponds to a distinct detection spectral region; correlating, with the aid of a programmable device, the obtained intensity values with a predetermined set of values that define a dynamic range of each detection spectral region; and predicting the presence and/or quantity of said analyte in the sample based on said correlating of the obtained intensity values with a predetermine set of values. In an embodiment, the plurality of intensity values comprise intensity values for red, green, and blue detection spectral regions. In another embodiment, the method further comprises selecting an illumination wavelength, and illuminating the sample with the selected illumination wavelength prior to and/or concurrently with obtaining the digital image. In another embodiment, the method further comprises, subsequent to obtaining the digital image, (a) selecting another illumination wavelength; (b) illuminating the sample with the other selected illumination wavelength; (c) obtaining another digital image of the sample, wherein the digital image comprises at least a two-dimensional array of pixels, and wherein each pixel comprises a plurality of intensity values, each of which corresponds to a distinct detection spectral region; and (d) predicting the presence and/or quantity of said analyte in the sample based on the obtained intensity values from the digital image and said another digital image.

Also, an aspect of the invention may be directed to a method of measuring an analyte concentration in a sample fluid comprising providing the sample contained in a container dimensioned with a plurality of distinct widths to permit transmission of light along a plurality of varying path lengths that correspond to the plurality of distinct widths; illuminating the container along at least one of the plurality of path lengths; and imaging the container to measure a first light intensity transmitted across said at least one of the plurality of path lengths, for the determination of the concentration of the analyte based on the measured first light intensity.

In accordance with another aspect of the invention, a method of detecting the presence or concentration of an analyte in a sample fluid contained in a container (e.g., cuvette) may comprise illuminating the container along a first region having a first path length to yield a first measurement of light intensity transmitted across the first path length; moving the sample fluid to another region in the container having another path length if the first measurement falls outside a predetermined dynamic range of transmitted light intensity; illuminating the container along the another region to yield another measurement of light intensity transmitted across the another path length; and optionally repeating second and third steps until a measurement of light intensity falls within the predetermined dynamic range, thereby detecting the presence or concentration of the analyte. In an embodiment, the method further comprises deconvoluting a line scan of the image, thereby detecting the presence or concentration of an analyte. In another embodiment, the sample is moved from a first region of the container having a first path length to a second region of the container having another path length by aspirating the sample. In another embodiment, an end of the container is attached to a pipette which is configured to aspirate the sample. In another embodiment, the sample is moved up or down the length of the container. In another embodiment, the container is a pipette tip. In another embodiment, the container is conically shaped. In another embodiment, the container has two open ends. In another embodiment, a first open end has a greater diameter than a second open end. In another embodiment, the container has a plurality of distinct widths to permit transmission of light along a plurality of varying path lengths. In another embodiment, the container volume is less than 100 microliters. In another embodiment, a plurality of distinct path lengths are imaged simultaneously.

A method may be provided as an additional aspect of the invention. The method may be provided for characterizing an analyte suspected to be present in a sample of biological fluid, said method comprising: providing said sample of biological fluid; allowing said analyte to react with one or more reagents that specifically react with said analyte to generate an optically detectable signal; and measuring said optically detectable signal with a plurality of detection spectral regions, wherein the presence of said optically detectable signal within a dynamic range of at least one detection spectral region is indicative of the concentration of said analyte in said sample of biological fluid. In an embodiment, the measuring is performed by an imaging device configured to measure a plurality of detection spectral regions. In another embodiment, the imaging device is configured to measure the plurality of detection spectral regions simultaneously. In another embodiment, the imaging device is configured to measure the plurality of detection spectral regions sequentially.

An aspect of the invention provides a method for increasing the accuracy of an assay comprising imaging a sample in a first tip to determine the volume of the first sample; imaging one or more reagents in a second tip to determine the volume of the one or more reagents; mixing the sample and the one or more reagents to form a reaction mixture; imaging the reaction mixture; correcting a calibration based on said determined volumes of the sample and the one or more reagents; and calculating a concentration of an analyte using the corrected calibration. In an embodiment, the method further comprises imaging the reaction mixture to determine the volume of the reaction mixture. In another embodiment, the imaging of the sample in the first tip is conducted using a camera configured to capture a side profile of the first tip. In another embodiment, imaging of the one or more reagents in the second tip is conducted using a camera configured to capture a side profile of the second tip. In another embodiment, the height of the sample and the one or more reagents is calculated based on the captured profiles. In another embodiment, determining the volume is based on the height of the sample and the one or more reagents and the known cross-sectional areas of the sample and the one or more reagents respectively. In another embodiment, the calibration is also based on the determined volume of the reaction mixture.

Another aspect of the invention provides a setup, comprising: a vessel configured to accept and confine a sample, wherein the vessel comprises an interior surface, an exterior surface, an open end, and an opposing closed end; and a tip configured to extend into the vessel through the open end, wherein the tip comprises a first open end and second open end, wherein the second open end is inserted into the vessel, wherein the vessel or the tip further comprises a protruding surface feature that prevents the second open end of the tip from contacting the bottom of the interior surface of the closed end of the vessel. In an embodiment, the surface feature is integrally formed on the bottom interior surface of the vessel. In another embodiment, the surface feature comprises a plurality of bumps on the bottom interior surface of the vessel. In another embodiment, the protruding surface feature is at or near the closed end.

Another aspect of the invention provides a sample processing apparatus comprising a sample preparation station, assay station, and/or detection station; a control unit having computer-executable commands for performing a point-of-service service at a designated location with the aid of at least one of said sample preparation station, assay station and detection station; and at least one centrifuge configured to perform centrifugation of a sample from a fingerstick. In an embodiment, the centrifuge is contained within the sample preparation station and/or the assay station. In another embodiment, the computer-executable commands are configured to perform the point-of-service service at a site selected from the group consisting of a retailer site, the subject's home, or a health assessment/treatment location.

Another aspect of the invention provides a method for dynamic feedback, said method comprising: taking an initial measurement of a sample within a container using a detection mechanism; based on said initial measurement, determining, using a processor, whether the sample concentration falls into a desired range, and determining, using a processor, (a) a degree of dilution to be performed if the sample concentration is higher than the desired range or (b) a degree of concentration to be performed if the sample concentration is lower than the desired range; and adjusting the sample concentration according to the determined degree of dilution or the determined degree of concentration. In an embodiment, the method further comprises taking a subsequent measurement of the sample within the container. In another embodiment, the method further comprises, based on the subsequent measurement determining, using a processor, whether the sample concentration falls into a desired range. In another embodiment, the subsequent measurement is made using the detection mechanism. In another embodiment, the method further comprises determining a characteristic of the sample based on the subsequent measurement. In another embodiment, the characteristic is selected from one or more of the following: the presence or concentration of an analyte, the presence or concentration of a cell, and the morphology of the cell. In another embodiment, the subsequent measurement is made using a separate detection mechanism from the initial detection mechanism. In another embodiment, the initial measurement provides a crude cell concentration measurement of the sample. In another embodiment, the subsequent measurement provides a measurement of cell concentration of the sample of greater resolution than the initial measurement. In another embodiment, the initial measurement is taken by imaging the sample. In another embodiment, the adjusting of the sample concentration permits detection of analyte that would otherwise fall outside the desired range.

Another aspect of the invention provides a method for providing quality control, said method comprising capturing an image of conditions under which a detection mechanism measures a characteristic of a sample; and determining, using a processor, based on the image whether there are undesirable conditions under which the detection mechanism is operated. In an embodiment, the undesirable conditions includes the presence of one or more undesirable materials. In another embodiment, the undesirable materials includes one or more of the following: bubbles, particles, fibers, debris, and precipitates that interfere with the measurement of the characteristic of the sample. In another embodiment, the detection mechanism is a different mechanism from a mechanism used to capture the image. In another embodiment, the image is captured using a camera. In another embodiment, the method further comprises providing an alert if an undesirable condition is detected. In another embodiment, the method further comprises adjusting the sample if an undesirable condition is detected. In another embodiment, the image includes an image of the sample. In another embodiment, the image includes an image of one or more of the following: the sample container or the detection mechanism.

Another aspect of the invention is an automated system for separating one or more components in a biological fluid comprising a centrifuge comprising one or more bucket configured to receive a container to effect said separating of one or more components in a fluid sample; and the container, wherein the container includes one or more shaped feature that is complementary to a shaped feature of the bucket. In an embodiment, the shaped feature of the bucket includes one or more shelf upon which a protruding portion of the container is configured to rest. In another embodiment, the bucket is configured to be capable of accepting a plurality of containers having different configurations, and wherein the shaped feature of the bucket includes a plurality of shelves, wherein a first container having a first configuration is configured to rest upon a first shelf, and a second container having a second configuration is configured to rest upon a second shelf.

Another aspect of the invention provides an assay unit comprising a first end and a second end; an outer surface; and an inner surface comprising one or more selected patterns each of which is immobilized thereon or therein with a capture reagent capable of capturing an analyte suspected to be present in a biological sample, wherein the first end and the second end are of different dimensions.

Another aspect of the invention provides an assay unit comprising an identifier that is used to determine (a) the one or more capture reagents immobilized on the inner surface; and (b) source of the biological sample if the assay unit contains said sample.

Another aspect of the invention provides an assay unit comprising a plurality of selected patterns, each pattern of said plurality comprises a distinct capturing agent.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof. The various compounds/devices disclosed herein can be used separately or conjunctively in any combination, for any methods disclosed herein alone or in any combinations.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing(s) of which:

DETAILED DESCRIPTION OF THE INVENTION

Figure 1:
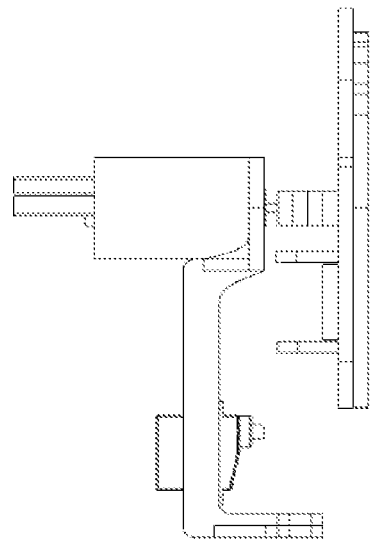
FIG. 1 shows a side view of a centrifuge.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention.

The invention provides mobile applications for system and methods for sample use maximization. Various aspects of the invention described herein may be applied to any of the particular applications set forth below or for any other types of diagnostic or therapeutic applications. The invention may be applied as a standalone system or method, or as part of an integrated pre-clinical, clinical, laboratory or medical application. It shall be understood that different aspects of the invention can be appreciated individually, collectively, or in combination with each other.

The devices and systems herein can provide an effective means for real-time detection of analytes present in a bodily fluid from a subject. The detection methods may be used in a wide variety of circumstances including identification and quantification of analytes that are associated with specific biological processes, physiological conditions, disorders or stages of disorders. As such, the systems have a broad spectrum of utility in, for example, drug screening, disease diagnosis, phylogenetic classification, parental and forensic identification, disease onset and recurrence, individual response to treatment versus population bases, and/or monitoring of therapy. The subject devices and systems are also particularly useful for advancing preclinical and clinical stage of development of therapeutics, improving patient compliance, monitoring ADRs associated with a prescribed drug, developing individualized medicine, outsourcing blood testing from the central laboratory to the home or on a prescription basis, and/or monitoring therapeutic agents following regulatory approval. The subject devices and system can be utilized by payors outsourcing blood tests from a central laboratory. The devices and systems can provide a flexible system for personalized medicine. Using the same system, a device can be changed or interchanged along with a protocol or instructions to a programmable processor of the systems to perform a wide variety of assays as described. The systems and devices described herein, while being much smaller and/or portable, embody novel features and offer many functions of a laboratory instrument.

In an aspect, a system of the invention comprises a device comprising assay units and reagent units, which include reagents, e.g., both liquid and/or solid phase reagents. In some embodiments, at least one of the whole device, an assay unit, a reagent unit, or a combination thereof is disposable. In a system of the invention, the detection of an analyte with the subject device is typically automated. Such automation can be effected by a built-in protocol or a protocol provided to the system by the manufacturer.

The devices and systems as described herein can offer many features that are not available in existing POC systems or integrated analysis systems. For example, many POC cartridges rely on a closed fluidic system or loop to handle small volumes of liquid in an efficient manner. The fluidic devices such as cartridges described herein can have open fluid movement between units within a given cartridge. For example, a reagent can be stored in a unit, a sample stored in a sample collection unit, a diluent stored in a diluent unit, and the capture surface can be in an assay unit, where in one state of cartridge, none of the units are in fluid communication with any of the other units. The units can be movable relative to each other in order to bring some units into fluid communication using a fluid transfer device of the system. For example, a fluid transfer device can comprise a head that engages an assay unit and brings the assay unit in fluidic communication with a reagent unit. In some cases, the head is a pipette head that moves the assay unit (e.g., tip) in fluid communication with a reagent unit.

Accordingly, in an embodiment, the present invention provides a method of detecting and/or measuring the concentration of an analyte in a bodily fluid or tissue sample, the method typically comprises the steps of providing a sample (e.g., blood, urine, saliva, tissue) to a device or system of the invention, allowing the sample to react within at least one assay unit of the device, and detecting the detectable signal generated from the analyte in the blood sample.

One aspect of the invention provides for analyzing samples using a point-of-care device that is configured to maximize sample utilization. For example, more than about 15, 25, 50, 75, or 100 assays can be performed on a sample having a volume of less than about 1, 20, 50, 100, or 500 µL. The sample can be a blood sample taken from a finger prick. The sample can be collected in a sealable capillary or tip. The sample can be prepared for one or more assays by subjecting the sample to a separation (e.g., centrifugation) and/or dilution process. The one or more assays can be prepared by combining the sample, which may have been separated and diluted, with one or more reagents in a reaction chamber. The reaction chamber can be a pipette tip, vial, a sample transfer device, and/or a cuvette. The one or more assays can be configured such that an optical signal can be measured which is indicative of the concentration of one or more analytes in the sample. The reaction chamber can contain a plurality of assays, which may be spatially separated. A plurality of optical signals can be generated within a single reaction chamber from one assay, or from a plurality of spatially separated assays. The one or more optical signals can be measured by a digital imaging camera that can measure a plurality of detection spectral regions or detection bands, e.g., red, green and blue. The optical signal can be measured on the assay reaction product in the reaction chamber, which can be a pipette tip or other sample containers. The systems, devices, and methods can be fully automated or semi-automated by programmable logic.

Another aspect of the invention provides for systems, devices, and methods for preparing samples for analysis. Samples can be prepared for analysis by one or more separation devices. For example, a sample can be prepared for analysis by centrifugation within a centrifuge. Other separations based on charge, size, hydrophobicity/hydrophilicity, and/or volatility can also be implemented.

One aspect of the invention provides for sample and reaction product analysis using image-based analysis. The system can include a camera that can measure an optical signal using one or more detection spectrum regions. For example, a camera can measure an optical signal using red, green, and blue detection spectrum regions. The measured signal can include three measured values that can be interpreted using one or more algorithms described herein. The use of more than one detection spectrum region can increase the dynamic range of an assay and can increase the accuracy of a measurement as compared to measurements using a single detection spectrum region.

The invention also provides for systems, devices, and methods for performing optical measurements on samples and assay reaction products that are contained within reaction chambers, each with a plurality of distinct path lengths. The reaction chambers can have a plurality of distinct path lengths such that a greater or lower amount of light absorbance is observed. The plurality of distinct path lengths (such as, for example, through the sample and/or reaction chamber) allows for an increase in the dynamic range of a selected assay protocol. The image of the reaction chamber can be analyzed as described herein to obtain information on the sample or the assay reaction products. The combination of utilizing the plurality of available path lengths within a single reaction chamber and the use of three channel detection spectrum regions greatly enhances the dynamic range of a given assay.

A system for performing sample preparation and analysis can include instrumentation, disposable components, and reagents. The system can accept samples and automatically performs a plurality of assays without user intervention. Where desired, the instrumentation can include a graphical user interface, a mechanism for introducing cartridges, which may be disposable, a motorized stage, which may have mobility in three dimensions, one or more single-head liquid handling devices, one or more multi-head liquid handling devices, one or more devices for performing sample preparation, optical sensors, which can include a PMT and/or an imaging device, temperature controllers, and communication devices. The disposable component can include a disposable cartridge that contains sample tips, tip seals, and reagents. In some embodiments, the disposable cartridge may also contain neutralizing assemblies configured to absorb and neutralize liquid assay products.

The instrumentation, disposable components, and reagents can be housed within a closeable environment, such as a case or a cabinet. In some embodiments, the case has a cross-sectional area less than about 4 $m^2$, 2 $m^2$, 1 $m^2$, 0.5 $m^2$, 0.1 $m^2$, 0.05 $m^2$, or lower. The invention provides for a distributed test system, such as a point-of-care device, which can include one or more of the following aspects:

1. Efficient (centrifugal) separation of blood and recovery of the separated plasma 2. Dilution of the plasma sample to one or more levels (for example 1:10, 1:100, 1:1000) so that each assay can be performed at an optimal dilution 3. Optimized distribution of sample to several different assays which may involve several different methodologies 4. Optimal assay protocols 5. Use of open-ended circular section cuvettes for sample analysis, mixing with reagents, incubation and presentation to optical systems 6. Analysis of assays using imaging technology (scanning and/or photography, and/or microscopy)

In one embodiment, the device of the invention is self-contained and comprises all reagents, liquid- and solid-phase reagents, required to perform a plurality of assays in parallel. Where desired, the device is configured to perform at least 2, 3, 4, 5, 6, 7, 8, 9, 10, 20, 30, 40, 50, 100, 200, 500, 1000 or more assays. One or more control assays can also be incorporated into the device to be performed in parallel if desired. Calibrators can also be provided for assay system calibration. Some examples of dried controls and calibrators useful for assay system calibration can include aqueous solutions of analytes, serum, or plasma samples with known levels of analytes, known quantities of such calibrators and controls can also be dried by lyophilization, vacuum drying, and other manufacturing processes (and dissolved during the assay).

By incorporating these components within a point-of-care system, a patient or user can have a plurality of analytes, for example more than about 10, 20, 30, 50, 75, 100, 150, or 200 analytes, quantified within less than about 0.5, 1, 2, 3, 4, 5, 10, 20, 30, 60, 120, 180, 240, 480 or 600 minutes.

The subject devices and systems can be utilized for conducting quantitative immunoassays, which can be completed in a short period of time. Other assay type can be performed with a device of the invention including, but not limited to, measurements of nucleic acid sequences and measurements of metabolite, such as cholesterol or electrolytes such as magnesium and chloride ions. In some embodiments, the assay is completed in no more than one hour, preferably less than 120, 60, 30, 15, 10, 5, 4, 3, 2, or 1 minute. In other embodiments, the assay is performed in less than 5 minutes. The duration of assay detection can be adjusted accordingly to the type of assay that is to be carried out with a device of the invention. For example, if needed for higher sensitivity, an assay can be incubated for more than one hour or up to more than one day. In some examples, assays that require a long duration may be more practical in other POC applications, such as home use, than in a clinical POC setting.

In other embodiments of the invention the reagent units of a subject device are configured to be a set of mix-and-match components. A reagent unit typically stores liquid or solid reagents necessary for conducting an assay that detect a given analyte. The assay units can sometimes (or optionally not always) comprise at least one capture surface capable of reacting with an analyte from the sample of bodily fluid. The assay unit may be a tubular tip with a capture surface within the tip. Examples of tips of the invention are described herein. Each individual assay and reagent unit can be configured for assay function independently. To assemble a device, the units can be assembled in a just-in-time fashion for use in an integrated device, which can take the format of cartridge.

A housing for a device of the invention can be made of a polymeric material, a metallic material or a composite material, such as, e.g., aluminum, polystyrene or other moldable or machinable plastic, and can have defined locations to place assay units and reagent units. The housing may include a metal or any other material. The housing may partially or entirely enclose the assay units and/or reagent units. The housing may support the weight of the assay units and/or reagent units. In an embodiment, the housing has means for blotting tips or assay units to remove excess liquid. The means for blotting can be a porous membrane, such as cellulose acetate, or a piece bibulous material such as filter paper.

In some embodiments, at least one of the components of the device may be constructed of polymeric materials. Non-limiting examples of polymeric materials include polystyrene, polycarbonate, polypropylene, polydimethysiloxanes (PDMS), polyurethane, polyvinylchloride (PVC), polysulfone, polymethylmethacrylate (PMMA), acrylonitrile-butadiene-styrene (ABS), and glass.

The device or the subcomponents of the device may be manufactured by variety of methods including, without limitation, stamping, injection molding, embossing, casting, blow molding, machining, welding, ultrasonic welding, and thermal bonding. In an embodiment, a device in manufactured by injection molding, thermal bonding, and ultrasonic welding. The subcomponents of the device can be affixed to each other by thermal bonding, ultrasonic welding, friction fitting (press fitting), adhesives or, in the case of certain substrates, for example, glass, or semi-rigid and non-rigid polymeric substrates, a natural adhesion between the two components.

A system as described can run a variety of assays, regardless of the analyte being detected from a bodily fluid sample. A protocol dependent on the identity of the device may be transferred from an external device where it can be stored to a reader assembly to enable the reader assembly to carry out the specific protocol on the device. In some embodiments, the device has an identifier (ID) that is detected or read by an identifier detector described herein. The identifier can enable two-way communication between the device and a sensor or receiving system. The identifier detector can communicate with a communication assembly via a controller which transmits the identifier to an external device. Where desired, the external device sends a protocol stored on the external device to the communication assembly based on the identifier. The protocol to be run on the system may comprise instructions to the controller of the system to perform the protocol, including but not limited to a particular assay to be run and a detection method to be performed. Once the assay is performed by the system, a signal indicative of an analyte in the bodily fluid sample is generated and detected by a detection assembly of the system. The detected signal may then be communicated to the communications assembly, where it can be transmitted to the external device for processing, including without limitation, calculation of the analyte concentration in the sample.

Systems, devices and methods for performing sample analysis using point-of-care devices and tips that can function as reaction chambers are described in U.S. Patent Publication No. 2009/0088336 and U.S. Provisional Application No. 60/997,460, each of which is incorporated herein by reference in its entirety for all purposes.

Sample Handling and Reaction Chambers

Samples, reagents, and assembled assays described herein can be handled and contained by a variety of reaction chamber types. A sample handing device and a reaction chamber can be a well, a tube, or an open ended tip, which may also be a cuvette. As used herein, a tip can also referred to as a sample tip, a cuvette tip, a reaction chamber, a cuvette, a capillary, a sample handing device, or a sample transfer device. Samples may be collected from a source into a tip or a tube. The tips may be sealed. Such seals may be permanent or reversible. Diluted samples can be combined with one or more reagents and mixed (as described in previous applications) within "assay elements" such as tips (open-ended cuvettes) or open or covered wells. Once the assay is ready for reading, the assay element can be presented to the optical system for image analysis or other types of reading. Alternatively, assay reaction mixtures can be transferred from one type of element to another. For example, assays incubated in tips can be blotted onto an absorbent or bibulous medium or assays incubated in wells can be aspirated into tips. Many assays can be processed in parallel. Assay readout can be serial or simultaneous depending on the assay protocol and/or incubation time. For assays involving measurement of a rate of change, the assay element can be presented to the optical system more than once at different times.

Fluid and Material Transfer Devices

A fluid transfer device can be part of a system. The fluid transfer device can comprise a plurality of heads. Any number of heads as is necessary to detect a plurality of analytes in a sample is envisioned for a fluid transfer device of the invention. In an example, a fluid transfer device has about eight heads mounted in a line and separated by a distance. In an embodiment, the heads have a tapered nozzle that engages by press fitting with a variety of tips, such as assay unit or sample collection units as described herein. The tips can have a feature that enables them to be removed automatically by the instrument and disposed into in a housing of a device as described after use. In an embodiment, the assay tips are clear and transparent and can be similar to a cuvette within which an assay is run that can be detected by an optical detector such as a photomultiplier tube or camera sensor.

In an example, a programmable processor (e.g., central processing unit, CPU) of a system can comprise or be configured to accept (such as, e.g., from a memory location) instructions or commands and can operate a fluid transfer device according to the instructions to transfer liquid samples by either withdrawing (for drawing liquid in) or extending (for expelling liquid) a piston into a closed air space. The processor can be configured to facilitate aspiration and/or dispensing. Both the volume of air moved and the speed of movement can be precisely controlled, for example, by the programmable processor.

Mixing of samples (or reagents) with diluents (or other reagents) can be achieved by aspirating components to be mixed into a common tube and then repeatedly aspirating a significant fraction of the combined liquid volume up and down into a tip. Dissolution of reagents dried into a tube can be done is similar fashion. Incubation of liquid samples and reagents with a capture surface on which is bound a capture reagent (for example an antibody) can be achieved by drawing the appropriate liquid into the tip and holding it there for a predetermined time. Removal of samples and reagents can be achieved by expelling the liquid into a reservoir or an absorbent pad in a device as described. Another reagent can then be drawn into the tip according to instructions or protocol from the programmable processor.

A system can comprise a holder or engager for moving the assay units or tips. An engager may comprise a vacuum assembly or an assembly designed to fit snugly into a boss of an assay unit tip. For example, a means for moving the tips can be moved in a manner similar to the fluid transfer device heads. The device can also be moved on a stage according to the position of an engager or holder.

In an embodiment, an instrument for moving the tips is the same as an instrument for moving a volume of sample, such as a fluid transfer device as described herein. For example, a sample collection tip can be fit onto a pipette head according to the boss on the collection tip. The collection tip can then be used to distribute the liquid throughout the device and system. After the liquid has been distributed, the collection tip can be disposed, and the pipette head can be fit onto an assay unit according to the boss on the assay unit. The assay unit tip can then be moved from reagent unit to reagent unit, and reagents can be distributed to the assay unit according to the aspiration- or pipette-type action provided by the pipette head. The pipette head can also perform mixing within a collection tip, assay unit, or reagent unit by aspiration- or syringe-type action.

In another embodiment, tips containing liquids including assay reaction mixtures can be disconnected from the pipetting device and "parked" at specific locations within the instrument or within a disposable unit. If needed, tips can be capped using a seal (as used in the centrifuge) to prevent liquids from draining out. In some embodiments, the seal can be a vinyl seal.

Exemplary Sample Tips

Figure 63:
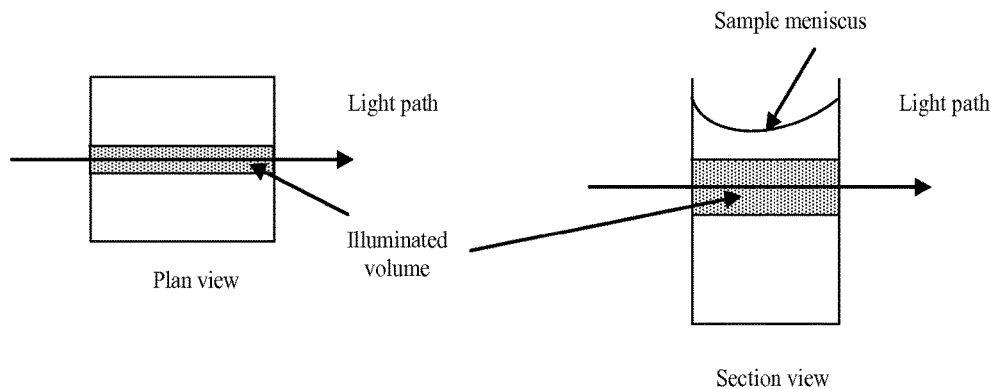
FIG. 63 shows a light path through a rectangular cuvette.
Figure 64:
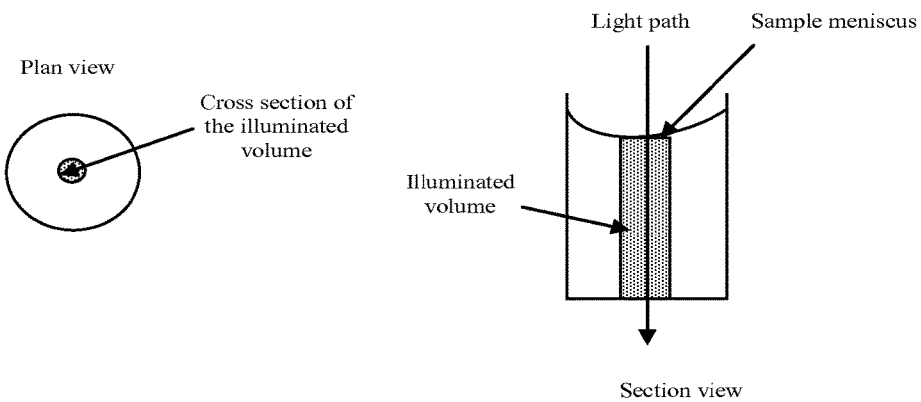
FIG. 64 shows a light path through a microtiter well.

A variety of container shapes can be utilized as sample tips, reaction chambers, and cuvettes. For example, a cuvette can be circular, cylindrical, square, rectangular, cubical, conical, pyramidal, or any other shape capable of holding a sample of fluid. Rectangular cuvettes where a light beam impinges at right angles to the cuvette surfaces as shown in plan and section views in FIG. 63 can be employed. In such rectangular cuvettes, the liquid sample that is illuminated is also rectangular and is defined by the cuvette. Cuvettes with circular cross-sections can also be used. For example, some types of microtiter plates where the illuminated sample volume is in part defined by the sample meniscus as shown below in plan and section view in FIG. 64.

Variable pathlength cuvettes can be used to optimize and extend the assay response and minimize the volume of sample required to measure the assay. Cuvettes can be longer in relation to their cross-section in at least one region. In some cases, the pathlength of a cuvette can be selected based on cuvette geometry and/or material. Different cuvettes can be selected for different assays.

Figure 65:
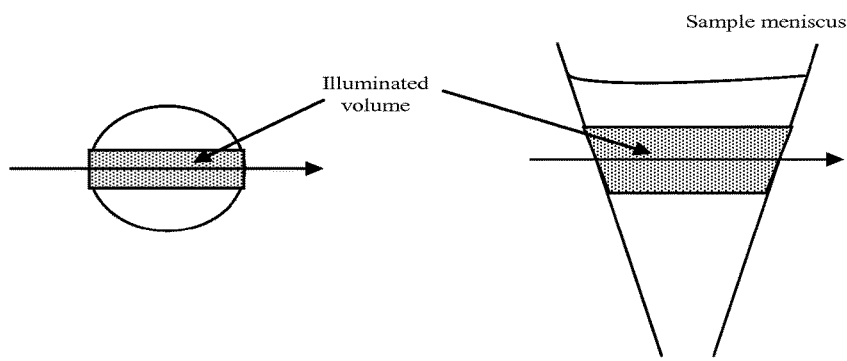
FIG. 65 shows a light path through a conically shaped cuvette.

In the present invention, one preferred version of the assay cuvette has a circular cross-section in the direction of the light beam as shown in FIG. 65. The use of a cuvette with a circular cross-section has several advantages, including, but not limited to the following:

1. The optical pathlength can be precisely defined. Dimensional precision of injection-molded parts have been found to be better than 1-2% CV. In conventional microtiter plates the unconstrained liquid meniscus can introduce imprecision in pathlength.

2. The open-ended character and circular section of the tips confers excellent fluid handling characteristics, making aspiration of liquids very precise.

3. The optical image of the tips provides for the ability to identify the tip location and boundaries of the liquid column and to locate very precisely the center of the tip where the signal is maximal.

4. More than one liquid sample can be incubated and analyzed in the same tip. This is because in the narrow part of the tip, very little material transfer occurs (in the axial direction) between adjacent "slugs" of liquid.

An exemplary tip may have the following general features:

Tip length: 0.5-4 cm
Tip OD: 0.2-1.0 cm
Tip ID: 0.1-0.5 cm
Tip capacity for liquids: 5-50 uL
Tip dimensional precision: generally better than 2% or +/−0.001 cm Tip configuration: The tip will generally have a feature that engages with a pipette (cylindrical) so as to form a fluid tight seal. There is a region generally cylindrical or conical which is used for imaging. Generally the optical part of the tip will have at least two different sections with different pathlengths. The lower end of the tip will typically be narrow so as to aid in retention of vertical liquid columns under gravity Tip material: Clear or uniformly specular plastic (polystyrene, polypropylene etc.) (transmission of light in the visible >80%)

For imaging purposes, the tip can generally be clear or translucent, but the tips do not have to be clear to work well as assay cuvettes when three-color analysis is used. Tip cuvettes which appear "cloudy" may function similarly to clear tips. The cloudy tips are made in injection molds with non-polished or textured surfaces or by adding some light scattering material to the plastic used to fabricate the tips. The light scattering intensity of such cloudy tips may be chosen to be not so great as to obscure the colored liquid to be measured. In general, the impact of light scattering on transmitted light can be selected to be less than 10, (20, and 30%) relative to the impact of the colored material. The light scattering effect can be selected such that the light scattering of the cloudy tips is uniform.

The tips and reaction chambers described herein can be comprised of a cylindrical (or conical) shaft about 2 cm in length and having an inner diameter of about 1-5 mm corresponding to a capacity of about 10-50 uL.

In one example, at the upper end of the cylinder is a truncated cylindrical "boss" fluidically connected to the cylinder and adapted so as to be able to engage with the tapered feature of a pipetter. The lower end of the tip may be narrowed to provide a feature that enables the tip to hold its liquid contents when oriented vertically and not attached to the pipetter. The tip may be a pointed tip. The external shape of the lower end of the tip is typically also somewhat pointed with the diameter being reduced from the main part of the cylindrical shaft toward the end so as to be capable of being fluidically sealed with a flexible (vinyl) cap into which the tip end is press fit. Tips are usually made of molded plastic (polystyrene, polypropylene and the like). The tips can be clear or translucent such that information about the sample can be acquired by imaging.

Figure 4:
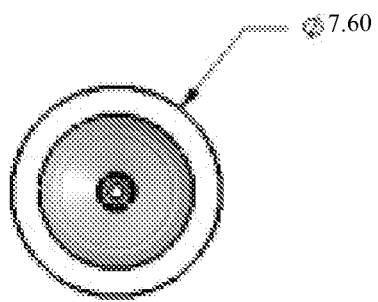
FIG. 4 shows a top view of a sample tip.
Figure 5:
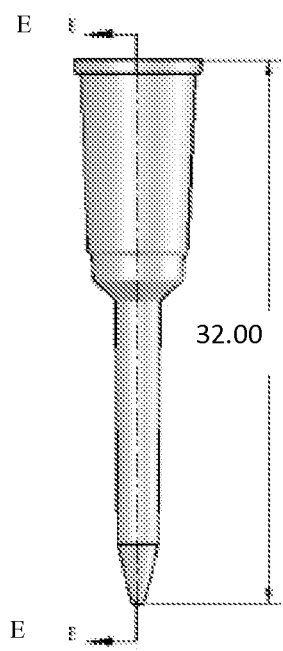
FIG. 5 shows a side view of a sample tip.
Figure 6:
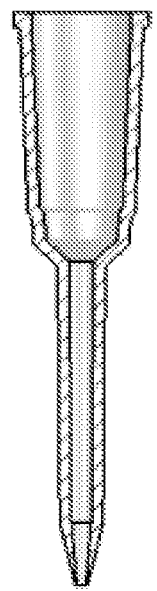
FIG. 6 shows a cross-sectional view of a sample tip.

FIG. 4, FIG. 5, and FIG. 6 show an example of a tip. The tip is configured with (1) an upper feature that can engage to form an air tight seal with a pipette head, (2) a basically cylindrical (actually conical with a very slight draft angle) shaft and a narrow, pointed lower tip. This tip can form a liquid-tight seal with a cap. The pointed shape aids in getting good conformance with the cap under moderate force. The material used is injection-molded polystyrene. The overall dimensions are: 32 mm long, about 7.6 mm largest outer diameter, useful capacity about 20 uL. The dimensions of the tip can be scaled to a larger volume. For example, for a 50 uL sample, the IDs can be increased by about 1.6-fold.

Sealing can be achieved using a cap made of vinyl or other materials which is easily press-fit to the narrow end of the sample containment means using force generated by motion of the instrument stage in the z-direction. A bubble of air can become trapped within the tip when the tip is capped. A centrifugation step can be used to drive the bubble to the top of the column of blood so as to eliminate the effects of the bubble. The dimensions of the tip and/or the dimensions of the tip holder in a centrifuge can be matched such that a tip can be secured for centrifugation.

Sample Preparation

The invention provides for systems, methods, and devices for the processing and analysis of samples can be collected from a variety of sources. For example, the sample can be collected from patients, animals, or the environment. The sample can be a bodily fluid. Any bodily fluids suspected to contain an analyte of interest can be used in conjunction with the system or devices of the invention. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid.

In some embodiments, the bodily fluid is a blood sample from a human patient. The blood source can be collected from a finger prick and have a volume of less than about 0.5, 1, 5, 10, 20, 50, 100, 200, 300, 400, 500, or 1000 uL.

A bodily fluid may be drawn from a patient and provided to a device in a variety of ways, including but not limited to, lancing, injection, or pipetting.

As used herein, the terms "subject" and "patient" are used interchangeably herein, and refer to a vertebrate, preferably a mammal, more preferably a human. Mammals include, but are not limited to, murines, simians, humans, farm animals, sport animals, and pets.

In one embodiment, a lancet punctures the skin and withdraws a sample using, for example, gravity, capillary action, aspiration, or vacuum force. The lancet may be part of the device, or part of a system or a stand-alone component. Where needed, the lancet may be activated by a variety of mechanical, electrical, electromechanical, or any other known activation mechanism or any combination of such methods. In another embodiment where no active mechanism is required, a patient can simply provide a bodily fluid to the device, as for example, could occur with a saliva sample. The collected fluid can be placed in the sample collection unit within the device. In yet another embodiment, the device comprises at least one microneedle which punctures the skin.

The volume of bodily fluid to be used with a device can be less than about 500 microliters, typically between about 1 to 100 microliters. Where desired, a sample of 1 to 50 microliters, 1 to 40 microliters, 1 to 30 microliters, 1 to 10 microliters or even 1 to 3 microliters can be used for detecting an analyte using the device. In an embodiment, the volume of bodily fluid used for detecting an analyte utilizing the subject devices or systems is one drop of fluid. For example, one drop of blood from a pricked finger can provide the sample of bodily fluid to be analyzed with a device, system or method described herein.

A sample of bodily fluid can be collected from a subject directly into a tip of the described herein, or can be later transferred to a tip.

Sample Dilution

In some instances, the configuration of the processor to direct fluid transfer effects a degree of dilution of the bodily fluid sample in the array of assay units to bring signals indicative of the plurality of analytes being detected within a detectable range, such that said plurality of analytes are detectable with said system. In an example, the bodily fluid sample comprises at least two analytes that are present at concentrations that differ by at least 1, 2, 5, 10, 15, 50, 100, 500, 1000, 10,000, $10^5$, $10^6$, $10^7$, $10^8$, $10^9$, or $10^{10}$ fold. In an example the bodily fluid sample is a single drop of blood. In an embodiment, the concentrations of at least two analytes present in a sample differs by up to 10 orders of magnitude (for example, a first analyte is present at 0.1 pg/mL and a second analyte is present at 500 ug/mL). In another example, some protein analytes are found at concentrations of greater than 100 mg/mL, which can extend the range of interest to about twelve orders of magnitude. In the case of measurement of nucleic acid analytes such as DNA and RNA using exponential amplification methods such as polymerase reaction, the number of copies of analyte can be increased by a billion fold prior to measurement.

Where desired, a degree of dilution of the bodily fluid sample can bring the signals indicative of the at least two analytes within the detectable range.

As described, the systems and devices herein can enable many features of the flexibility of laboratory setting in a POC environment. For example, samples can be collected and manipulated automatically in a table top size or smaller device or system. A common issue in POC devices is achieving different dilution ranges when conducting a plurality of assays, wherein the assays may have significantly different sensitivity or specificity. For example, there may be two analytes in a sample, but one analyte has a high concentration in the sample and the other analyte has a very low concentration. As provided, the systems and devices herein can dilute the sample to significantly different levels in order to detect both analytes. Alternatively, a sample may be split into two or more samples, which may enable individual analytes to be detected at various levels of dilution.

For example, if the analyte is in a high concentration, a sample can be serially diluted to the appropriate detection range and provided to a capture surface for detection. In the same system or device, a sample with an analyte in a low concentration may not need to be diluted. In this manner, the assay range of the POC devices and systems provided herein can be expanded from many of the current POC devices.

In POC assay systems using disposable cartridges containing the diluent there is often a practical limit to the extent of dilution. For example, if a small blood sample is obtained by fingerstick (for example, about 20 microliters) is to be diluted and the maximum volume of diluent that can be placed in a tube is 250 microliters, the practical limit of dilution of the whole sample is about 10-fold. In an example herein, a system can aspirate a smaller volume of the sample (for example about 2 microliters) making the maximum dilution factor about 100-fold. For many assays, such dilution factors are acceptable but for an assay like that of CRP (as described in the examples herein) there is a need to dilute the sample much more. Separation-based ELISA assays can have an intrinsic limitation in the capacity of the capture surface to bind the analyte (for example about a few hundred ng/ml for a typical protein analyte). Some analytes are present in blood at hundreds of micrograms/ml. Even when diluted by 100-fold, the analyte concentration may be outside the range of calibration. In an exemplary embodiment of a system, device, and fluid transfer device herein, multiple dilutions can be achieved by performing multiple fluid transfers of the diluent into an individual assay unit or sample collection unit. For example, if the concentration of an analyte is very high in a sample as described above, the sample can be diluted multiple times until the concentration of the analyte is within an acceptable detection range. The systems and methods herein can provide accurate measurements or estimations of the dilutions in order to calculate the original concentration of the analyte.

Sample Separation

In some embodiments of the invention, a sample can be prepared for analysis by an initial separation step. For example, if the assay is to analyze DNA, a DNA separation step can be employed to eliminate or reduce contaminants or unwanted source material. The separation step can utilize chromatography, centrifugation, liquid-liquid extraction, solid-liquid extraction, affinity binding, or any other mechanisms known to one skilled in the art.

In some embodiments, a blood sample to be analyzed is first processed by separating the plasma component from the blood sample. This step can be performed using a variety of techniques, such as filtration, centrifugation, and affinity binding. Centrifugation can be an efficient method for separation of blood sample components, and can be employed in the present invention.

Plasma Separation

Blood can be introduced into a close ended or sealable tip in a variety of ways, for example samples can be provided in a tube and a sealable tip can receive the sample from the tube via capillary action or via pneumatic force. One preferred means of introduction is the use of capillary action. Alternatively, container used to hold the sample for centrifugal separation can be configured with only one opening as in a conventional centrifuge.

The tip, once filled with blood, can be moved automatically to a location in a disposable cartridge where there is a sealing element. The sealing element can be a small "cup" made of a deformable (pliant) material (vinyl, silicone or the like) conformed to fit on the lower end of the tip and to seal it. The tip is pressed into the seal by the instrument thus forming a liquid-tight junction. The sealed tip is then moved to a small centrifuge (typically located in and forming part of the instrument) and press-fit into a positioning feature in the centrifuge rotor such that the lower (sealed) end of the tip butts up to a rigid shelf that will support the tip during the centrifugation step.

The centrifuge rotor can be circular having about 10 cm in diameter. The mass of the blood-containing tip is either (1) small relative to the rotor or (2), where desired, balanced by a counter weight located on the opposite part of the rotor such that any vibration during the centrifugation step is minimized One exemplary orientation of the centrifuge rotor is vertical (axis of rotation horizontal). The rotor is mounted in a drive shaft with is driven by an electric motor.

Centrifugation can be achieved by spinning the rotor at about 15,000 rpm for 5 minutes. During this process, the particular elements in the blood (red cells and white cells) sediment to the sealed end of the tip and form a closely packed column with cell free plasma separated at the part of the tip distal from the seal.

The tip containing the separated sample can then be placed vertically in a location accessible to a fluid handling device comprised of a narrow pipette tip ("sample acquisition tip") mounted on a pipetting device in turn mounted on an x-y-z stage.

Plasma can now be efficiently recovered from the centrifuged sample. This is achieved by moving the sample acquisition tip vertically along the axis of the centrifuge tip so that it comes into fluid contact with the plasma and can draw the plasma upwards using, e.g., pneumatic means.

Optionally, this operation can be monitored using a camera or other imaging device which can be used both to measure the sample hematocrit and to provide information as to the location of the plasma/red cell boundary to the stage/pipetter controller. With the aid of imaging the separated blood, a narrow pipette tip fitted to a pipette is slowly moved vertically down, such that the tip is directed axially down the sample containment means until it contacts the plasma. The tip is then moved further until it is close (within less than about 3, 2, 1, 0.5, or 0.1 mm) of the packed cell interface. At the same time, plasma is aspirated into the narrow pipette tip under computer control. The plasma can be aspirated simultaneously while moving the narrow pipette tip into the plasma column so that the plasma does not become displaced into the upper part of the sample containment means. The aspiration can be controlled to avoid air being aspirated during the plasma removal step.

In general, a pipette tip with a very narrow end, such as those used to apply samples to an electrophoresis system, can be used to aspirate the plasma from the centrifuged sample tip. The narrow tip is typically conical or tapered and has dimensions 1-3×0.1-0.5 cm (length×diameter) and made of any of a variety of materials (polypropylene, polystyrene etc.). The material can be clear or translucent in the visible. One end of the tip engages with a pipetting device. The other is very narrow (0.05-0.5 mm OD) such that it can move into the sample tip without touching the inner surface of the sample tip. Even if there is contact between the plasma aspiration tip and the sample tip, plasma aspiration is not hindered.

Figure 7:
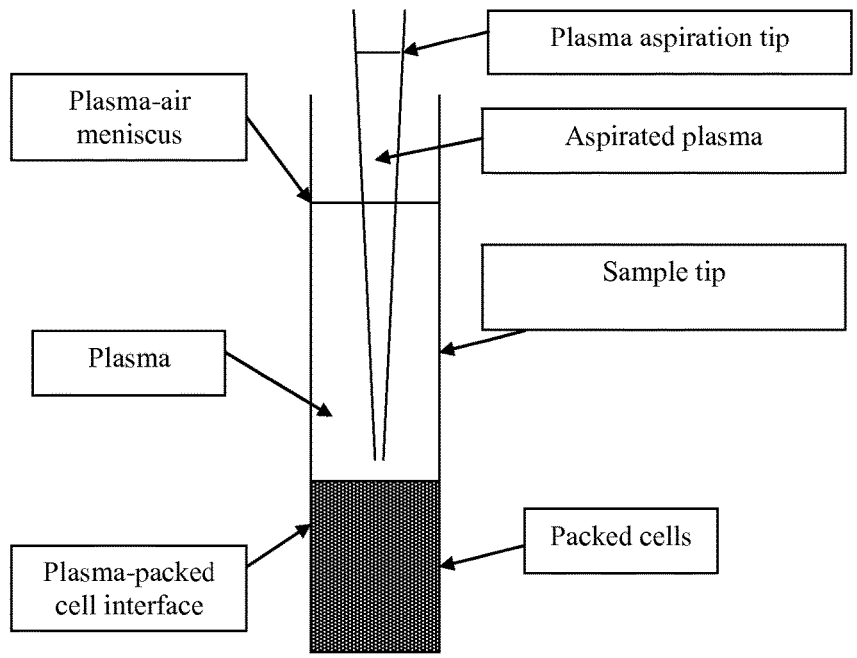
FIG. 7 shows a diagram of a sample tip positioned in a sample above a plasma/packed cell interface.

A schematic of the plasma aspiration process at the stage where the plasma aspiration tip is located just above the plasma-packed cell interface during the aspiration step is shown in FIG. 7.

In this way we have found that almost all of the plasma can be removed leaving as little as e.g. 1 uL in the centrifuged sample tip. This corresponds to about 11 uL of plasma (90% recovery) from 20 uL of blood with a 40% hematocrit. Additionally the quality of the plasma sample (with respect to hemolysis, lipemia and icteria) can be determined from an image of the centrifuged sample.

The aspirated plasma can be moved to other locations for dilution and mixing with assay reagents so that assays for analytes industry but not limited to metabolites, electrolytes, protein biomarkers, drugs and nucleic acids may be performed.

Separation of White Blood Cells

A further use of the invention is to isolate and concentrate the white cells from blood. In one aspect of the invention, the blood sample is first subject to a process which lyses the red cells (and optionally fixes the white cells) by adding a reagent (For example, BD Pharmlyse™ 555899 or BD FACS™ Lysing Solution 349202) to the blood and mixing. Following a brief incubation, the lysed sample is subject to centrifugation as described above such that the white cells are concentrated at the sealed end of the blood tip. The lysed red cell solution can then be removed by aspiration. Recovery of the white cells is achieved by either (1) addition of a small amount of a buffer solution and repeated up and down aspiration to re-suspend the cells followed by displacement into a receptacle or (2) removal of the seal and downward displacement of the packed cells into a receptacle using air pressure.

An alternate scheme allows recovery of white cells without lysis of the red cells. After centrifugation of blood (as is well known) the white cells form a layer on top of the packed red cells known as the Buffy Coat. Following removal of most of the plasma (as above) the white cells can be efficiently recovered by (1) optionally adding a small volume (e.g. about 5 uL) of isotonic buffer, or (2) using the residual plasma and re-suspending the white cells by repeated aspiration and/or mechanical stirring using the sample acquisition tip. Once suspended, the resulting mixture of white cells together with a small proportion of red cells also re-suspended can be acquired by aspiration for analysis of the white cells. In this way most of the white cells (typically all) can be recovered with only a small (contaminating) quantity of red cells (typically less than 5% of the original).

Centrifuges

Figure 2:
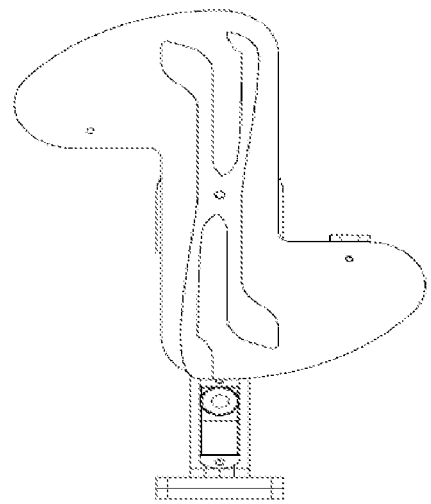
FIG. 2 shows a face on view of a centrifuge.
Figure 3:
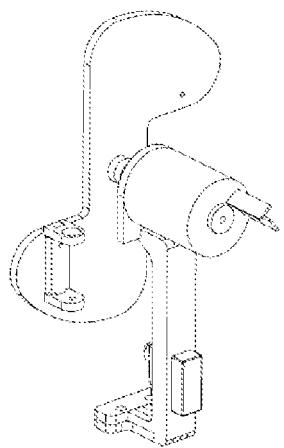
FIG. 3 shows a perspective view of the back of a centrifuge.

FIG. 1, FIG. 2, and FIG. 3 show scale perspectives of a centrifuge (FIG. 1—side view, FIG. 2—front face view, FIG. 3—rear view) that can be integrated into the system. The centrifuge may contain an electric motor capable of turning the rotor at 15,000 rpm. One type of centrifuge rotor is shaped somewhat like a fan blade is mounted on the motor spindle in a vertical plane. Affixed to the rotor is an element which holds the sample holding means (tip) and provides a ledge or shelf on which the end of the tip distal to the motor axis rests and which provides support during the centrifugation so that the sample cannot escape. The tip may be further supported at its proximal end by a mechanical stop in the rotor. This can be provided so that the force generated during centrifugation does not cause the tip to cut through the soft vinyl cap. The tip can be inserted and removed by standard pick and place mechanisms but preferably by a pipette. The rotor is a single piece of acrylic (or other material) shaped to minimize vibration and noise during operation of the centrifuge. The rotor is (optionally) shaped so that when it is oriented in particular angles to the vertical, other movable components in the instrument can move past the centrifuge. The sample holding means are centrifugally balanced by counter masses on the opposite side of the rotor such that the center of rotational inertia is axial relative to the motor. The centrifuge motor may provide positional data to a computer which can then control the rest position of the rotor (typically vertical before and after centrifugation).

Figure 8:
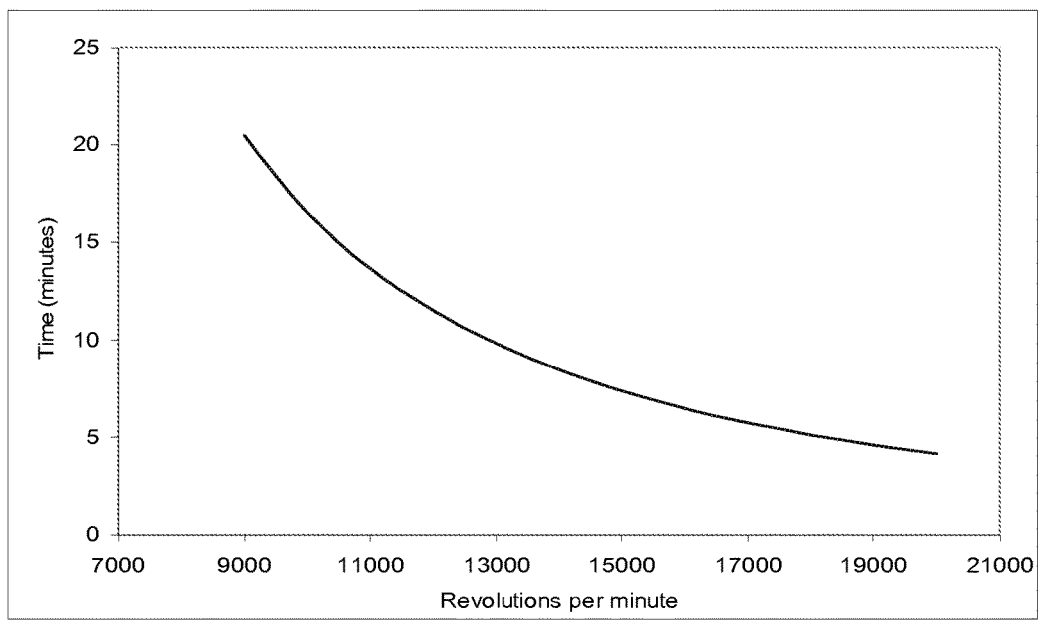
FIG. 8 shows a graph of centrifugation time as a function of revolutions per minute.
Figure 9:
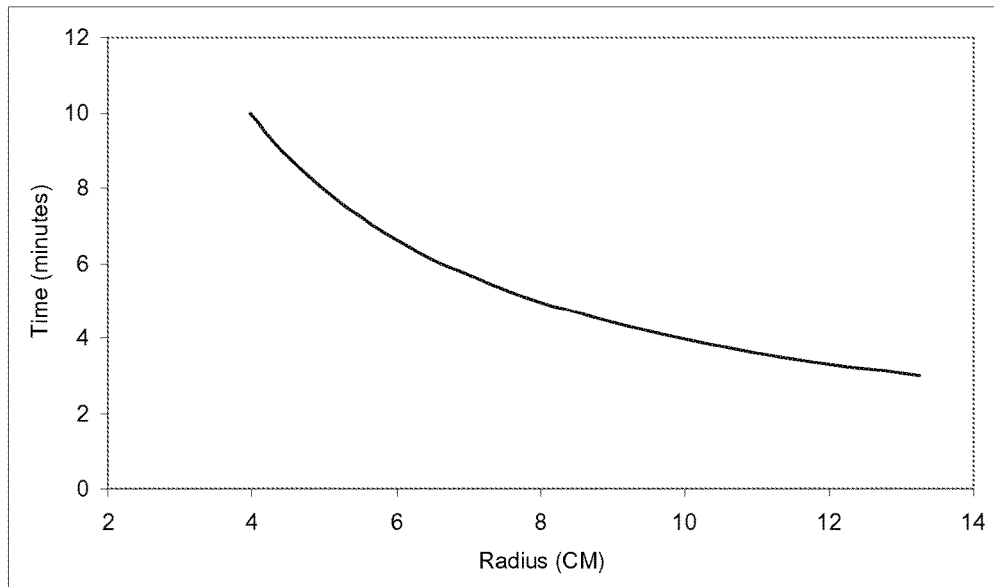
FIG. 9 shows a graph of centrifugation time as a function of the radius of the centrifuge rotor.

As may be seen from the two graphs in FIG. 8 and FIG. 9, to minimize centrifugation time (without generating too much mechanical stress during centrifugation) according to published standards (DIN 58933-1; for the U.S. the CLSI standard H07-A3 "Procedure for Determining Packed Cell Volume by the Microhematocrit Method"; Approved Standard—Third Edition) convenient dimensions for the rotor are in the range of about 5-10 cm spinning at about 10-20 thousand rpm giving a time to pack the red cells of about 5 min.

An exemplary equation for calculating centrifugation force is shown below:

$$RCF = \frac{r(2\pi N)^2}{g}$$

Where:
g is earth's gravitational acceleration,
r is the rotational radius,
N is the rotational speed, measured in revolutions per unit of time.
Where:
$r_{cm}$ is the rotational radius measured in centimeters (cm),
$N_{RPM}$ is rotational speed measured in revolutions per minute (RPM).

$$RGF = 1.118 \times 10^{-6} r_{cm} N_{RPM}^2$$

In some embodiments, a centrifuge may be a horizontally oriented centrifuge with a swinging bucket design. In some preferable embodiments, the axis of rotation of the centrifuge is vertical. In alternate embodiments, the axis of rotation can be horizontal or at any angle. The centrifuge may be capable of simultaneously spinning two or more vessels and may be designed to be fully integrated into an automated system employing computer-controlled pipettes. In some embodiments, the vessels may be close-bottomed. The swinging bucket design may permit the centrifugation vessels to be passively oriented in a vertical position when stopped, and spin out to a fixed angle when spinning. In some embodiments, the swinging buckets may permit the centrifugation vessels to spin out to a horizontal orientation. Alternatively they may spin out to any angle between a vertical and horizontal position (e.g., about 15, 30, 45, 60, or 75 degrees from vertical. The centrifuge with swinging bucket design may meet the positional accuracy and repeatability requirements of a robotic system a number of positioning systems are employed.

A computer-based control system may use position information from an optical encoder in order to spin the rotor at controlled slow speeds. Because an appropriate motor could be designed for high-speed performance, accurate static positions need not be held using position feedback alone. In some embodiments, a cam in combination with a solenoid-actuated lever may be employed to achieve very accurate and stable stopping at a fixed number of positions. Using a separate control system and feedback from Hall-Effect sensors built into the motor, the velocity of the rotor can be very accurately controlled at high speeds.

Because a number of sensitive instruments must function simultaneously within the assay instrument system, the design of the centrifuge preferably minimizes or reduces vibration. The rotor may be aerodynamically designed with a smooth exterior—fully enclosing the buckets when they are in their horizontal position. Also, vibration dampening can be employed in multiple locations in the design of the case.

Rotor

A centrifuge rotor can be a component of the system which may hold and spin the centrifugation vessel(s). The axis of rotation can be vertical, and thus the rotor itself can be positioned horizontally. However, in alternate embodiments, different axes of rotation and rotor positions can be employed. There are two components known as buckets positioned symmetrically on either side of the rotor which hold the centrifugation vessels. Alternative configurations are possible in which buckets are oriented with radial symmetry, for example three buckets oriented at 120 degrees. Any number of buckets may be provided, including but not limited to 1, 2, 3, 4, 5, 6, 7, 8, or more buckets. The buckets can be evenly spaced from one another. For example, if n buckets are provided where n is a whole number, then the buckets may be spaced about 360/n degrees apart from one another. In other embodiments, the buckets need not be spaced evenly around one another or with radial symmetry.

Figure 111:
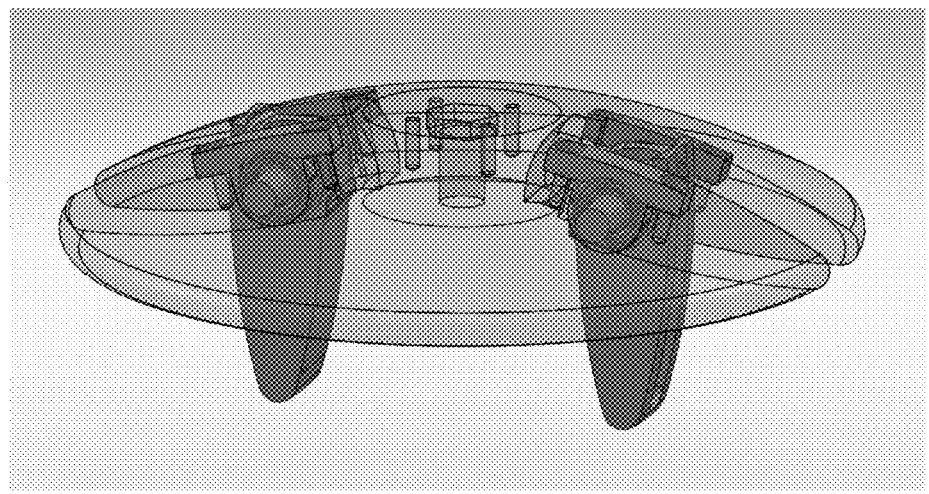
FIG. 111 shows an example of a rotor at rest with buckets vertical.
Figure 112:
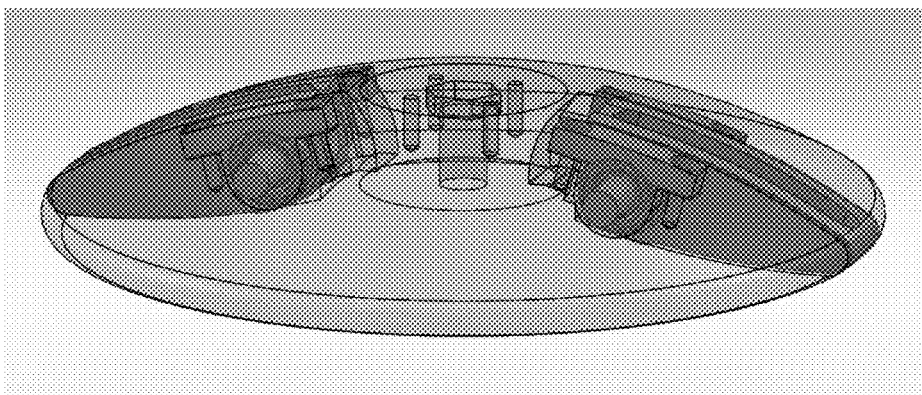
FIG. 112 shows an example of a rotor at a speed with buckets at a small angle to horizontal.

When the rotor is stationary, these buckets, influenced by gravity, may passively fall such as to position the vessels vertically and to make them accessible to the pipette. FIG. 111 shows an example of a rotor at rest with buckets vertical. In some embodiments, the buckets may passively fall to a predetermined angle that may or may not be vertical. When the rotor spins, the buckets are forced into a nearly horizontal position or to a predetermined angle by centrifugal forces. FIG. 112 shows an example of a rotor at a speed with buckets at a small angle to horizontal. There can be physical hard stops for both the vertical and horizontal positions acting to enforce their accuracy and positional repeatability.

The rotor may be aerodynamically designed with a disk shape, and as few physical features as possible in order to minimize vibration caused by air turbulence. To achieve this, the outer geometry of the bucket may exactly match that of the rotor such that when the rotor is spinning and the bucket can be forced horizontal the bucket and rotor can be perfectly aligned.

To facilitate plasma extraction, the rotor may be angled down toward the ground relative to the horizon. Because the angle of the bucket can be matched to that of the rotor, this may enforce a fixed spinning angle for the bucket. The resulting pellet from such a configuration could be angled relative to the vessel when placed upright. A narrow extraction tip may be used to aspirate plasma from the top of the centrifugation vessel. By placing the extraction tip near the bottom of the slope created by the angle pellet, the final volume of plasma can be more efficiently extracted without disturbing the sensitive buffy coat.

A variety of tubes designs can be accommodated in the buckets of the device. In some embodiments, the various tube designs may be closed ended. Some are shaped like conventional centrifuge tubes with conical bottoms. Other tube designs may be cylindrical. Tubes with a low ratio of height to cross-sectional area may be favored for cell processing. Tubes with a large ratio (>10:1) may be suitable for accurate measurement of hematocrit and other imaging requirements. However, any height to cross-sectional area ratio may be employed. The buckets can be made of any of several plastics (polystyrene, polypropylene), or any other material discussed elsewhere herein. Buckets have capacities ranging from a few microliters to about a milliliter. The tubes may be inserted into and removed from the centrifuge using a "pick and place" mechanism.

Control System

Due to the spinning and positioning requirements of the centrifuge device, a dual control system approach may be used. To index the rotor to specific rotational orientations, a position based control system may be implemented. In some embodiments, the control system may employ a PID (Proportional Integral Derivative) control system. Other feedback control systems known in the art can be employed. Positional feedback for the position controller may be provided by a high-resolution optical encoder. For operating the centrifuge at low to high speeds, a velocity controller may be implemented, while employing a PID control system tuned for velocity control. Rotational rate feedback for the velocity controller may be provided by a set of simple Hall-Effect sensors placed on the motor shaft. Each sensor may generate a square wave at one cycle per motor shaft rotation.

Stopping Mechanism

To consistently and firmly position the rotor in a particular position, a physical stopping mechanism may be employed. In one embodiment, the stopping mechanism may use a cam, coupled to the rotor, along with a solenoid-actuated lever. The cam may be shaped like a circular disk with a number of "C" shaped notches machined around the perimeter. To position the centrifuge rotor, its rotational velocity may first be lowered to, at most, 30 RPM. In other embodiments, the rotational velocity may be lowered to any other amount, including but not limited to about 5 rpm, 10 rpm, 15 rpm, 20 rpm, 25 rpm, 35 rpm, 40 rpm, or 50 rpm. Once the speed is sufficiently slow, the lever may be actuated. At the end of the lever is a cam follower which may glide along the perimeter of the cam with minimal friction. Once the cam follower reaches the center of a particular notch in the cam, the force of the solenoid-actuated lever can overcome that of the motor and the rotor may be brought to a halt. At that point the motor may be electronically braked, and, in combination with the stopping mechanism a rotational position can be very accurately and firmly held indefinitely.

Centrifuge Buckets

Figure 113:
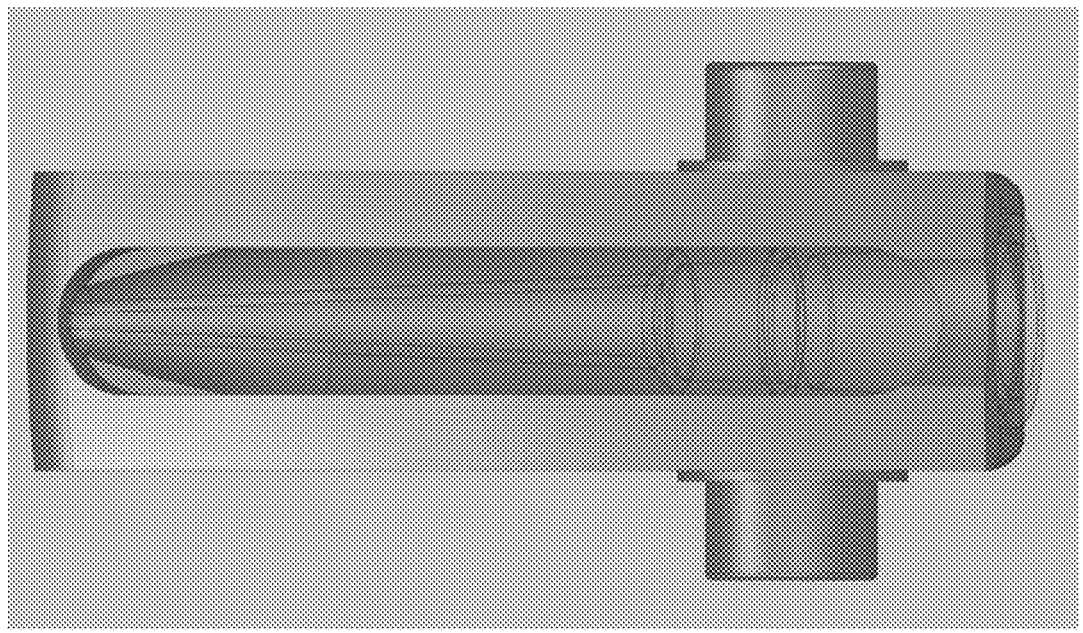
FIG. 113 shows an example of a bucket configuration.
Figure 114:
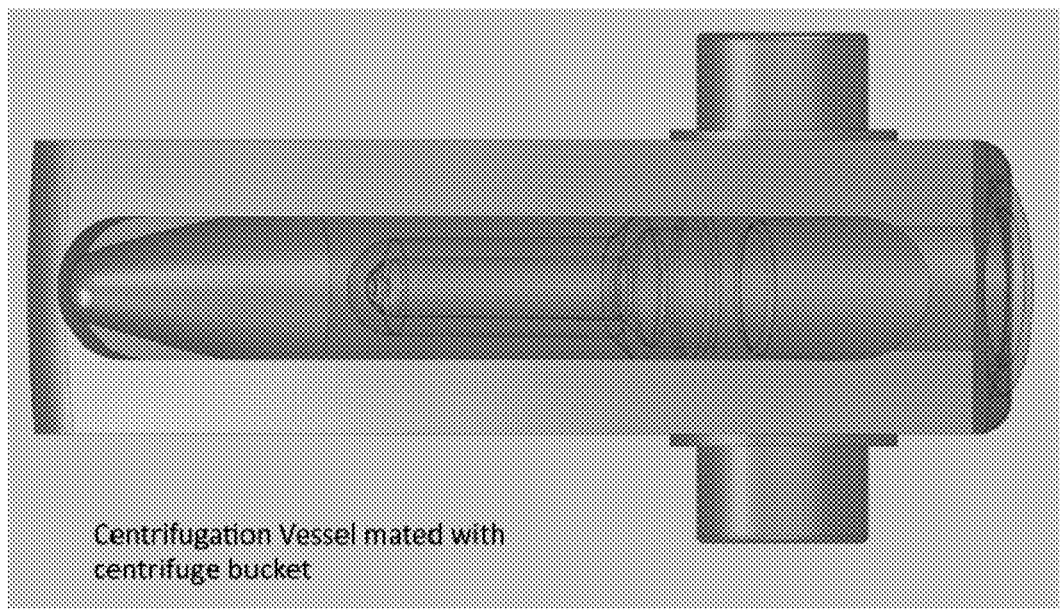
FIG. 114 shows an example of a centrifugation vessel mated with the bucket.
Figure 115:
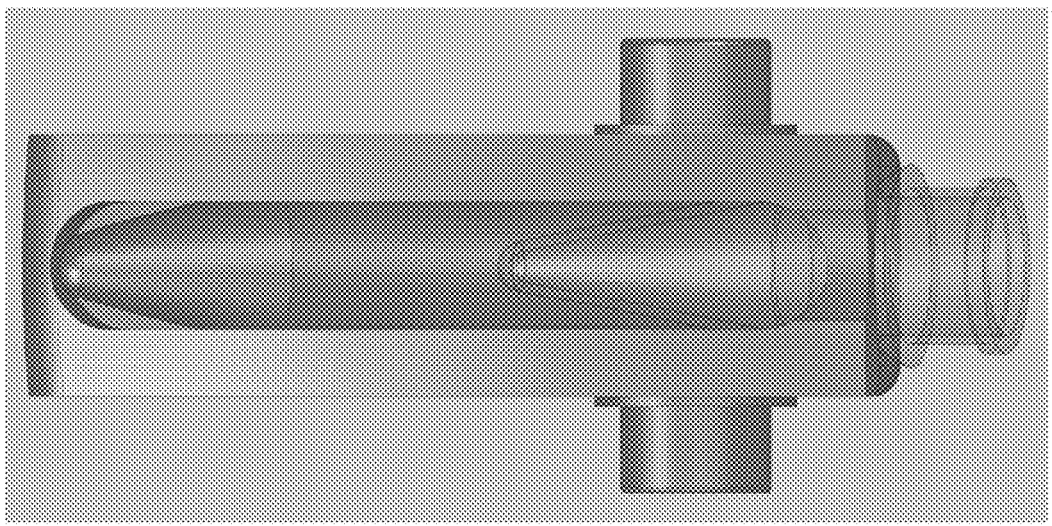
FIG. 115 shows an example of another centrifugation vessel that can be mated with the bucket.

The centrifuge swing-out buckets may be configured to accommodate different type of centrifuge tubes. In preferable embodiments, the various tube types may have a collar or flange at their upper (open) end. This collar or flange feature may rests on the upper end of the bucket and support the tube during centrifugation. As shown in FIGS. 113, 114, and 115, conical and cylindrical tubes of various lengths and volumes can be accommodated. FIGS. 113, 114, and 115 provide examples of buckets and other bucket designs may be employed. For example, FIG. 113, shows an example of a bucket configuration. The bucket may have side portions that mate with the centrifuge and allow the bucket to swing freely. The bucket may have a closed bottom and an opening at the top. FIG. 114 shows an example of a centrifugation vessel mated with the bucket. As previously mentioned, the bucket may be shaped to accept various configurations of centrifugation vessels. The centrifugation vessel may have one or more protruding member that may rest upon the bucket. The centrifugation vessel may be shaped with one or more feature that may mate with the centrifugation bucket. The feature may be a shaped feature of the vessel or one or more protrusion. FIG. 115 shows an example of another centrifugation vessel that can be mated with the bucket. As previously described, the bucket can have one or more shaped feature that may allow different configurations of centrifugation vessels to mate with the bucket.

Figure 116:
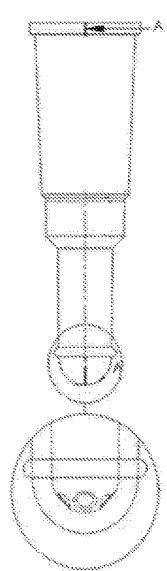
FIG. 116 shows an example of a centrifugation vessel.
Figure 116:
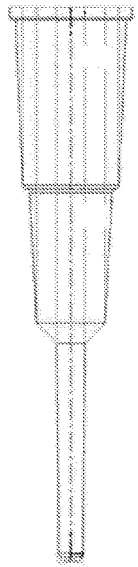
Figure 117:
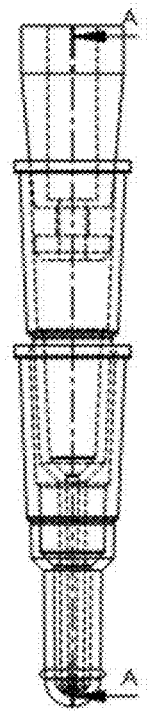
FIG. 117 shows an example of an extraction tip.
Figure 117:
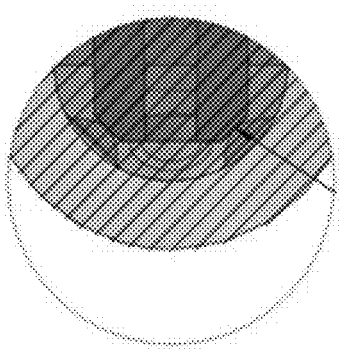
Figure 118:
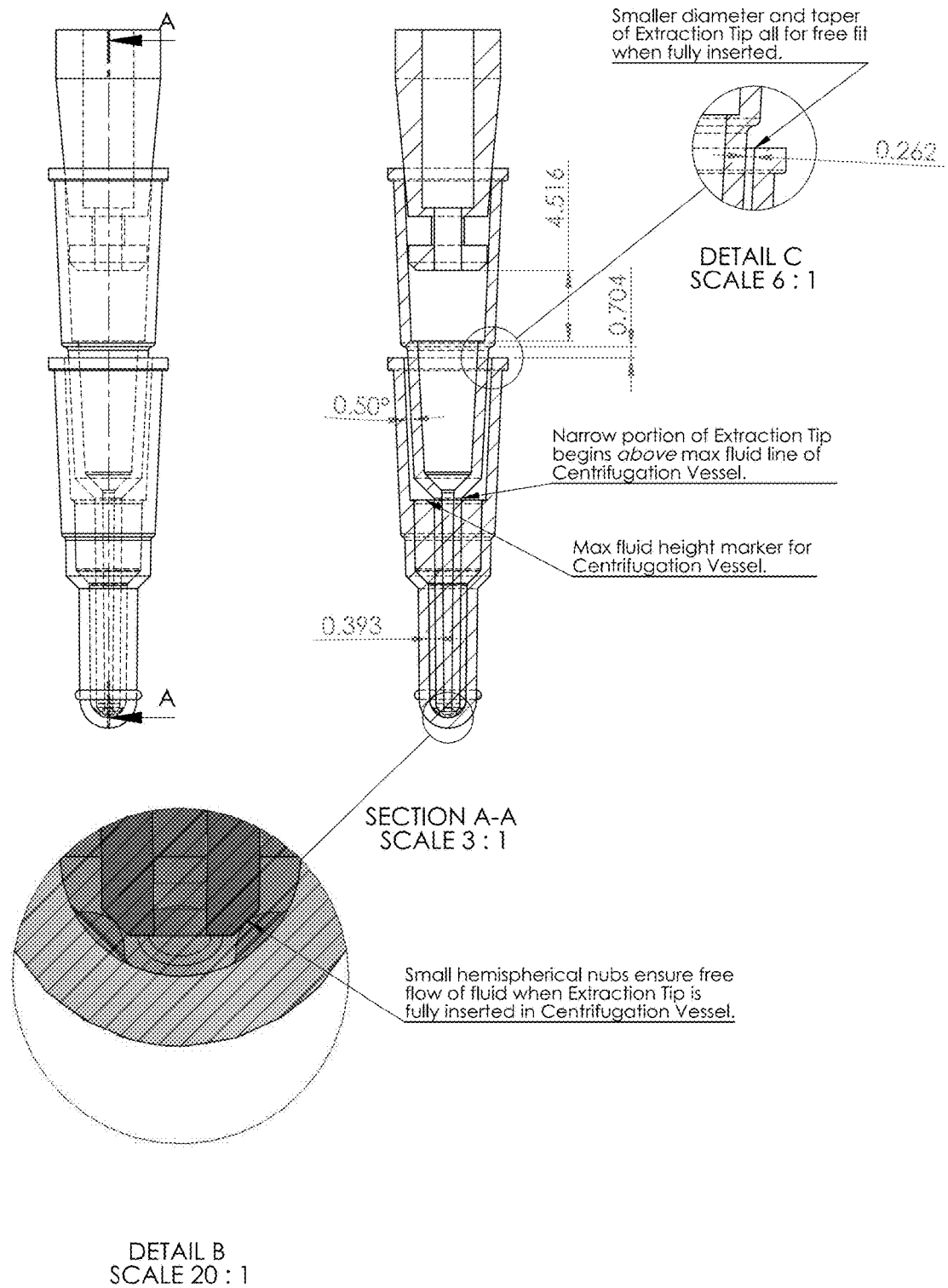
FIG. 118 provides an example of how the centrifugation vessel and extraction tip may mate.

Centrifuge Tubes and Sample Extraction Means:

The centrifuge tube and extraction tip may be provided individually and can be mated together for extraction of material following centrifugation. The centrifugation tube and extraction tip may be designed to deal with complex processes in an automated system. FIG. 116 shows an example of a centrifugation vessel. FIG. 117 shows an example of an extraction tip. FIG. 118 provides an example of how the centrifugation vessel and extraction tip may mate. Any dimensions are provided by way of example only, and other dimensions of the same or differing proportions may be utilized.

The system can enable one or more of the following:
1. Rapid processing of small blood samples (typically 5-50 uL)
2. Accurate and precise measurement of hematocrit
3. Efficient removal of plasma
4. Efficient re-suspension of formed elements (red and white blood cells)
5. Concentration of white cells (following labeling with fluorescent antibodies and fixation plus lysis of red cells)
6. Optical confirmation of red cell lysis and recovery of white cells Centrifugation Vessel and Extraction Tip Overview A custom vessel and tip may be used for the operation of the centrifuge in order to satisfy the variety of constraints placed on the system. The centrifugation vessel may be a closed bottom tube designed to be spun in the centrifuge. In some embodiments, the centrifugation vessel may be the vessel illustrated in FIG. 116 or may have one or more features illustrated in FIG. 116. It may have a number of unique features enabling the wide range of required functionality including hematocrit measurement, RBC lysing, pellet re-suspension and efficient plasma extraction. The extraction tip may be designed to be inserted into the centrifugation vessel for precise fluid extraction, and pellet re-suspension. In some embodiments, the extraction tip may be the tip illustrated in FIG. 117 or may have one or more features illustrated in FIG. 117. Exemplary specifications for each tip are discussed herein.

Centrifugation Vessel

The centrifugation vessel may be designed to handle two separate usage scenarios, each associated with a different anti-coagulant and whole blood volume.

A first usage scenario may require that 40 uL of whole blood with Heparin be pelleted, the maximum volume of plasma be recovered, and the hematocrit measured using computer vision. In the case of 60% hematocrit or below the volume of plasma required or preferable may be about 40 uL*40%=16 uL.

In some embodiments, it will not be possible to recover 100% of the plasma because the buffy coat must not be disturbed, thus a minimum distance must be maintained between the bottom of the tip and the top of the pellet. This minimum distance can be determined experimentally but the volume (V) sacrificed as a function of the required safety distance (d) can be estimated using: $V(d)=d*\pi 1.25 \text{ mm}^2$. For example, for a required safety distance of 0.25 mm, the sacrificed volume could be 1.23 uL for the 60% hematocrit case. This volume can be decreased by decreasing the internal radius of the hematocrit portion of the centrifugation vessel. However, because in some embodiments, that narrow portion must fully accommodate the outer radius of the extraction tip which can be no smaller than 1.5 mm, the existing dimensions of the centrifugation vessel may be close to the minimum.

Along with plasma extraction, in some embodiments it may also be required that the hematocrit be measured using computer vision. In order to facilitate this process the total height for a given volume of hematocrit may be maximized by minimizing the internal diameter of the narrow portion of the vessel. By maximizing the height, the relationship between changes in hematocrit volume and physical change in column height may be optimized, thus increasing the number of pixels that can be used for the measurement. The height of the narrow portion of the vessel may also be long enough to accommodate the worst-case scenario of 80% hematocrit while still leaving a small portion of plasma at the top of the column to allow for efficient extraction. Thus, 40 uL*80%=32 uL may be the required volume capacity for accurate measurement of the hematocrit. The volume of the narrow portion of the tip as designed may be about 35.3 uL which may allow for some volume of plasma to remain, even in the worst case.

A second usage scenario is much more involved, and may require one, more, or all of the following:
 whole blood pelleted
 plasma extracted
 pellet re-suspended in lysing buffer and stain
 remaining white blood cells (WBCs) pelleted
 supernatant removed
 WBCs re-suspended
 WBC suspension fully extracted In order to fully re-suspend a packed pellet, experiments have shown one can physically disturb the pellet with a tip capable of completely reaching the bottom of the vessel containing the pellet. A preferable geometry of the bottom of the vessel using for re-suspension seems to be a hemispherical shape similar to standard commercial PCR tubes. In other embodiments, other vessel bottom shapes may be used. The centrifugation vessel, along with the extraction tip, may be designed to facilitate the re-suspension process by adhering to these geometrical requirements while also allowing the extraction tip to physically contact the bottom.

During manual re-suspension experiments it was noticed that physical contact between the bottom of the vessel, and the bottom of the tip may create a seal that prohibits fluid movement. A delicate spacing may be used in order to both fully disturb the pellet, while allowing fluid flow. In order to facilitate this process in a robotic system, a physical feature may be added to the bottom of the centrifugation vessel. In some embodiments, this feature may comprise four small hemispherical nubs placed around the perimeter of the bottom portion of the vessel. When the extraction tip is fully inserted into the vessel and allowed to make physical contact, the end of the tip may rest on the nubs, and fluid is allowed to freely flow between the nubs. This may result in a small amount of volume (~0.25 uL) lost in the gaps.

During the lysing process, in some implementations, the maximum expected fluid volume is 60 uL, which, along with 25 uL displaced by the extraction tip may demand a total volume capacity of 85 uL. A design with a current maximum volume of 100 uL may exceed this requirement. Other aspects of the second usage scenario require similar or already discussed tip characteristics.

The upper geometry of the centrifugation vessel may be designed to mate with a pipette nozzle. Any pipette nozzle described elsewhere herein or known in the art may be used. The external geometry of the upper portion of the vessel may exactly match that of a reaction tip which both the current nozzle and cartridge may be designed around. In some embodiments, a small ridge may circumscribe the internal surface of the upper portion. This ridge may be a visual marker of the maximum fluid height, meant to facilitate automatic error detection using computer vision system.

In some embodiments, the distance from the bottom of the fully mated nozzle to the top of the maximum fluid line is 2.5 mm. This distance is 1.5 mm less than the 4 mm recommended distance adhered to by the extraction tip. This decreased distance may be driven by the need to minimize the length of the extraction tip while adhering to minimum volume requirements. The justification for this decreased distance stems from the particular use of the vessel. Because, in some implementations, fluid may be exchanged with the vessel from the top only, the maximum fluid it will ever have while mated with the nozzle is the maximum amount of whole blood expected at any given time (40 uL). The height of this fluid may be well below the bottom of the nozzle. Another concern is that at other times the volume of fluid in the vessel may be much greater than this and wet the walls of up to the height of the nozzle. In some embodiments, it will be up to those using the vessel to ensure that the meniscus of any fluids contained within the vessel do not exceed the max fluid height, even if the total volume is less than the maximum specified. In other embodiments, other features may be provided to keep the fluid contained within the vessel.

Any dimensions, sizes, volumes, or distances provided herein are provided by way of example only. Any other dimension, size, volume or distance may be utilized which may or may not be proportional to the amounts mentioned herein.

The centrifugation vessel can be subjected to a number of forces during the process of exchanging fluids and rapidly inserting and removing tips. If the vessel is not constrained, it is possible that these forces will be strong enough to lift or otherwise dislodge the vessel from the centrifuge bucket. In order to prevent movement, the vessel should be secured in some way. To accomplish this, a small ring circumscribing the bottom exterior of the vessel was added. This ring can easily be mated with a compliant mechanical feature on the bucket. As long as the retaining force of the nub is greater than the forces experienced during fluid manipulations, but less than the friction force when mated with the nozzle then the problem is solved.

Extraction Tip

The Extraction Tip may be designed to interface with the centrifugation vessel, efficiently extracting plasma, and re-suspending pelleted cells. Where desired, its total length (e.g., 34.5 mm) may exactly match that of another blood tip including but not limited to those described in U.S. Ser. No. 12/244,723 (incorporated herein by reference) but may be long enough to physically touch the bottom of the centrifugation vessel. The ability to touch the bottom of the vessel may be required in some embodiments, both for the re-suspension process, and for complete recovery of the white cell suspension.

The required volume of the extraction tip may be determined by the maximum volume it is expected to aspirate from the centrifugation vessel at any given time. In some embodiments, this volume may be approximately 60 uL, which may be less than the maximum capacity of the tip which is 85 uL. In some embodiments, a tip of greater volume than required volume may be provided. As with the centrifugation vessel, an internal feature circumscribing the interior of the upper portion of the tip may be used to mark the height of this maximum volume. The distance between the maximum volume line and the top of the mated nozzle may be 4.5 mm, which may be considered a safe distance to prevent nozzle contamination. Any sufficient distance to prevent nozzle contamination may be used.

The centrifuge may be used to sediment precipitated LDL-cholesterol. Imaging may be used to verify that the supernatant is clear, indicating complete removal of the precipitate.

Figure 119:
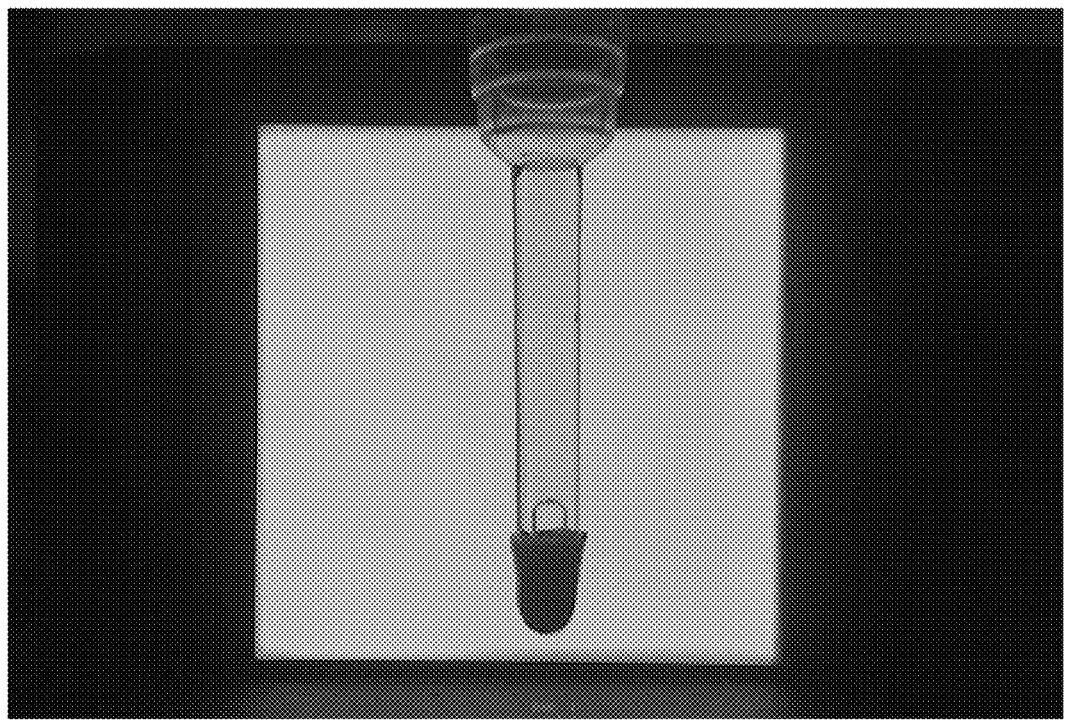
FIG. 119 is an image that was taken of the original reaction mixture prior to centrifugation.
Figure 120:
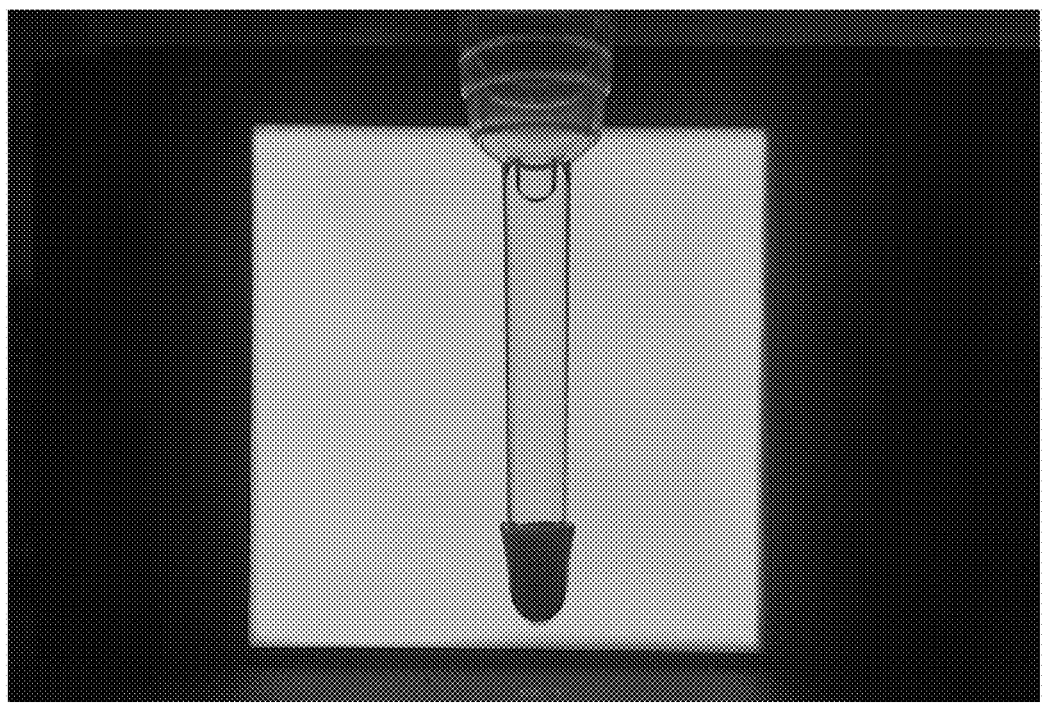
FIG. 120 is another image that was taken of the original reaction mixture prior to centrifugation
Figure 121:
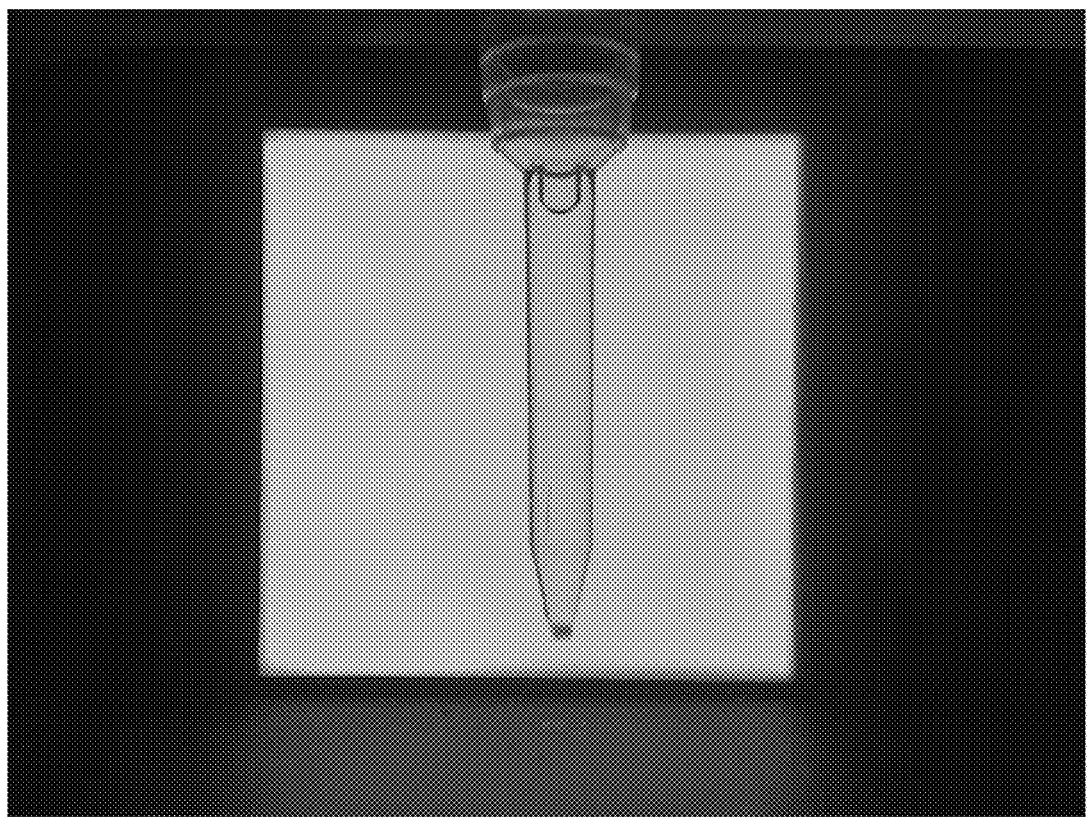
FIG. 121 is an additional image that was taken of the original reaction mixture prior to centrifugation

In one example, plasma may be diluted (e.g., 1:10) into a mixture of dextran sulfate (25 mg/dL) and magnesium sulfate (100 mM), and may be then incubated for 1 minute to precipitate LDL-cholesterol. The reaction product may be aspirated into the tube of the centrifuge, capped then and spun at 3000 rpm for three minutes. FIGS. 119, 120, and 121 are images that were taken of the original reaction mixture prior to centrifugation (showing the white precipitate), following centrifugation (showing a clear supernatant) and of the LDL-cholesterol pellet (after removal of the cap), respectively.

Other examples of centrifuges that can be employed in the present invention are described in U.S. Pat. Nos. 5,693,233, 5,578,269, 6,599,476 and U.S. Patent Publication Nos. 2004/0230400, 2009/0305392, and 2010/0047790, which are incorporated by reference in their entirety for all purposes.

Example Protocols

Many variations of protocol may be used for centrifugation and processing. For example, a typical protocol for use of the centrifuge to process and concentrate white cells for cytometry may include one or more of the following steps. The steps below may be provided in varying orders or other steps may be substituted for any of the steps below:

1. Receive 10 uL blood anti-coagulated with EDTA (pipette injects the blood into the bottom of the centrifuge bucket)
2. Sediment the red and white cells by centrifugation (<5 min×10,000 g).
3. Measure hematocrit by imaging
4. Remove plasma slowly by aspiration into the pipette (4 uL corresponding to the worst case scenario [60% hematocrit]) without disturbing the cell pellet.
5. Re-suspend the pellet after adding 20 uL of an appropriate cocktail of up to five fluorescently labeled antibodies[1] dissolved in buffered saline+BSA (1 mg/mL) (total reaction volume about 26 uL[2]).

[1] Concentration will be adjusted appropriately to deal with the different volume ratio relative to standard laboratory method (specifically about 5×lower)

[2] If necessary, this volume can be bigger to have optimal staining but not more than 50 uL.

6. Incubate for 15 minutes at 37 C.
7. Prepare lysing/fixative reagent by mixing red cell lysing solution (ammonium chloride/potassium bicarbonate) with white cell fixative reagent (formaldehyde).
8. Add 30 uL lysing/fixative reagent (total reaction volume about 60 uL).
9. Incubate 15 minutes at 37 C
10. Sediment the white cells by centrifugation (5 min, 10,000 g).
11. Remove the supernatant hemolysate (about 57 uL).
12. Re-suspend the white cells by adding 8 uL buffer (isotonic buffered saline).
13. Measure the volume accurately.
14. Deliver sample (c 10 uL) to cytometry.

The steps may include receiving a sample. The sample may be a bodily fluid, such as blood, or any other sample described elsewhere herein. The sample may be a small volume, such as any of the volume measurements described elsewhere herein. In some instances, the sample may have an anti-coagulant.

A separation step may occur. For example, a density-based separation may occur. Such separation may occur via centrifugation, magnetic separation, lysis, or any other separation technique known in the art. In some embodiments, the sample may be blood, and the red and white blood cells may be separated.

A measurement may be made. In some instances, the measurement may be made via imaging, or any other detection mechanism described elsewhere herein. For example, the hematocrit of a separated blood sample may be made by imaging. Imaging may occur via a digital camera or any other image capture device described herein.

One or more component of a sample may be removed. For example, if the sample is separated into solid and liquid components, the liquid component may be moved. The plasma of a blood sample may be removed. In some instances, the liquid component, such as plasma, may be removed via a pipette. The liquid component may be removed without disturbing the solid component. The imaging may aid in the removal of the liquid component, or any other selected component of the sample. For example, the imaging may be used to determine where the plasma is located and may aid in the placement of the pipette to remove the plasma.

In some embodiments, a reagent or other material may be added to the sample. For example, the solid portion of the sample may be resuspended. A material may be added with a label. One or more incubation step may occur. In some instances, a lysing and/or fixative reagent may be added. Additional separation and/or resuspending steps may occur. As needed, dilution and/or concentration steps may occur.

The volume of the sample may be measured. In some instances, the volume of the sample may be measured in a precise and/or accurate fashion. The volume of the sample may be measured in a system with a low coefficient of variation, such as coefficient of variation values described elsewhere herein. In some instances, the volume of the sample may be measured using imaging. An image of the sample may be captured and the volume of the sample may be calculated from the image.

The sample may be delivered to a desired process. For example, the sample may be delivered for cytometry.

In another example, a typical protocol that may or may not make use of the centrifuge for nucleic acid purification may include one or more of the following steps. The system may enable DNA/RNA extraction to deliver nucleic acid template to exponential amplification reactions for detection. The process may be designed to extract nucleic acids from a variety of samples including, but not limited to whole blood, serum, viral transfer medium, human and animal tissue samples, food samples, and bacterial cultures. The process may be completely automated and may extract DNA/RNA in a consistent and quantitative manner. The steps below may be provided in varying orders or other steps may be substituted for any of the steps below:

1. Sample Lysis. Cells in the sample may be lysed using a chaotropic-salt buffer. The chaotropic-salt buffer may include one or more of the following: chaotropic salt such as, but not limited to, 3-6 M guanidine hydrochloride or guanidinium thiocyanate; sodium dodecyl sulfate (SDS) at a typical concentration of 0.1-5% v/v; ethylenediaminetetraacetic acid (EDTA) at a typical concentration of 1-5 mM; lysozyme at a typical concentration of 1 mg/mL; proteinase-K at a typical concentration of 1 mg/mL; and pH may be set at 7-7.5 using a buffer such as HEPES. In some embodiments, the sample may be incubated in the buffer at typical temperature of 20-95° C. for 0-30 minutes. Isopropanol (50%-100% v/v) may be added to the mixture after lysis.

2. Surface Loading. Lysed sample may be exposed to a functionalized surface (often in the form of a packed bed of beads) such as, but not limited to, a resin-support packed in a chromatography style column, magnetic beads mixed with the sample in a batch style manner, sample pumped through a suspended resin in a fluidized-bed mode, and sample pumped through a closed channel in a tangential flow manner over the surface. The surface may be functionalized so as to bind nucleic acids (e.g. DNA, RNA, DNA/RNA hybrid) in the presence of the lysis buffer. Surface types may include silica, and ion-exchange functional groups such as diethylaminoethanol (DEAE). The lysed mixture may be exposed to the surface and nucleic acids bind.

3. Wash. The solid surface is washed with a salt solution such as 0-2 M sodium chloride and ethanol (20-80% v/v) at pH 7.0-7.5. The washing may be done in the same manner as loading.

4. Elution. Nucleic acids may be eluted from the surface by exposing the surface to water or buffer at pH 7-9. Elution may be performed in the same manner as loading.

Many variations of these protocols or other protocols may be employed by the system. Such protocols may be used in combination or in the place of any protocols or methods described herein.

In some embodiments, it is important to be able to recover the cells packed and concentrated by centrifugation for cytometry. In some embodiments, this may be achieved by use of the pipetting device. Liquids (typically isotonic buffered saline, a lysing agent, a mixture of a lysing agent and a fixative or a cocktail of labeled antibodies in buffer) may be dispensed into the centrifuge bucket and repeatedly aspirated and re-dispensed. The tip of the pipette may be forced into the packed cells to facilitate the process. Image analysis aids the process by objectively verifying that all the cells have been re-suspended.

Use of the Pipette and Centrifuge to Process Samples Prior to Analysis:

In accordance with an embodiment of the invention, the system may have pipetting, pick-and-place and centrifugal capabilities. Such capabilities may enable almost any type of sample pretreatment and complex assay procedures to be performed efficiently with very small volumes of sample.

Specifically, the system may enables separation of formed elements (red and white cells) from plasma. The system may also enable re-suspension of formed elements. In some embodiments, the system may enable concentration of white cells from fixed and hemolysed blood. The system may also enable lysis of cells to release nucleic acids. In some embodiments, purification and concentration of nucleic acids by filtration through tips packed with (typically beaded) solid phase reagents (e.g. silica) may be enabled by the system. The system may also permit elution of purified nucleic acids following solid phase extraction. Removal and collection of precipitates (for example LDL-cholesterol precipitated using polyethylene glycol) may also be enabled by the system.

In some embodiments, the system may enable affinity purification. Small molecules such as vitamin-D and serotonin may be adsorbed onto beaded (particulate) hydrophobic substrates, then eluted using organic solvents. Antigens may be provided onto antibody-coated substrates and eluted with acid. The same methods can be used to concentrate analytes found at low concentrations such as thromboxane-B2 and 6-keto-prostaglandin F1α. Antigens may be provided onto antibody or aptamer-coated substrates and then eluted.

In some embodiments, the system may enable chemical modification of analytes prior to assay. To assay serotonin (5-Hydroxytryptamine) for example, it may be required to convert the analyte to a derivative (such as an acetylated form) using a reagent (such as acetic anhydride). This may be done to produce a form of the analyte that can be recognized by an antibody.

Liquids can be moved using the pipette (vacuum aspiration and pumping). The pipette may be limited to relatively low positive and negative pressures (approximately 0.1-2.0 atmospheres). A centrifuge can be used to generate much higher pressures when needed to force liquids through beaded solid phase media. For example, using a rotor with a radius of 5 cm at a speed of 10,000 rpm, forces of about 5,000×g (about 7 atmospheres) may be generated, sufficient to force liquids through resistive media such as packed beds. Any of the centrifuge designs and configurations discussed elsewhere herein or known in the art may be used.

Measurement of hematocrit with very small volumes of blood may occur. For example, inexpensive digital cameras are capable of making good images of small objects even when the contrast is poor. Making use of this capability, the system of the present invention may enable automated measurement of hematocrit with a very small volume of blood.

For example, 1 uL of blood may be drawn into a microcap glass capillary. The capillary may then be sealed with a curable adhesive and then subject to centrifugation at 10,000×g for 5 minutes. The packed cell volume may be easily measured and the plasma meniscus (indicated by an arrow) may also be visible so hematocrit can be accurately measured. This may enable the system to not waste a relatively large volume of blood to make this measurement. In some embodiments, the camera may be used "as is" without operation with a microscope to make a larger image. In other embodiments, a microscope or other optical techniques may be used to magnify the image. In one implementation, the hematocrit was determined using the digital camera without additional optical interference, and the hematocrit measured was identical to that determined by a conventional microhematocrit laboratory method requiring many microliters of sample. In some embodiments, the length of the sample column and of that of the column of packed red cells can be measured very precisely (+/−<0.05 mm) Given that the blood sample column may be about 10-20 mm, the standard deviation of hematocrit may be much better than 1% matching that obtained by standard laboratory methods.

Figure 122:
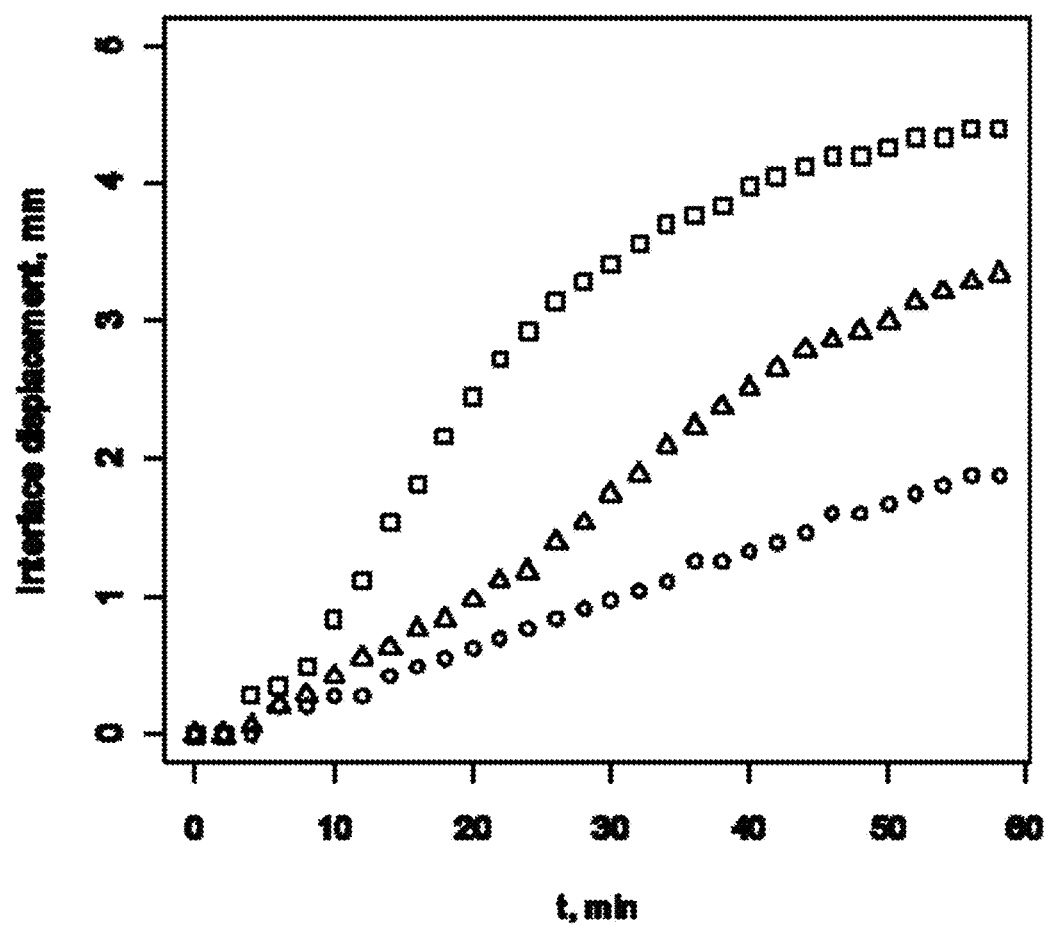
FIG. 122 shows results as distance of the interface from the plasma meniscus.

The system may enable measurement of erythrocyte sedimentation rate (ESR). The ability of digital cameras to measure very small distances and rates of change of distances may be exploited to measure ESR. In one example, three blood samples (15 uL) were aspirated into "reaction tips". Images were captured over one hour at two-minute intervals. Image analysis was used to measure the movement of the interface between red cells and plasma. FIG. 122 shows results as distance of the interface from the plasma meniscus.

The precision of the measurement may be estimated by fitting the data to a polynomial function and calculating the standard deviation of the difference between the data and the fitted curve (for all samples). In the example, this was determined to be 0.038 mm or <2% CV when related to the distance moved over one hour. Accordingly, ESR can be measured precisely by this method. Another method for determination of ESR is to measure the maximum slope of the distance versus time relationship.

Assay Preparation

In some embodiments, tips can be designed to accommodate a plurality of reactions or assays. Simultaneous measurement of several different assay mixtures and one or more controls or one or more calibrators can be made within one tip of the present invention. In doing this we exploit the ability to sample several liquid sources by sequential aspiration of liquids into the same tip. Effective segmentation and separation of the liquids is greatly improved by aspirating in sequence a small volume of air and a small volume of a wash solution which cleans the surface of the tips prior to aspiration of the next liquid of interest.

As described above, tips can have conical shapes. In some embodiments, an assay can require oxygen as a reactant. In such reactions, increasing availability of oxygen within a reaction can be achieved by moving the sample and/or assay mixture to a wide part of tip to increase surface area to volume ratio.

Figure 93:
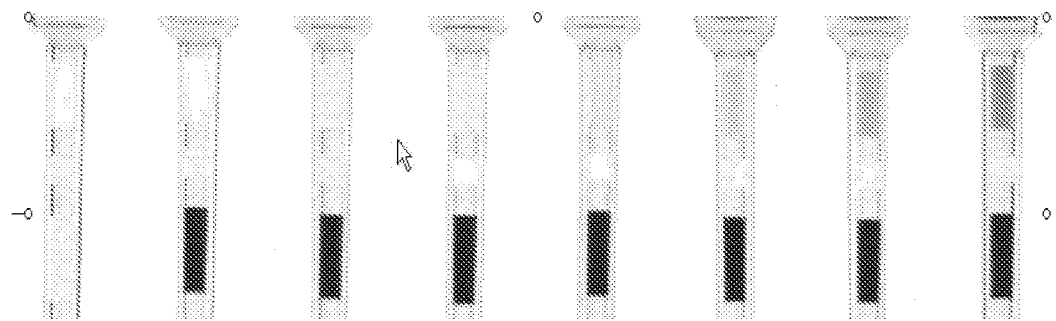
FIG. 93 shows an image of tips containing solutions of bromophenol blue and water.
Figure 94:
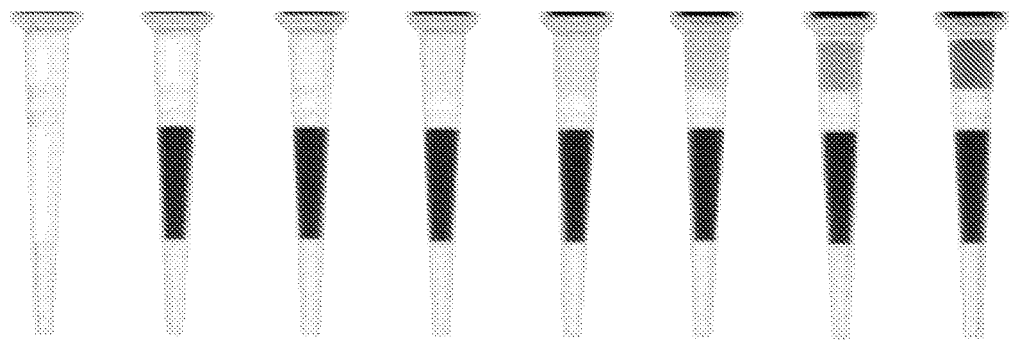
FIG. 94 shows an image of additional tips that may contain solutions of bromophenol blue and water.

In FIG. 93 and FIG. 94, solutions of bromphenol blue were aspirated into tips. The uppermost segments (aspirated first) 6 uL are from a two-fold dilution series (highest concentration (0.0781 mg/mL) to the right of the image, with the exception of the left-most tip which is a water blank). Then air (2 uL), wash solution (2 uL) respectively were aspirated followed by a 6 uL volume of a fixed concentration control solution (0.625 mg/mL).

Using this approach several alternative assay configurations can be achieved, for example:

1. Simultaneous measurement of reagent and/or sample blank and assay
2. Simultaneous measurement of sample, blank and control
3. Within-tip calibration of assay The table below illustrates some "multiplex types" in which preferred combinations of assays, controls and calibrators are assembled within a tip.

colored product from one sample to the next is minimized by either or both:

1. Reading the liquid column in the middle portion well away from that part that first comes into contact with the preceding sample
2. Washing the tip between samples.

In order to measure the extent of 'carry-over' from one liquid segment to the next, the following procedure was be performed. A small amount (e.g. 6 uL) of a high concentration of bromphenol blue (e.g. 0.625 mg/mL) was aspirated into tips, followed by 2 uL of air and 2 uL of wash solution. Finally 6 uL of serial two-fold dilutions of bromphenol blue is aspirated with the following results (highest concentration (0.0781 mg/mL) to the right; left most tip is a water blank).

Figure 96:
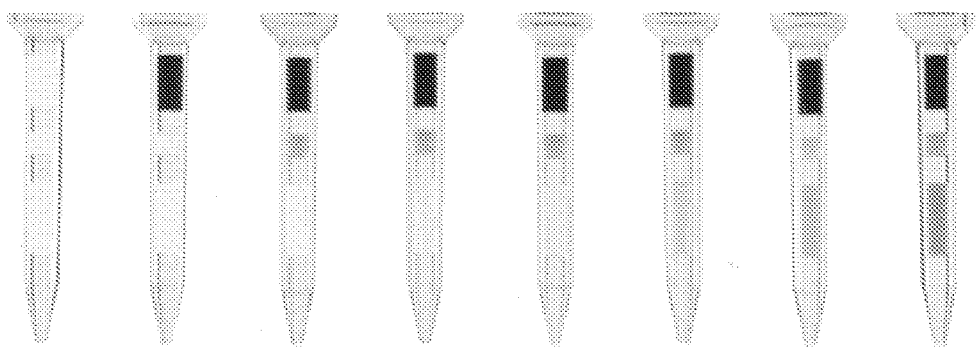
FIG. 96 shows an image of tips containing solutions of bromophenol blue and water.
Figure 97:
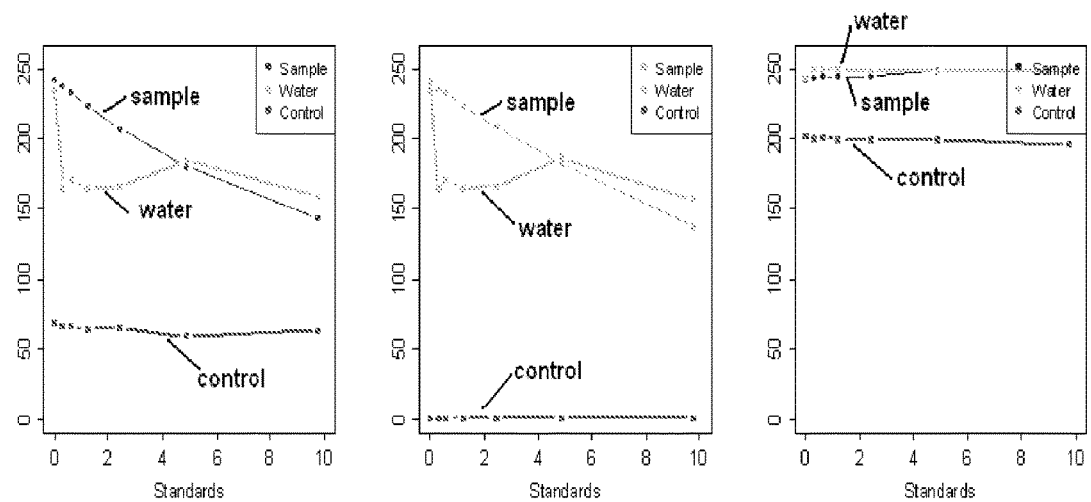
FIG. 97 shows a graph of signal response for sample, water, and control in multiple standards. The samples may be aqueous calibrators containing known concentrations of analyte.

As can be seen from the images shown in FIG. 96 and the 3-color analysis shown in FIG. 97, measurable amounts of the high concentration solution is transferred into the wash solution.

Average carry-over (from high concentration control to the water wash) is calculated at 1.4%. Since, in effect, the leading zone (proximal to the earlier slug) of a later slug of liquid acts as second wash step and the color reading is taken at a location remote from this leading zone (typically at a central zone of the slug), the effective carryover from one slug to the next is typically much less than 1% and therefore generally insignificant. When the dilution series is measured using only dilution series samples to fill the tips, results are identical with those obtained above. The above represents a "stress test" designed to evaluate the extent of carry-over.

Figure 98:
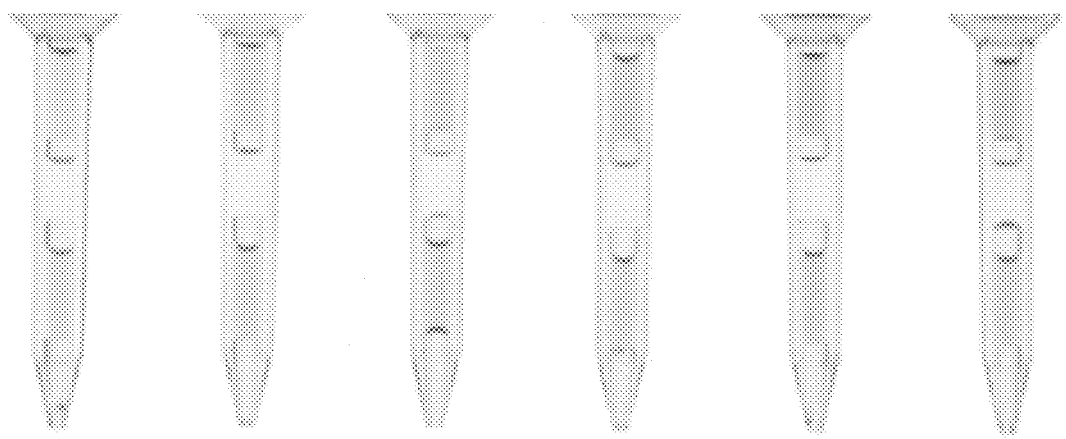
FIG. 98 shows tips containing assays for both $Ca^{2+}$ (upper region of the tip) and $Mg^{2+}$ (lower region of the tip).

FIG. 98 shows a tip containing reaction products for two commercially available assays for ionized calcium, Ca2+ (upper segment) and magnesium Mg2+ (lower segment) that were aspirated into tips for measurement. Ca2+ concentrations used in this experiment are 0, 2.5, 5, 10, 20, and 40 mg/dL; Mg2+ concentrations are 0, 1.25, 2.5, 5, 10, 20 mg/dL. Assay reaction mixtures (6 uL [Ca2+] and 4 uL [Mg2+]) are well separated using 2 uL of air, 3 uL of wash and a further 4 uL of air. Results for each assay read in this way are essentially identical to those measured having only one assay reaction mixture per tip.

As noted above, the present invention allows for simultaneous evaluation of a plurality of assays. Images can be made of many assay cuvettes in the same field of view. Specifically, simultaneous evaluation of assays and controls in the same assay cuvette can be performed. Simultaneous evaluation of several assays in the same assay cuvette can be also performed.

Reaction Environment

| | Zone # | | | | | | | | | | |
| --- | --- | --- | --- | --- | --- | --- | --- | --- | --- | --- | --- |
| Multiplex Type | 1 Top | 2 | 3 | 4 | 5 | 6 | 7 | 8 | 9 | 10 | 11 Bottom |
| Assay with controls | Air | Control1 | Air | Wash | Air | Assay | Air | Wash | Control2 | | |
| Three assays | Air | Assay1 | Air | Wash | Air | Assay2 | Air | Wash | Air | Assay3 | Air |
| Calibration series | Air | Cal1 | Air | Wash | Air | Cal2 | Air | Wash | Air | Cal3 | Air |
| Assay with blank | Air | Assay | Air | Wash | Air | Blank | Air | | | | |

Figure 95:
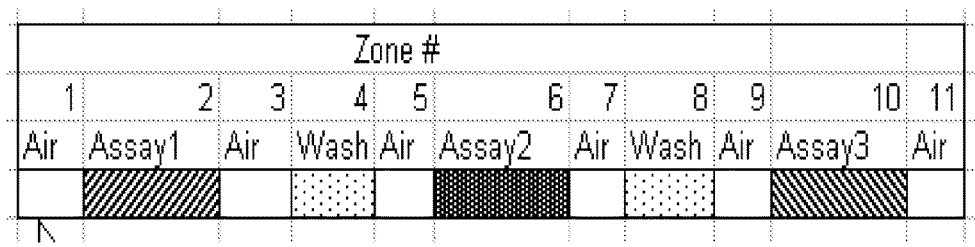
FIG. 95 shows an schematic of a tip containing reaction mixtures to perform multiple assays.

Case 2 is shown in FIG. 95.

Serial measurements of blank solutions, sample, controls and calibrators can also be made with single tips. In this scenario, the tip is filled with the first solution, read then emptied. The tip can then be re-filled and read with other samples etc. in sequence. The impact of "carry-over" of A system can comprise a heating block for heating the assay or assay unit and/or for control of the assay temperature. Heat can be used in the incubation step of an assay reaction to promote the reaction and shorten the duration necessary for the incubation step. A system can comprise a heating block configured to receive an assay unit of the invention. The heating block can be configured to receive a plurality of assay units from a device of the invention. For example, if 8 assays are desired to be run on a device, the heating block can be configured to receive 8 assay units. In some embodiments, assay units can be moved into thermal contact with a heating block using the means for moving the assay units. The heating can be performed by a heating means known in the art.

Protocol Optimization

Assay protocols for analyzing samples can be optimized in a variety of manners. When multiple assays are to be run on a sample, all protocols can be optimized to the most stringent reaction conditions, or each assay protocol can be optimized based on the desired performance of a particular assay.

In some embodiments, a single protocol that can be designed to meet the test requirements under all possible use cases. For example, on a multiplex cartridge, a single protocol may be specified based on the case when all tests on the cartridge are to be performed (i.e., the limiting case). This protocol can be designed to meet the minimal test requirements, such as the precision and dynamic range for each test on the cartridge. However, this approach can be suboptimal for alternate use cases, for example, when only a subset of tests on the cartridge is to be performed. In these cases, by using more sample, some assays can achieve improved performance in terms of sensitivity and precision. There can be a trade-off between how much sample is allocated to an assay and assay sensitivity. For example, an assay which has a sensitivity of 1 unit/mL when the sample is diluted 1:100 may be able to detect 0.1 unit/mL if the dilution factor is increased to 1:10. One downside of using a lower dilution factor in a multiplexed assay system with restricted sample volume can be that the fraction of the sample required for this assay is increased by 10-fold even when using the minimal volume to perform the assay. Likewise, assay precision may be improved by using a higher sample concentration. For example, an assay which results in a signal of (say) 0.1 absorbance+/−0.02 (20% signal imprecision) at its limit of detection can be improved by use of 10 times the sample concentration such that the signal produced is 10 times greater giving a signal of 0.1+/−0.02 OD at an analyte concentration ten times lower and at signal of 1.0, +/−0.02 the imprecision is now only 2%. The reason this is the case is that typically assay signal (at the lower range of analyte concentrations) is directly proportional to the analyte concentration (and therefore to the sample concentration) whereas the signal imprecision can be typically related to the square root of the signal and so increases as the square root of analyte concentration (and sample concentration). Thus, the coefficient of variation (CV) of the signal can be inversely proportional to the square root of the signal; such that a 10-fold increase in signal corresponds to approximately three-fold decrease in signal CV. Since concentration CV is typically directly related to signal CV, the concentration CV will decrease with increased sample concentration (decreased dilution).

Protocols can be optimized to specific use cases rather than the typical one-size fits all approach described above. For example, the protocol may be optimized to enhance the precision of each test being performed in the multiplex device. Moreover, some tests may be prioritized relative to other tests for optimization. Protocol optimization can be pre-computed for use cases that are known a priori. Protocol optimization can also be performed in real-time for new use cases not known a priori. System validation can be performed to span the suite of use cases.

One example of protocol optimization is described below comparing two uses cases. For both use cases, 8 uL of undiluted sample is available to run the required tests. In this example, the multiplex cartridge has 20 tests on board, where 5 of the tests require 1:5 dilution and 15 of the tests require 1:25 dilution.

In the first use case, all tests are required to be run on the sample. The protocol in this use case (Use-case B) is as follows:

1) Prepare 1:5 dilution (8 uL sample+32 uL diluent)
2) Prepare 1:25 dilution (15 uL 1:5 sample+60 uL diluent)
3) For each test (n=20), mix 5 uL of appropriately diluted sample with 10 uL of the reagent This protocol results in concentration imprecision of 10% CV for all 20 tests, meeting the minimal requirements. The sample usage is 1 uL for each 1:5 dilution assay and 0.2 uL for each 1:25 dilution assay (for a total of 5*1+15*0.2=8 uL, using all the available sample).

In the second use case (Use-case "B") with the same cartridge type, only 10 tests are required to be run for the sample, not all 20. Moreover, all these 10 tests would be performed at the 1:25 dilution level in use-case A. The protocol is optimized for this use case to maximize precision for all the tests by using a lower dilution (1:5). The optimized protocol for this specific use case is as follows:

1) Prepare 1:5 dilution (8 uL sample+32 uL diluent)
2) For each test (n=10), mix 4 uL of diluted sample with 11 uL of reagent Sample usage is 0.8 uL undiluted sample per assay for a total of 8 uL. Since the sample concentration in the assay is increased by 5-fold relative to that for use-case A, the assay sensitivity is improved by a factor of 5 and the assay imprecision is reduced by about 2.4 (5^0.5) fold to about 4.5%.

By re-optimizing the protocol, in use case B employs 5-times as much original sample for each test, thereby improving overall performance. Note that the above discussion does not account for any imprecision due to errors in metering of volumes but only addresses errors due to imprecision in measurement of optical signal. Use-case B would have a lower imprecision due to imprecision in volumes since it uses fewer pipetting steps. For example if the volume imprecision introduces 5% imprecision in the reported analyte concentration in both use cases there would be a total analyte imprecision of 11.2% (10^2+5^2)^0.5 in use-case A compared with 6.5% (4.5^2+5^2)^0.5 in use-case B (assuming, as is generally true, that factors causing imprecision in assays aggregate as the square root of the sum of squares of each source of imprecision).

The effects illustrated above can more easily be seen in the case of luminescence-based assays where the assay signal is expressed as a number of photons emitted per unit time. As is the case for counting of radioactive emissions in for example radioimmunoassay, the signal imprecision is equal to the square root of the signal and thus the signal CV is 100/(square root of signal). For example, a signal of 10,000 counts will have a CV of 1%. In many assays which produce photons (for example chemiluminescence immunoassays, the signal is almost exactly proportional to analyte concentration, at least at the lower concentration range). Thus the measured analyte imprecision scales with 1/(square root of signal) for concentrations significantly above the limit of detection. In assays which utilize dilution of the sample, the measured analyte imprecision will therefore scale as 1/(sample dilution). For example, an assay using a 1:100 dilution of sample will have signal and concentration CVs about 3.2 fold (10^0.5) higher than an assay using a dilution 1:10 (and will also have a sensitivity about 10-times higher).

Reaction Chemistries

A variety of assays may be performed on a fluidic device according to the present invention to detect an analyte of interest in a sample. Where a label is utilized in the assay, one may choose from a wide diversity of labels is available in the art that can be employed for conducting the subject assays. In some embodiments labels are detectable by spectroscopic, photochemical, biochemical, electrochemical, immunochemical, or other chemical means. For example, useful nucleic acid labels include the, fluorescent dyes, electron-dense reagents, and enzymes. A wide variety of labels suitable for labeling biological components are known and are reported extensively in both the scientific and patent literature, and are generally applicable to the present invention for the labeling of biological components. Suitable labels include, enzymes, fluorescent moieties, chemiluminescent moieties, bioluminescent labels, or colored labels. Reagents defining assay specificity optionally include, for example, monoclonal antibodies, polyclonal antibodies, aptamers, proteins, nucleic acid probes or other polymers such as affinity matrices, carbohydrates or lipids. Detection can proceed by any of a variety of known methods, including spectrophotometric or optical tracking of fluorescent, or luminescent markers, or other methods which track a molecule based upon size, charge or affinity. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Thus, a label includes without limitation any composition detectable by spectroscopic, photochemical, biochemical, immunochemical, nucleic acid probe-based, electrical, optical thermal, or other chemical means.

In some embodiments the label (such as a colored compound, fluor or enzyme) is coupled directly or indirectly to a molecule to be detected, according to methods well known in the art. In other embodiments, the label is attached to a receptor for the analyte (such as an antibody, nucleic acid probe, aptamer etc.). As indicated above, a wide variety of labels are used, with the choice of label depending on the sensitivity required, ease of conjugation of the compound, stability requirements, available instrumentation, and disposal provisions. Non-radioactive labels are often attached by indirect means. Generally, a receptor specific to the analyte is linked to a signal-generating moiety. Sometimes the analyte receptor is linked to an adaptor molecule (such as biotin or avidin) and the assay reagent set includes a binding moiety (such as a biotinylated reagent or avidin) that binds to the adaptor and to the analyte. The analyte binds to a specific receptor on the reaction site. A labeled reagent can form a sandwich complex in which the analyte is in the center. The reagent can also compete with the analyte for receptors on the reaction site or bind to vacant receptors on the reaction site not occupied by analyte. The label is either inherently detectable or bound to a signal system, such as a detectable enzyme, a fluorescent compound, a chemiluminescent compound, or a chemiluminogenic entity such as an enzyme with a luminogenic substrate. A number of ligands and anti-ligands can be used. Where a ligand has a natural anti-ligand, for example, biotin, thyroxine, digoxigenin, and cortisol, it can be used in conjunction with labeled, anti-ligands. Alternatively, any haptenic or antigenic compound can be used in combination with an antibody.

Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl groups, and umbelliferone. Chemiluminescent compounds include dioxetanes, acridinium esters, luciferin, and 2,3-dihydrophthalazinediones, such as luminol.

Methods of detecting labels are well known to those of skilled in the art. Thus, for example, where the label is fluorescent, it may be detected by exciting the fluorochrome with light of an appropriate wavelength and detecting the resulting fluorescence by, for example, microscopy, visual inspection, via photographic film, by the use of electronic detectors such as digital cameras, charge coupled devices (CCDs) or photomultipliers and phototubes, or other detection devices. Similarly, enzymatic labels are detected by providing appropriate substrates for the enzyme and detecting the resulting reaction product spectroscopically or by digital imaging (the subject of the present invention). Finally, simple colorimetric labels are often detected simply by observing the color associated with the label. For example, colloidal gold sols often appear pink, while various beads doped with dyes are strongly colored.

In some embodiments the detectable signal may be provided by luminescence sources Luminescence is the term commonly used to refer to the emission of light from a substance for any reason other than a rise in its temperature. In general, atoms or molecules emit photons of electromagnetic energy (e.g., light) when they transition from an excited state to a lower energy state (usually the ground state). If the exciting agent is a photon, the luminescence process is referred to as photoluminescence or fluorescence. If the exciting cause is an electron, the luminescence process can be referred to as electroluminescence. More specifically, electroluminescence results from the direct injection and removal of electrons to form an electron-hole pair, and subsequent recombination of the electron-hole pair to emit a photon Luminescence which results from a chemical reaction is usually referred to as chemiluminescence. Luminescence produced by a living organism is usually referred to as bioluminescence. If photoluminescence is the result of a spin allowed transition (e.g., a single-singlet transition, triplet-triplet transition), the photoluminescence process is usually referred to as fluorescence. Typically, fluorescence emissions do not persist after the exciting cause is removed as a result of short-lived excited states which may rapidly relax through such spin allowed transitions. If photoluminescence is the result of a spin forbidden transition (e.g., a triplet-singlet transition), the photoluminescence process is usually referred to as phosphorescence. Typically, phosphorescence emissions persist long after the exciting cause is removed as a result of long-lived excited states which may relax only through such spin-forbidden transitions. A luminescent label may have any one of the above-described properties.

Suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety of conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca] benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include—N-alkyl acridinum esters and dioxetanes. Alternatively, luciferins may be used in conjunction with luciferase or lucigenins to provide bioluminescence. Especially preferred chemiluminescent sources are "luminogenic" enzyme substrates such as dioxetane-phosphate esters. These are not luminescent but produce luminescent products when acted on by phosphatases such as alkaline phosphatase. The use of luminogenic substrates for enzymes is particularly preferred because the enzyme acts as an amplifier capable of converting thousands of substrate molecules per second to product. Luminescence methods are also preferred because the signal (light) can be detected both very sensitively and over a huge dynamic range using PMTs.

The term analytes as used herein includes without limitation drugs, prodrugs, pharmaceutical agents, drug metabolites, biomarkers such as expressed proteins and cell markers, antibodies, serum proteins, cholesterol and other metabolites, electrolytes, metal ions, polysaccharides, nucleic acids, biological analytes, biomarkers, genes, proteins, hormones, or any combination thereof. Analytes can be combinations of polypeptides, glycoproteins, polysaccharides, lipids, and nucleic acids.

The system can be used to detect and/or quantify a variety of analytes. For example, analytes that can be detected and/or quantified include Albumin, Alkaline Phosphatase, ALT, AST, Bilirubin (Direct), Bilirubin (Total), Blood Urea Nitrogen (BUN), Calcium, Chloride, Cholesterol, Carbon Dioxide ($CO_2$), Creatinine, Gamma-glutamyl-transpeptidase (GGT), Globulin, Glucose, HDL-cholesterol, Hemoglobin, Homocysteine, Iron, Lactate Dehydrogenase, Magnesium, Phosphorous, Potassium, Sodium, Total Protein, Triglycerides, and Uric Acid. The detection and/or quantification of these analytes can be performed using optical, electrical, or any other type of measurements.

Of particular interest are biomarkers which are associated with a particular disease or with a specific disease stage. Such analytes include but are not limited to those associated with autoimmune diseases, obesity, hypertension, diabetes, neuronal and/or muscular degenerative diseases, cardiac diseases, endocrine disorders, metabolic disorders, inflammation, cardiovascular diseases, sepsis, angiogenesis, cancers, Alzheimer's disease, athletic complications, and any combinations thereof.

Of also interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are analytes that are indicative of a microorganism, virus, or Chlamydiaceae. Exemplary microorganisms include but are not limited to bacteria, viruses, fungi and protozoa. Analytes that can be detected by the subject method also include blood-born pathogens selected from a non-limiting group that consists of *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influenzae, Staphylococcus simulans, Streptococcus pneumoniae* and *Candida albicans*.

Analytes that can be detected by the subject method also encompass a variety of sexually transmitted diseases selected from the following: gonorrhea (*Neisseria gonorrhoeae*), syphilis (*Treponena pallidum*), clamydia (*Clamyda tracomitis*), nongonococcal urethritis (*Ureaplasm urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

Additional analytes that can be detected by the subject methods encompass a diversity of respiratory pathogens including but not limited to *Pseudomonas aeruginosa*, methicillin-resistant *Staphylococcus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae*, and *Mycobacterium tuberculosis*.

Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, Triglycerides, Tryptase, Low density lipoprotein Cholesterol, High density lipoprotein Cholesterol, Cholesterol, IGFR.

Exemplary liver markers include without limitation LDH, (LD5), Alanine-aminotransferase (ALT), Arginase 1 (liver type), Alpha-fetoprotein (AFP), Alkaline phosphatase, Lactate dehydrogenase, and Bilirubin.

Exemplary kidney markers include without limitation TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markers include without limitation Troponin I (TnI), Troponin T (TnT), Creatine dinase (CK), CKMB, Myoglobin, Fatty acid binding protein (FABP), C-reactive protein (CRP), Fibrinogen D-dimer, S-100 protein, Brain natriuretic peptide (BNP), NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancrease markers include without limitation Amylase, Pancreatitis-Associated protein (PAP-1), and Regeneratein proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx), Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type I N propeptide, Osteocalcin (bone gla-protein), Alkaline phosphatase, Cathepsin K, COMP (Cartilage Oligimeric Matrix Protein), Osteocrin, Osteoprotegerin (OPG), RANKL, sRANK, TRAP 5 (TRACP 5), Osteoblast Specific Factor 1 (OSF-1, Pleiotrophin), Soluble cell adhesion molecules, sTfR, sCD4, sCD8, sCD44, and Osteoblast Specific Factor 2 (OSF-2, Periostin).

In some embodiments markers according to the present invention are disease specific. Exemplary cancer markers include without limitation PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, CAA pancreatic, Neuron-specific enolase, Angiostatin DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine.

Exemplary infectious disease conditions include without limitation: Viremia, Bacteremia, Sepsis, and markers: PMN Elastase, PMN elastase/α1-PI complex, Surfactant Protein D (SP-D), HBVc antigen, HBVs antigen, Anti-HBVc, Anti-HIV, T-supressor cell antigen, T-cell antigen ratio, T-helper cell antigen, Anti-HCV, Pyrogens, p24 antigen, Muramyl-dipeptide.

Exemplary diabetes markers include without limitation C-Peptide, Hemoglobin A1c, Glycated albumin, Advanced glycosylation end products (AGEs), 1,5-anhydroglucitol, Gastric Inhibitory Polypeptide, Glucose, Hemoglobin A1c, ANGPTL3 and 4.

Exemplary inflammation markers include without limitation Rheumatoid factor (RF), Antinuclear Antibody (ANA), C-reactive protein (CRP), Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4, Von Willebrand factor.

In some embodiments a marker may be therapy specific. Markers indicative of the action of COX inhibitors include without limitation TxB2 (Cox-1), 6-keto-PGF-1-alpha (Cox 2), 11-Dehydro-TxB-1a (Cox-1).

Other markers of the present invention include without limitation Leptin, Leptin receptor, and Procalcitonin, Brain S100 protein, Substance P, 8-Iso-PGF-2a.

Exemplary geriatric markers include without limitation, Neuron-specific enolase, GFAP, and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4), Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, amd sTfR (soluble Transferrin Receptor).

Exemplary markers of Lipid metabolism include without limitation Apo-lipoproteins (several), Apo-A1, Apo-B, Apo-C-CII, Apo-D, Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII: Anti-hemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1).

Exemplary monoclonal antibodies include those for EGFR, ErbB2, and IGF1R.

Exemplary tyrosine kinase inhibitors include without limitation Ab1, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary Serine/Threonine Kinase Inhibitors include without limitation AKT, Aurora A/B/B, CDK, CDK (pan), CDK1-2, VEGFR2, PDGFRb, CDK4/6, MEK1-2, mTOR, and PKC-beta.

GPCR targets include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

Cholesterol

Figure 52:
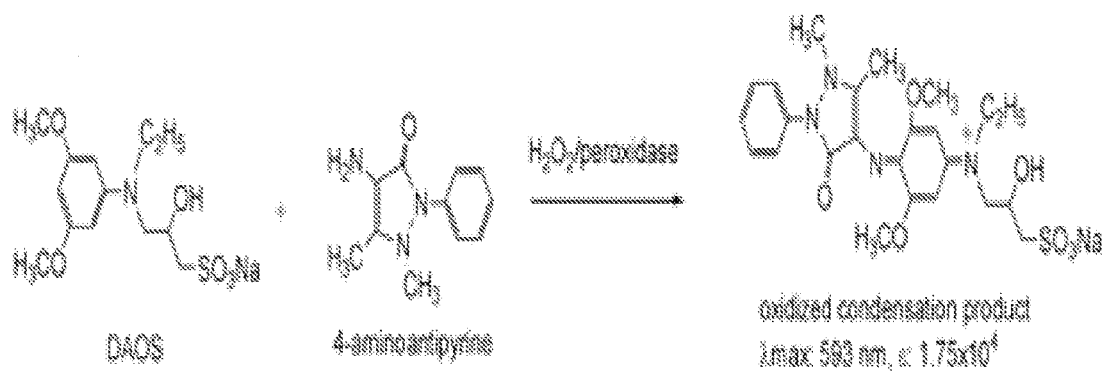
FIG. 52 shows a schematic of a chemical reaction that produces a colored product.
Figure 53:
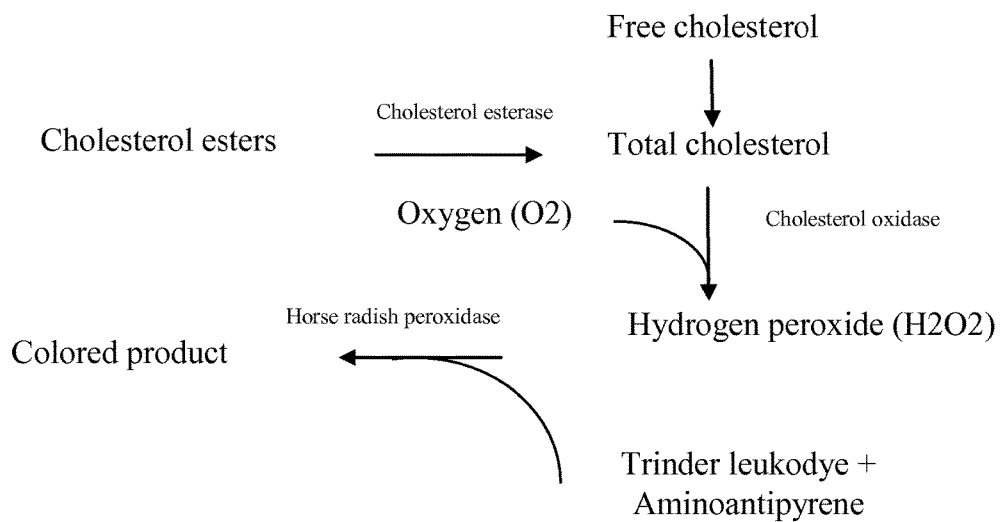
FIG. 53 shows a schematic of a chemical reaction that produces a colored product from cholesterol.

Measurement of metabolites can be performed by production of a colored product using oxidases (such as cholesterol oxidase) (to make H2O2) and horse-radish peroxidase plus a chromogen (such as N-Ethyl-N-(2-hydroxy-3-sulfopropyl)-3,5-dimethoxyaniline, sodium salt ["DAOS" plus amino anti-pyrene] to form a colored product such as a Trinder dye). One example of such chemistry is shown in FIG. 52 and FIG. 53.

NADH or NADPH

Production or consumption of NADH or NADPH are frequently used in clinical assays. This is because these coenzymes are common substrates for enzymes. For example, measurement of enzymes of clinical interest such as lactate dehydogenase (LDH) can be measured by the rate of production of NADH. Since NADH absorbs light maximally at 340 nm and (1) polystyrene and other plastics transmit light poorly in the near UV, (2) White light sources produce little light in the near UV and (3) camera and scanner sensors have low sensitivity to near UV light, it is not practical to measure NADH by three color image analysis. To deal with this issue NADH can be converted to a colored product using tetrazolium salts such as Water Soluble Tetrazolium (e.g.WST-1 (Dojindo Molecular Technologies) plus an "electron mediator" such as 1-Methoxyphenazine methosulfate (PMS).

Figure 54:
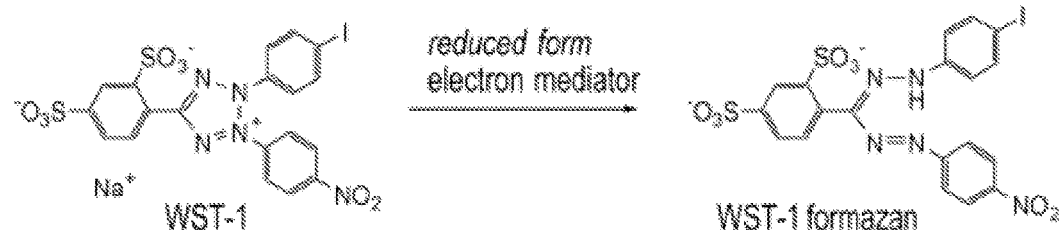
FIG. 54 shows a schematic of a chemical reaction that uses reducing equivalents to produce a colored product.

In some embodiments, assays that produce or consume NADH or NADPH can be paired with other reactions that allow for colorimetric measurement. For example, NADH or NADPH can be used to reduce compounds such as 2-(4-Iodophenyl)-3-(4-nitrophenyl)-5-(2,4-disulfophenyl)-2H-tetrazolium, monosodium salt (WST-1) to a colored formezan dye as shown below with the use of phenazine methosulfate as an electron mediator, as shown in FIG. 54.

Figure 73:
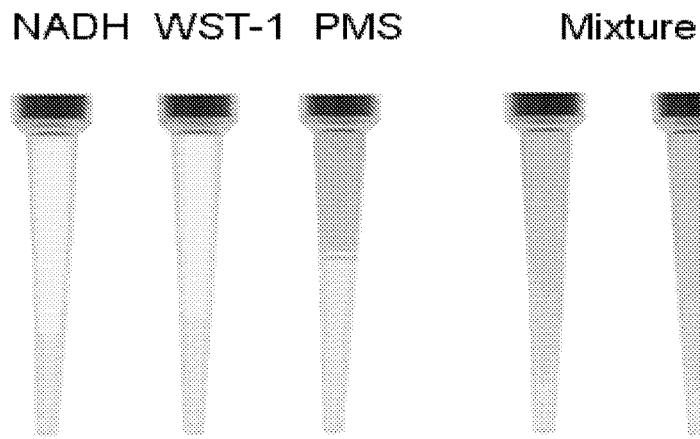
FIG. 73 shows tips that each separately contain reagents NADH, WST-1, PMS, and two tips containing a mixture of the reagents.

As shown in FIG. 73, when NADH, WST-1 and PMS are combined at millimolar concentrations, a yellow product (shown in tips indicated as Mixture) is formed.

Figure 74:
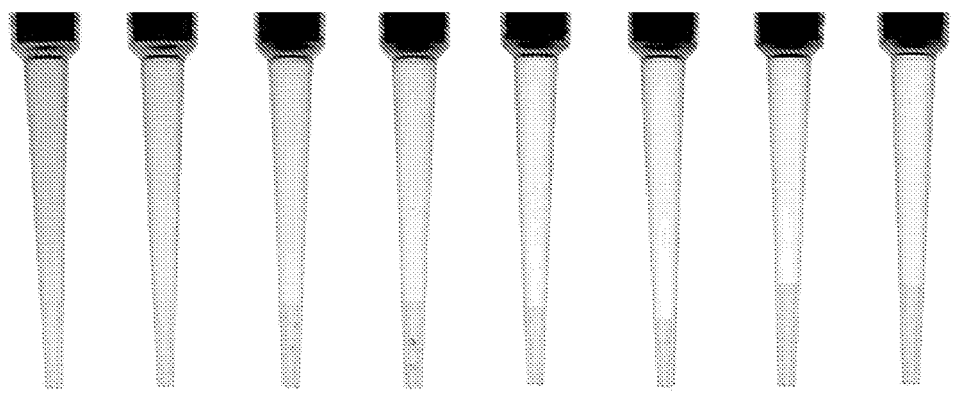
FIG. 74 shows a digital image of tips containing two-fold decreasing concentration of lactate dehydrogenase (LDH) from left to right.
Figure 75:
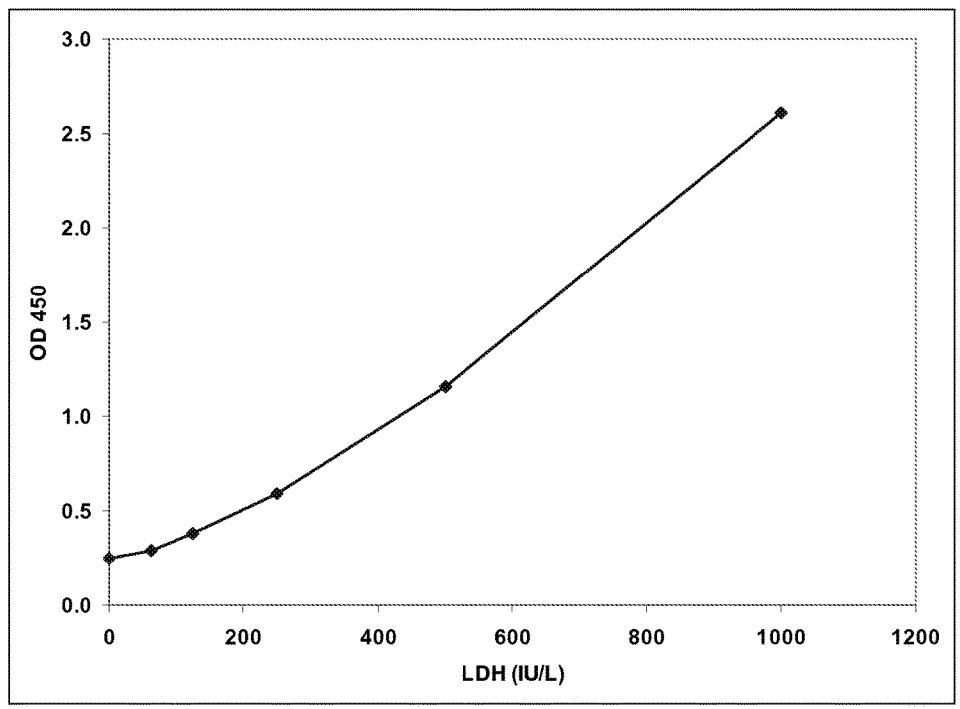
FIG. 75 shows a graph of optical density measured at 450 nm as a function of LDH.

Using this chemistry, an assay for LDH was set up. Lactate (mM), NAD (mM) and LDH were combined and incubated at 37 C for 10 minutes before addition of WST-1 and PMS. A good dose-response to LDH was obtained as shown in FIG. 74 for two-fold serial dilutions of LDH (1000 IU/L) (left to right) corresponding to the OD 450 nm values shown in the graph in FIG. 75.

Alkaline Phosphatase

In other embodiments, assays utilizing enzymes such as alkaline phosphatase can be measured using a chromogenic substrate such as p-nitrophenyl phosphate. The enzymatic reaction can make p-nitrophenol which is yellow in alkaline conditions.

Metal Ions

Figure 55:
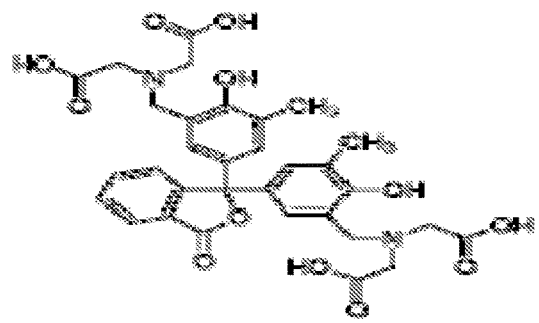
FIG. 55 shows an example of a compound that changes color upon being complexed with a metal ion.

Measurements can also be performed on assays that form colored complex, such as between a metal ion a chelating dye which changes color on binding. For example, o-Cresolphthalein Complexone (shown in FIG. 55) forms a complex with calcium, which has a different color than the reagent. The general scheme of such assays is: Chelating dye (color 1)+$M^{N+}$⇌Chelating dye: $M^{N+}$:(Color 2)

Optical signals can also be measured for metal ion assays using metal-dependant enzymes. For example, sodium ions can be determined enzymatically via sodium dependent β-galactosidase activity with o-nitro-phenyl galactoside (ONPG) as the substrate. The absorbance at 405 nm of the product o-nitrophenol is proportional to the sodium concentration.

ELISAs

Assays can be performed for analytes by color-forming ELISAs. Many ELISA methods are known which generate color using enzymes such as horseradish peroxidase, alkaline phosphatase and (β-galactosidase with chromogenic substrates such as o-phenylene diamine, p-nitrophenyl phosphate, and o-nitrophenyl galactoside respectively. Such assays can be readily performed and read by the subject invention.

Luminogenic Immunoassays

Luminogenic immunoassays can also be performed. Assays can utilize chemiluminogenic entities such as an enzyme with a luminogenic substrate. For example, chemiluminescent compounds include dioxetanes, acridinium esters, luciferin, and 2,3-dihydrophthalazinediones, such as luminol.

Furthermore, suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety of conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include N-alkyl acridinum esters and dioxetanes. Alternatively, luciferins may be used in conjunction with luciferase or lucigenins to provide bioluminescence.

Nucleic Acid Amplification

Assays that can be performed also include nucleic acid amplification. Among these assays, isothermal amplification and Loop-Mediated Isothermal Amplification Assays (LAMP) are examples. Nucleic acid amplification can be used to produce visibly turbid, fluorescent or colored assay reaction products for analytes such as nucleic acid targets (genes etc.). Nucleic acid amplification technology can be used for isothermal amplification of specific DNA and RNA targets. Additional information on isothermal nucleic acid amplification is described in Goto et al., "Colorimetric detection of loop-mediated isothermal amplification reaction by using hydroxy naphthol blue", BioTechniques, Vol. 46, No. 3, March 2009, 167-172.

Nucleic acid amplification can be used to measure DNA and, coupled with the use of reverse transcriptase, RNA. Once the reaction has occurred, the amplified product can be detected optically using intercalating dyes or chromogenic reagents that react with released pyrophosphate generated as a side product of the amplification.

The reaction can be visualized by changes (increases) in color, fluorescence or turbidity. Very small copy numbers of DNA can be detected in less than one hour. This technology can advantageously be read out in the present invention using three-color image analysis. As shown below, images of isothermal nucleic acid amplification assay reaction products can be measured by (1) back lit-illumination (transmission optics) measuring absorbance of light, (2) images captured by a digital camera of light transmitted through a reaction product or (3) fluorescent light images generated by illumination of reaction products with a UV source (or any other appropriate light source) captured by a digital camera.

The nucleic acid amplification assay is generally performed in a "one-pot" format where sample and reagents are combined in a sealed tube and incubated at elevated temperature. In some formats, the reaction can be monitored in real time by changes in optical properties. In other assay formats the reaction is stopped and reaction products visualized after adding a chromogenic or fluorogenic reagent. The present invention allows for the reading of nucleic acid amplification assay products directly in the reaction vessel or after aspiration into the tips described herein.

Turbidity

The invention also provides for optical turbidimetric assays. For example, immunoassays can be set up by measurement of the agglutination of small latex particles (50-300 nm). In these assays the particles can be coated with an antigen and/or antibody and agglutination occurs when a binding counterpart in the sample such as antibody or antigen is added. Assays can be set up as direct (e.g. antibody on the particle reacting with a multi-epitope protein or biomarker) or the competitive mode (e.g. drug hapten on particle reacts with anti-drug antibody in competition with free drug in the sample). The dispersion of latex becomes more turbid and the turbidity can be measured as decreased transmission of light using 3-color optics.

Similarly, assays based on the agglutination of large latex particles (diameter about 1 um) or red blood cells can be measured. Assay configuration is similar to turbidimetric assays as disclosed above, but the measurement can be by image analysis (scanner or camera measurement) using software to interpret the number and size of the agglutinates.

Reagents for performing reaction chemistries can be included in the cartridges described here, such as in pipette tips. The reagents can be stored as liquids or in dried, lyophilized, or glassy forms.

Localized Reagents

In some embodiments, the location and configuration of a reaction site is an important element in an assay device. Most, if not all, disposable immunoassay devices have been configured with their capture surface as an integral part of the device.

In one embodiment, a molded plastic assay unit is either commercially available or can be made by injection molding with precise shapes and sizes. For example, the characteristic dimension can be a diameter of 0.05-3 mm or can be a length of 3 to 30 mm. The units can be coated with capture reagents using method similar to those used to coat microtiter plates but with the advantage that they can be processed in bulk by placing them in a large vessel, adding coating reagents and processing using sieves, holders, and the like to recover the pieces and wash them as needed.

The assay unit (e.g. encompassing the tip disclosed herein, tips, vessels, or any other containers) can offer a rigid support on which a reactant can be immobilized. The assay unit is also chosen to provide appropriate characteristics with respect to interactions with light. For example, the assay unit can be made of a material, such as functionalized glass, Si, Ge, GaAs, GaP, SiO2, SiN4, modified silicon, or any one of a wide variety of gels or polymers such as (poly)tetrafluoroethylene, (poly)vinylidenedifluoride, polystyrene, polycarbonate, polypropylene, polymethylmethacrylate (PMMA), acrylonitrile-butadiene-styrene (ABS), or combinations thereof. In an embodiment, an assay unit comprises polystyrene. In some embodiments, the assay unit may be formed from a homogeneous material, heterogeneous material, clad material, coated material, impregnated material, and/or embedded material. Other appropriate materials may be used in accordance with the present invention. A transparent reaction site may be advantageous. In addition, in the case where there is an optically transmissive window permitting light to reach an optical detector, the surface may be advantageously opaque and/or preferentially light scattering. In some embodiments, the assay unit may be formed from a transparent material. Alternatively, a portion of the assay unit may be formed from a transparent material.

The assay unit may have a reagent coated thereon and/or impregnated therein. In some embodiments, the reagent may be a capture reagent capable of immobilizing a reactant on a capture surface. The reactant may be a cell and/or analyte, or any other reactant described elsewhere herein. In some embodiments, the reagent may be a molecule that may be a cell capture agent. A cell capture agent may anchor to the surface of desired cells during fluid transport. In some embodiments, the capture reagents may be an antibody, peptide, organic molecule (e.g., which may have a lipid chain, lipophilic molecule), polymer matrix, protein, protein composite, glycoprotein, that may interact with the cell membrane. Capture reagents may be molecules, cross-linked molecules, nanoparticles, nanostructures, and/or scaffolds. In some embodiments, microstructures may be provided that may become an analysis mechanism in a vessel. Capture reagents (which may include capture structures formed by the assay unit material) may allow cells to be tethered, bound, and/or trapped.

The capture reagents may immobilize a reactant, such as a cell, during processing. Capture techniques may be chemical, physical, electrical, magnetic, mechanical, size-related, density-related, or any combination thereof. In some embodiments, the capture reagents may be used to concentrate reactants, such as cells, at a desired location. For example, an assay unit may be coated with the capture reagents, which may cause cells to be captured at the assay unit surface, thus concentrating the cells on the captured surface. The capture reagents may keep the captured reactant immobilized on the cell surface. This may aid in keeping the reactants (e.g., cells, analytes) stationary during imaging.

Immobilizing the reactants may be useful for applications where there may be long acquisition times for reactions and/or detection. For example, a number of imaging applications may require extended exposure times (~1 min) or imaging of small objects (<1 um) which may have significant Brownian motion.

In some embodiments, the capture reagents may be formed from materials that may provide little or no background for imaging. In some instances, the material of the assay unit may provide little or no background for imaging. The capture reagents may be selected so that they do not interfere with, or only have a small interference with, imaging and/or detection.

A reactant immobilized at the capture surface can be anything useful for detecting an analyte of interest in a sample of bodily fluid. For instance, such reactants include, without limitation, nucleic acid probes, antibodies, cell membrane receptors, monoclonal antibodies, antisera, and aptamers reactive with a specific analyte. Various commercially available reactants such as a host of polyclonal and monoclonal antibodies specifically developed for specific analytes can be used.

One skilled in the art will appreciate that there are many ways of immobilizing various reactants onto a support where reaction can take place. The immobilization may be covalent or noncovalent, via a linker moiety, or tethering them to an immobilized moiety. Non-limiting exemplary binding moieties for attaching either nucleic acids or proteinaceous molecules such as antibodies to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art. Surface immobilization can also be achieved via a Poly-L Lysine tether, which provides a charge-charge coupling to the surface.

The assay units can be dried following the last step of incorporating a capture surface. For example, drying can be performed by passive exposure to a dry atmosphere or via the use of a vacuum manifold and/or application of clean dry air through a manifold or by lyophilization.

A capture surface may be applied to an assay unit using any technique. For example, the capture surface may be painted on, printed on, electrosprayed on, embedded in the material, impregnating the material, or any other technique. The capture reagents may be coated to the assay unit material, incorporated in the material, co-penetrate the material, or may be formed from the material. For example, a reagent, such as a capture reagent may be embedded in a polymer matrix that can be used as a sensor. In some embodiments, one or more small particles, such as a nanoparticle, a microparticle, and/or a bead, may be coated and/or impregnated with reagents. In some embodiments, the capture reagents may be part of the assay unit material itself, or may be something that is added to the material.

In many embodiments, an assay unit is designed to enable the unit to be manufactured in a high volume, rapid manufacturing processes. For example, tips can be mounted in large-scale arrays for batch coating of the capture surface into or onto the tip. In another example, tips can be placed into a moving belt or rotating table for serial processing. In yet another example, a large array of tips can be connected to vacuum and/or pressure manifolds for simple processing.

A capture reagent may be applied to an assay unit during any point in the process. For example, the capture reagent may be applied to the assay unit during manufacturing. The capture reagent may be applied to the assay unit prior to shipping the assay unit to a destination. Alternatively, the capture reagent may be applied to the assay unit after the assay unit has been shipped. In some instances, the capture reagent may be applied to the assay unit at a point of use, such as a point of service location.

In some embodiments, the capture reagent may cover an entire surface or region of the assay unit. The capture reagent may be provided on an inner surface of the assay unit. In some embodiments, the capture reagent may cover portions or sections of an assay unit surface. The capture reagent may be provided on a surface in a pattern. A unit may have portions of the surface that have a capture reagent applied thereon, and portions of the surface that do not have a capture reagent applied thereon. For example, there may be coated and non-coated regions. A capture reagent may be applied in a surface in accordance with a geometric choice of how the capture reagent is to be applied. For example, the capture reagent may be applied in dots, rows, columns, arrays, regions, circles, rings, or any other shape or pattern. The capture reagents may be applied at desired positions on the surface.

A plurality of capture reagents may optionally be applied to an assay unit. In some embodiments, the plurality of capture reagents may be applied so that the different capture reagents do not overlap (e.g., the different capture reagents are not applied to the same region or area). Alternatively, they may overlap (e.g., the different capture reagents may be applied to the same region or area). Space without any capture reagents may or may not be provided between regions with different capture reagents. The different capture reagents may be used to immobilize different reactants. For example, different capture reagents may be used to immobilize different cells and/or analytes on the capture surface. By using a plurality of capture reagents patterned in selected regions, a plurality of reactants may be detected from the same assay unit. In some embodiments, two or more, three or more, four or more, five or more, seven or more, ten or more, fifteen or more, twenty or more, thirty or more, forty or more, fifty or more, seventy or more, 100 or more, 150 or more, 200 or more, or 300 or more different capture reagents may be applied to a surface of an assay unit. The different capture reagents may be applied in any pattern or shape. For example, different capture reagents may be applied as an array or series of rings on an inner surface of an assay unit. For example, different capture reagents may be applied on an inner surface of a tip, vessel, container, cuvette, or any other container described elsewhere herein.

The location of the different capture reagents on the assay unit may be known prior to detection of the captured reactants. In some embodiments, the assay unit may have an identifier that may indicate the type of assay unit and/or the pattern of capture agents therein. Alternatively the location of the different capture reagents of the assay unit may not be known prior to detection of the captured reactants. The location of the different capture reagents may be determined based on detected patterns of captured reactants.

The capture reagents may be applied using any technique, such as those described elsewhere herein. In some instances, masking or lithographic techniques may be used to apply different capture reagents.

Any description herein of a capture reagent and/or coating applied to an assay unit may apply to any other units or containers described elsewhere herein, including but not limited to tips, vessels, cuvettes, or reagent units.

Reagent Assemblies

In many embodiments of the invention the reagent units are modular. The reagent unit can be designed to enable the unit to be manufactured in a high volume, rapid manufacturing processes. For example, many reagent units can be filled and sealed in a large-scale process simultaneously. The reagent units can be filled according to the type of assay or assays to be run by the device. For example, if one user desires different assays than another user, the reagent units can be manufactured accordingly to the preference of each user, without the need to manufacture an entire device. In another example, reagent units can be placed into a moving belt or rotating table for serial processing.

In another embodiment, the reagent units are accommodated directly into cavities in the housing of a device. In this embodiment, a seal can be made onto areas of housing surrounding the units.

Reagents according to the present invention include without limitation wash buffers, enzyme substrates, dilution buffers, conjugates, enzyme-labeled conjugates, DNA amplifiers, sample diluents, wash solutions, sample pretreatment reagents including additives such as detergents, polymers, chelating agents, albumin-binding reagents, enzyme inhibitors, enzymes, anticoagulants, red-cell agglutinating agents, antibodies, or other materials necessary to run an assay on a device. An enzyme-labeled conjugate can be either a polyclonal antibody or monoclonal antibody labeled with an enzyme that can yield a detectable signal upon reaction with an appropriate substrate. Non-limiting examples of such enzymes are alkaline phosphatase and horseradish peroxidase. In some embodiments, the reagents comprise immunoassay reagents. In general, reagents, especially those that are relatively unstable when mixed with liquid, are confined separately in a defined region (for example, a reagent unit) within the device.

In some embodiments, a reagent unit contains approximately about 5 microliters to about 1 milliliter of liquid. In some embodiments, the unit may contain about 20-200 microliters of liquid. In a further embodiment, the reagent unit contains 100 microliters of fluid. In an embodiment, a reagent unit contains about 40 microliters of fluid. The volume of liquid in a reagent unit may vary depending on the type of assay being run or the sample of bodily fluid provided. In an embodiment, the volumes of the reagents do not have to predetermined, but must be more than a known minimum. In some embodiments, the reagents are initially stored dry and dissolved upon initiation of the assay being run on the device.

In an embodiment, the reagent units can be filled using a siphon, a funnel, a pipette, a syringe, a needle, or a combination thereof. The reagent units may be filled with liquid using a fill channel and a vacuum draw channel. The reagent units can be filled individually or as part of a bulk manufacturing process.

In an embodiment, an individual reagent unit comprises a different reagent as a means of isolating reagents from each other. The reagent units may also be used to contain a wash solution or a substrate. In addition, the reagent units may be used to contain a luminogenic substrate. In another embodiment, a plurality of reagents are contained within a reagent unit.

In some instances, the setup of the device enables the capability of pre-calibration of assay units and the reagent units prior to assembly of disposables of the subject device.

Aptamer Binding Assays

The subject invention enables a variety of assay methods based on the use of binding elements that specifically bind to one or more analytes in a sample. In general, a binding element is one member of a binding pair capable of specifically and selectively binding to the other member of the binding pair in the presence of a plurality of different molecules. Examples of binding elements include, but are not limited to, antibodies, antigens, metal-binding ligands, nucleic acid probes and primers, receptors and reactants as described herein, and aptamers. In some embodiments, a binding element used to detect an analyte is an aptamer. The term "aptamer" is used to refer to a peptide, nucleic acid, or a combination thereof that is selected for the ability to specifically bind one or more target analytes. Peptide aptamers are affinity agents that generally comprise one or more variable loop domains displayed on the surface of a scaffold protein. A nucleic acid aptamer is a specific binding oligonucleotide, which is an oligonucleotide that is capable of selectively forming a complex with an intended target analyte. The complexation is target-specific in the sense that other materials, such as other analytes that may accompany the target analyte, do not complex to the aptamer with as great an affinity. It is recognized that complexation and affinity are a matter of degree; however, in this context, "target-specific" means that the aptamer binds to target with a much higher degree of affinity than it binds to contaminating materials. The meaning of specificity in this context is thus similar to the meaning of specificity as applied to antibodies, for example. The aptamer may be prepared by any known method, including synthetic, recombinant, and purification methods. Further, the term "aptamer" also includes "secondary aptamers" containing a consensus sequence derived from comparing two or more known aptamers to a given target.

In general, nucleic acid aptamers are about 9 to about 35 nucleotides in length. In some embodiments, a nucleic acid aptamer is at least 4, 5, 6, 7, 8, 9, 10, 11, 12, 13, 14, 15, 20, 25, 30, 35, 40, 45, 50, 55, 60, 65, 70, 80, 90, 100, or more residues in length. Although the oligonucleotides of the aptamers generally are single-stranded or double-stranded, it is contemplated that aptamers may sometimes assume triple-stranded or quadruple-stranded structures. In some embodiments, a nucleic acid aptamer is circular, such as in US20050176940. The specific binding oligonucleotides of the aptamers should contain the sequence-conferring specificity, but may be extended with flanking regions and otherwise derivatized or modified. The aptamers found to bind to a target analyte may be isolated, sequenced, and then re-synthesized as conventional DNA or RNA moieties, or may be modified oligomers. These modifications include, but are not limited to incorporation of: (1) modified or analogous forms of sugars (e.g. ribose and deoxyribose); (2) alternative linking groups; or (3) analogous forms of purine and pyrimidine bases.

Nucleic acid aptamers can comprise DNA, RNA, functionalized or modified nucleic acid bases, nucleic acid analogues, modified or alternative backbone chemistries, or combinations thereof. The oligonucleotides of the aptamers may contain the conventional bases adenine, guanine, cytosine, and thymine or uridine. Included within the term aptamers are synthetic aptamers that incorporate analogous forms of purines and pyrimidines. "Analogous" forms of purines and pyrimidines are those generally known in the art, many of which are used as chemotherapeutic agents. Non-limiting examples of analogous forms of purines and pyrimidines (i.e. base analogues) include aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyl-uracil, 5-methoxyaminomethyl-2-thiouracil, beta-D-mannosylqueosine, 5-methoxyuracil, 2-methyl-thio-N6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, 5-pentynyl-uracil, and 2,6-diaminopurine. The use of uracil as a substitute base for thymine in deoxyribonucleic acid (hereinafter referred to as "dU") is considered to be an "analogous" form of pyrimidine in this invention.

Aptamer oligonucleotides may contain analogous forms of ribose or deoxyribose sugars that are known in the art, including but not limited to 2' substituted sugars such as 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, locked nucleic acids (LNA), peptide nucleic acid (PNA), acyclic analogs and abasic nucleoside analogs such as methyl riboside.

Aptamers may also include intermediates in their synthesis. For example, any of the hydroxyl groups ordinarily present may be replaced by phosphonate groups, phosphate groups, protected by a standard protecting group, or activated to prepare additional linkages to additional nucleotides or substrates. The 5' terminal OH is conventionally free but may be phosphorylated; OH substituents at the 3' terminus may also be phosphorylated. The hydroxyls may also be derivatized to standard protecting groups. One or more phosphodiester linkages may be replaced by alternative linking groups. These alternative linking groups include, but are not limited to embodiments wherein P(O)O is replaced by P(O)S ("thioate"), P(S)S ("dithioate"), P(O)NR 2 ("amidate"), P(O)R, P(O)OR', CO or CH 2 ("formacetal"), wherein each R or R' is independently H or substituted or unsubstituted alkyl (1-20 C.) optionally containing an ether (—O—) linkage, aryl, alkenyl, cycloalkyl, cycloalkenyl or aralkyl.

One particular embodiment of aptamers that are useful in the present invention is based on RNA aptamers as disclosed in U.S. Pat. Nos. 5,270,163 and 5,475,096, which are incorporated herein by reference. The aforementioned patents disclose the SELEX method, which involves selection from a mixture of candidate oligonucleotides and stepwise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with a target, such as a target analyte, under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule. In some embodiments, negative screening is employed in which a plurality of aptamers are exposed to analytes or other materials likely to be found together with target analytes in a sample to be analyzed, and only aptamers that do not bind are retained.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. In some embodiments, two or more aptamers are joined to form a single, multivalent aptamer molecule. Multivalent aptamer molecules can comprise multiple copies of an aptamer, each copy targeting the same analyte, two or more different aptamers targeting different analytes, or combinations of these.

Aptamers can be used as diagnostic and prognostic reagents, as reagents for the discovery of novel therapeutics, as reagents for monitoring drug response in individuals, and as reagents for the discovery of novel therapeutic targets. Aptamers can be used to detect, modify the function of, or interfere with or inhibit the function of one or more target analytes. The term "analytes" as used herein includes without limitation drugs, prodrugs, pharmaceutical agents, drug metabolites, biomarkers such as expressed proteins and cell markers, antibodies, serum proteins, cholesterol and other metabolites, electrolytes, metal ions, polysaccharides, nucleic acids, biological analytes, biomarkers, genes, proteins, hormones, or any combination thereof. Analytes can be combinations of polypeptides, glycoproteins, polysaccharides, lipids, and nucleic acids. Aptamers can inhibit the function of gene products by any one of, but not limited to only, the following mechanisms: (i) modulating the affinity of a protein-protein interaction; (ii) modulating the expression of a protein on a transcriptional level; (iii) modulating the expression of a protein on a post-transcriptional level; (iv) modulating the activity of a protein; and (v) modulating the location of a protein. The precise mechanism of action of peptide aptamers can be determined by biochemical and genetic means to ascertain their specific function in the context of their interaction with other genes, and gene products.

Aptamers can be used to detect an analyte in any of the detection schemes described herein. In one embodiment, apatamers are covalently or non-covalently coupled to a substrate. Non-limiting examples of substrates to which aptamers may be coupled include microarrays, microbeads, pipette tips, sample transfer devices, cuvettes, capillary or other tubes, reaction chambers, or any other suitable format compatible with the subject detection system. Biochip microarray production can employ various semiconductor fabrication techniques, such as solid phase chemistry, combinatorial chemistry, molecular biology, and robotics. One process typically used is a photolithographic manufacturing process for producing microarrays with millions of probes on a single chip. Alternatively, if the probes are pre-synthesized, they can be attached to an array surface using techniques such as micro-channel pumping, "ink-jet" spotting, template-stamping, or photocrosslinking. An exemplary photolithographic process begins by coating a quartz wafer with a light-sensitive chemical compound to prevent coupling between the quartz wafer and the first nucleotide of the DNA probe being created. A lithographic mask is used to either inhibit or permit the transmission of light onto specific locations of the wafer surface. The surface is then contacted with a solution which may contain adenine, thymine, cytosine, or guanine, and coupling occurs only in those regions on the glass that have been deprotected through illumination. The coupled nucleotide bears a light-sensitive protecting group, allowing the cycle can be repeated. In this manner, the microarray is created as the probes are synthesized via repeated cycles of deprotection and coupling. The process may be repeated until the probes reach their full length. Commercially available arrays are typically manufactured at a density of over 1.3 million unique features per array. Depending on the demands of the experiment and the number of probes required per array, each wafer, can be cut into tens or hundreds of individual arrays.

Other methods may be used to produce the biochip. The biochip may be a Langmuir-Bodgett functionalized glass, germanium, silicon, PTFE, polystyrene, gallium arsenide, gold, silver, membrane, nylon, PVP, or any other material known in the art that is capable of having functional groups such as amino, carboxyl, Diels-Alder reactants, thiol or hydroxyl incorporated on its surface. These groups may then be covalently attached to crosslinking agents, so that the subsequent attachment of the nucleic acid ligands and their interaction with target molecules will occur in solution without hindrance from the biochip. Typical crosslinking groups include ethylene glycol oligomer, diamines, and amino acids. Alternatively, aptamers may be coupled to an array using enzymatic procedures, such as described in US20100240544.

In some embodiments, aptamers are coupled to the surface of a microbead. Microbeads useful in coupling to oligonucleotides are known in the art, and include magnetic, magnetizable, and non-magnetic beads. Microbeads can be labeled with 1, 2, 3, 4, 5, 6, 7, 8, 9, 10, or more dyes to facilitate coding of the beads and identification of an aptamer joined thereto. Coding of microbeads can be used to distinguish at least 10, 50, 100, 200, 300, 400, 500, 600, 700, 800, 900, 1000, 1500, 2000, 5000, or more different microbeads in a single assay, each microbead corresponding to a different aptamer with specificity for a different analyte.

In some embodiments, reagents are coupled to the surface of a reaction chamber, such as a tip. For example, the interior surface of a tip may be coated with an aptamer specific for a single analyte. Alternatively, the interior surface of a tip may be coated with two or more different aptamers specific for different analytes. When two or more different aptamers are coupled to the same interior tip surface, each of the different aptamers may be coupled at different known locations, such as forming distinct ordered rings or bands at different positions along the axis of a tip. In this case, multiple different analytes may be analyzed in the same sample by drawing a sample up a tip and allowing analytes contained in the sample to bind with the aptamers coated at successive positions along the tip. Binding events can then be visualized as described herein, with the location of each band in a banding pattern corresponding to a specific known analyte.

Figure 136:
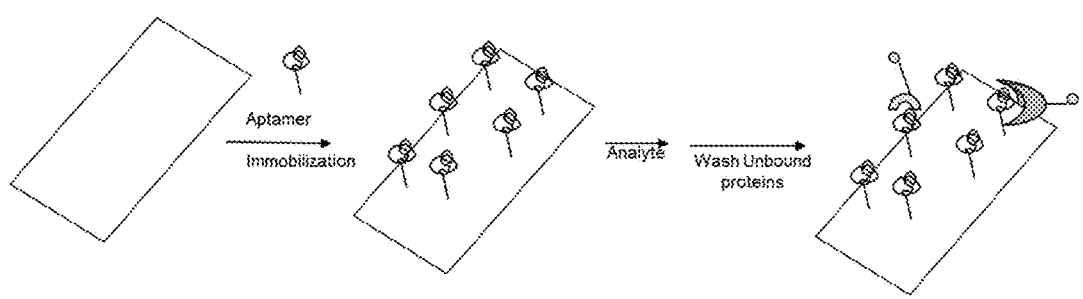
FIG. 136 illustrates an example detection process of the invention using an array.
Figure 137:
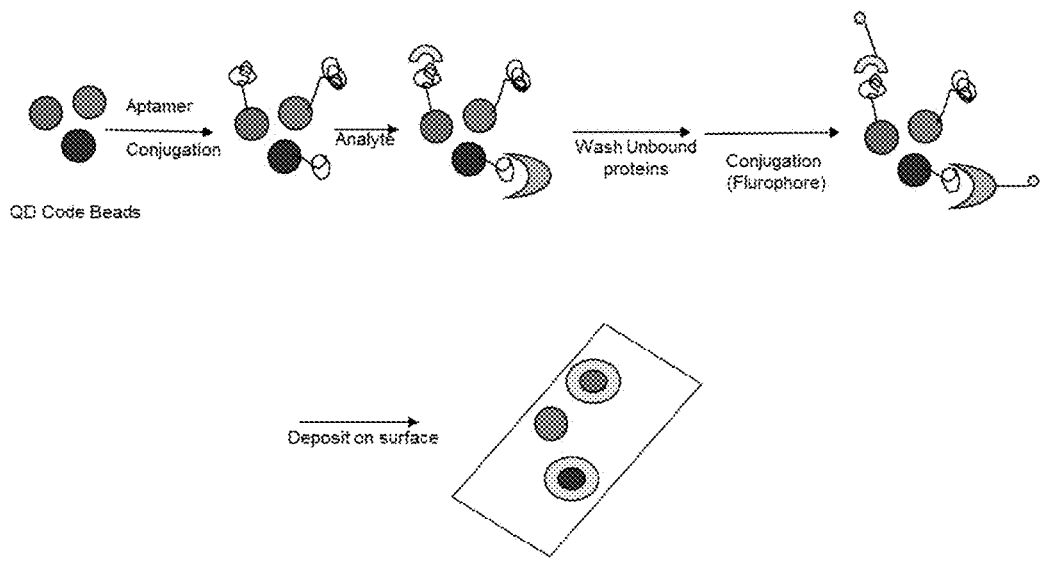
FIG. 137 illustrates an example detection process of the invention using beads.
Figure 137:
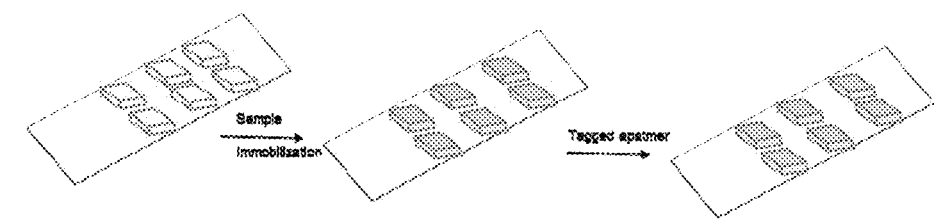

In some embodiments, binding of one or more aptamers to one or more target analytes is detected using an optical feature. In some embodiments, the optical feature is fluorescence. In some embodiments, a sample containing analytes to be analyzed is treated with a labeling compound to conjugate the analytes with a fluorescent tag. Binding can then be measured by fluorescence to detect presence and optionally quantity of one or more analytes, such as illustrated in FIG. 136 in combination with aptamers coupled to an array, and in FIG. 137 in combination with aptamers coupled to coded beads. In some embodiments, the sample is treated with a labeling compound to conjugate the analytes with a linker. Upon binding the linker is functionalized with a fluorescent tag and the positive event is measured by fluorescence. In some embodiments, the analyte binding domain of an aptamer is partially hybridized to a complentary probe that is fluorescently labeled. Upon binding to the analyte, the complementary probe is released, which results in an optically measurable decrease in fluorescent signal. In some embodiments, an aptamer is fluorescently labeled and is partially hybridized to a complementary probe labeled with a quencher that is in proximity to the fluorescent label. Upon binding to the analyte, the complementary probe is released resulting in a measurable increase in fluorescence of the label conjugated to the aptamer. In some embodiments, the aptamer is partially hybridized to a complementary probe, which hybridization occludes a domain containing a secondary structure. Upon binding to the analyte, the complementary probe is released, and the secondary structure is made available to an intercalating dye used to produce a measurable signal. Labels useful in the detection of binding between an apatamer and an analyte in a binding pair can include, for example, fluorescein, tetramethylrhodamine, Texas Red, or any other fluorescent molecule known in the art. The level of label detected at each address on the biochip will then vary with the amount of target analyte in the mixture being assayed.

In some embodiments, the displaced complementary probe is conjugated to one member of an affinity pair, such as biotin. A detectable molecule is then conjugated to the other member of the affinity pair, for example avidin. After the test mixture is applied to the biochip, the conjugated detectable molecule is added. The amount of detectable molecule at each site on the biochip will vary inversely with the amount of target molecule present in the test mixture. In another embodiment, the displaced complementary probe will be biotin labeled, and can be detected by addition of fluorescently labeled avidin; the avidin itself will then be linked to another fluorescently labeled, biotin-conjugated compound. The biotin group on the displaced oligonucleotide can also be used to bind an avidin-linked reporter enzyme; the enzyme will then catalyze a reaction leading to the deposition of a detectable compound. Alternatively, the reporter enzyme will catalyze the production of an insoluble product that will locally quench the fluorescence of an intrinsically-fluorescent biochip. In another embodiment of the displacement assay, the displaced complementary probe will be labeled with an immunologically-detectable probe, such as digoxigenin. The displaced complementary probe will then be bound by a first set of antibodies that specifically recognize the probe. These first antibodies will then be recognized and bound by a second set of antibodies that are fluorescently labeled or conjugated to a reporter enzyme. Many variations on these examples are known or will now occur to those skilled in the art. Assays analogous to "double-sandwich" ELISAs can also be set up using combinations of antibodies and aptamers as receptors. For example, a capture surface can be functionalized with an aptamer and the detection reagent can be an enzyme-labeled antibody. Conversely, the antibody can be on the capture surface and the detection reagent a labeled aptamer.

Figure 138:
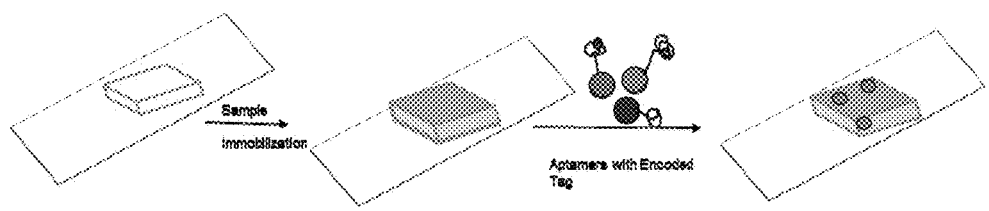
FIG. 138 illustrates an example detection process of the invention using tagged aptamers.

In some embodiments, a sample containing an analyte to be analyzed is dispersed into a three-dimensional hydrogel matrix. The hydrogel matrix can be activated to covalenly trap proteins and small molecules. After a wash of the excess and unbound sample, fluorescently labeled aptamers can be introduced for the detection of the specific analytes present, such as illustrated in FIG. 138. In some embodiments, the three-dimensional hydrogel matrix is divided in small subsets or microwells to which a single aptamer can be added to undergo a specific analysis of the analyte present. In some embodiments, aptamers are labeled with a set of coded quantum dots or fluorescent tags corresponding to a unique signature. In some embodiments, labeled aptamers are added to the three-dimensional matrix simultaneously with the sample.

In some embodiments, an aptamer is used instead of an antibody in an ELISA assay. In general, a sample is exposed to a surface and specifically or non-specifically coupled thereto. In a sandwich ELISA, an analyte is specifically coupled to a surface by binding to first antibody that is coupled to the surface. In a typical ELISA, the analyte, whether bound specifically or non-specifically, is then detected by binding to a second antibody carrying a label. In an aptamer ELISA, the first antibody, second antibody, or both are replaced with aptamers specific for an analyte.

Imaging Analysis of Samples and Assay Reaction Products

Figure 92:
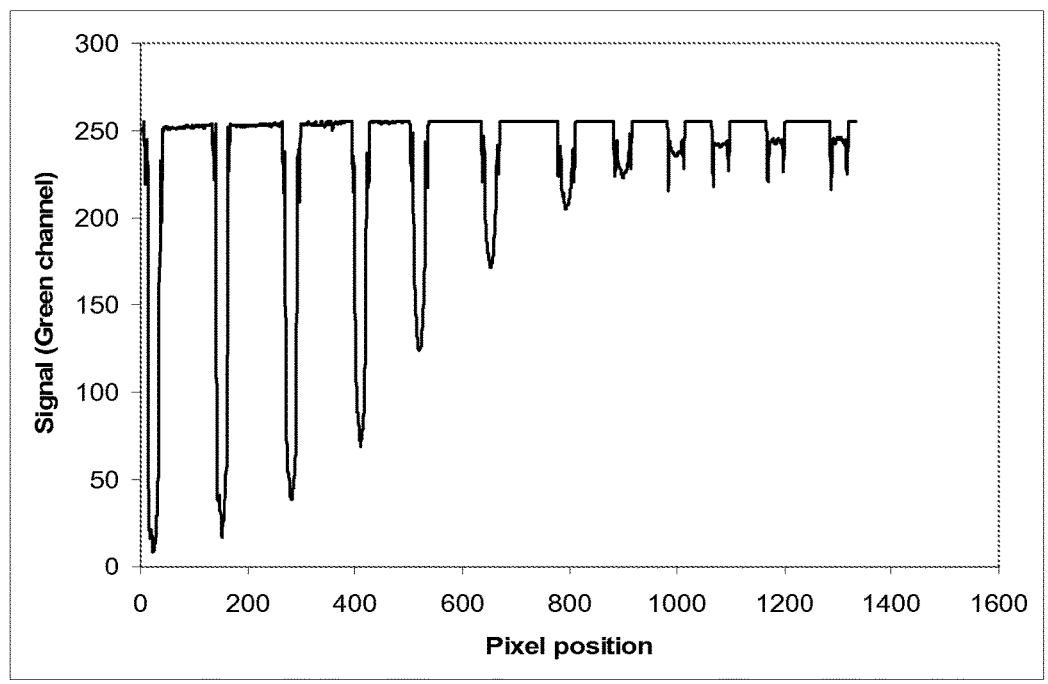
FIG. 92 shows a graph of green channel signal response as a function of pixel position.

In some embodiments of the invention, analysis of sample and the assay reaction products can be performed using digital imaging. The assay cuvettes can be aligned for measurement and scanned or imaged in a single operation. In the instrumented system of the invention this is achieved automatically by mechanical components. Assay cuvettes are located at defined locations in a cartridge and moved to the scanner maintaining the same orientation and spacing. The graph shown in FIG. 92 corresponds to the green channel response over the width of the cuvette. As shown, the edges of the cuvettes are well-defined, as is the location corresponding to the middle of the cuvette.

The images obtained by scanning or imaging can be a two-dimensional array of pixels, where each pixel comprises a plurality of intensity values corresponding to a distinct detection spectral region (e.g., red, blue, green). The images can be interpreted by line-scans, which may correspond to a horizontal portion of a tip. If the tip is circular-shaped, then an effective absorbance can be determined by deconvoluting the line-scan over an appropriate function. Example functions include parabolic functions, and functions for circles. In some embodiments, the images can be data-averaged over multiple images taken of a tip or a sample over a range of physical locations.

In an embodiment, a sensor is provided to locate an assay unit relative to a detector when an assay is detected.

Figure 61:
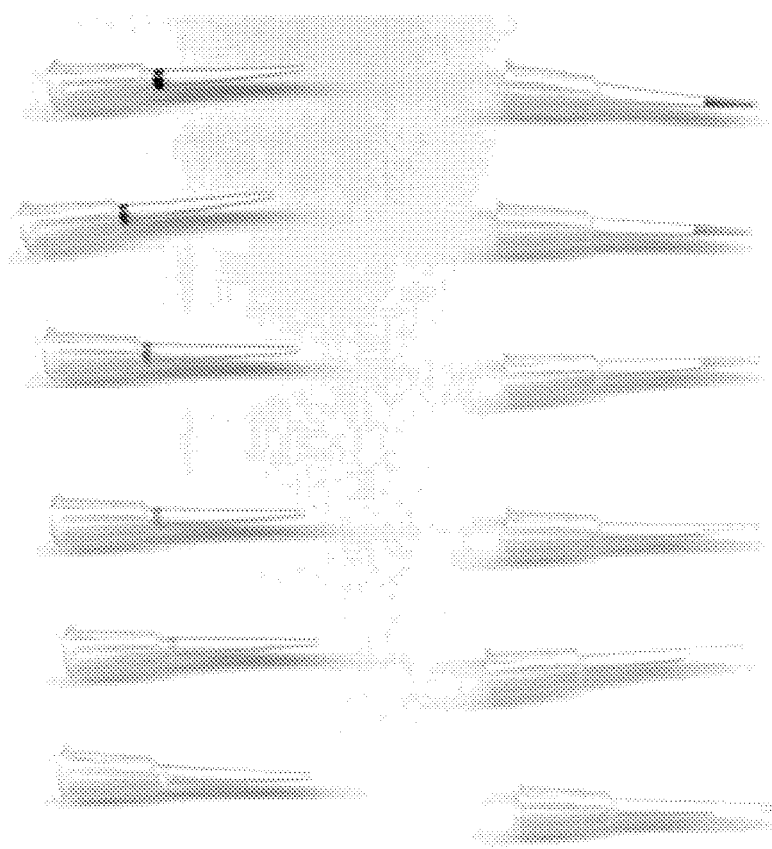
FIG. 61 shows a series of tips containing bromophenol blue solutions.
Figure 62:
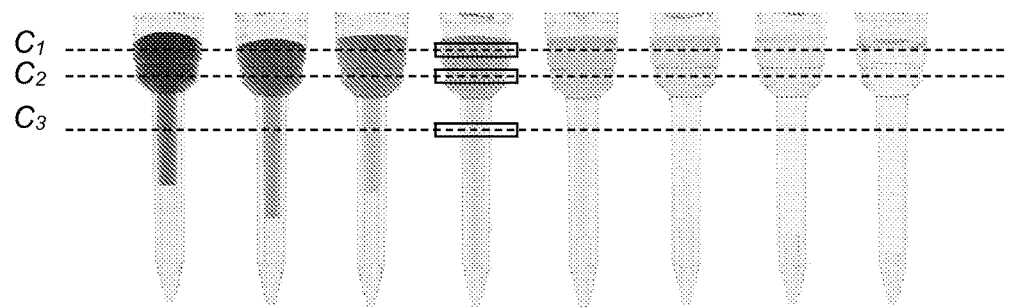
FIG. 62 is an illustration of tips having a plurality of distinct optical path lengths.

As shown in FIG. 61 and FIG. 62, bromophenol blue solutions were aspirated into a set of conical tips and imaged with front face illumination (light source and detector on the same side of the object). Small volumes (5 uL) of serial dilutions of a 0.78 mg/mL solution were used with the highest concentration at the top of the image. In FIG. 61, tips on the left have the sample located at the widest location in the conical tip whereas tips on the right have the sample at the narrowest. The image in FIG. 61 was taken using a scanning optical system.

FIG. 62 shows tips that were imaged using a back-lit configuration (light source and detector on opposite sides of the imaged object). The back-lit configuration can be preferred because of the higher image quality.

As shown in FIG. 61 and FIG. 62, the effective optical path length of a colored solution can be varied by changing tip design. In particular, the pathlength can be varied within a single tip to increase sensitivity of measurement of light absorbance (long pathlength) or to increase the dynamic range of the measurement. The pathlength can be changed, for example, by changing the diameter of the tip.

An additional feature of the tip design can be that it enables assays to be read with a very small volume of assay reaction product requiring a very small volume of sample. Typically, assay reaction mixtures are incubated in a narrow part of a tip which provides a high ratio of liquid/air surface area to volume, thus minimizing evaporation. The small volume can then be moved to a wide part of the tip for measurement of the colored product thus maximizing the optical pathlength available (and thereby increasing the absorbance of light) for a given reaction mixture volume.

For example in the table below, we compare reading an assay reaction mixture of 10 uL in which a 1 uL sample is diluted 1:10. In the tips of the current invention, incubation of an assay mixture can be achieved in a 13 mm length of tip region having a diameter of 1 mm then be moved to a 3 mm diameter region for color measurement. In comparison with using a microtiter plate of standard dimensions (typical of 384-well plates) to incubate and read the same assay, the area of liquid surface exposed to air (allowing evaporation) is about 5 times less and the optical pathlength is about twice as great.

| | | |
|---|---|---|
| Sample volume | 1.00 uL | |
| Dilution factor | 10.00 fold | |
| Reaction volume | 10.00 uL | |
| Tips | | |
| Tip diameter | 1.00 mm | For incubation |
| Exposed surface area | 1.57 mm^2 | For incubation |
| Length of liquid column | 12.73 mm | For incubation |
| Tip diameter | 3.00 | Pathlength for reading |
| Length of liquid column | 1.41 mm | For reading |
| Microtiter Plate | | |
| Well diameter | 3.00 mm | |
| Exposed surface area | 7.07 mm^2 | |
| Length of liquid column | 1.41 mm | Pathlength |

Optimizing Optical Path Length

Spectroscopic measurements of colored solutes are traditionally measured by recording the fraction of light transmitted through a cuvette at the absorbance wavelength maximum. The data are then transformed to give Absorbance (A) or optical density (OD) values. According to Beer's law, $A(\lambda max) = \epsilon M * l * Concentration$ where $\epsilon M$ is the molar extinction product (L/Mole.cm), l is the optical pathlength (cm) and Concentration is in molar units. OD=A for l=1. This is done to provide a measure, A, which is directly proportional to solute concentration.

There are two significant limitations of absorbance measurements for assaying solute concentrations. At low concentrations, the change in transmission is small and therefore imprecise because of variations in the background (or blank) transmission. At high concentrations transmission is very low (for example at A=3, the transmitted light is 1/1000th of the input light. Any "stray" light or other forms of signal noise have a significant effect on the measurement and the response to concentration becomes non-linear and imprecise. Typically, absorbance measurements are regarded as precise and accurate over a range from about 0.1 to about 2.0 (a 20-fold range).

The method of the present invention overcomes these problems to a significant degree by enabling facile measurements of color over a very wide dynamic range (up to 1000-fold):

1. At different pathlengths: low concentrations can be measured at long pathlengths and high concentrations at short pathlengths.

2. In different color channels: low concentrations can be measured in the best matching color channel and high concentrations in color channels mismatched to the color.

Figure 79:
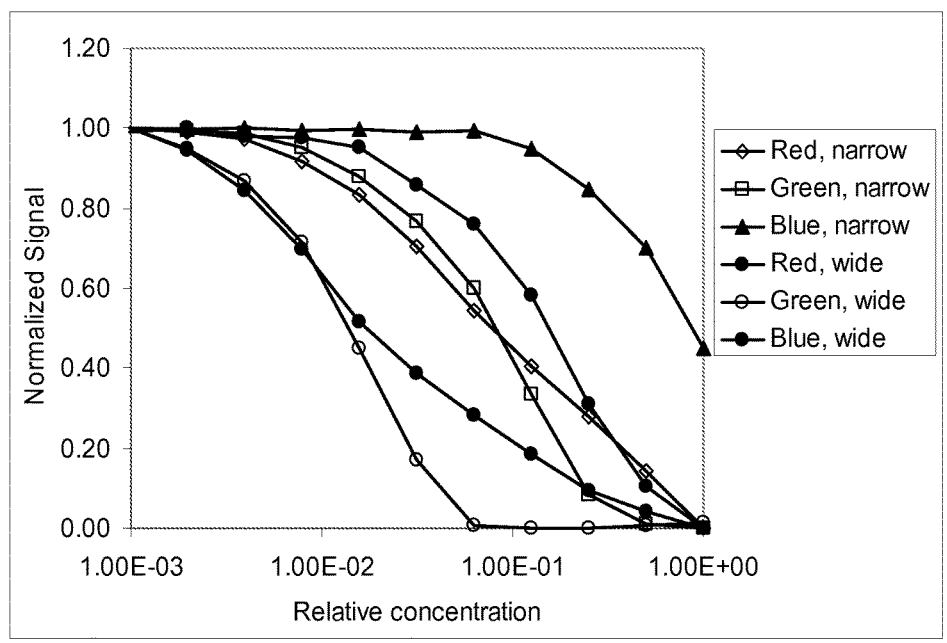
FIG. 79 shows normalized signal as a function of relative concentration measured for narrow and wide path lengths using red, green, and blue color channels.

This is illustrated by the data shown in FIG. 79. Bromphenol blue solutions serially diluted from a 5 mg/mL stock were analyzed using the three-color method in tips at two locations, one with a maximum pathlength (also "path length" herein) of about 5 mm ("wide"), the other of about 1 mm ("narrow"). Signals in the three color channels were normalized to their highest and lowest levels as shown in the graph below. An algorithm to optimally extract the concentration of the analyte (bromphenol blue) was set up as follows:

1. For normalized signals in the range 10% maximum<signal<90% maximum, compute a value concentration=$a+b*Log(signal)+c*(Log(signal))^2$ where a b and c are arbitrary constants. This operation was performed for each color at both pathlengths.

2. Using a well-known optimization routine (for example "Solver" in Microsoft Excel), compute the best-fit values of a, b and c for all colors and pathlengths.

3. Average the computed concentration values for all colors and both pathlengths.

Figure 80:
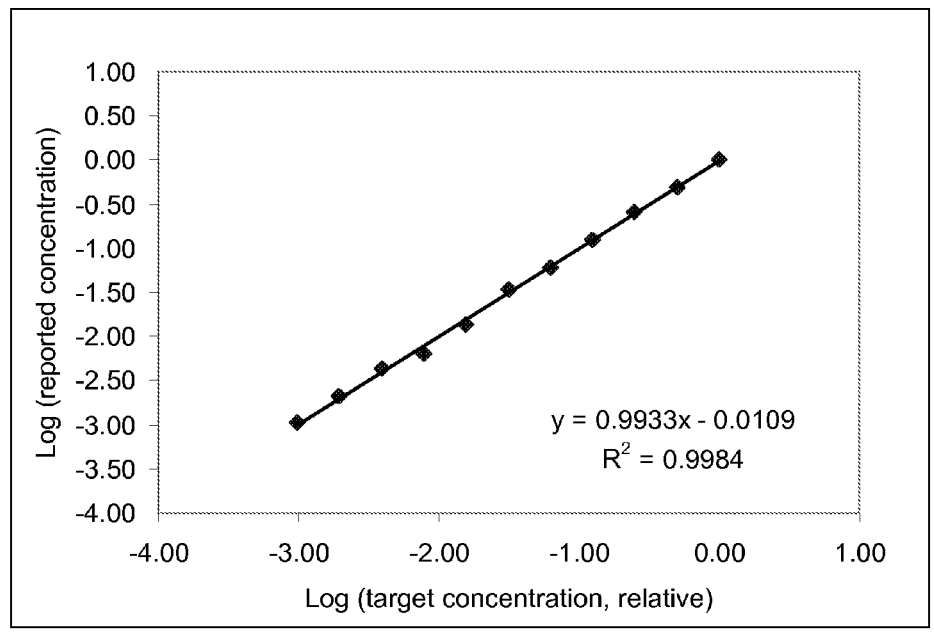
FIG. 80 shows a graph of log of measured concentration as a function of actual concentration, illustrating the accuracy of the measurement algorithm.

As shown in FIG. 80, the method yielded accurate results across a 1000-fold concentration range. When the algorithm was used to compute concentration values for replicate measurements (N=3), the average CV was 3.5%.

Measurements can be made at various pathlengths. In some cases, pathlengths are at least partially dependent on container (e.g., cuvette, tip, vial) geometry. The container geometry and/or features in the container, such as scattering features, may affect the optical path and path length in the container.

Multi-Color Analysis

Figure 71:
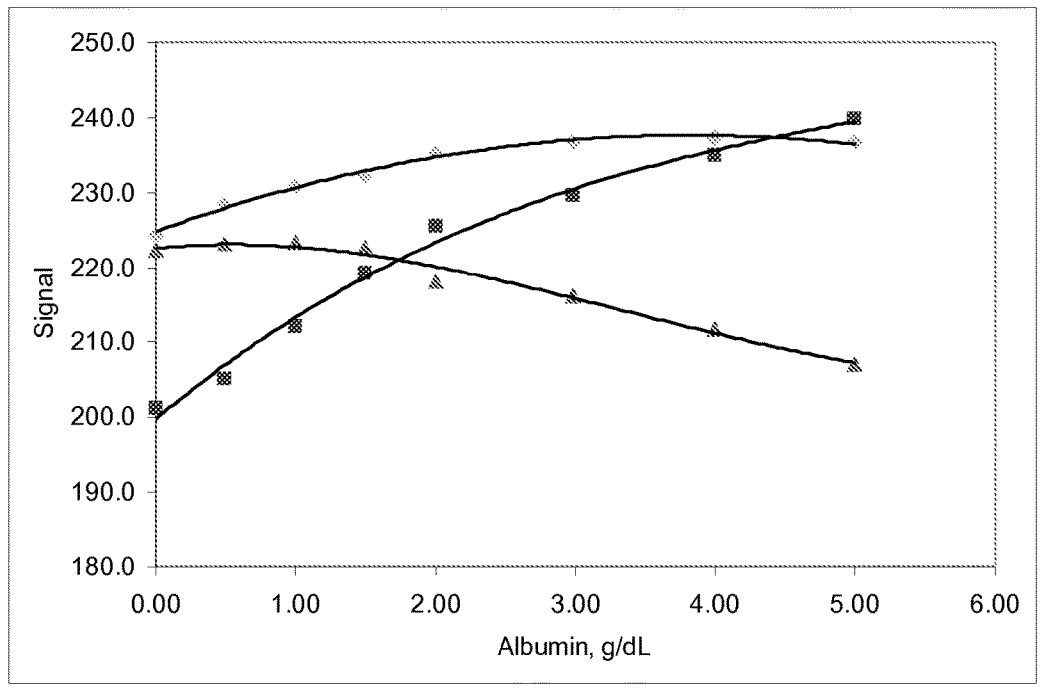
FIG. 71 shows a graph of signal response as measured by red (squares), green (diamonds), and blue (triangles) color channels as a function of albumin concentration.

Scanners and cameras have detectors that can measure a plurality of different colors channel detection spectrum regions (e.g., red, green, and blue). Because the spectral width of each of these channels is wide and color chemistries produce colored products with wide band widths, colored reaction products can be detected using a plurality of channel detection spectrums. For example, FIG. 71 shows the response of red (squares), green (diamonds), and blue (triangles) detection channel spectrums as a function of analyte concentration. The signals produced by each detector correspond to light intensity within each detection spectrum and are typically expressed as a number from 0 to 255. When white light is transmitted through a circular section cuvette containing a colored solute as shown above, light is absorbed and the light intensity reduced so that the detector responses change.

Figure 66:
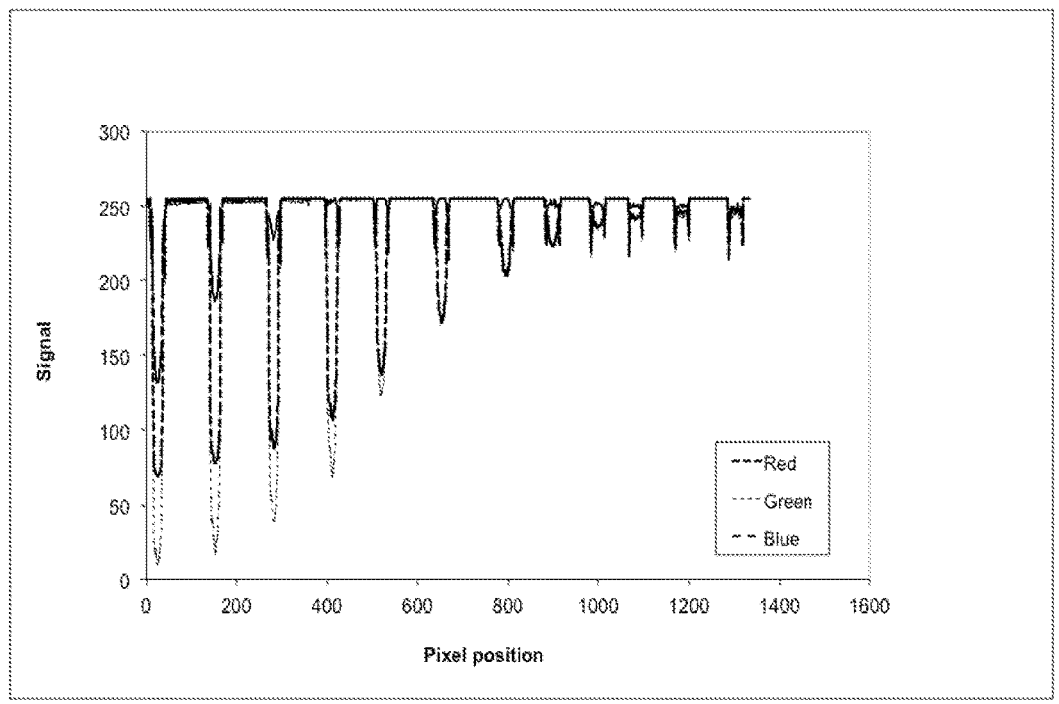
FIG. 66 shows a graph of light intensity as a function of location as measured on tips containing samples with varying concentration of bromophenol blue solutions for red, green, and blue color channels.
Figure 67:
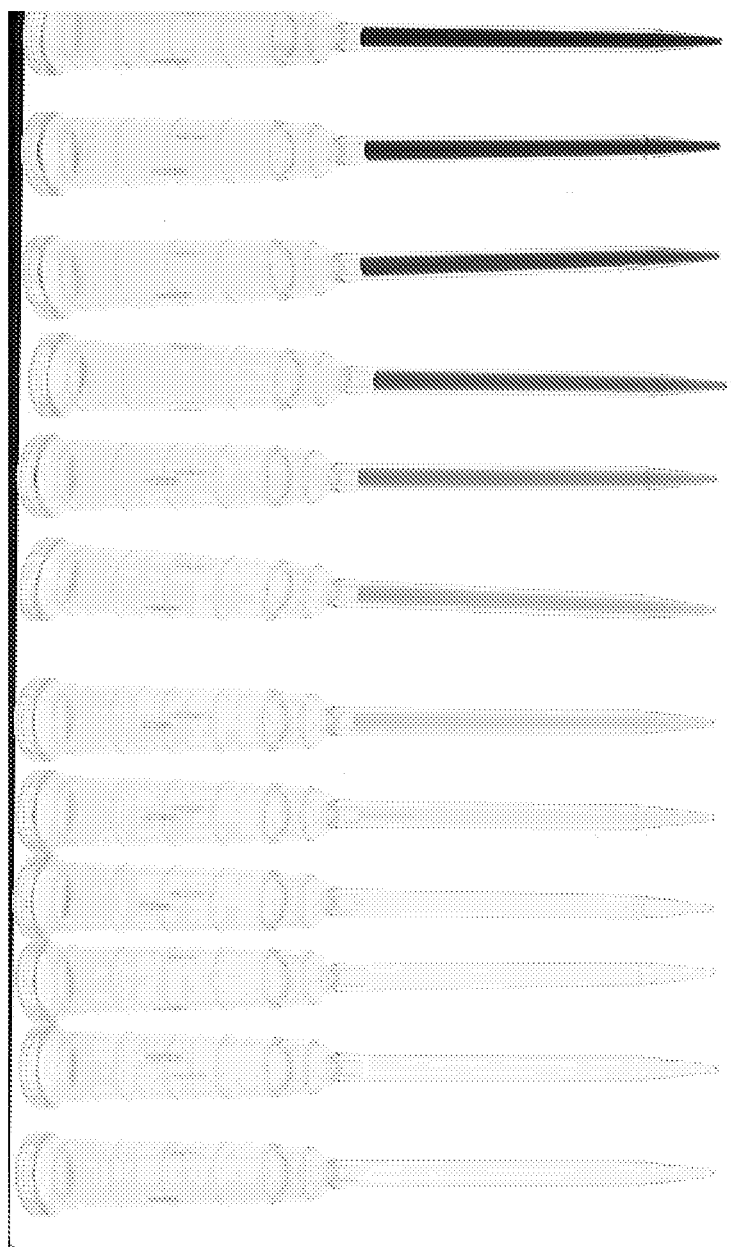
FIG. 67 shows an image of the tips that were analyzed in FIG. 66.
Figure 68:
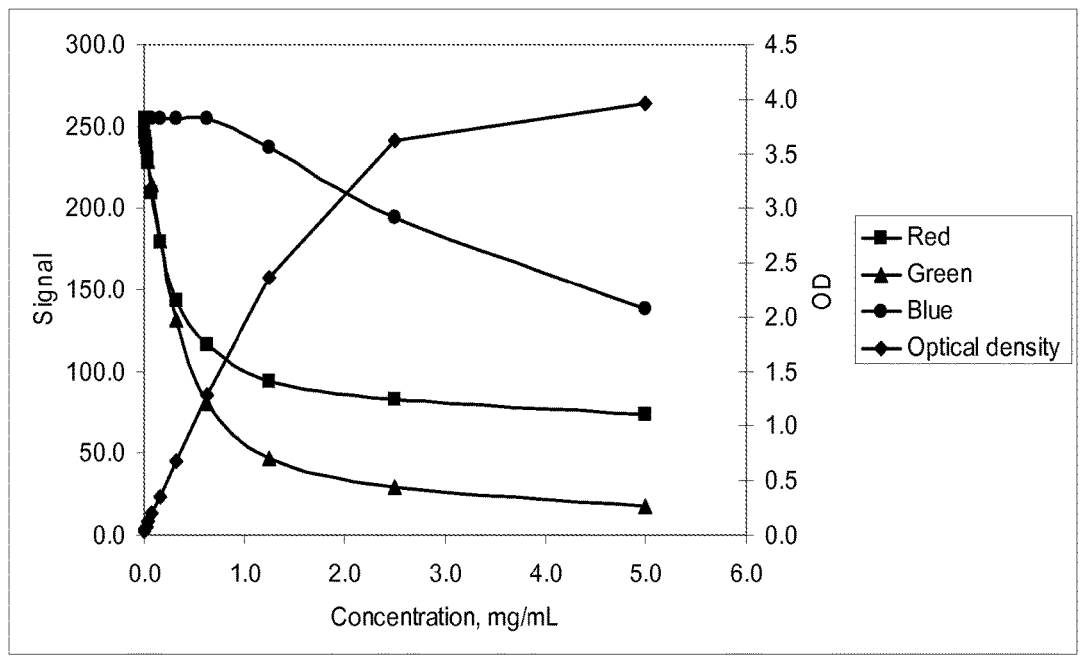
FIG. 68 shows a graph of signal as a function of bromophenol blue concentration as measured by red, green, and blue color channels. The optical density may be measured at 589 nm.

For example, when bromphenol blue dissolved in alkaline buffer at concentrations ranging from 0 to 5 mg/mL and scanned at the location indicated "C3" in FIG. 62, signals shown in FIG. 66, which are the detector responses averaged over a zone corresponding to seven pixels along the length of the cuvette. The signals were recorded on an Epson backlit scanner. FIG. 66 shows the three color responses for a set of 11 cuvettes containing 2-fold serial dilutions of a 5 mg/mL bromphenol blue solution and a "blank" solution (arranged left to right on the image). The image of the scanned tips is shown in FIG. 67. The signal in each channel corresponding to the solution is reduced to an extent related to the optical path. Accordingly, the maximum change in signal is seen at the center of the cuvette. When signals in the central region of the cuvette were averaged (over the zone shown by the small rectangles for the fourth cuvette from the left) and plotted against the bromophenol blue concentration, the dose-responses shown FIG. 68 were observed. In each color "channel" the signal declined smoothly with concentration. The green signal changed most and the blue signal least. Corresponding optical densities measured in an M5 spectrometer (Molecular Devices) at the wavelength of maximal absorbance (e.g., 589 nm) are also shown. At the highest concentrations, the spectrophotometer response becomes not linear and changes very little with concentration. A similar effect was noted in the scanner green and red channel responses. The blue channel response in contrast, is very slight until the highest concentrations.

According to Beer's law, absorbance of a solution is equal to $\epsilon$M*Concentration*pathlength. Absorbance is defined as Log 10(Transmission/Blank Transmission), where blank transmission is that corresponding to that for the solvent. Strictly Beer's law applies to a parallel beam of monochromatic light (in practice a band width of a few nm) passing normally through a rectangular cuvette. Spectrophotometers respond linearly to concentration up to Absorbance values about 1.5. At higher absorbance, instrument response becomes non-linear due to "stray light" and other effects. Optical density is defined as absorbance for a one cm optical pathlength.

Figure 69:
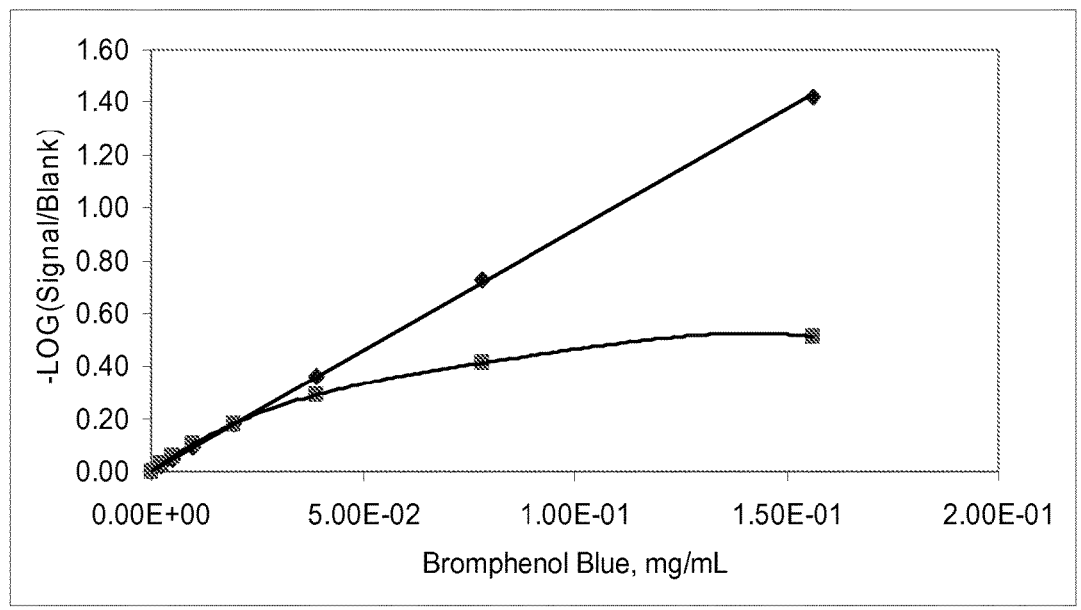
FIG. 69 shows a log scale graph of signal response as a function of bromophenol blue concentration as measured by blue (diamonds) and red (squares) color channels.

When the color signal data from the above experiment was transformed according to an expression that linearizes optical transmission so as to obtain an absorbance value proportional to concentration in conventional spectrophotometry (−Log(signal/blank signal), the graph shown in FIG. 69 was obtained for the green (squares) and red (diamonds) channels.

The green channel data followed Beer's law but the red channel data did not reaching a plateau level at for a sample having about 2 mg/mL in a fashion similar to that of the OD response of the spectrophotometer.

Improved Assay Utilization by Three-Color Analysis and Optimization of Optical Path Length Assay results from reaction setups that would otherwise provide uninterpretable data can be salvaged using the present invention. The present invention allows for increased dynamic range and sensitivity of assays by the combination of optical pathlength optimization and three-color analysis. The inability to salvage data plagued by reduced dynamic range is a major problem in assay management, especially in the context of samples being evaluated for diagnostic or therapy management purposes is that assays have a limited dynamic range or limited range of analyte values that can be reported with good confidence. There are two main reasons why an assay result may not be available from laboratory-based assay systems or from distributed test situations. Namely the analyte value is too high or too low to be reported. This may in some circumstances be rectified in clinical laboratories by re-analyzing a portion of a retained sample using a different dilution. In distributed testing typically there is no recourse but to recall the patient, obtain a new sample and use a different (laboratory) method. This is because assay systems use fixed protocols and fixed levels of sample dilution. In either situation, it is very inconvenient and expensive to rectify the problem. Moreover, valuable information pertinent to proper diagnosis and/or therapy management may be lost with resultant harm to the patient.

In the system of the present invention, these problems are eliminated by monitoring assays during their execution, recognizing any problem and modifying either the optical pathlength used to measure the assay product or making use of the different sensitivity levels of the three color channels to the assay color and in turn to the analyte sensitivity.

Specifically when the assay reaction product is measured if the measured signal is either too high or too low, the system can respond by:

1. making the measurement with a different pathlength (moving the optical cuvette relative to the optical system such that the pathlength is either bigger or smaller). This can be performed by (a) making a measurement at a standard, first location, (b) reporting the result to the software managing the assay (in instrument and/or on a remote server), (c) recognizing a problem condition, and (d) modifying the read position and making a second measurement; and/or 2. emphasizing a more or less sensitive color channel in signal analysis. This can be implemented automatically by suitable assay analysis algorithms.

Color Calibration

The signal responses can be calibrated to allow for computation of the concentration of the colored species from imaging data. To obtain a data transform predictive of the concentration of the colored solute, the following procedure can be used. In other embodiments, other methods may also be used.

1. For each channel for all concentrations, the transform −Log(signal/blank signal) was computed and designated "A".

2. For all concentrations, a further transform ("C") was computed as a*A+b*A^2+c*A^3 (initially values for a, b and c were set at arbitrary values).

3. For all concentrations, C values for the three color channels were summed and designated Cestimate.

4. The sum of square differences between the target (known) concentration and Cestimate was computed over all concentrations.

5. Values of a, b and c parameters for all channels were derived by a well-known algorithm which minimized the sum of the square differences.

Figure 70:
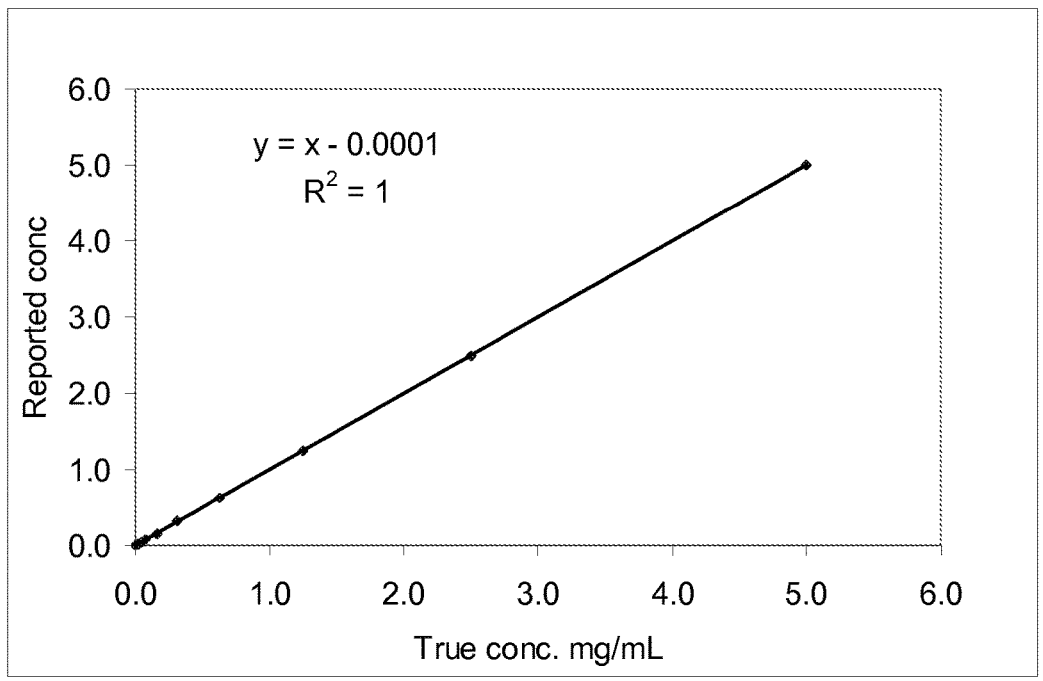
FIG. 70 shows a graph of concentration measured by color analysis of digital images as a function actual concentration.

The results shown in FIG. 70 demonstrates accurate calibration of the scanner response over the entire concentration range.

Other automated calibration algorithms have been developed and found to be equally effective. For example, the following is an example of calibration for a cholesterol assay performed in a reaction tip.

The measured signal is decomposed into Red (R), Green (G), and Blue (B) color channels. Calibration equations are computed to optimize the accuracy, precision, and dynamic range according to assay design requirements.

In this assay example, only Red and Green channels are utilized to compute concentration. These two signals are transformed to compute an intermediate variable (F) as follows:

$$F=p_1+p_2 \cdot G+p_3 \cdot G^2+p_4 \cdot R+p_5 \cdot R^2,$$

where $p_i$ are calibration parameters.

Finally, the signal F is used to compute the concentration (C) via a linear transformation:

$$C=(F-p_6)/p_7,$$

where C is the calculated concentration, and $p_6$ and $p_7$ are calibration parameters, in this case, representing the intercept and slope parameters of a linear relationship, respectively.

When the same approach was followed for a large set of assays for a variety of analytes which produced colored products spanning the entire visible spectrum (λmax from 400-700 nm), comparable results were obtained.

In conventional transmission spectrophotometric measurements, a "blank" value is used to normalize the measurement. Method (1) Blanks are typically constructed by measuring a sample that is equivalent to the sample but does not have any of the component to be measured. The measurement is typically made in the same cuvette as that which will be used for the sample or an optically equivalent cuvette. Thus in a spectrophotometric assay, one would combine all the reagents in the same concentrations using the same protocol substituting a zero analyte solution for the sample. Method (2) uses a two step process making measurements against an absolute reference such as air (which will never vary in absorbance) and measuring both sample and blank against the absolute reference. The sample absorbance is then calculated by subtraction of the blank value from that of the sample. Method (3) is to collect spectra of the sample or assay reaction product and reference the measured absorbance (or transmission) at an optimal wavelength (usually that for maximum absorbance for the measured species) against the absorbance at a wavelength where the species to be measured is known to have zero absorbance. The absorbance is the difference between those recorded at the two wavelengths.

Digital imaging and three-color analysis can be employed, but in some embodiments can be modified according to the digital (pixilated) character of the assay signal. Namely:

1. For each pixel in the image and for each color a white standard is imaged and the intensities of the signal adjusted to a value corresponding to no absorbance. This can be done by the following exemplary procedure:
   a. adjusting the intensity of the light source
   b. adjusting the sensitivity of the detector (preferred), or
   c. software adjustment (not preferred by itself)

A preferred approach is a combination of (b) and (c) above. First, adjust the detector in the analog realm, and then fine tune the result in the digital realm.

For the analog adjustment, the gain and offset of the amplifiers between the light sensors and the analog-to-digital section are adjusted to ensure maximum resolution of the digitization. The lower end of the light range of interest will be set to zero and the high end of the range will be set to just below saturation of the sensor.

Subsequently, the images may be fine-tuned in the digital domain. A preferred approach, specifically, would be to use what is called the "two-image calibration" for an m×n image. The mechanism is to first collect a black image by blocking all light to the detector. We'll call this image BLACK[m,n]. A second calibration image is recorded consisting of light at the maximum end of the sensitivity range. We'll call this image WHITE[m,n]. Thus a corrected image a[m,n] could be constructed, pixel-wise, as:

$$a[m, n] = \frac{c[m, n] - \text{BLACK}[m, n]}{\text{WHITE}[m, n] - \text{BLACK}[m, n]}$$

Note that this digital correction does not improve the dynamic range of the digitized data, but adjusts the values so that the full white and black references are consistent.

2. An image of a physical blank in a tip can be used as a pixel-by-pixel and color by color blank. The blank can be:
   a. Air;
   b. Water;
   c. Blank assay reaction product (no analyte);
   d. Sample blank (no assay reagents); or
   e. Some combination of the above;

3. The signal from a color channel where there is a zero or weak response can be used to normalize signals from the other channels.

Figure 104:
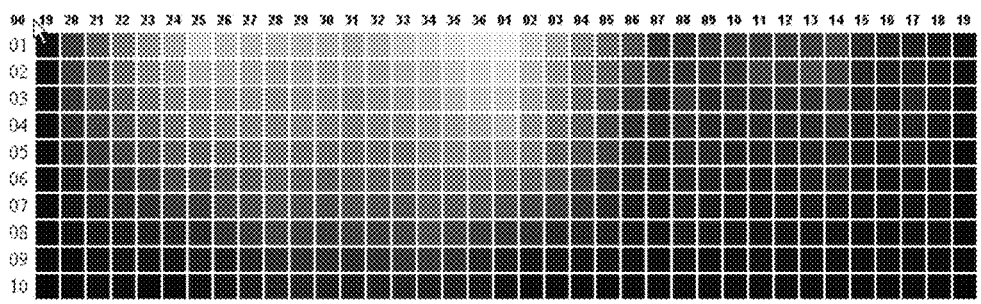
FIG. 104 shows an array of printed dyes that can be used to calibrate the optical setup.

A further method of controlling and normalizing the optics is to image a set of physical (stable) standards before or during an assay. For example, an array of printed dyes (shown in FIG. 104) can be made corresponding to a set of standard colors with standard intensities (similar to standard color "wheels" used to calibrate cameras and scanners).

Such standards may be measured using reflectance from an opaque surface or (preferred) by transmission through a clear film.

Depending on the stability of the optics, calibration and normalization of the optics may be (1) a one-time exercise, (2) performed at regular intervals or (3) performed for each assay.

Calibrating a Digital Imager Range

In some embodiments, methods may be provided for calibrating a digital imager used for imaging optical densities.

In testing the optical density of an analyte, it may be desirable to make use of as much of the dynamic range of the imager as possible. Under normal use, the setup may comprise a relatively homogenous illuminated white background, the imager and the analyte to be tested in a transparent cuvette between them. Operationally, the test may comprise placing the cuvette between the imager and the white backlight source and measure the amount of light absorbed by the analyte in the cuvette. To maximize the full dynamic range of the sensor, the background may be sensed as the maximum intensity measurable. It may be desirable to take care to not saturate the sensor because then information could be lost since when the sensor is saturated, and attenuation may not be correctly measured. The system may be configured to efficiently maximize the measured values of the backlight while minimizing number of saturated pixels.

Figure 128:
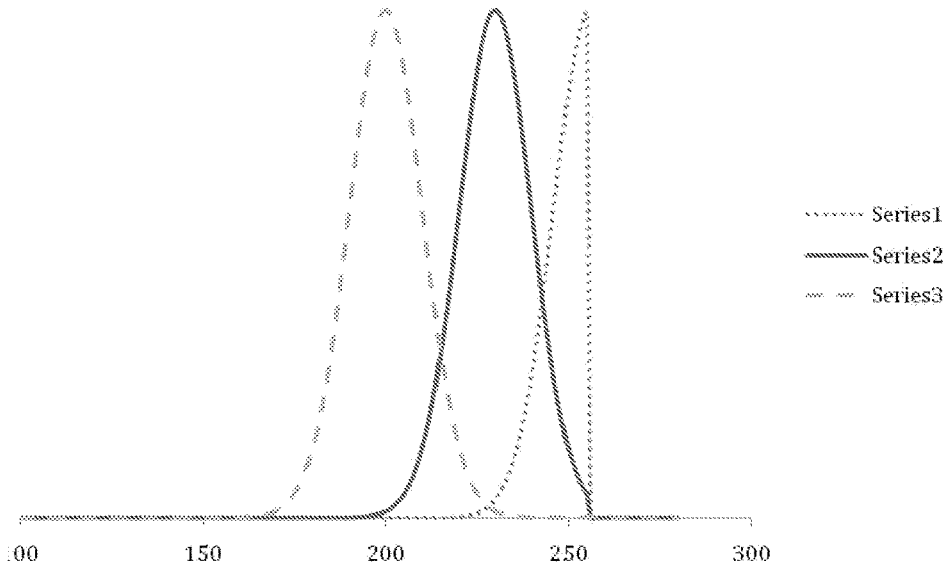
FIG. 128 shows variation in light distribution.

The illuminated background may emit white light of equal intensity over its entire surface. The light output may vary somewhat, producing a normal distribution of pixel intensities as detected by the imager. This is illustrated by the curves shown in FIG. 128. For this example, the sensor may return a value from 0 to 256 from each pixel as an indicator of the amount of light it receives. Each pixel may saturate at a value of 256. That is, regardless of further increasing of light intensity or sensor sensitivity, only a value of 256 may be recorded. Series 1 in FIG. 128, the dotted line, shows where the light is too intense, cutting off the normal curve. Series 3, the dashed line, shows that all pixels are correctly reading intensity, but that the imager sensitivity is lower than it might be for maximum dynamic range. The majority of the pixels are at a value of less than 200. Series 2 represents the desired settings, where the mean of the distribution is as high as possible, but that a sufficiently small number of pixels are saturated.

In one embodiment, the intensity of the backlight may be held constant while the imager's settings may be adjusted. For the purpose of imager sensitivity, two controls may be used: exposure time and gain. Exposure time may be the amount of time that the sensor pixels are permitted to collect photons before the value is read out. For a given amount of light, the readout value may be larger when the exposure time is made longer. This control may be the "coarse" control for the application. Gain may be the control adjusting the amount of amplification applied to the sensor signal.

Increasing gain may increase the value of the signal from the sensor. Gain may be the "fine" control.

An exemplary procedure for setting the imager's sensitivity parameters may include one or more of the following steps:
1. Set exposure time to value known to be below saturation. Set gain to highest usable value.
2. Binary search starting upwards adjust exposure time to find the setting where not all of the pixels in the region of interest of the image are saturated. This may be detected by observing the point at which the mean pixel value becomes less than 256.
3. Back gain down incrementally until there are sufficiently few pixels that are at the saturation limit. The number of pixels at an acceptable level will be determined by the shape of the distribution. Wide standard deviation will increase the number of pixels permitted to be saturated.

Next, the white balance may be corrected. There are three groups of sensors in a digital imager. Members of each group collect light of a different wavelength, red, green or blue. When detecting white light, the sensors would preferably see equal values or red, green and blue. The white balance control adjusts the relative gains of the red and blue channel. Since the light coming from the backlight is defined as white, the procedure would be to simply adjust the white balance until the channels read the same values. In practice, the green channel is typically left unadjusted, and the red and blue channels are changed in opposite directions to each other as the control is changed. However, in other embodiments, another channel, such as the red channel or blue channel may be left unadjusted while the other two channels may be changed.

Finally, the images may be fine-tuned in the digital domain. A preferable approach, specifically, would be to use what is called the "two-image calibration" for an m×n image, as previously described.

Assays making a variety of colored products have been analyzed in the subject invention. Colors from those with low wavelength absorption maxima (yellow) to high wavelength maxima (blue) have been successfully measured. Wavelength maxima for some representative assays were: 405, 450, 500, 510, 540, 570, 612 and 620 nm demonstrating the ability to read color over the entire visible spectrum.

Figure 129:
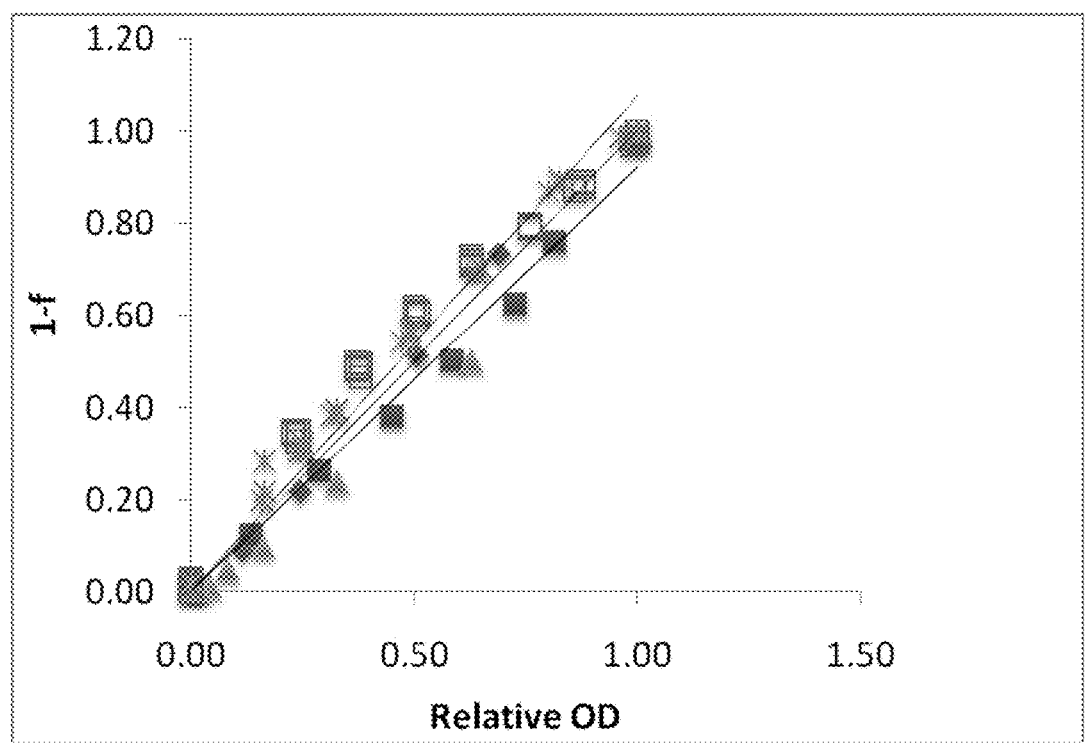
FIG. 129 shows data from five assays.

Colors may be quantified using average data for many pixels (typically about 1000). A parameter (f) which produces a good fit (e.g., greatest $R^2$) to the dose-response data may be selected. The parameter may be first fitted to the form $a1+b1*R+c1*R^2+b2*G+c2*G^2+b3*B+c2*B^2$ where a, b, c are constants and R, G and B are color intensity values for red, green and blue channels respectively. The parameter f may then be derived by forcing it to have a maximum value of 1 and a minimum value of 0. Parameter f is related to transmission of light through the colored reaction product. As would be expected, f may be closely related to the parameter optical density (OD) used in spectrophotometry to quantify an absorbing species. When 1-f measured by 3-color imaging is plotted against OD measured at the absorption maximum for the same assay reaction products in a microtiterplate in a spectrophotometer, it may be observed that 1-f is essentially linearly related to OD. In FIG. 129, such data for five assays is presented. OD may be normalized as "relative OD"=(OD−OD min)/(ODmax−OD min). In some cases, there is a somewhat curved relationship but the correlation coefficient (R) is usually >0.99.

Figure 130:
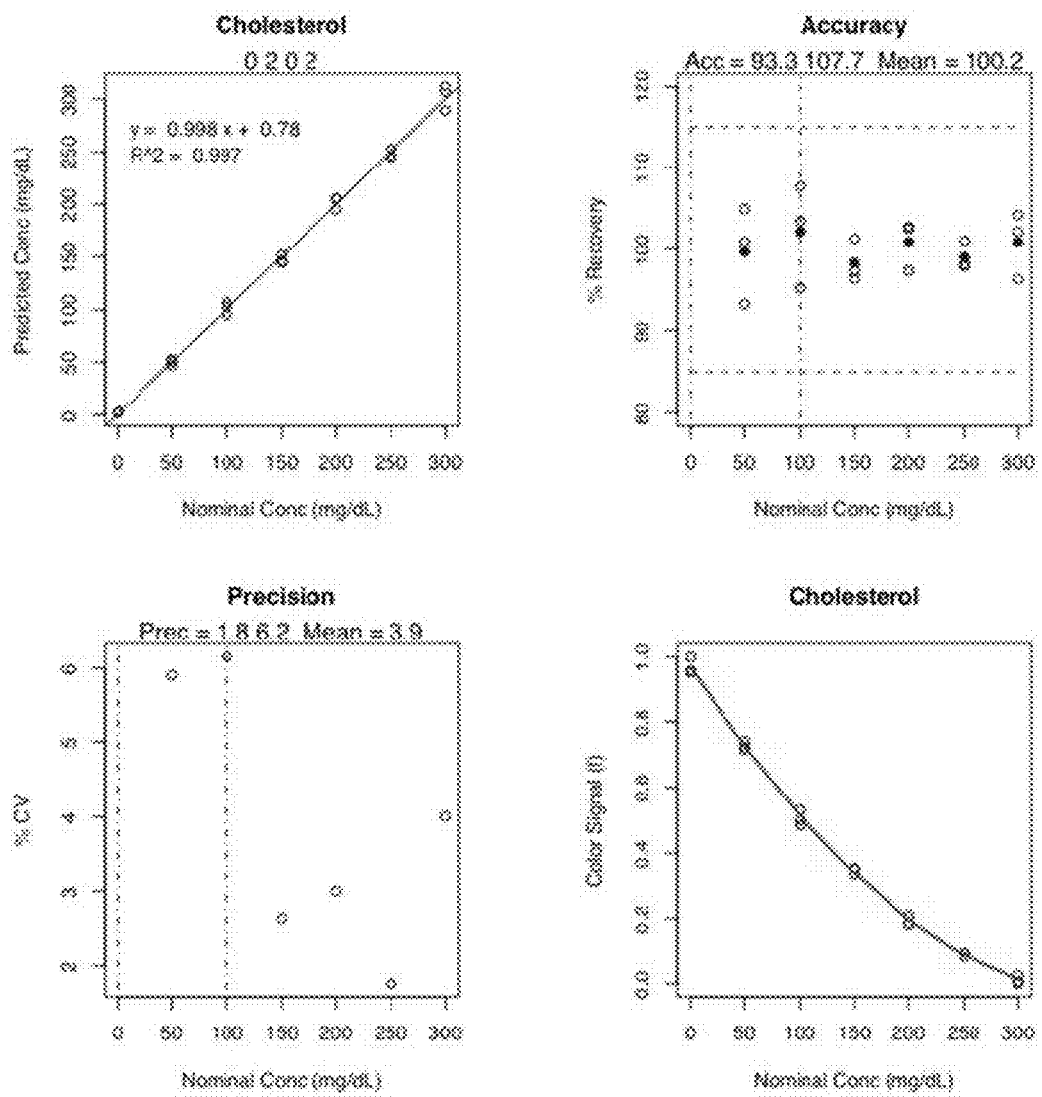
FIG. 130 shows a parameter plotted against concentration of the analyte, as well as graphs relating to accuracy, precision, and predicted concentration.

The parameter f may be used to calibrate assays measured by 3-color image analysis. When plotted against concentration of the analyte, a smooth calibration relationship may be shown in FIG. 130 for a representative cholesterol assay. An equation of the form concentration=$a+b*f+c*f^2$ (where a, b and c are constants) relating concentration to f is derived and as shown in FIG. 130, the calculated concentration is essentially identical to that of the "nominal" (expected, desired) value (regression line slope close to 1.0, intercept close to 0.0 and $R^2$=0.998. Also shown in FIG. 130 are graphs of assay accuracy and precision. Accuracy is close to 100% (mean 100.2%) and imprecision (represented by CV %) is low (less than 10%, average CV 3.9%).

Simultaneous Imaging of Assays

As shown in FIG. 56, FIG. 57, FIG. 58, FIG. 59, and FIG. 60, several assay elements (tips, wells, blots) can be imaged in parallel. In general, the elements can be placed at known locations in a cartridge or mounted on a subsystem of the instrument, so that a particular element can be associated with a particular assay. Even if the elements are not perfectly oriented or located, image analysis can be used to rectify any such miss-positioning by locating features of the assay elements.

Figure 56:
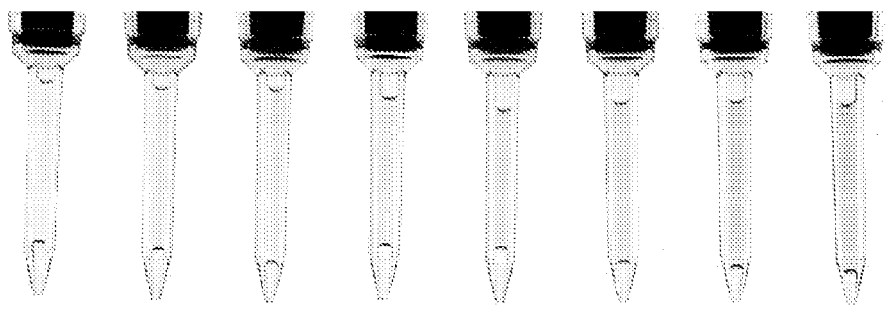
FIG. 56 shows a series of images of tips with two-fold decreasing concentration of albumin from right to left, except for the left-most tip, which has no albumin.
Figure 57:
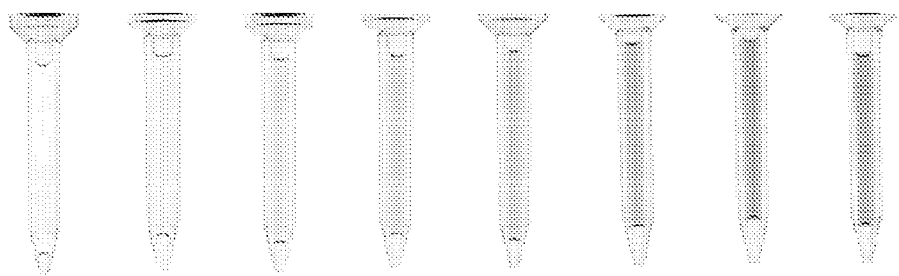
FIG. 57 shows a series of images of tips with two-fold decreasing concentration of cholesterol from right to left, except for the left-most tip, which has no cholesterol.

Commercially available assays for albumin (FIG. 56) and cholesterol (FIG. 57) were used according to the manufacturer's directions. A series of analyte concentrations in the range of clinical interest was measured using a series of calibrators in which the analyte concentration was reduced two-fold from the highest concentration. In FIG. 56 and FIG. 57, analyte concentration was highest on the right and the furthest left tip corresponded to zero analyte. The volume of assay reaction mixture aspirated into the tips was 20 uL.

Figure 58:
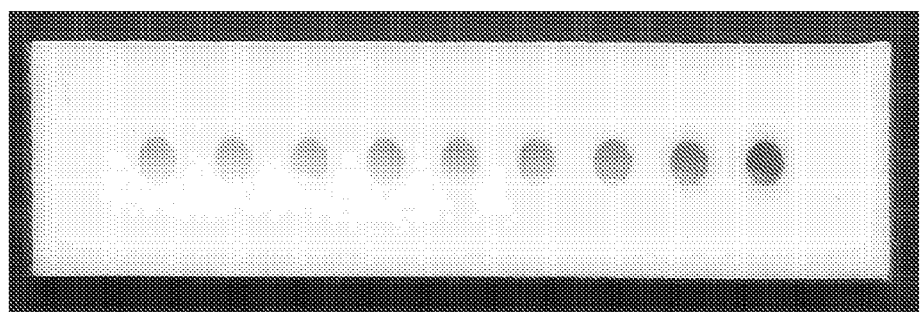
FIG. 58 shows a series of hemispherical wells machined from a block of white opaque plastic, which each well having two-fold decreasing concentration of analyte from right to left, except for the left-most well, which has no analyte. In some embodiments, the analyte may be calcium.
Figure 59:
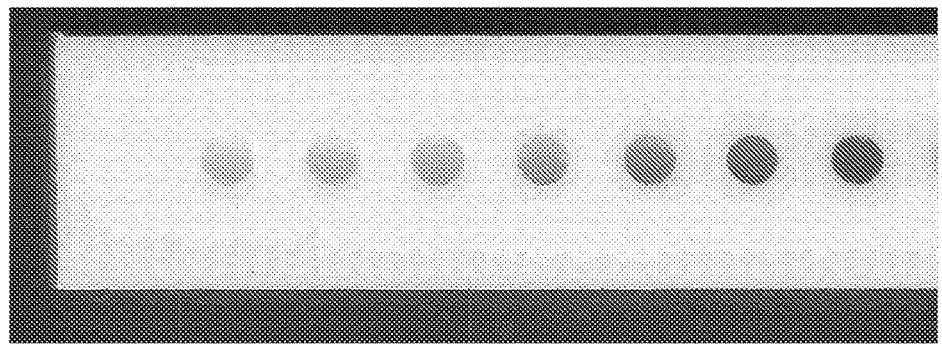
FIG. 59 shows a series of hemispherical wells machined from a block of white opaque plastic, which each well having two-fold decreasing concentration of analyte from right to left, except for the left-most well, which has no analyte. In some embodiments, the analyte may be magnesium.
Figure 60:
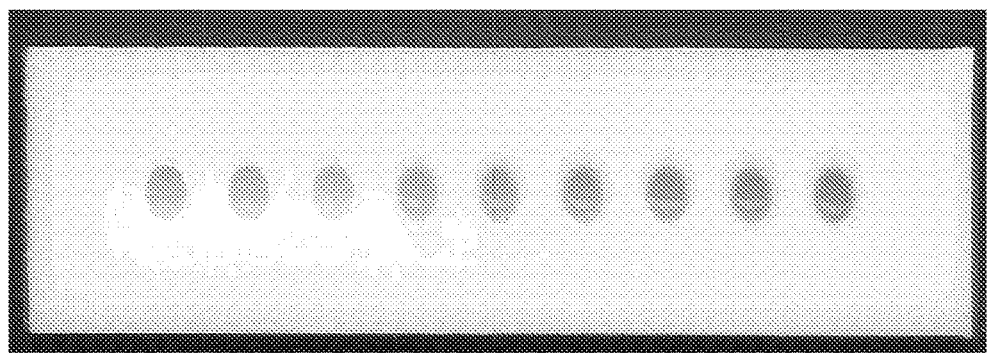
FIG. 60 shows a series of hemispherical wells machined from a block of white opaque plastic, which each well having two-fold decreasing concentration of analyte from right to left, except for the left-most well, which has no analyte. In some embodiments, the analyte may be urea.

FIG. 58, FIG. 59, and FIG. 60 show wells that can be imaged in parallel. A set of shallow hemispherical wells was made by machining a block of white opaque plastic. Three commercially available color forming assays were performed in these wells and reaction products imaged. As above, the wells to the far right have the highest analyte concentration and each adjacent well has a two-fold lower concentration except the left-most well which has zero analyte. Seven uL of assay reaction product were introduced into each well.

Reaction products can also be imaged after blotting them onto porous membranes or paper and imaging once the liquid has soaked into the medium. It is also possible to use any of a variety of assay chemistries impregnated into paper or membranes and to image the resulting reaction products following addition of sample.

Analyzing Turbidity

Turbidimetry is performed by measuring the reduction in the intensity of the incident light after it passes through the sample being measured. This technique is used where the result of the assay is a dispersed precipitate that increases the opacity of the liquid.

Figure 72:
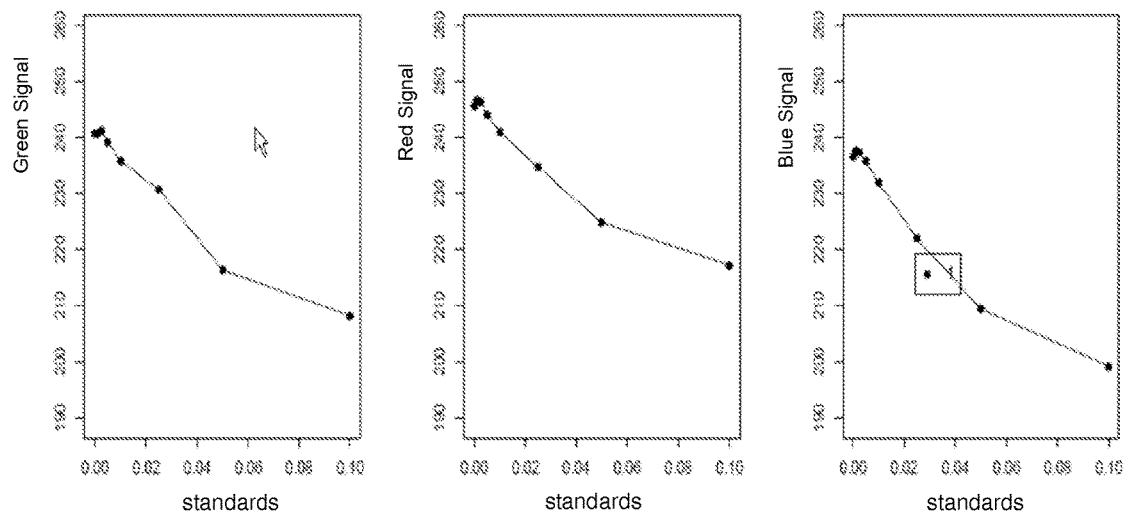
FIG. 72 shows three graphs of signal response as measured for green, red, and blue color channels for polystyrene latex particles.

Turbidimetry can be measured in latex agglutination assays. As a model of latex agglutination assay responses, polystyrene latex particles (1 um diameter) were dispersed in buffer at the given (w/v) concentrations and subject to three-color image analysis. As can be seen in FIG. 72, a good response was found in all three channels and could be used to measure the latex particle concentration and agglutination of latex.

Analyzing Agglutination

Similarly to turbidity analysis, the system can be used to measure agglutination, hemagglutination, and the inhibition thereof.

Figure 77:
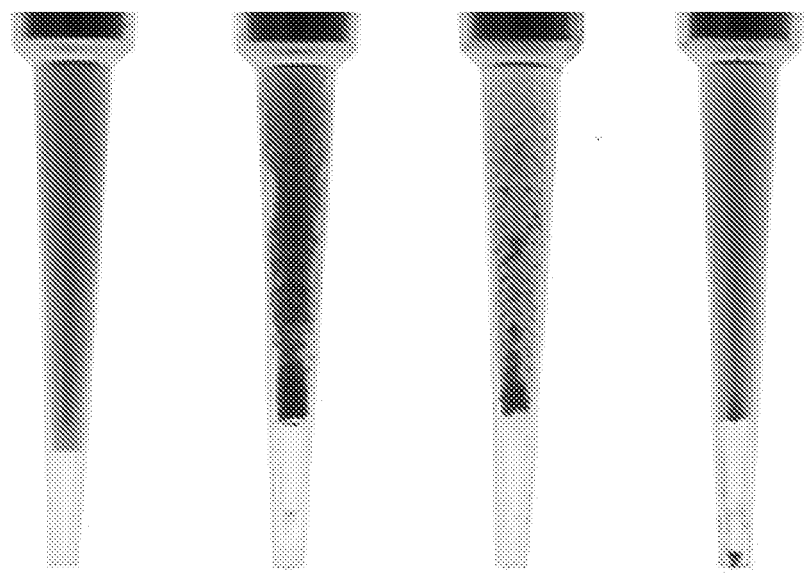
FIG. 77 shows tips containing blood samples mixed with blood typing reagents for Anti-A, Anti-B, Anti-D, and Control (from left to right).
Figure 78:
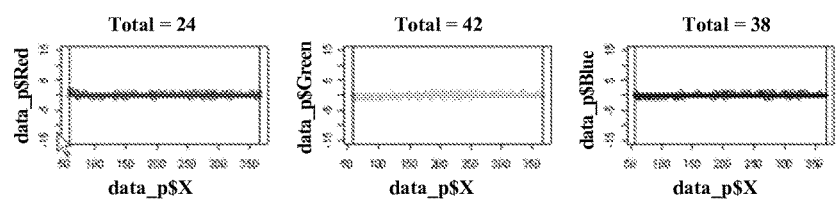
FIG. 78 shows measured signals for signal as a function of position for red (left column), green (middle column), and blue (right column) for samples mixed with Anti-A, Anti B, Anti-D, and Control reagents.
Figure 78:
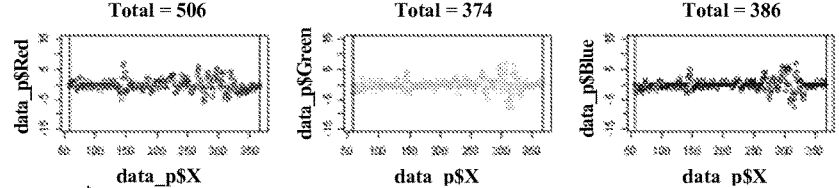
Figure 78:
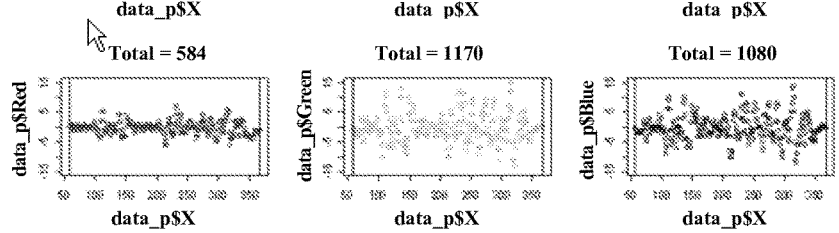
Figure 78:
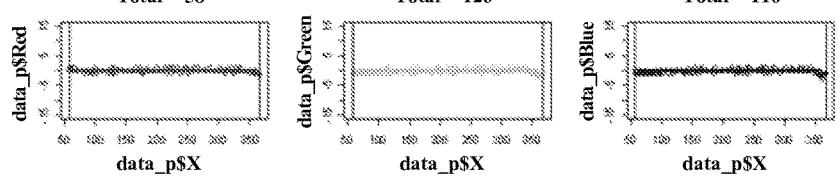

The system can be used to perform blood typing by red blood cell agglutination. Blood was diluted and mixed with blood typing reagents (anti-A, anti-B, anti-D) from a commercial typing kit. As shown below for a B+blood, the appropriate agglutination responses can easily be seen when the mixtures are imaged. Moreover, when the images shown in FIG. 77 were scanned along the vertical axis of the tips, a quantitative measure of agglutination could be obtained by measuring the variance of the three-color signals, as shown in FIG. 78. Greater variance indicated agglutination and can be detected in each color channel. It is evident that the method can be used to measure the extent of such agglutination reactions.

Shape Recognition

Images can be analyzed for shape recognition. Shape recognition can be performed at normal magnification and at very high magnification. Under high magnification image analysis may be used to recognize the size and shape of cells. These techniques are commonly used in cell counting to determine relative concentrations of red blood cells, white blood cells and platelets. Under normal magnification, shape recognition is used to observe the state of the sample. Bubble and other defect recognition methods are used to ensure that measured liquid amounts are aspirated and dispensed correctly.

Analyzing Samples on Solid Phase Substrates

Figure 76:
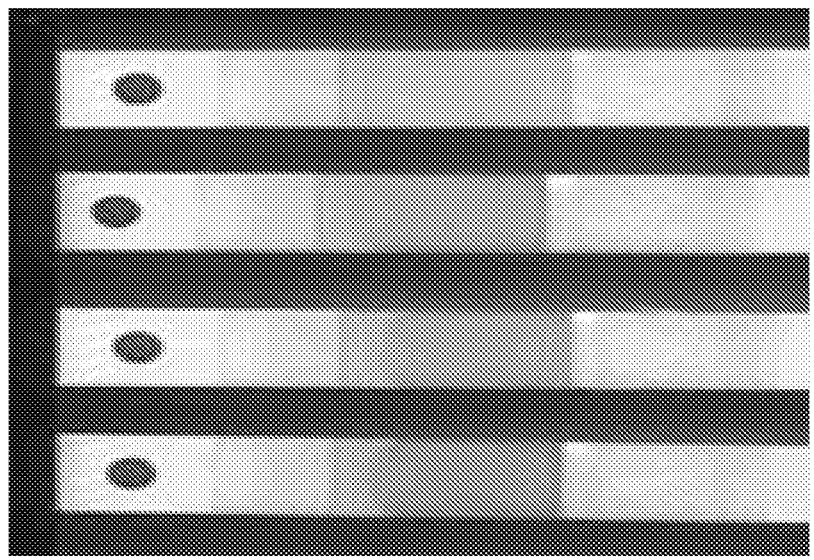
FIG. 76 shows solutions of potassium chloride added to potassium assay strips.

Digital imaging with front-face illumination can also be used to read out assay responses on solid phase substrates as shown in FIG. 76. Solutions of potassium chloride (0, 2, 4 and 8 mM) were added to Reflotron™ potassium assay strips (Boehringer-Mannheim/Roche) designed for use in a reflectance assay system.

Analyzing Sample Quality

Figure 99:
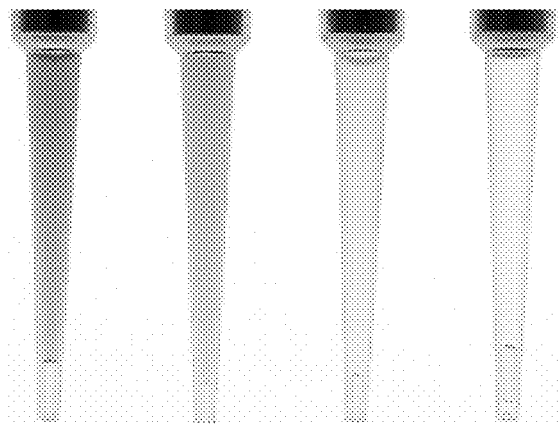
FIG. 99 shows four tips with various types of serum samples: hemolyzed (reddish in color), lipemic (gray), icteric (yellow in color), and normal (from left to right).

Certain sample characteristics can render assay results invalid. For example, hemolysis causes potassium ions to leak from red cells into plasma causing the measured plasma or serum potassium ion concentrations to be falsely high. Similarly, icteria and lipemia can interfere with several color-forming chemistries by altering the measured absorbances. In the present invention, we can detect and quantify such interfering substances using image analysis. Assays which would give false results can then be either (1) eliminated from the list of results delivered by the analytical system or (2) optical signals can be corrected to account for the measured level of interferent. An image of different types of serum samples is shown in FIG. 99 (from left to right: Hemolyzed, Lipemic, Icteric (yellow) and "normal").

Digital Data Analysis

Conventional methods for data generation and calibration in assay methods which generate and/or change color typically measure an analog signal representing the change in absorbance characteristics of an assay mixture generated by mixing a sample with reagents. Some portion of the reaction mixture is illuminated and the light transmitted through or reflected from that portion impinges on a detector and evaluated as an analog signal. The quality of the assay as determined by the volume and quality of the sample, sample processing, assembly of the assay into the assay mixture and of the physical element used to present the mixture to the optical system rely on an assumed quality of the physical system used.

In the present invention, we can image (1) the sample, (2) sample processing processes, and (3) the assay mixture and collect the data as a set of one or more digital images. Each pixel in the image of the assay mixture represents a very small fraction of the total but by averaging the 3-color signal from many pixels, we collect an assay signal at least as good as that obtained by conventional analog methods. Where however, conventional methods lose information by averaging, the present invention both aggregates the information and retains the detail lost by conventional methods. In this context, color-based assays include assays for: Metabolites, Electrolytes, Enzymes, Biomarkers (using immunoassay), Drugs (using immunoassay), and Nucleic acid targets (using "LAMP" technology). The same principles can be applied to assays using fluorescence and/or luminescence.

Volume Confirmation and Correction

The volume of a sample, or any other material, such as a liquid or a solid, can be determined optically. This can be performed by imaging a container whose internal dimensions are known and mathematically determining sample volume from observed segment of the container occupied. Solid measurements are primarily used to measure solids that are centrifuged down. The most common case is reading the volume of centrifuged red blood cells to determining hematocrit level. Examples 6-11 and 16 describe the use of imaging analysis to calculate sample volumes and other measurements. This can allow for improved assay results. For example, if the target volume to be used is 10 uL and the technology of the invention determines that the actual volume is 8 uL, the assay system can correct the results for the volume (in this example, the concentration of analytes calculated on the presumption of a 10 uL sample would be multiplied by 10/8).

Knowledge of actual sample and reagent volumes can be performed by imaging the sample and reagents and can be used to correct the calculations used to detect and/or quantify analytes in the sample.

As shown in many examples above, the use of imaging allows samples and assay mixtures to be evaluated for quality and assay response. Additionally, imaging of 'tips' used as reaction vessels and sample acquisition methods enables (1) the accurate and precise measurement of sample and reagent volumes and (2) the use of such data to correct any inaccuracies and or imprecision in assay results due to volume errors. To achieve this, tips can have accurately and precisely known geometry (as is the case for tips made by injection molding). Replicate measurements of tips using imaging has demonstrated that their dimensions are precise to better than about 1%. It is thus possible to measure the volume of liquid samples and reagents in such tips with corresponding precision. If the pipetting of samples and reagents is less accurate and precise, correction of results knowing the actual volumes (by image measurement) is possible.

For example, consider an assay in which the response is directly proportional to analyte concentration (as is true for many of the assays discussed herein). A sample volume error of 10% would lead to an error of 10% in the value reported by the analytical system. If however, the inaccurately dispensed sample volume is measured accurately (say to within 2% of the actual value), the system response can be corrected so as to reduce the error from 10% to 2%. Corresponding corrections can be made for volume errors in reagent volumes. The correction algorithm can depend on the response of the assay system to volume or knowledge of each assay component (sample, reagents), but this information can easily be determined during assay development and validation.

Thus, the invention provides a variety of advantages over conventional techniques. In the generation of the "assay signal", the present invention can detect physical defects in the assay cuvette, defects in the assay mixture (bubbles and the like). Once these defects are identified (image analysis) the assay result can be rejected so that false results do not occur or (preferred) the effect of the defect can be eliminated and an accurate assay signal computed.

In the assembly of the assay mixture, any and all defects can be detected including: incorrect sample type (e.g. blood versus plasma), incorrect sample volume, for a blood sample, failure to separate plasma from formed elements (red and white cells), sample factors that may compromise the quality of the assay result (e.g., lipemia, icteria, hemolysis, presence of precipitates, or other unidentified in-homogeneities), defects in assembly of the assay mixture (e.g., presence of bubbles, failure to mix adequately (non-uniformity of color)), mechanisms for retrospective quality evaluation and preservation of detailed archival information, mechanisms for measuring sample and reagent volumes (and to correct for inaccuracies and/or imprecision in such volumes).

Assessing Therapeutic Agents

In a separate embodiment, devices and methods for monitoring more than one pharmacological parameter useful for assessing efficacy and/or toxicity of a therapeutic agent is provided. For example, a therapeutic agent can include any substances that have therapeutic utility and/or potential. Such substances include but are not limited to biological or chemical compounds such as simple or complex organic or inorganic molecules, peptides, proteins (e.g. antibodies) or a polynucleotides (e.g. anti-sense). A vast array of compounds can be synthesized, for example polymers, such as polypeptides and polynucleotides, and synthetic organic compounds based on various core structures, and these can also be included as therapeutic agents. In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies. For example, small molecule drugs are often measured by mass-spectrometry which can be imprecise. ELISA (antibody-based) assays can be much more accurate and precise.

Physiological parameters according to the present invention include without limitation parameters such as temperature, heart rate/pulse, blood pressure, and respiratory rate. Pharmacodynamic parameters include concentrations of biomarkers such as proteins, nucleic acids, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters in real time from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the pharmacodynamic (PD) parameters fall outside the desired range during a treatment regime, immediate action may have to be taken as well.

Being able to monitor the rate of change of an analyte concentration or PD or PK parameters over a period of time in a single subject, or performing trend analysis on the concentration, PD, or PK parameters, whether they are concentrations of drugs or their metabolites, can help prevent potentially dangerous situations. For example, if glucose were the analyte of interest, the concentration of glucose in a sample at a given time as well as the rate of change of the glucose concentration over a given period of time could be highly useful in predicting and avoiding, for example, hypoglycemic events. Such trend analysis has widespread beneficial implications in drug dosing regimen. When multiple drugs and their metabolites are concerned, the ability to spot a trend and take proactive measures is often desirable.

In some embodiments, the present invention provides a business method of assisting a clinician in providing an individualized medical treatment. A business method can comprise post prescription monitoring of drug therapy by monitoring trends in biomarkers over time. The business method can comprise collecting at least one pharmacological parameter from an individual receiving a medication, said collecting step is effected by subjecting a sample of bodily fluid to reactants contained in a fluidic device, which is provided to said individual to yield a detectable signal indicative of said at least one pharmacological parameter; and cross referencing with the aid of a computer medical records of said individual with the at least one pharmacological parameter of said individual, thereby assisting said clinician in providing individualized medical treatment.

The devices, systems, and methods herein allow for automatic quantification of a pharmacological parameter of a patient as well as automatic comparison of the parameter with, for example, the patient's medical records which may include a history of the monitored parameter, or medical records of another group of subjects. Coupling real-time analyte monitoring with an external device which can store data as well as perform any type of data processing or algorithm, for example, provides a device that can assist with typical patient care which can include, for example, comparing current patient data with past patient data. Therefore, also provided herein is a business method which effectively performs at least part of the monitoring of a patient that is currently performed by medical personnel.

Optical Setup for Sample and Reaction Product Imaging

Figure 100:
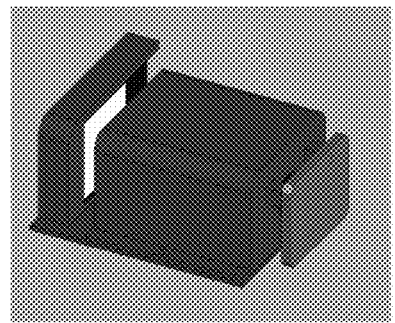
FIG. 100 shows a schematic of a camera and optical components.
Figure 101:
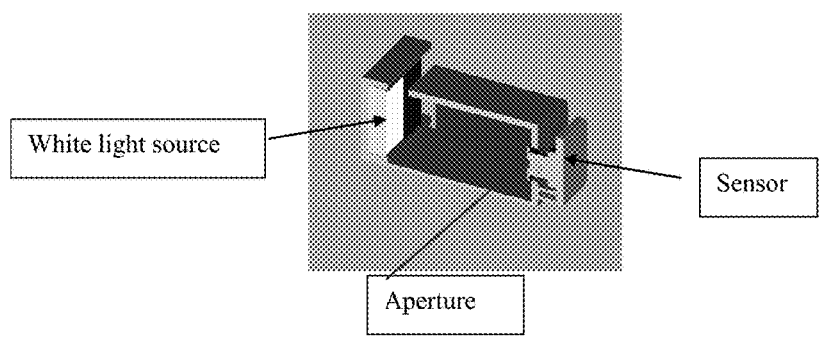
FIG. 101 shows a cross-sectional view of a camera and optical components including a white light source, an aperture, and a sensor.

Sample and reaction product analysis can be performed using an optical setup. The optical setup can includes a light source, an aperture, and a sensor or a detector. A schematic for an optical setup is shown in FIG. 100 and FIG. 101. In some embodiments, the camera can be a Logitech C600 Webcamera, the camera sensor can be a ⅓" 2.0 MP (1600× 1200) CMOS: (MI-2010-SOC), the lens can be glass with a standard object distance webcam lens (Lens-to-Object distance: 35 mm). The light source can be a Moritex White Edge Illuminator MEBL-Cw25 (white) operating at 9.4 volts. Camera images can be taken in a sequence where 1, 2, 3 4, or more tips are moved by an x-y-z stage into the optical path.

In an embodiment, the detector is a reader assembly housing a detection assembly for detecting a signal produced by at least one assay on the device. The detection assembly may be above the device or at a different orientation in relation to the device based on, for example, the type of assay being performed and the detection mechanism being employed. The detection assembly can be moved into communication with the assay unit or the assay unit can be moved into communication with the detection assembly.

The sensors can be PMTs, wide range photo diodes, avalanche photodiodes, single frequency photo diodes, image sensors, CMOS chips, and CCDs. The illumination sources can be lasers, single color LEDs, broad frequency light from fluorescent lamps or LEDs, LED arrays, mixtures of red, green, and blue light sources, phosphors activated by an LED, fluorescent tubes, incandescent lights, and arc sources, such as a flash tube.

In many instances, an optical detector is provided and used as the detection device. Non-limiting examples include a photodiode, photomultiplier tube (PMT), photon counting detector, avalanche photo diode, or charge-coupled device (CCD). In some embodiments a pin diode may be used. In some embodiments a pin diode can be coupled to an amplifier to create a detection device with a sensitivity comparable to a PMT. Some assays may generate luminescence as described herein. In some embodiments chemiluminescence is detected. In some embodiments a detection assembly could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

A detector can also comprise a light source, such as a bulb or light emitting diode (LED). The light source can illuminate an assay in order to detect the results. For example, the assay can be a fluorescence assay or an absorbance assay, as are commonly used with nucleic acid assays. The detector can also comprise optics to deliver the light source to the assay, such as a lens or fiber optics.

In some embodiments, the detection system may comprise non-optical detectors or sensors for detecting a particular parameter of a subject. Such sensors may include temperature, conductivity, potentiometric signals, and amperometric signals, for compounds that are oxidized or reduced, for example, $O_2$, $H_2O_2$, and $I_2$, or oxidizable/reducible organic compounds.

The illumination can be back lit, front lit, and oblique (side) lit. Back lighting can be used in general chemistry for the purpose of detecting either light absorption (colorimetry) or scattering (turbidity). The arrangement takes two forms, a broad, evenly illuminated rear field, and a specifically shaped beam that is interrupted by the subject. Front lit illumination can be used for reflectance and fluorescence excitation. In reflectance, a subject is lit from the front by a light source are measured by observing the light reflected from the subject. The colors absorbed produce the same information as a liquid illuminated by a back light. In reflectance, a subject can also be illuminated using oblique lighting. The use of oblique (from the side) illumination gives the image a 3-dimensional appearance and can highlight otherwise invisible features. A more recent technique based on this method is Hoffmann's modulation contrast, a system found on inverted microscopes for use in cell culture. Oblique illumination suffers from the same limitations as bright field microscopy (low contrast of many biological samples; low apparent resolution due to out of focus objects), but may highlight otherwise invisible structures.

In fluorescence excitation, subjects can be illuminated from the front for the purpose of fluorescence illumination. These are usually single color lights, most commonly lasers. The Confocal Laser Scanning Microscope is a common embodiment of this. Oblique lighting can also be used in fluorescence excitation. In fluorescence cytometry, the subjects are often excited at an angle, usually 90 degrees, from which the decay photons will appear. This form of lighting enables scatter detection directly behind the subject (back lit) as well as the fluorescence emissions exiting from the side.

Figure 102:
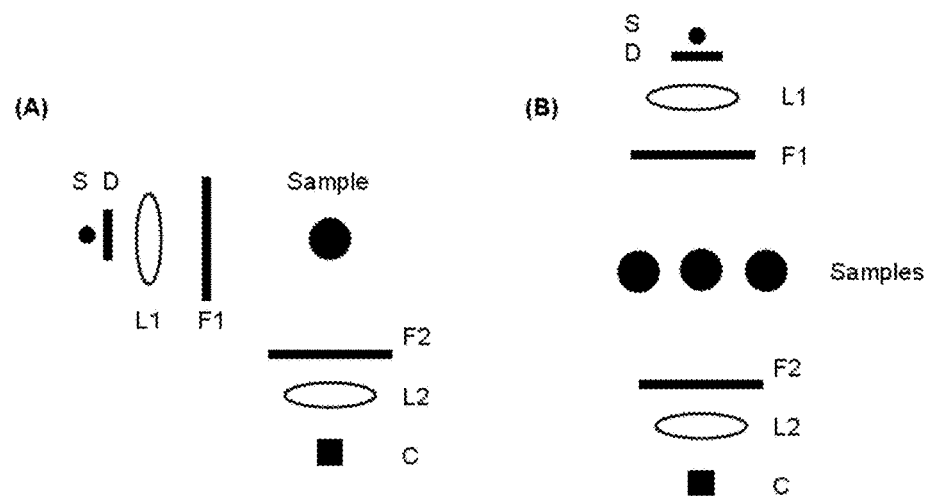
FIG. 102 shows a schematic of an optical setup for measuring light signal using (A) a sensor that is positioned to detect light at a perpendicular angle to an excitation beam, and (B) a sensor that is positioned in line with an excitation beam.

In some embodiments, fluorescent light is imaged at 90 degrees to the excitation beam. In FIG. 102A, a photon source (S), typically a high-intensity LED, passes through a beam diffuser (D) and a shaping lens (L1), producing a collimated or slowly diverging excitation beam. The excitation beam passes through a band-pass filter (F1) and illuminates the sample, consisting of a vessel (tube, cuvette, or pipette tip) containing a solution with a fluorescently-labeled sample. Isotropically-emitted fluorescence is spectrally separated from excitation light with a long- or band-pass filter (F2) appropriate to pass Stokes-shifted fluorescence. Light is then imaged through a lens (L2) onto a digital camera (C) or other detector. Fluorescence intensity is extracted from the resulting images via image analysis.

Images taken using the optical setup shown in FIG. 102A produces single-tube images (as shown in FIG. 103A. Successive experiments show the difference in fluorescence intensity from Negative and Positive LAMP experiments using intercalating dye.

Figure 103:
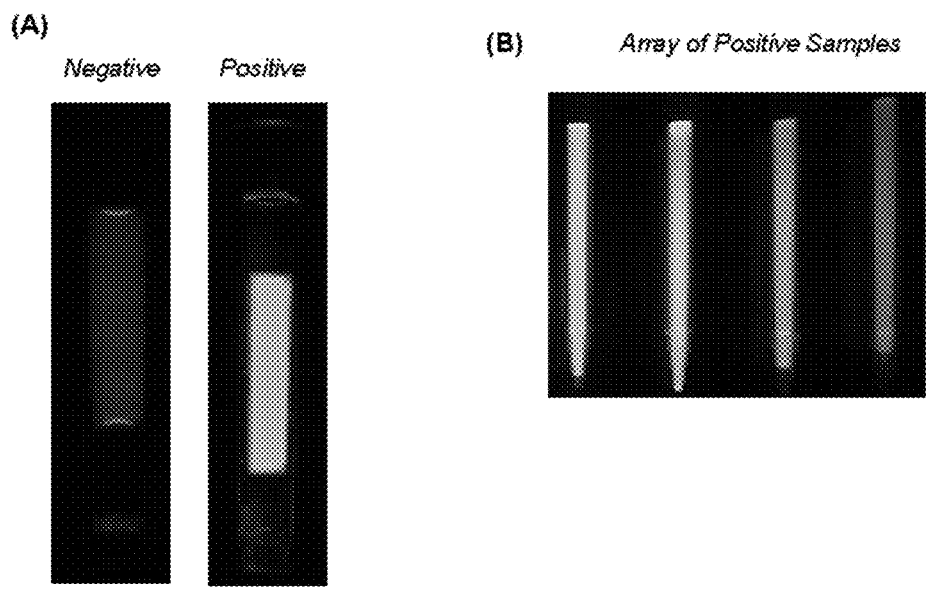
FIG. 103 shows images taken using (A) an excitation beam perpendicular to a sensor and (B) an excitation beam that is in line with a sensor.

In other embodiments, transmitted light is imaged after optical filtering to remove the light at the exciting wavelength. In FIG. 102B, a photon source (S), typically a high-intensity LED, passes through a beam diffuser (D) and a shaping lens (L1), producing slowly divergent, elliptical excitation beam. The excitation beam passes through a band-pass filter (F1) and illuminates the samples, presented as an array of sample vessels (tube, cuvette, or pipette tip), each containing a solution with a fluorescently-labeled sample. Isotropically-emitted fluorescence is spectrally separated from excitation light with a long- or band-pass filter (F2) appropriate to pass Stokes-shifted fluorescence. Light is then imaged through a camera lens (L2) onto a digital camera (C). Fluorescence intensity is extracted from the resulting images via image analysis. The optical setup shown in FIG. 103 can be used to produces array images of multiple tubes simultaneously (as shown in FIG. 103B).

For colorimetry, the preferred embodiment for sensing is backlighting the subject with white light with the result sensed by an imaging sensor. In this case the transmissive color absorption is measured.

For Turbidimetry, the preferred embodiment for sensing is backlighting the subject with white light with the result sensed by an imaging sensor. For turbidimetry, the reduction of the intensity of the transmitted light is measured.

Luminometry utilizes no illumination method as the subject emits its own photons. The emitted light can be weak and can be detecting using an extremely sensitive sensor such as a photomultiplier tube (PMT).

In some embodiments, imaging may occur using fluorescence, darkfield illumination, or brightfield illumination. Such imaging can be used for cytometry or other applications. Epi-fluorescence illumination may be achieved by the use of three illumination sources of differing wavelengths. Further, two different sources can be used simultaneously, if required. Consequently, the imaging platform can be used to image a large variety of fluorescent dyes. The combination of illumination sources and emission optics can be configured to achieve a plurality of spectrally independent channels of imaging.

Darkfield illumination may be achieved by the use of a ringlight (located either above or below the sample), a darkfield abbe condenser, a darkfield condenser with a toroidal mirror, an epi-darkfield condenser built within a sleeve around the objective lens, or a combination of ringlight with a stage condenser equipped with a dark stop. Fundamentally, these optical components create a light cone of numerical aperture (NA) greater than the NA of the objective being used. The choice of the illumination scheme depends upon a number of considerations such as magnification required, mechanical design considerations, size of the imaging sensor etc. A ringlight based illumination scheme generally provides uniform darkfield illumination over a wider area while at the same time providing sufficient flexibility in mechanical design of the overall system.

Brightfield illumination may be achieved by the use of a white light source along with a stage-condenser to create Koehler illumination.

In some embodiments, an automatic filter wheel may be employed. The automatic filter wheel allows control of the imaging optical path to enable imaging of multiple fluorophores on the same field of view.

In some embodiments, image based auto-focusing may take place. An image-based algorithm may be used to control the z-position (e.g., vertical position) of an objective (i.e., its distance from the sample) to achieve auto-focusing. Briefly, a small image (for example, 128×128 pixels) is captured at a fast rate using darkfield illumination. This image may be analyzed to derive the auto-focus function which is measure of image sharpness. Based on a fast search algorithm the next z-location of the objective is calculated. The objective may be moved to the new z-location and another small image may be captured. This closed-loop system does not require the use of any other hardware for focusing. The microscope stage may be connected to computer-controlled stepper motors to allow translation in the X and Y directions (e.g., horizontal directions). At every location, the desired number of images is captured and the stage is moved to the next XY position.

Imaging or other sensing may be performed with the aid of a detector. A detector can include a camera or other sensing apparatus configured to convert electromagnetic radiation to an electronic signal. In an example, a camera can be a charge-coupled (CCD) or electron-multiplying CCD (EMCCD) camera. A detector may be a sensor, such as an active pixel sensor or CMOS sensor. A detector may include a photo-multiplier tube for detecting a signal.

The detector can be in optical communication with a sample container (e.g., cuvette, tip, vial). In some cases, the detector is in direct line of sight of the sample container. In other cases, the detector is in optical communication with the sample container with the aid of one or more optics, such as lenses, mirrors, collimators, or combinations thereof.

Cell counting can be performed using imaging and cytometry. In situations where the subjects may be bright-field illuminated, the preferred embodiment is to illuminate the subjects from the front with a white light and to sense the cells with an imaging sensor. Subsequent digital processing will count the cells. Where the cells are infrequent or are small, the preferred embodiment is to attach a fluorescent marker, and then illuminating the subject field with a laser. Confocal scanning imaging is preferred. For flow cytometry, the subjects are marked with fluorescent markers and flowed past the sensing device. There are two types of sensors, one is position such that the subject is back lit, measuring beam scatter to determine presence of a cell. The other sensor, aligned so that the illumination is from the side, measures the fluorescent light emitted from the marked subjects. Further description is provided below relating to imaging methodology for cytometry.

End-User Systems

A device and system may, after manufacturing, be shipped to the end user, together or individually. The device or system of the invention can be packaged with a user manual or instructions for use. In an embodiment, the system of the invention is generic to the type of assays run on different devices. Because components of the device can be modular, a user may only need one system and a variety of devices or assay units or reagent units to run a multitude of assays in a point-of-care or other distributed testing environment. In this context, a system can be repeatedly used with multiple devices, and it may be necessary to have sensors on both the device and the system to detect such changes during shipping, for example. During shipping, pressure or temperature changes can impact the performance of a number of components of the present system, and as such a sensor located on either the device or system can relay these changes to, for example, the external device so that adjustments can be made during calibration or during data processing on the external device. For example, if the temperature of a fluidic device is changed to a certain level during shipping, a sensor located on the device could detect this change and convey this information to the system when the device is inserted into the system by the user. There may be an additional detection device in the system to perform these tasks, or such a device may be incorporated into another system component. In some embodiments information may be wirelessly transmitted to either the system or the external device, such as a personal computer or a television. Likewise, a sensor in the system can detect similar changes. In some embodiments, it may be desirable to have a sensor in the shipping packaging as well, either instead of in the system components or in addition thereto. For example, adverse conditions that would render an assay cartridge or system invalid that can be sensed can include exposure to a temperature higher than the maximum tolerable or breach of the cartridge integrity such that moisture penetration.

In an embodiment, the system comprises a communication assembly capable of transmitting and receiving information wirelessly from an external device. Such wireless communication may be Bluetooth or RTM technology. Various communication methods can be utilized, such as a dial-up wired connection with a modem, a direct link such as a T1, ISDN, or cable line. In some embodiments, a wireless connection is established using exemplary wireless networks such as cellular, satellite, or pager networks, GPRS, or a local data transport system such as Ethernet or token ring over a local area network. In some embodiments the information is encrypted before it is transmitted over a wireless network. In some embodiments the communication assembly may contain a wireless infrared communication component for sending and receiving information. The system may include integrated graphic cards to facilitate display of information.

In some embodiments the communication assembly can have a memory or storage device, for example localized RAM, in which the information collected can be stored. A storage device may be required if information cannot be transmitted at a given time due to, for example, a temporary inability to wirelessly connect to a network. The information can be associated with the device identifier in the storage device. In some embodiments the communication assembly can retry sending the stored information after a certain amount of time.

In some embodiments an external device communicates with the communication assembly within the reader assembly. An external device can wirelessly or physically communicate with a system, but can also communicate with a third party, including without limitation a patient, medical personnel, clinicians, laboratory personnel, or others in the health care industry.

In some embodiments the system can comprise an external device such as a computer system, server, or other electronic device capable of storing information or processing information. In some embodiments the external device includes one or more computer systems, servers, or other electronic devices capable of storing information or processing information. In some embodiments an external device may include a database of patient information, for example but not limited to, medical records or patient history, clinical trial records, or preclinical trial records. An external device can store protocols to be run on a system which can be transmitted to the communication assembly of a system when it has received an identifier indicating which device has been inserted in the system. In some embodiments a protocol can be dependent on a device identifier. In some embodiments the external device stores more than one protocol for each device. In other embodiments patient information on the external device includes more than one protocol. In some instances, the external server stores mathematical algorithms to process a photon count sent from a communication assembly and in some embodiments to calculate the analyte concentration in a bodily fluid sample.

In some embodiments, the external device can include one or more servers as are known in the art and commercially available. Such servers can provide load balancing, task management, and backup capacity in the event of failure of one or more of the servers or other components of the external device, to improve the availability of the server. A server can also be implemented on a distributed network of storage and processor units, as known in the art, wherein the data processing according to the present invention reside on workstations such as computers, thereby eliminating the need for a server.

A server can includes a database and system processes. A database can reside within the server, or it can reside on another server system that is accessible to the server. As the information in a database may contain sensitive information, a security system can be implemented that prevents unauthorized users from gaining access to the database.

One advantage of some of the features described herein is that information can be transmitted from the external device back to not only the reader assembly, but to other parties or other external devices, for example without limitation, a PDA or cell phone. Such communication can be accomplished via a wireless network as disclosed herein. In some embodiments a calculated analyte concentration or other patient information can be sent to, for example but not limited to, medical personnel or the patient.

Accordingly, the data generated with the use of the subject devices and systems can be utilized for performing a trend analysis on the concentration of an analyte in a subject which changes over time.

Another advantage as described herein is that assay results can be substantially immediately communicated to any third party that may benefit from obtaining the results. For example, once the analyte concentration is determined at the external device, it can be transmitted to a patient or medical personnel who may need to take further action. The communication step to a third party can be performed wirelessly as described herein, and by transmitting the data to a third party's hand held device, the third party can be notified of the assay results virtually anytime and anywhere. Thus, in a time-sensitive scenario, a patient may be contacted immediately anywhere if urgent medical action may be required.

As described elsewhere herein, imaging may be used for detection. Imaging can be used to detect one or more characteristic of a sample. For example, imaging may be used to detect the presence or absence of a sample. The imaging may be used to detect the location, placement, volume or concentration of a sample. The imaging may be used to detect the presence, absence, and/or concentration of one or more analytes in the sample.

In some embodiments, a single measurement may be used to capture various information about a sample and/or analytes. For example, a single measurement may be used to capture information about the volume of a sample and the concentration of an analyte within the sample. A single measurement may be used to capture information about the presence and/or concentration of a plurality of analytes and/or types of analytes within the sample. A single image may be used to capture information relating to one, two, or more of the information or types of information described herein.

Such imaging and detection may provide more precise and accurate assays, which may be advantageous in situations with small sample volumes, such as those described elsewhere herein. Additional examples of volumes of sample may include 5000 µL or less, 2500 µL or less, 2000 µL or less, 175 µL or less, 150 µL or less, 100 µL or less, 80 µL or less, 70 µL or less, 60 µL or less, 50 µL or less, 30 µL or less, 20 µL or less, 15 µL or less, 10 µL or less, 8 µL or less, 5 µL or less, 1 µL or less, 500 nL or less, 300 nL or less, 100 nL or less, 50 nL or less, 10 nL or less, 1 nL or less, 500 pL or less, 250 pL or less, 100 pL or less, 50 pL or less, 10 pL or less, 5 pL or less, or 1 pL or less. In some embodiments, the sample volume may include less than or equal to about 3 drops from a fingerstick, less than or equal to about 2 drops from a fingerstick, or less than or equal to about 1 drop from a fingerstick. Such small volumes may be useful in point of service applications.

Such imaging and/or detection may yield assays with low coefficient of variation. A coefficient of variation may be the ratio between the standard deviation and an absolute value of the mean. In an embodiment, a reaction and/or assay may have a coefficient of variation (CV) (also "relative standard deviation" herein) less than or equal to about 20%, 15%, 12%, 10%, 9%, 8%, 7%, 6%, 5%, 4%, 3%, 2%, 1%, 0.5%, 0.3%, or 0.1%. A single reaction and/or assay, or a procedure with a plurality of reactions and/or assays may have a coefficient of variation of less than or equal to about 20%, 15%, 12%, 10%, 9%, 8%, 7%, 6%, 5%, 4%, 3%, 2%, 1%, 0.5%, 0.3%, or 0.1%. In some embodiments, an imaging and/or detection step, or a procedure with a plurality of imaging and/or detection steps may have a coefficient of variation of less than or equal to about 20%, 15%, 12%, 10%, 9%, 8%, 7%, 6%, 5%, 4%, 3%, 2%, 1%, 0.5%, 0.3%, or 0.1%.

In some embodiments, the use of imaging with a device that may be placed at a point of service location may improve the overall performance of the device. The accuracy and/or precision may be improved and/or the coefficient of variation may be reduced. The performance of the device may be improved when handling small samples, such as those volumes described herein. The imaging may be used in combination with other detection systems, in combination with other processes, or as a standalone system. Improvement in performance may include a decrease in the coefficient of variation of about 15%, 12%, 10%, 9%, 8%, 7%, 6%, 5%, 4%, 3%, 2%, 1%, 0.5%, 0.3%, or 0.1%.

Imaging may be useful for various detection types for one or more types of assays or sample handling procedures. Examples of such assays or sample handling procedures may include centrifugation, separation, cytometry, immunoassay, ELISA, nucleic acid assay, enzymatic assay, colorimetry, or any other type of assay or reaction described elsewhere herein.

Imaging systems may provide multiple advantages over other methods for data collection, data processing, and results interpretation. Imaging systems may maximize, or increase the efficiency of, the use of small samples and enhancing system-level performance. Imaging systems may be used for detection as standalone systems or may be used in combination with other detection systems or mechanisms.

In some systems, sensors and systems may be used (such as photodiodes and photomultiplier tubes and associated optics/devices) that typically do not provide any spatial information about the sample being interrogated. Rather, these systems may collect information about the sample after the information has been spatially integrated, typically losing spatial information related to the sample. While integrating the signal in space from the sample may augment the signal levels being detected by the sensor, advances in sensitivity of optical and other sensors may negate the need for such integration. Imaging for detection may be used in the place of such sensors, or may be used in conjunction with such sensors.

Imaging systems may be used that may advantageously have one or more of the following features. Imaging sensors may have sensitivity and dynamic range that meet and/or exceed that of conventional non-imaging sensors. Imaging devices may maintain spatial aspects of the sample being interrogated, providing significant ability for post processing. Post processing can include QA/QC (e.g., quality control, such as automated error detection and/or review by pathologist), and/or image analysis to extract specific sample features. The imaging device can utilize 3D, 2D, 1D (line sensors), and/or point sensors with a means to translate the sample relative to the collection optics/sensor to enable the spatial reconstruction of the sample. Data collected from the imaging device can be processed to extract very specific information, such as morphological features of the sample (such as cell counts), data from select regions of the image (peak fluorescence across a sample or in a cell within the image). Data collected from the imaging device can be processed to improve the sensitivity and resolution of the measurement. Data collected from the imaging device can enable the assessment of signal variation across the sample being imaged. The data may be post processed to calculate mean, standard deviation, maximum, minimum, and/or other applicable statistics across the sample or within any regions of interest identified in the sample images. Imaging devices enable the exploration of changes in the sample over time by collecting multiple images and comparing changes in the images over time and space, such as would be evident in an aggregation processes (such as for an assay of prothrombin time) or other (e.g., chemical, physical, biologic, electrical, morphological) changes in the sample over time and space. Imaging devices may enable more rapid data acquisition of arrays, tissue sections, and other assay/sample configurations.

Cytometry Application

In some embodiments, any of the embodiments described herein may be adapted to enable the system to perform cytometry. Cytometry (e.g., enumeration and function analysis of cells) in the system may be performed using image analysis. Blood can be processed using the pipette and centrifuge as described previously herein. Typically, a known measured volume of blood (1-50 uL) may first be centrifuged and the plasma fraction removed. The cell fraction may then be re-suspended into buffer by use of the pipette repeatedly to dispense and aspirate. A cocktail of fluorescent antibodies may be directed to selected cell markers (such as CD45, CD4 etc.). Following a brief incubation, a reagent which may act as a fixative for the white cells and a lysing agent for red cells can be added. Following another incubation white cells may be collected by centrifugation and the supernatant hemolysate removed by aspiration. The stained white cells can be re-suspended in a measured volume of buffer (typically less than the original blood volume (say 1-20 uL) and dispensed into transparent capillary channels for image analysis. Typically up to three or even five or more cell types can be imaged using antibodies having different fluorescent labels or and/or antibodies labeled with different fluor/protein ratios. When more cell types have to be counted or analyzed, more than one reaction mixture can be used. In some embodiments, a reaction mixture can be used to count or analyze various numbers of cell types.

In some embodiments, the capillary channels are typically about 10-100 um deep, 0.5-2 mm wide and 0.5-5 cm long. The capillary channels may have other dimensions, including but limited to other dimensions described elsewhere herein. The stained cell dispersion may fill the channel usually by capillary action and the cells may be allowed to settle on the lower channel surface. The channels can be illuminated with one or more lasers or other light sources (e.g., LEDs). The optical train may have one or more optical elements, such as dichroic mirrors or lenses, and may or may not magnify the field of view. In some embodiments, the field of view may be magnified 2-100 fold. A series of images may be collected typically representing a field of view of about 1 mm×0.5 mm and which contains 1-10,000 cells (ideally, 300 cells of interest) imaged onto a sensor having an area of about 1000×1000 pixels (1 million total).

A series of images representing adjacent sections of channel may be collected. A mechanical stage can be used to move the channels relative to the light source. In some cases, a servo-mechanism may move the stage in a vertical direction so as to focus the image. In some embodiments, the light source or one or more optical elements may move relative to the stage to focus the image. Images are usually made using one or more combinations of light sources and optical filters. The light sources may be turned on and off and filters moved into the light path as needed. Preferably up to 1000 cells of any given type may be counted. In other embodiments, various numbers of cells of any given type may be counted, including but not limited to more than, less than, or equal to about 1 cell, 5 cells, 10 cells, 30 cells, 50 cells, 100 cells, 150 cells, 200 cells, 300 cells, 500 cells, 700 cells, 1000 cells, 1500 cells, 2000 cells, 3000 cells, 5000 cells. Cells may be counted using available counting algorithms. Cells can be recognized by their characteristic fluorescence, size and shape. Pattern recognition algorithms may be employed to exclude stained cell debris and in most cases where there are cells which are aggregated these can either be excluded from the analysis or interpreted as aggregates.

A cytometry platform may be an integrated automated microscopy device capable of the following tasks in a fully automated, controlled environment. One or more of the following tasks may occur in cytometry applications. The following tasks may occur in the order they appear or in alternate orders or other tasks may be substitute as appropriate.

1. Isolation of blood cells of the desired type
2. Labeling of cells with fluorescent and/or colored dyes and/or beads
3. Confinement of cell suspension in an optically compatible cuvette
4. Imaging of cells using fluorescence microscopy, darkfield illumination, and/or brightfield illumination
5. Automated analysis of images to extract desired cellular attributes
6. Automated analysis of extracted information using advanced statistical and classification methods to derive clinically reportable information.

In the following sections, each of these tasks is discussed in greater detail; images and sketches are provided wherever deemed necessary.

1. Isolation of Blood Cells of the Desired Type.

Blood cells of a desired type may be isolated in accordance with one or more embodiments described elsewhere herein. For example, such isolation may occur as referred to in previous descriptions relating to the cytometry or the centrifuge.

2. Labeling of Cells with Fluorescent and/or Colored Dyes and/or Beads.

Figure 123:
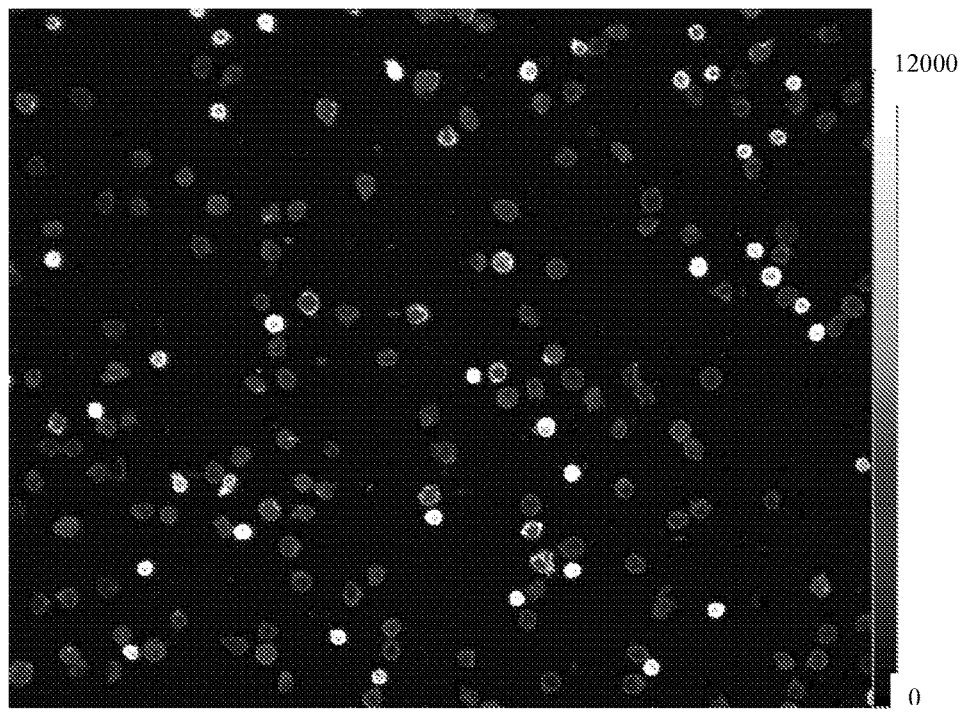
FIG. 123 provides an example of a fluorescence micrograph showing labeled leukocytes.

Specific fluorescent dyes may be employed. Cells of interest can be incubated with pre-aliquoted solutions of fluorescently labeled binders (e.g., antibodies, aptamers, etc.) which are specific to markers on these cells. A key consideration may be pairing 'bright" or high extinction coefficient and high quantum yield fluors with markers for which cells have a lower binding capacity; and vice versa. For example, the marker CD22 may be expressed on B-lymphocytes at about one tenth the level as CD45. Given this relative expression, CD22 may be labeled with a "bright" dye and CD45 may be labeled with the "dimmer" dye. The markers to be labeled using this technique can be either intracellular or cell-surface markers. The sensitivity of detection and quantification can be improved by using a secondary labeling scheme for low expression markers. Briefly, a primary binder may be conjugated with another molecule which can be specifically recognized by a secondary binder. A secondary binder labeled with a higher number of fluorophores can then bind the primary binder in situ and enhance fluorescence signal. One scheme for achieving this may be the use of biotin conjugated anti-CD22 antibody which may be in turn recognized by an anti-biotin antibody that is labeled with fluorescein isothiocyanate (FITC). The use of can dramatically enhance fluorescence signal. FIG. 123 provides an example of a fluorescence micrograph showing labeled leukocytes. The example illustrates a fluorescence micrograph of Alexa-Fluor 647-anti-CD45 labeled human leukocytes in a fixed, lysed blood sample. The pseudocolor scheme is used to enhance perception of the different between 'bright' cells (with high CD45 expression) and 'dim' cells (with low CD45 expression).

Color stains of cell smears may also be employed within the system. For example, the manual procedure given in StainRITE™ Wright-Giemsa Stain (Polysciences Inc.) can be automated and read in the devices of the subject invention.

In some embodiments, non-specific fluorescent dyes can be used. For the purposes of differentiating leukocyte subpopulations, the platform can also use fluorescent dyes which may bind to nucleic acids (e.g., SYTO, Hoechst) or lipid membranes (e.g., Di1, DiD, FM-4-64).

3. Confinement of Cell Suspension in an Optically Compatible Cuvette.

In some embodiments, cytometry cuvettes may be designed to confine a pre-labeled cell suspension of fixed volume into a 'channel' fabricated so as to provide an optically clear imaging material above and below the cells. Sample may be introduced into the channel via a sample entry port. At some distance from the sample entry port, an air vent may allow the release of air pressure and flow of sample into the channel.

The channel dimensions may be designed to hold a pre-defined known volume of fluid, regardless of the volume dispensed at the sample entry port. Each cuvette may have multiple channels of same and/or different volumes, each with at least one sample entry port and at least one air vent.

The concentration of cells of interest in the sample can be adjusted during sample preparation such that after confinement in the cuvette, a desired number of cells per field of view in the imaging system can be achieved. One method for doing this may be to image a container with the cell dispersion and measure turbidity. Using a pre-established relationship between turbidity and cell count, the cell density can be calculated. Typically, the cell dispersion will be made in a volume of buffer such that with the lowest likely cell count, and the cell concentration will be greater than optimal for image-based cell counting. More buffer may then be added to bring the dispersion to the optimal level.

The imaging area of the cuvette may be designed so as to provide a sufficient number of cells for the application of interest. For example, counting the abundant RBCs may require counting of only 1000-2000 cells and hence a diluted sample and only a small imaging area in the cuvette. However, counting rare myeloblasts may require in some cases the ability to image more than 100,000 (total) cells. In such a scenario, the system may concentrate the cell suspension so that 100,000 cells may be imaged with a reasonable number of fields of view. Therefore, the channel on the cuvette dedicated to RBC imaging will be smaller than the one dedicated to imaging myeloblasts.

The cuvette may be designed to be picked up by a standard pipetting mechanism in an automated fashion to allow the transfer of the cuvette to the imaging platform. The pipetting mechanism's tip ejector can eject the cuvette from the pipetting mechanism onto the imaging platform. Registration of cuvette to imaging platform may take place in two steps. Upon transfer of the cuvette to the imaging platform, static registration features on the cuvette may interface with mating features on the imaging platform to align the cuvette parallel to the imaging platform's optical axis (X,Y registration). Registration may then be completed by a mechanism located on the imaging platform. This mechanism may bias the cuvette against a planar surface perpendicular to the imaging platform's optical axis (Z registration), thereby constraining the sample within the imaging platform's focal range.

4. Imaging of Cells Using Fluorescence, Darkfield Illumination, Brightfield Illumination.

The method of imaging the cells may also be applied to other applications of the invention described elsewhere herein. The imaging techniques, as previously described, can be used for other imaging uses.

Illumination Capabilities:

The cytometry platform may be designed to have three types of illumination schemes: epi-fluorescence, darkfield and brightfield. The modular nature of the setup also allows integration of phase-contrast and differential-interference contrast (DIC).

Epi-fluorescence illumination may be achieved by the use of three laser lines (e.g., 488 nm, 532 nm and 640 nm), but the modular nature of the system also allows for integration of other light sources, such as other laser sources, LEDs and standard arc-lamps (e.g. Xenon, Mercury and Halogen). Further, two different sources can be used simultaneously, if required. Consequently, the cytometry platform can be used to image a large variety of fluorescent dyes. The combination of illumination sources and emission optics can be configured to achieve various numbers (e.g., 3-5) spectrally independent channels of imaging.

Figure 124:
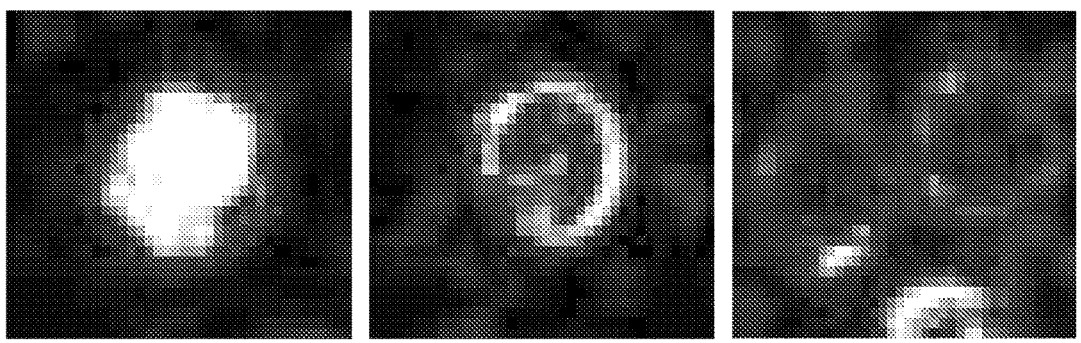
FIG. 124 provides an example of intracellular patterns using darkfield images.

Darkfield illumination may be achieved by the use of a ringlight (located either above or below the sample), a darkfield abbe condenser, a darkfield condenser with a toroidal mirror, an epi-darkfield condenser built within a sleeve around the objective lens, or a combination of ringlight with a stage condenser equipped with a dark stop. Fundamentally, these optical components can create a light cone of numerical aperture (NA) greater than the NA of the objective being used. The choice of the illumination scheme depends upon a number of considerations such as magnification required, mechanical design considerations, or size of the imaging sensor. A ringlight based illumination scheme generally provides uniform darkfield illumination over a wider area while at the same time providing sufficient flexibility in mechanical design of the overall system. FIG. 124 provides an example of intracellular patterns using darkfield images. The example shows different intracellular patterns in darkfield images of human leukocytes. (a) A strong scattering pattern due to presence of granules in eosinophils, (b) a polymorphonuclear neutrophil with characteristic nucleolar lobes and (c) cells that do not scatter light to a significant degree (lymphocytes or basophils)

Figure 126:
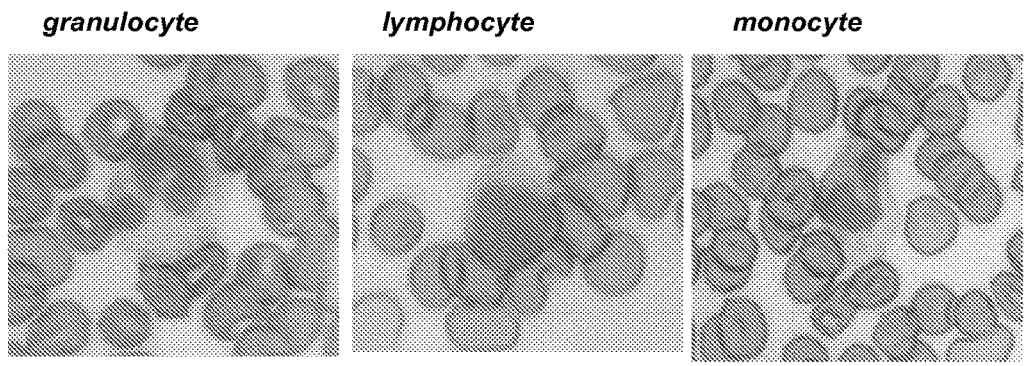
FIG. 126 provides an example of brightfield images of human whole blood.

Brightfield illumination may be achieved by the use of a white light source along with a stage-condenser to create Koehler illumination. FIG. 126 provides an example of brightfield images of human whole blood. The example shows brightfield images of a human whole blood smear stained with the Wright-Giemsa staining method. Characteristic patterns of staining of human leukocytes are apparent. The characteristically shaped red cells can also be identified in these images.

Automatic Filter Wheel:

An automatic filter wheel may allow control of the imaging optical path to enable imaging of multiple fluorophores on the same field of view.

Image Based Auto-Focusing:

The cytometry platform may use an image-based algorithm to control the z-position (e.g., vertical position) of the objective (i.e., its distance from the sample) to achieve auto-focusing. Briefly, a small image (for example, 128×128 pixels) may be captured at a fast rate using darkfield illumination. This image may be analyzed to derive the auto-focus function which may be used to measure of image sharpness. Based on a fast search algorithm the next z-location of the objective may be calculated. The sample may be moved to the new z-location and another small image may be captured. In some embodiments, this closed-loop system does not require the use of any other hardware for focusing.

Translation of Stage:

The microscope stage may be connected to computer-controlled stepper motors to allow translation in the X and Y directions (e.g., horizontal directions). At every location, the desired number of images may be captured and the stage may be moved to the next XY position.

Imaging Sensor:

A camera with a CCD, EMCCD, CMOS or in some cases a photo-multiplier tube can be used to detect the signal.

5. Analysis of Images to Extract Desired Cellular Attributes.

The cytometry platform may use different illumination techniques to acquire images that reveal diverse properties and features of the cells. Labeling with cell-marker specific binders may reveal the degree of expression of that particular marker on the cell surface or in the cell. Darkfield image may reveal the light scattering properties of the cell. The internal and external features of the cell which scatter more light appear brighter and the features which scatter lesser amounts of light appear darker in a darkfield image. Cells such as granulocytes have internal granules of size range (100-500 nm) which can scatter significant amount of light and generally appear brighter in darkfield images. Furthermore, the outer boundary of any cell may scatter light and may appear as a ring of bright light. The diameter of this ring may directly give the size of the cell. Brightfield images of cells can reveal cell size, phase-dense material within the cells and colored features in the cell if the cells have been previously stained.

An image processing library may extract one or more of the following information for each cell (but is not limited to the following):

1. Cell size
2. Quantitative measure of cell granularity (also popularly called side scatter, based on flow cytometry parlance)
3. Quantitative measure of fluorescence in the each spectral channel of imaging, after compensating for cross-talk between spectral channels
4. Shape of the cell, as quantified by standard and custom shape attributes such as aspect ratio, Feret diameters, Kurtosis, moment of inertia, circularity, solidity etc.
5. Color, color distribution and shape of the cell, in cases where the cells have been stained with dyes (not attached to antibodies or other types of receptor).
6. Intracellular patterns of staining or scattering or color that are defined as quantitative metrics of a biological feature, for example density of granules within cells in a darkfield image, or the number and size of nucleolar lobes in a Giemsa-Wright stained image of polymorphonuclear neutrophils etc.
7. Co-localization of features of the cell revealed in separate images The image processing algorithms utilized in this step may use combinations of image filtering, edge detection, template matching, automatic thresholding, morphological operations and shape analysis of objects.

6. Analysis of Extracted Information using Advanced Statistical and Classification Methods to Derive Clinically Reportable Information.

Any number of measured attributed may be extracted from images of cells. For example, measured attributes of each cell extracted from the images can range from 7-15, thus creating a 7 to 15 dimensional space within which each cell is a point. If n measured attributes are extracted from the images, an n dimensional space may be provided, within which each cell is a point.

Based on data acquired for a large number of cells (e.g., 100-100,000 cells) a complex n-dimensional scattered data set may be generated.

Statistical methods may be used for clustering cells into individual separate populations in this n-dimensional space. These methods may also use state-of-the-art knowledge from cell biology and hematology to aid in clustering and cell population identification.

Figure 125:
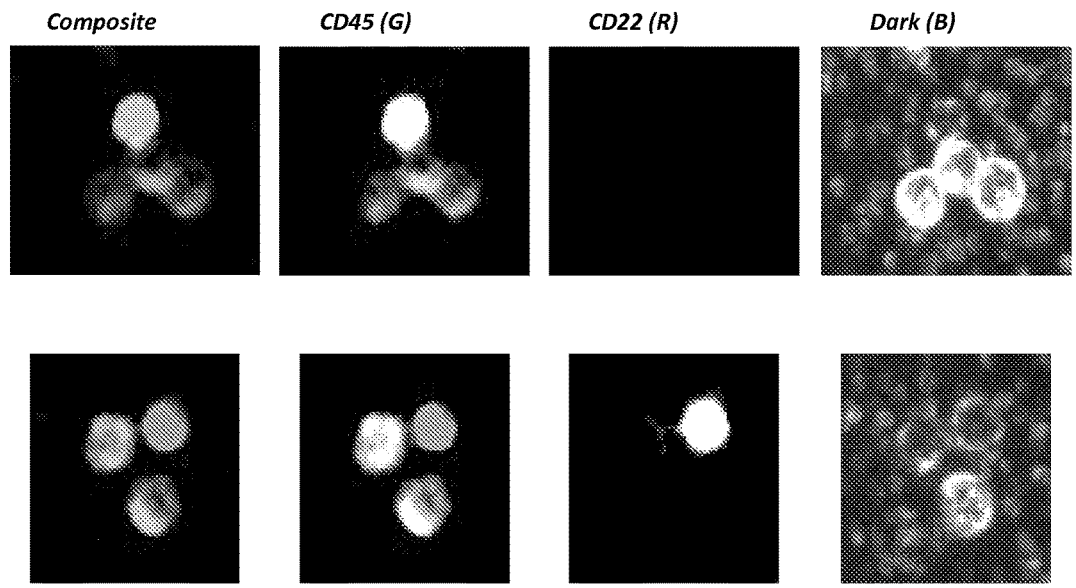
FIG. 125 provides an example of multi-parameter acquisition of data from labeled cell samples.

FIG. 125 provides an example of multi-parameter acquisition of data from labeled cell samples. Human leukocytes were labeled with the pan-leukocyte marker anti-CD45-Alexa Fluor 700 (shown here in green) and the B-cell marker anti-CD22-APC (shown here in red). The individual channels show different patterns of CD45, CD22 expression and side scatter. Cells which are positive for CD22 and CD45 (B-lymphocytes) show the characteristically low side scatter. On the other hand cells such as neutrophils and eosinophils which have high side scatter do not show labeling for CD22.

Figure 127:
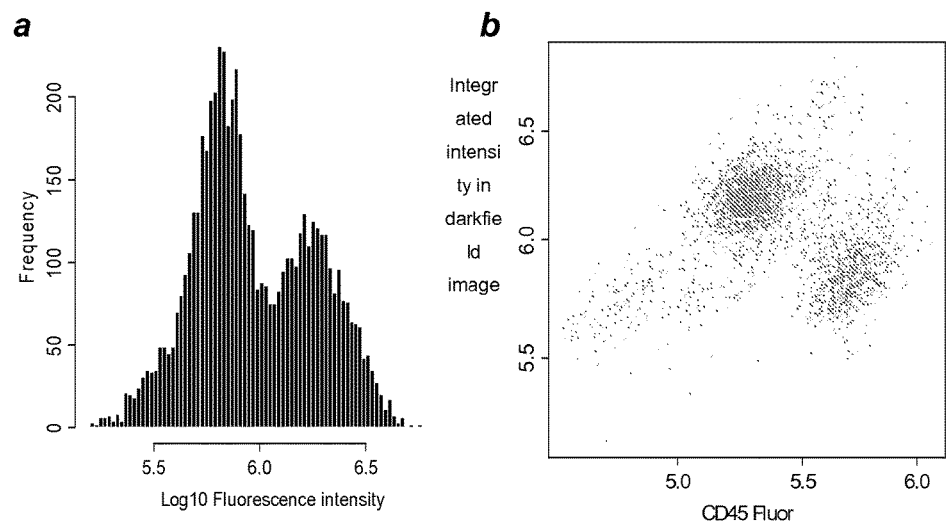
FIG. 127 provides an example of quantitative multi-parametric data acquisition and analysis.

FIG. 127 provides an example of quantitative multi-parametric data acquisition and analysis. For example, a histogram may be provided which may show distribution of CD45 intensity on human leukocytes. Any other graphical data distribution techniques may be employed to shows the distribution. In some embodiments, a scatter plot of side scatter may be provided. The side scatter may be determined by dark-field image analysis versus CD45 fluorescence intensity for a human leukocyte sample. The side scatter plot may show two main populations of granulocytes (top left) and lymphocytes (bottom right).

Foregoing sections describe the main components and capabilities of the cytometry platform and applications. Based on these capabilities, a wide gamut of cell-based assays can be designed to work on this platform. For example, an assay for performing a 5-part leukocyte differential may be provided. The reportables in this case may be number of cells per microliter of blood for the following types of leukocytes: monocytes, lymphocytes, neutrophils, basophils and eosinophils. The basic strategy for development of this assay on the cytometry platform may be to convert this into a problem where some attributes of leukocytes are measured such as side scatter, CD45 fluorescence intensity, or CD20 fluorescence intensity so that leukocytes can be segregated into (e.g., 5) different populations in this n-dimensional space. The regions made around a cluster of cells can be positioned on a scatter plot in 2-dimensional space are called "gates" after flow cytometry parlance. An example labeling and "gating" strategy is as follows:

| Marker | Label | Purpose |
| --- | --- | --- |
| CD2/CRTH2/CD19/CD3 cocktail | PE-Cy7 | Identification of lymphocytes, labeling of basophils and eosinophils |
| CD45 | Alexa-Fluor 647 | Pan-leukocyte marker to label all leukocytes |
| CD14/CD36 cocktail | FITC | Identification of monocytes |

| Cell type | "Gate" |
| --- | --- |
| Basophils | CD2/CRTH2/CD19/CD3 pos, SSC low, CD45 intermediate, CD14/CD36 low |
| Eosinophils | CD2/CRTH2/CD19/CD3 pos, SSC high, CD45 high, CD14/CD36 low |
| Neutrophils | CD2/CRTH2/CD19/CD3 neg, SSC high, CD45 intermediate (less Eosinopils) |
| Lymphocytes | CD2/CRTH2/CD19/CD3 pos, SSC low, CD45 high, CD14/CD36 low |
| Monocytes | CD2/CRTH2/CD19/CD3 neg, SSC int, CD45 int, CD14/CD36 pos |

The cytometry platform and analysis system described herein may advantageously permit automated sample preparation and execution based on ordered sample. The systems and methods described may also enable specific identification of cells as opposed to VCS (volume, conductivity and scatter), which can increase confidence in identification and reduce instances for confirmatory testing. The image analysis described herein may also permit preservation of cell images for later confirmation, analysis as required. There may also advantageously be availability of morphological features of the cell. In some embodiments, dynamic adjustment of sample prep and imaging parameters to deal with cell samples of wide range of concentrations may be provided.

In some embodiments, the centrifuge may be used to prepare and concentrate cell populations. A method may include the use of the centrifuge for cell preparation and the imaging and analysis system described elsewhere herein.

In some embodiments, a combination of dark-field imaging and imaging of cells stained with multiple fluorescent antibodies may be used. Such a combination may give the equivalent of FACS analysis in a much simpler and less expensive device than other techniques.

In accordance with some embodiments of the invention, the systems and methods described herein may enable one or more of the following features. Such features may be advantageous for various applications. In some embodiments, automated sample inspection and processing may be enabled. Such sample inspection and processing may include one or more of the following: sample quality, sample volume measurement, dilution (and measurement of dilution factors), and separation of red and white cells from plasma.

An automated chemical/assay related process may also be employed. This may include precipitation, mixing or sedimentation.

In some embodiments, there may be automated measurement of any and all assays that produce luminescence or change light (e.g., color chemistry). These may include one or more of the following: spectrophotometry, fluorimetry, luminometry, turbidimetry, nephelometry, refractometry, 3-color image analysis, polarimetry, measurement of agglutination, image analysis (which may employ one or more of the following: camera, digital camera, scanner, lens-less photography, 3-D photography, video photography), or microscopy.

Automated quality control and/or calibration of assays may also be provided within the systems and methods described herein.

In some embodiments, two-way communication may be provided. Such communication may enable record keeping of all assay steps. The two-way communication may also enable changes in assay protocols to optimize or increase completion of multiple assays.

Quality Control/Complementary Applications

In some embodiments, imaging may be used in conjunction with one or more other measurements or detection steps. The imaging may be complementary to other techniques, procedures, reactions, and/or assays. For example, imaging may be used to perform one or more quality control check or step for any other action, such as a sample preparation, assay, or detection step. Imaging may be used for the facilitation of other detections. Imaging may be used to improve the accuracy and/or precision of collected data. The imaging may be a quality control aspect to verify data, results, and/or any measurements. The imaging may be a control mechanism or improvement mechanism. Imaging may be used to detect one or more condition that may affect collected data and/or the accuracy and/or precision of the data. Thus, imaging may improve sample preparation, assay, and/or detection procedures. This may be particularly advantageous in situations where there are small sample volumes, such as volumes described elsewhere herein.

In an example, a detection step may occur to determine the presence and/or concentration of an analyte. Detection may occur of one or more signal that may be representative of data that may be useful for subsequent qualitative and/or quantitative evaluation. Detection may or may not include the detection of visible light. Detection may include the measurement of energy from anywhere along the electromagnetic spectrum (e.g., infra-red, microwave, ultraviolet, gamma ray, x-ray, visible light). Detection may occur using any type of sensor, which may include an optical sensor, temperature sensor, motion sensor, pressure sensor, electricity sensor, acoustic sensor, chemical sensor, spectrometer, or any other sensor described elsewhere herein, or any combination thereof. In some embodiments, detection may or may not include a spatial distribution of light and/or energy. In some instances, detection may or may not include an energy density distribution.

Imaging may be capable of detecting one or more condition under which the detection takes place. Imaging may be used to detect the condition of a sample, reagent, container, portion of the device that may be used in the detection. In some embodiments, the imaging may be visible imaging. For example, imaging may include capturing a snapshot, photo, and/or picture. Imaging may include capturing a spatial distribution of energy along the electromagnetic spectrum. The energy along the electromagnetic spectrum may include visible light, or may include other ranges (e.g., infra-red, ultraviolet, or any other described herein). For example, a spatial distribution of visible light may include a two-dimensional image. In some embodiments, imaging may include the use of an image capture device, which is described in greater detail elsewhere herein. Some examples of image capture devices may include a camera, such as a lens-less (computational) camera (e.g., Frankencamera) or open-source camera. An image capture device may be capable of capturing signals that may be capable of generating a one-dimensional, two-dimensional, or three-dimensional representation of the item that is imaged. In some cases, an image capture device may be a motion-sensing input device configured to provide a three-dimensional or pseudo three-dimensional representation of an object.

The imaging technique may be the same or may be different from the detection mechanism utilized. In some instances, different types of detection mechanisms are used between the detection step and the quality control imaging step. In some instances, detection may include an energy band assessment or energy density distribution, such as from a spectrometer, while quality control imaging may include a spatial distribution of visible light, such as from a camera.

Sensitive detection may be achieved by imaging. For example, an imaging device may be able to capture an image to within 1 mm, 500 micrometer (um), 200 um, 100 um, 75 um, 50 um, 25 um, 15 um, 10 um, 7 um, 5 um, 1 um, 800 nanometer (nm), 700 nm, 500 nm, 300 nm, 100 nm, 50 nm, 30 nm, 10 nm, 5 nm, 1 nm, 500 picometer (pm), 300 pm, or 100 pm. In an example, the imaging may be achieved by a camera which may have a resolution of greater than or equal to about 2 megapixels, 4 megapixels, 6 megapixels, 8 megapixels, 10 megapixels, 12 megapixels, 15 megapixels, 20 megapixels, 25 megapixels, 30 megapixels, 40 megapixels, or 50 megapixels, or more.

Imaging may be used to detect an error or other fault state. Imaging may be used to determine a condition that may increase the likelihood of an error and/or result in inaccuracies and/or imprecision. For example, imaging may be used to determine the presence and/or absence of one or more undesirable materials. Examples of undesirable materials may include bubbles, particles, fibers, particulates, debris, precipitates, or other material that may affect a measurement. In another example imaging may be used to determine if a volume of sample, reagent, or other material falls within a desired range, or whether a sample, reagent, or other material is located in a desired location. The imaging may be used to determine the concentration of a sample, reagent or other material, or whether the sample, reagent, or other material falls into a desired concentration range.

In one example, an enzymatic assay may be performed on a small volume of sample. Examples of volume values may be provided elsewhere herein. A spectrometer or other detection method or mechanism described herein may be used to perform a detection step for the enzymatic assay. An imaging step may occur to determine the conditions under which the detection is occurring. For example, the imaging step may determine whether there are undesired particulates, such as bubbles, or any other undesired conditions. The imaging step may verify whether the assay is operating as it should. The imaging step may confirm whether the operating conditions under which the assay is occurring and/or detection is being performed falls within desired tolerances or optimized conditions. In some examples, the imaging may include taking a snapshot of a reaction occurring in a container. The captured image may be analyzed for any undesirable and/or desirable conditions. In some instances, the captured image may be analyzed automatically in a computer assisted method. One or more processor may aid with the analysis of the captured image, in some cases using one or more routines implemented by way of machine-executable code stored in a memory location. The imaging may be used for quality control without requiring the intervention of a human.

The imaging may provide intelligence for a system. The imaging step may provide intelligence on the conditions under which sample preparation, assay, and/or detection occurs. The detection methods may provide more reliable, accurate, and/or precise measurements from a point of service device or component of the device, when utilizing the imaging in a quality control procedure. The quality control may be beneficial when small volumes are utilized.

Dynamic Feedback

In some embodiments, dynamic feedback may be provided during a sample processing step. For example, dynamic feedback may occur during a sample preparation step, assay step, and/or detection step. In some embodiments, dynamic feedback may be provided via imaging. Alternatively, dynamic feedback may occur via any other detection mechanism, such as those described elsewhere herein. In some embodiments, a dynamic feedback mechanism may utilize optical detection, electromechanics, impedance, electrochemistry, microfluidics, or any other mechanism or combination thereof.

Dynamic feedback may optionally utilize imaging or other detection mechanisms. The dynamic feedback may be involved in automated decision making for a system. For example, an image may be captured, and data may be captured that may be considered in the determination of a step. A sensor, such as an imaging sensor, may capture physical information which may be utilized in the determination of a subsequent step or procedure. Such subsequent steps or procedures may be determined on the fly in an automated fashion.

In an example, dynamic dilution may occur. A container, such as a cuvette or any other container described herein, may have a sample therein. A dynamic feedback mechanism (e.g., imaging, spectrophotometer, or other detection mechanism) may determine the concentration of a sample. In some embodiments, the determination may be a rough or crude determination. The initial determination may be a ballpark determination that may provide feedback that may put the sample into a condition for more precise or fine-tuned detection and/or analysis. In an example, the dynamic feedback mechanism may be an imaging method that may use an initial fluorescence detection to do the initial estimate for concentration.

The dynamic feedback mechanism may determine whether the sample concentration falls within an acceptable range. In one example, the concentration may be a cell concentration. A rough cell count may be performed to determine cell concentration. One or more signal from the dynamic feedback mechanism may be used for the cell count. In some embodiments, cells may be provided in a wide range of concentrations. In some instances, the concentrations may vary on over 1, 2, 3, 4, 5, 6, 7 or more orders of magnitude. In some embodiments, depending on the cell or analyte to be measured and/or analyzed, different concentrations may be provided within the same sample. Based on the determined concentration, the sample may be diluted or concentrated and/or amplified. For example, if the concentration is higher than a desired range, the sample may be diluted. If the concentration is lower than a desired range, the sample may be concentrated and/or amplified. The degree of dilution and/or concentration/amplification may be determined on the fly, based on the estimated concentration.

The degree of dilution and/or concentration/amplification may be determined in an automated fashion. Dynamic feedback may be automated. The dynamic feedback mechanism (e.g., imaging or other detection mechanism) may provide data which may be analyzed to determine an operational condition. For example, a sample concentration may be determined based on the dynamic feedback mechanism. A processor may be provided, capable of receiving and/or processing one or more signals from the dynamic feedback mechanism. Based on the received signals the processor may determine the concentration and whether the concentration falls within a desired range. If the concentration falls within the desired range, the processor may determine that no further dilution or concentration/amplification is needed. If the concentration is higher than the desired range, the processor may determine that dilution is needed. The processor may determine the degree of dilution needed based on how far the concentration falls outside the desired range. If the concentration is lower than the desired range, the processor may determine that concentration (or amplification) is needed. The processor may determine the degree of amplification needed based on how far the concentration falls below the desired range. Such determinations may be based on tangible computer readable media which may include code, logic, or instructions for performing one or more steps. Such determinations may be automated and thus made without requiring the intervention of a human. This may apply to any operational condition, and need not be limited to sample concentration, such as cell concentration.

In some embodiments, after an initial feedback measurement and dilution or concentration/amplification step, a more precise measurement may be taken. For example, a more precise measurement of cell counting may occur after the sample is determined to be in a desirable range. In some embodiments, a sample may reach a desirable range after a single dilution and/or concentration/amplification step. In other embodiments, additional feedback steps may occur and additional dilution and/or concentration/amplification steps may be provided, as necessary. For example, if an initial determination yields that a sample has a high concentration, a dilution step may occur. Following the dilution step, an additional feedback step may optionally occur. If the sample concentration does not fall into the desired (or otherwise predetermined) range, an additional dilution or concentration/amplification step may occur, depending on whether the measured concentration is above or below the desired range, respectively. This may be repeated as many times as necessary for the sample to fall into the desired range. Alternatively, feedback steps may or may not be repeated, or may be repeated a fixed number of times. In some embodiments, each feedback step may occur with a greater degree of precision. Alternatively, the same degree of precision may be utilized in each of the feedback steps.

In some embodiments, when a sample concentration (e.g., cell concentration, analyte concentration) falls into a desired range, the sample may be analyzed effectively. For example, the sample cell concentration may have a desired range that may be beneficial for imaging. A desired number of cells per field of view may be provided.

Cell quantification and enumeration by imaging can enhanced by controlling the cells density during imaging, thus limiting crowding and clustering of cells. Consequently the range of analyte concentration over which the assay is linear can be maximized or increased. In order to extend the assay linear range, the dynamic system may perform a prior, non-destructive measurement on the sample using a method which has a high dynamic range to provide determine a rough cell concentration in the sample. An algorithm may then calculate the dilution ratio required to bring the cell concentration in the acceptable range for the main measurement. Dilution and/or concentration/amplification may be provided accordingly, thereby providing dynamic dilution and/or concentration.

Such dynamic feedback, such as dynamic dilution, may be advantageous in systems utilizing small volumes. In some embodiments, a total sample volume may include any of the volumes described elsewhere herein. In some instances, the volumes for a particular portion of a sample to be analyzed may have any of the volumes described elsewhere herein. Dynamic dilution may assist with providing low coefficient of variation. For example, a coefficient of variation for a sample preparation, assay, and/or detection step may have a coefficient of variation value as described elsewhere herein. This may be advantageous in point of service devices, which may utilize small volumes, and/or have low coefficients of variation.

Dynamic feedback may advantageously permit non-destructive testing of a sample. This may be advantageous in systems using small volumes. The same sample may be used for the initial feedback detection and for subsequent detections. The same sample may under initial feedback detection and subsequent detections within the same container (e.g., cuvette, vial, tip). A vessel may be provided with a sample that is outside a desired and/or detectable range in its initial state. For example, a concentration of one or more analytes and/or cells may fall outside a desired and/or detectable concentration range initially. The same sample may be measured within the range in the same vessel. In some embodiments, the concentration of the one or more analytes and/or cells may later fall within a desired and/or detectable range in the same vessel. In some embodiments, one or more intervening steps, such as dilution and/or concentration/amplification may be performed on the sample in order to get the sample into the desired and/or detectable range. Such intervening steps may be performed in an automated fashion.

In some embodiments, dilution may be provided to the sample in an automated fashion. For example, a diluent may be dispensed into a container holding the sample and mixed with the sample to effect a new sample volume. In some cases, the diluent includes a single diluent. In other cases, the diluent includes a plurality of diluents. The diluent can be dispensed into the container with the aid of a pumping system, valves and/or fluid flow channels for facilitating the flow, such as a microfluidic system having one or more microfluidic channels and/or one or more microfluidic pumps. The microfluidic system may include one or more mechanical and/or electromechanical components, such as a mechanical pumping system having one or more actuated (e.g., pneumatically actuated) valves for facilitating the flow of a fluid. The pumping system in some cases includes a mechanical pump configured to facilitate fluid flow. The pumping system can include one or more sensors for measuring and relaying operating parameters, such as fluid flow rate, concentration, temperature and/or pressure, to a control system. In an example, the diluent is dispensed into the container with the aid of a microfluidic system having a mechanical pump coupled to a microfluidic channel bringing the container in fluid communication with a diluent reservoir.

In some cases, a pumping system is provided to release a diluent based on a measured sample dilution. The sample dilution can be measured with the aid of a sensor, such as, for example, a light sensor. In an example, the light sensor is coupled with a light source for directing a beam of light through the sample, and subsequently measuring sample dilution based at least in part on the scattering of light through the sample. If the measured sample (e.g., cell, tissue) concentration is above a predetermined limit (or threshold), then the pumping system directs a diluent (e.g., water) from a diluent reservoir to a container holding the sample.

In some embodiments, dynamic dilution is electronically automated with the aid of a fluid flow system having a pump (e.g., microfluidic pump) in fluid communication with a fluid flow channel (e.g., microfluidic channel), and further including one or more valves for regulating fluid flow. The automation of dilution can be used to test and/or adjust calibration settings, such as preset dilution fluid volumes used to effect a desired concentration.

In some situations, the pump comprises one or more valves, such as pneumatically-actuated valves. The pump, fluid flow channel and one or more valves bring a diluent reservoir in fluid communication with a container configured to hold a sample. The one or more valves and/or the pump can be in electrical communication with a control system having a processor for regulating the flow of diluent from the diluent reservoir to the to regulate the concentration of the sample.

Dynamic feedback advantageously enables the automated regulation of sample concentration while minimizing, if not eliminating, user involvement. In some cases, the concentration of a sample is automatically regulated (e.g., diluted or amplified) without any user involvement. Such minimal user involvement can provide low coefficient of variation in imaging and overall system use, as described elsewhere herein.

In an example, dynamic feedback system is used to regulate the concentration of cells in a fluid sample using imaging. With the sample provided in a sample container, such as cuvette, the imaging is used to measure the concentration of cells in the fluid sample. The measured concentration can be a rough (or ballpark) measurement of concentration. The dynamic feedback system then dilutes the fluid sample by providing a diluent into the sample container. This may minimize, if not eliminate, any disturbance to (or destruction of) the cells upon dilution. An optional measurement of the concentration of cells in the fluid sample can then be made to measure the concentration following dilution. In some situations, following dilution a reaction can take place in the same sample container that was used to dilute the sample. In some situations, the reaction may take place in cases in which the dilution is not optimal.

In some cases, during dynamic feedback a rough measurement of sample concentration is made with the aid of a spectrometer, and a more precise measurement of sample concentration is made with the aid of an imaging device. The imaging device can include a light source (e.g., coherent light, such as a laser, or incoherent light) and a camera, such as a charge-coupled device (CCD) camera. In an example, following the rough measurement, the dynamic feedback system coarse adjusts the concentration of the sample by providing the diluent, and subsequently makes the more precise measurement. The sample concentration can be further adjusted by providing smaller volumes of a diluent (i.e., fine adjustment) in relation to the volume of the diluent provided during coarse adjustment. Alternatively, the rough measurement of sample concentration is made with the aid of an imaging device, and the more precise measurement is made with the aid of a spectrometer. Coarse and fine adjustment Dynamic feedback systems provided herein can be configured to concentrate/amplify (i.e., increase the concentration of) a sample, such as cells in a fluid sample. In some cases, this is accomplished with the aid of centrifugation or field-induced separation (e.g., electric field separation, magnetic separation).

In some situations, the concentration of a sample is made using an imaging device, with the location of the imaging device selected to select a desired path length and/or focal point. In some cases, the location of one or more optics associated with the imaging device are adjusted to provide a desired path length and/or focal point. In some cases, a lens-less camera is used for image capture, which can computationally provide image analysis and various focal points.

Dynamic dilution can be performed on various sample volumes. In some cases, if a sample volume is above a predetermined limit, the sample can be distributed in multiple sample containers (e.g., cuvettes) for sequential or parallel processing and/or imaging.

Self-Learning

The dynamic feedback mechanism may result in self-learning by the system. For example, for a dynamic dilution/concentration system, an initial feedback measurement may be made. Based on the feedback measurement, the sample may have no action, may be diluted, or may be concentrated/amplified. Subsequent measurements and/or detection may occur. The subsequent measurements and/or detection may or may not be additional feedback measurements. Based on the subsequent measurements, a determination may be made whether the action taken (e.g., no action, dilution, concentration/amplification) was correct and/or whether the correct degree of action was taken (e.g., enough dilution or concentration/amplification). For example, an initial feedback mechanism may determine that the sample concentration is high and needs to be diluted. The sample may be diluted by a particular amount. A subsequent measurement may be taken (e.g., image of the sample may be taken). If the degree of dilution does not bring the sample into the desired range (e.g., dilution was too much or too little), the system may receive an indication that for subsequent dynamic dilutions/concentrations with the same or similar initial feedback mechanisms, a different degree of dilution may be used. If the degree of dilution does bring the sample into the desired range, the system may receive a confirmation that the amount of dilution should be used for subsequent dilutions for the same or similar type of initial feedback measurement.

Data points may be gathered based on initial conditions and subsequent actions, which may assist with determining appropriate actions to take in subsequent dynamic feedback situations. This may cause the system to self-learn over time on steps to take in particular dynamic situations. The self-learning may apply to individualized situations. For example, the self-learning system may learn that a particular individual from whom the sample is drawn, may require different degrees of dilution/concentration than another individual. The self-learning may apply to groups of individuals having one or more characteristic. For example, the self-learning system may learn that an individual using a particular type of drug may require different degrees of dilution/concentration than another individual. The self-learning system may also be generalized. For example, the system may become aware of a pattern that people of a particular demographic or having particular characteristics may or may not required different degrees of dilution and/or concentration. The system may draw on past data points, individuals' records, other individuals' records, general health information, public information, medical data and statistics, insurance information, or other information. Some of the information may be publicly available on the Internet (e.g., web sites, articles, journals, databases, medical statistics). The system may optionally crawl web sites or databases for updates to information. In some embodiments, self-learning may occur on the device, the cloud or an external device. As additional data is gathered, it may be uploaded to the cloud or external device, and may be accessible by the self-learning system.

Image Capture and/or Manipulation Devices

In some embodiments, sample preparation, processing and/or analysis is performed with the aid of image capture and/or manipulation devices, including electromagnetic radiation (or light) capture and/or manipulation devices, such as imaging devices or spectrometers. In some cases, an imaging device can be used in association with a spectrometer. A spectrometer can be used to measure properties of light over a select portion of the electromagnetic spectrum, which may be used for spectroscopic analysis, such as materials analysis. An imaging (or image capture) device can be used to measure sample concentration, composition, temperature, turbidity, flow rate, and/or viscosity.

In an example, an image capture device may be a digital camera. Image capture devices may also include charge coupled devices (CCDs) or photomultipliers and phototubes, or photodetector or other detection device such as a scanning microscope, whether back-lit or forward-lit. In some instances, cameras may use CCDs, CMOS, may be lens-less (computational) cameras (e.g., Frankencamera), open-source cameras, or may use any other visual detection technology known in the art. In some instances, an imaging device may include an optical element that may be a lens. For example, the optical element is a lens which captures light from the focal plane of a lens on the detector. Cameras may include one or more optical elements that may focus light during use, or may capture images that can be later focused. In some embodiments, imaging devices may employ 2-d imaging, 3-d imaging, and/or 4-d imaging (incorporating changes over time). Imaging devices may capture static images or dynamic images (e.g., video). The static images may be captured at one or more points in time. The imaging devices may also capture video and/or dynamic images. The video images may be captured continuously over one or more periods of time.

In some cases, an image capture device is a computational camera that is used to measure the concentration of a plurality of samples within a relatively short period of time, such as at once. In some embodiments, the computational camera may have an optical which may be different from a lens. In an example, the computation camera1 is a lens-less camera that takes a photograph of a plurality of samples in staggered sample containers (e.g., cuvettes). The concentration of a sample in a particular sample container can then be calculated by, for example, mathematically rendering the image to select a focal point at or adjacent to a portion of the image having the particular sample container, and deriving the sample concentration from the rendered image. Such mathematical manipulation of an image, as may be acquired with the aid of a lens-less camera, can provide other information at various points in space within the field of view of the lens-less camera, which may include points in space that may be extrapolated from scattered light. In some embodiments, the final signal may be analyzed by complex algorithms. One example of such a setup is a computational camera with optical elements which may produce a Fourier-transformed image on the detector. The resulting "image" can be analyzed to extract required information. Such a detector would enable one to obtain rich information from the imaged subject. Obtaining different features from the image, for example, information at a different focal length could be done purely through software, simplifying the imaging hardware and providing more rapid and informative data acquisition.

Electromagnetic radiation capture and/or manipulation devices can be used in various applications provided herein, such as measuring sample concentration, including dynamic dilution. In an example, a light capture and/or manipulation device includes a light source, such as a coherent light source (e.g., laser), coupled with a light sensor, such as a CCD camera, for capturing scattered light, as may emanate from a sample upon the light source being directed through the sample. This can be used to measure the concentration of the sample. The light sensor can be configured to capture (or sense) various wavelengths of light, such as red, green and blue, or other color combinations, such as combinations of red, orange, yellow, green, blue, indigo and violet, to name a few examples. In some situations, the light sensor is configured to sense light having wavelengths at or greater than infrared or near infrared, or less than or equal to ultraviolet, in addition to the visible spectrum of light.

Light capture and/or manipulation devices can be used to collect information at particular points in time, or at various points in time, which may be used to construct videos having a plurality of still images and/or sound (or other data, such as textual data) associated with the images.

Light capture and/or manipulation devices, including computational (or lens-less) cameras, can be used to capture two-dimensional images or three-dimensional (or pseudo three-dimensional) images and/or video.

In some embodiments, an image capture and/or manipulation device perturbs an object and measures a response in view of the perturbation. The perturbation can be by way of light (e.g., x-rays, ultraviolet light), sound, an electromagnetic field, an electrostatic field, or combinations thereof. For example, perturbation by sound can be used in acoustic imaging. Acoustic imaging may use similar principles to diagnostic ultrasound used in medicine. Acoustic imaging may function similarly to a regular microscope but may use acoustic waves. A source of ultrasound may produce waves that can travel through the sample and get reflected/scattered due to heterogeneities in the elastic properties of the sample. The reflected waves may be "imaged" by a sensor. A variant of this method may include "photo-acoustic imaging" where the acoustic waves traveling through the sample may cause local compression and extension of the sample. This compression/extension may cause a change in the refractive index of the sample material which can be detected by measuring/imaging the reflection of a laser beam by the sample.

In some situations, an imaging device can be used to measuring the volume of a cell. In an example, the combination of a light source and CCD camera is used to capture a still image of a cell. A computer system digitizes the still image and draws a line across the cell, such as through the center of the cell. The computer system then measures the distance between the points at which the line intersects the boundaries of the cell (or cell wall or membrane) to provide an estimate of the diameter of the cell, which may be used to estimate the volume of the cell.

The imaging device may utilize line scanning microscopy to enable sample illumination with a thin line or spot of coherent laser light, so that power from the source can be concentrated in a small area giving high power densities. The detector geometry may be matched with the line or spot. Then the line/spot may be scanned across the sample so that different parts of it can be imaged. Each scanned line can then be concatenated to form the whole image (e.g., in a similar manner like a document scanner). This method may be advantageous as an analytical/imaging method for one or more of the following reasons: (1) high power density of illumination, (2) relatively high speeds can be obtained from line scanning as opposed to spot scanning, (though both may be slower than full-frame or classical imaging), (3) high precision and/or accuracy of analytical measurements on the sample such as fluorescence, absorbance, luminescence, (4) combination with spectral or hyper-spectral imaging such that a complete spectrum of the sample can be acquired for each pixel, (5) on-the-fly adjustment of resolution, (i.e. without changing any elements, a sample can be scanned at low or high lateral resolution as desired), or (6) can provide high depth of field to allow imaging of tissue samples.

In some embodiments, an imaging device is configured to detect light emanating from an ionization (fluorescence or luminescence) event, such as via scintillation. In an example, a scintillator is coated on or embedded in a material comprising a sample container. Upon a sample binding to (or otherwise interacting with the scintillator), the scintillator emanates light (e.g., fluorescent light) that is detected by a detector of the imaging device. This may be used to measure the radioactive decay (e.g., alpha and/or beta decay) of certain samples.

In some situations, an imaging device is a field effect transistor for detecting charged particles, such as ions. Alternatively, the imaging device may be a thermal detector for measuring a heat change, which may be used to construct a heat map, for example.

In some situations, a sample container comprises one or more wells for immobilizing a sample. The sample container may be coupled with an imaging device for imaging a sample immobilized in the one or more wells. Sample immobilization can be facilitated with the aid of beads having surface binding agents (e.g., antibodies) or surface binding agents, which may be disposed, for example, at bottom portions of wells. The wells can have diameters on the order of nanometers to micrometers or greater.

In some embodiments, sample detection and/or analysis is facilitated with the aid of image enhancement species, such as dyes. A dye may bind to a sample provide an optical, electrical or optoelectronic signal that can be detected by a detector of an imaging device. In an example, a dye binds to a cell and fluoresces, which is recorded by a detector. By measuring fluorescence, the spatial distribution and/or concentration of cells can be measured. Image enhancement species can aid in achieving improved signal-to-noise during image acquisition (or capture). A dye can bind to a cell with the aid of surface receptors and/or antibodies.

In some cases, the use of dyes can generate background fluorescence, which may distort an image—the fluorescence sample may be difficult to resolve from the fluorescing background. In such a case, image acquisition can be enhanced by contacting a sample in a fluid with a fluorescent dye. Unbound dye is removed with the aid of a centrifuge (or magnetic or electric separation), which separates the sample from the unbound dye. The centrifuge may be integrated in a point of service device having the imaging device. The sample can then be re-suspended in a fluid and subsequently imaged with the aid of the imaging device.

In some cases, image acquisition can be enhanced by using dynamic feedback in addition to, or in place of, the use of image enhancement species. In an example, the concentration of the sample is optimized with the aid of dilution and/or amplification prior to image acquisition.

Sample separation can be facilitated with the aid of a centrifuge. As an alternative, sample separation can be performed with the aid of a magnetic or electric field. For instance, a magnetic particle can bind to a cell, which in the presence of a magnetic field can be used to attract the cell towards the source of magnetic attraction.

Systems and methods provided herein can be applied to various types of samples, such as cells as may be derived from tissue (e.g., skin, blood), saliva or urine. In an example, dynamic feedback and/or imaging can be applied to tissue samples or cell samples derived from such tissue samples.

EXAMPLES

Example 1

Nucleic Acid Amplification by Loop-Mediated Isothermal Amplification (LAMP)

To evaluate the ability of the three-color image analysis method for both fluorescence and absorption to read LAMP assays the following experiments were performed.

Lamp Reaction Conditions

The LAMP reaction was carried out in a total volume of 25 µL in 500 uL PCR tubes (VWR, West Chester, Pa.). The reaction mixture included 0.8 µM of primer 1 and primer 2, 0.2 µM of primer 3 and primer 4, 400 µM each dNTP (Invitrogen, Carlsbad, Calif.), 1M betaine (Sigma, St. Louis, Mo.), 1× Thermopol Buffer (New England Biolabs, Ipswitch, Mass.), 2 mM MgSO4 (Rockland Immunochemicals, Gilbertsville, Pa.), 8U Bst DNA polymerase large fragment (New England Biolabs, Ipswitch, Mass.), and a given amount of template DNA (varied between ~10 and ~10^9 copies). In the case of negative control approximately 10^9 copies of irrelevant DNA was added.

Reaction Conditions

The reaction was incubated at 65° C. for 1 hour in sealed tubes. The polymerase was then inactivated by heating the reaction product to 80° C. for 5 minutes.

Product Detection and Visualization

SYBR Green I stain (Invitrogen, Carlsbad, Calif.) stock was diluted 100 fold, 5 µL was mixed with 10 µL of the completed LAMP reaction product mixed, and incubated for 5 minutes at room temperature. The reaction products were then read out in the following way:

Fluorescence readout: PCR tubes or pipette tips containing the mixture, were illuminated with 302 nm UV light and fluorescent emission (λmax~524 nm) imaged by a digital camera (Canon EOS T1i, 18-55 mm, Canon, Lake Success, N.Y.).

Figure 81:
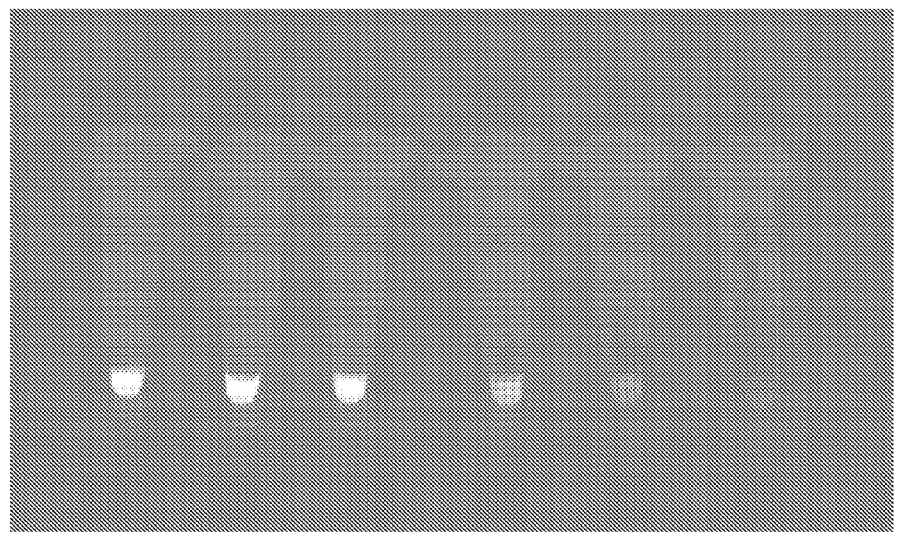
FIG. 81 shows a fluorescence image of assay products in tubes.
Figure 82:
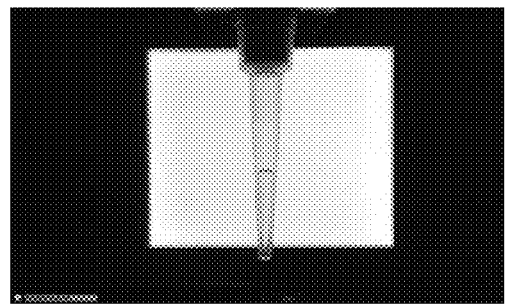
FIG. 82 shows an image of reaction products in tips.
Figure 83:
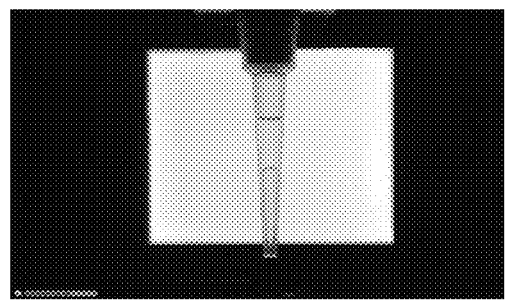
FIG. 83 shows an image of reaction products in tips.
Figure 84:
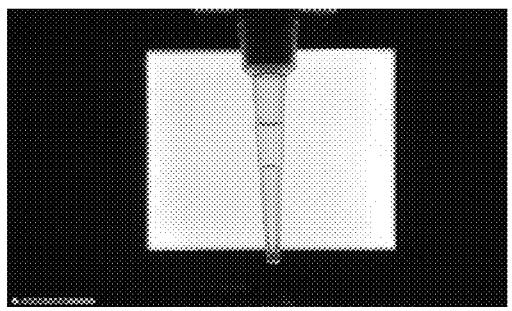
FIG. 84 shows an image of reaction products in tips.
Figure 85:
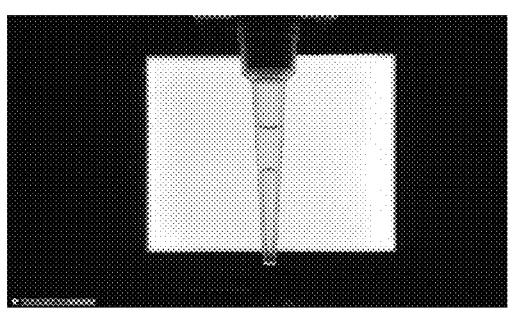
FIG. 85 shows an image of reaction products in tips.
Figure 86:
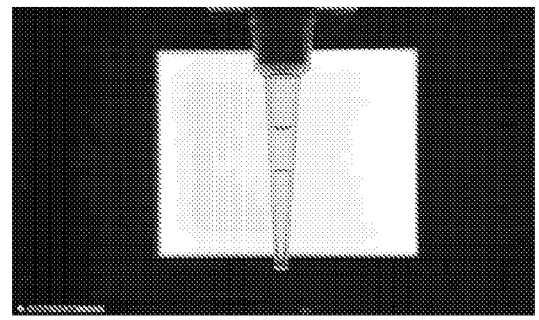
FIG. 86 shows an image of reaction products in tips.
Figure 87:
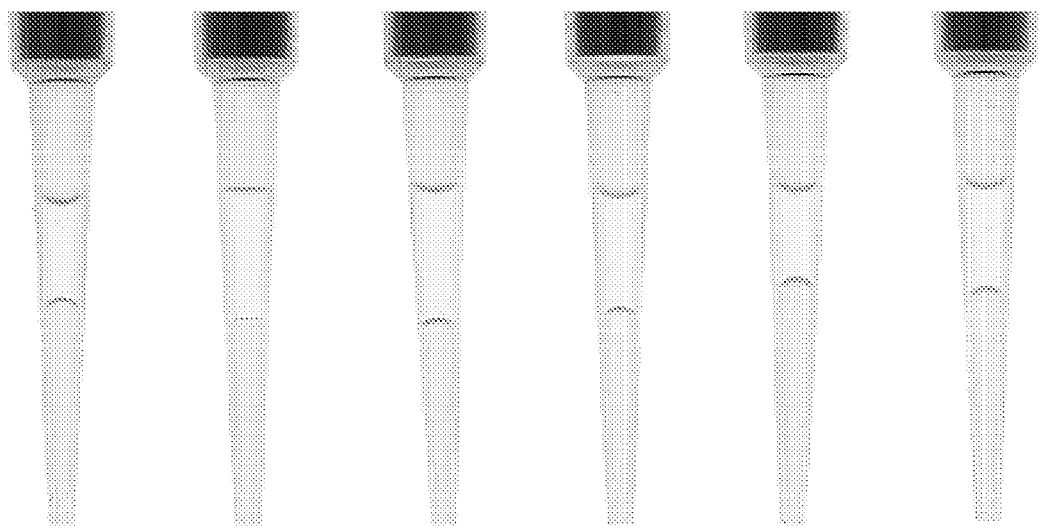
FIG. 87 shows an image of reaction products in tips.

Color readout: Reaction products were aspirated into tips and imaged using a digital camera Results:

A fluorescence image of assay products in tubes is shown in FIG. 81.

Figure 89:
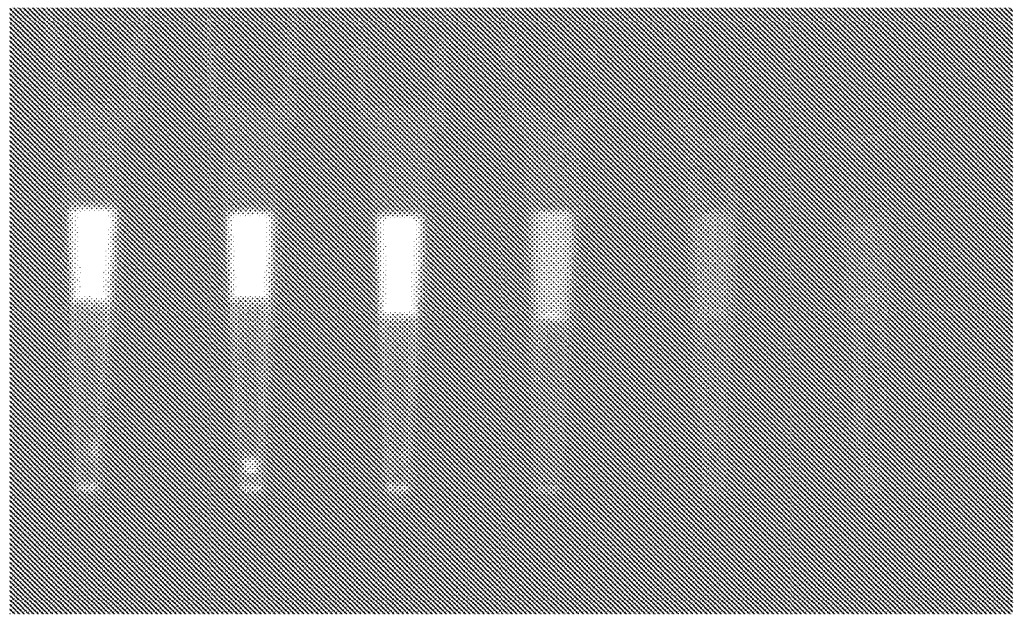
FIG. 89 shows a fluorescence image of reaction products in tips.

A fluorescence image of the assay product in tips is shown in FIG. 89.

Figure 88:
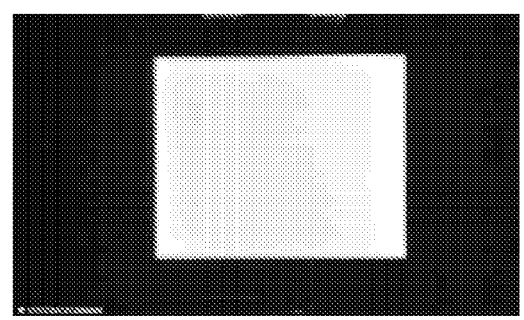
FIG. 88 shows a background color image obtained for calibration.

Color images of the assay products in tips are shown in FIG. 82, FIG. 83, FIG. 84, FIG. 85, FIG. 86, and FIG. 87. FIG. 88 shows a background color image obtained for calibration.

Figure 90:
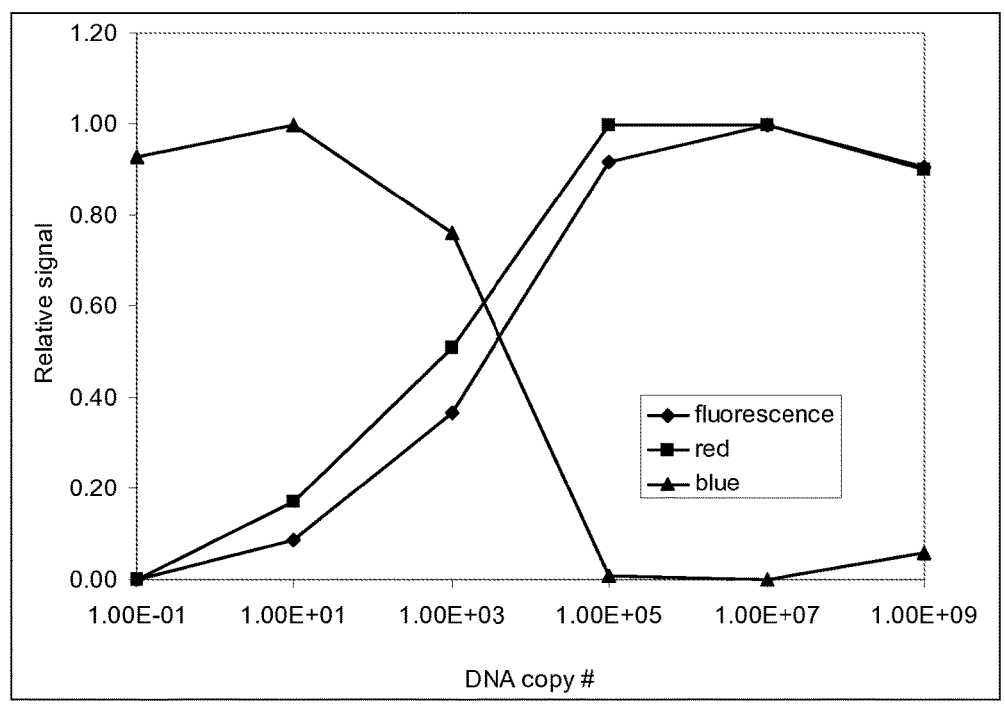
FIG. 90 shows red and blue color channel response and fluorescence response as a function of DNA copy number.

FIG. 90 shows a comparison of LAMP dose-responses obtained by measurement of "bulk" fluorescence (conventional fluorometry) and responses for two color channels obtained by camera. As is evident, the color method shows a response comparable to that of fluorimetry.

Figure 91:
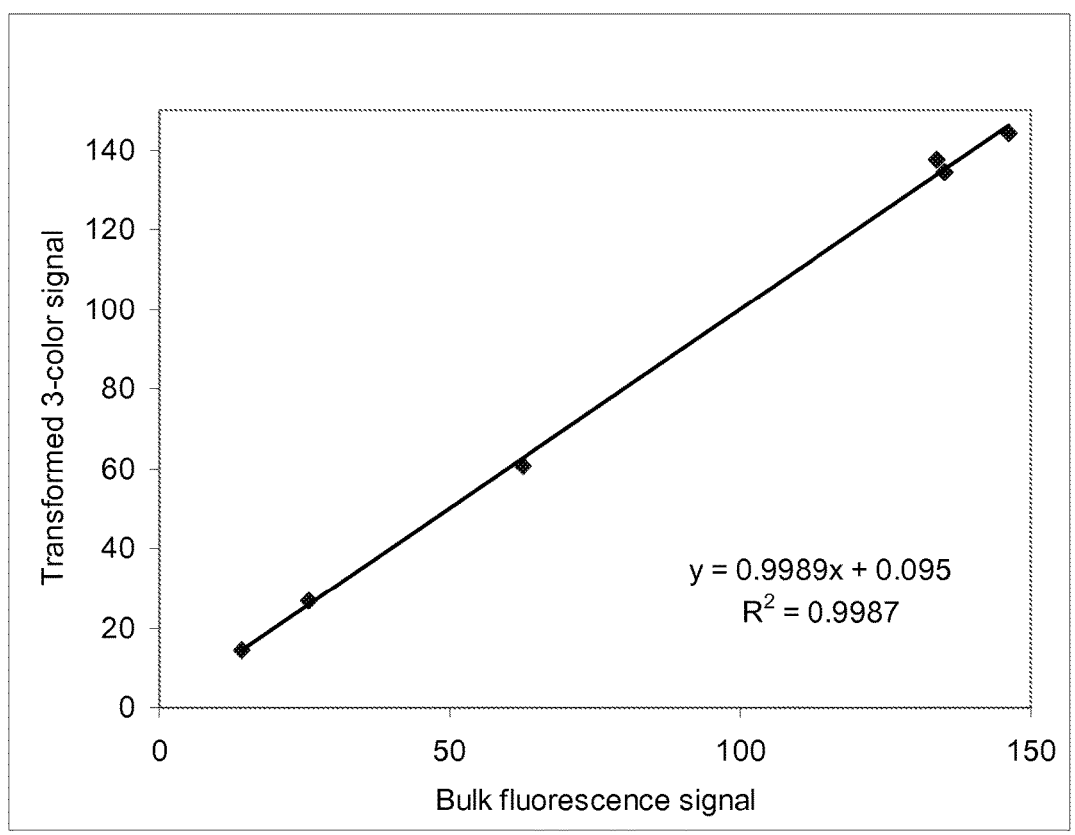
FIG. 91 shows graph of transformed 3-color signal as a function of fluorescence signal.

When the color images were analyzed and calibrated according to methods described herein using all thee color channels, the close correspondence of the calibrated color signal with the fluorescence signal is evident as shown in FIG. 91.

Example 2

System Maximizing Sample Utilization

A system for maximizing sample utilization can have the following characteristics:
1. Efficient separation of blood into plasma and efficient recovery of the plasma
   a. Separation is achieved by centrifugation in a capillary tube
2. Dilution of the plasma to a few pre-established levels appropriate to both high and low sensitivity assays
3. Minimizing the volume of each assay reaction mixture required for each assay
   a. Using an open-ended low volume cuvette suitable for assay incubations while precluding evaporation
      i. Cuvette is long relative to width
   b. Within said low volume cuvettes enabling increase in assay signal sensitivity by modifying the optical pathlength
      i. Cuvette is conical or has features where the width is wide and narrow
   c. When needed, achieving said increase in assay signal sensitivity by moving the reaction product (which does not fill the cuvette) to selected locations having greater pathlength at the time of optical measurement
      i. Cuvette internal volume is much larger than the volume of the assay mixture
4. Use of either or both variable pathlength and 3-color channel analysis to increase the useful dynamic range of assays Example 3

Point-of-Care Assay Device

A point of care assay device can include of single-use disposable cartridges an instrument which processes samples and operates the assays and a server remote from the instrument, the measurement and detection system comprising:

A disposable cartridge containing
  Sample-acquisition and metering methods (such as a sample tip)
An instrument housing containing
  A light imaging sensor (such as a cell-phone camera having a light source (e.g., a flash) and a CCD image collecting device)
  A mechanism for moving said tip to a location where said light imaging sensor can acquire images
Uploading said images wirelessly (or by other methods) to a server remote from the instrument
Image interpreting software capable of:
  Measuring volumes from the two-dimensional images
  Distinguishing sample types
Using said sample type and/or volume data as part of an operating algorithm to:
  Provide prompts to system users as to sample integrity
  Provide any needed prompts to provide an augmented or replacement sample
  Interpret signal data from said instrument in terms of assay results making allowance for sample type and/or sample volume
The system can optionally include additional mechanisms for processing and/or imaging of samples acquired by users into a "sample acquisition device (capillary)" comprising:
  Mechanisms for accepting the capillary in a defined location and moving said capillary to another defined location where an image can be acquired
  Mechanisms for ejecting substantially all the sample into the said cartridge at a defined location Example 4

Analysis of a Capillary Containing a Blood Sample

Samples are acquired by users by touching the distal end of the capillary to a drop of blood (typically as a fingerstick). The capillary usually fills by capillary action provided there is sufficient blood. In one version of the invention, the user places the capillary at a latching location on the cartridge then inserts the cartridge onto a slide in the instrument then activates an assay by pressing a screen button on the instrument GUI. All subsequent assay steps are automated. The instrument moves the cartridge inside its housing and closes the door through which the cartridge was inserted. In this version of the invention, the instrument moves a component for grasping the capillary and moving it to a location in front of a digital camera equipped with a flash light source a CCD. An image of the capillary is taken using flash illumination and sent wirelessly to the server which interprets the image in terms of type, location and quantity of sample. If preset criteria are met the server instructs the instrument to continue the assay. If the sample is not appropriate the capillary is returned to the cartridge which is ejected and the server causes the GUI to display an appropriate prompt. The user may then (1) add more sample or (2) obtain a fresh sample and use a new capillary. Once the user indicates by the GUI that corrective action has been taken and the capillary/cartridge has been re-inserted into the instrument, the server instructs the instrument to resume assay processing. The criterion for appropriate volume of sample is usually that the volume is more than the minimum required for the assay. Thus in some assays for example, 10 uL of sample can be used, so typically the sample is regarded as adequate if the measured volume is >12 uL.

In a second version of the invention which may be implemented alone or in combination with the first, image acquisition is used to measure the volume of sample taken from the original sample by the instrument. In the assay sequence, sample is ejected from the capillary into a sample well in the cartridge either (1) by the user, or (2) by the instrument. Then an exact volume is taken from sample well using a second tip either by capillary action or (preferred) pneumatic methods. At this stage the type of the sub-sample and the sub-sample volume is measured (as above) by imaging the tip. If the sample type and volume is acceptable (target +/−<5%), the assay proceeds. If not, the assay may be aborted and the user prompted to take remedial action. Sample types that may be discriminated are blood and plasma or serum and others. The imaging system makes the distinction by observing the much greater contrast between blood (opaque) and the tip (transparent) than is the case for plasma and serum. In the event that the sample volume while not at the target level is still sufficient for the assay to give satisfactory results (in the above example, a volume>5 uL would be acceptable if the target volume is 10 uL). The assay algorithm that calculates the analyte concentration then uses a correction function Conc. (true)=Conc. (observed assuming target volume)*Target volume/Measured volume.

Blood can easily be detected and its volume measured by creating a pixel map of the tip and counting the dark pixels then comparing with a previously established number for the target volume. Even though sample types serum and plasma (and other aqueous non-blood samples) are transparent, the imaging system can still detect the presence of sample due to the change in refraction that occurs over the sample meniscus and the difference in refractive index between the tip material and the sample. Alternatively a dye may be added to the sample by providing a dried dye formulation coated within the capillary which is dissolved by the sample Other methods for measuring the volume of sample include locating the top and bottom of each meniscus and using simple geometric techniques (as described herein). Bubbles within the sample liquid column can be recognized and measured by the methods discussed above and the appropriate volume subtracted from the total volume occluded by the sample.

The methods given above measure the sample within the sample capillary or pendent from the end of the capillary (as described herein). After the sample is measured and accepted by the system it is ejected by pipetting/pneumatic methods within the instrument. Once this has happened, the tip can be imaged again and any residual sample measured. The volume that actually is used in the assay is the difference between the total volume and the residual volume.

Another particular problem in POC assay systems especially when used by non-technically trained users is the presence of sample on the outside of the sample capillary. This can be imaged and measured using the invention and the user prompted to remove excess blood.

The effectiveness of sample acquisition and delivery in assay devices depends on the liquid handling techniques used. Automated devices may use (1) pneumatic aspiration and ejection (as in many laboratory single and multi-channel pipetting devices that use disposable tips; pneumatic methods may use positive or negative pressure (vacuum)), (2) positive displacement (as in a syringe), ink jet-like technology and the like. Samples and other liquids such as reagents can be (3) drawn out of reservoirs by capillary action or (4) wicking into porous media. Liquids (samples and/or reagents) may be ejected with or without contacting other liquids. For example, if the sample is to be diluted, the sample tip can be dipped into the diluent or displaced into air so as to drop into a dry well or a well containing diluent. The performance of all of the above systems and methods may be verified and/or measured using the invention.

In other embodiments, the capillary can be imaged by a user outside the instrument with an external camera. Volume measurements can be scaled to the size of the capillary. Such an externally oriented camera can be used for recognition of the user/patient so that results can more reliably be attributed to the correct patient. The method may also be used to verify appropriate medication is being used (image the pill container or pill or alternatively the bar code reader in the instrument may be used for this purpose).

The invention may also be used to measure location and volumes of reagent aspirated into assay tips. In some cases dyes may be added to reagents to make them more easily imaged (improved contrast).

In assays where plasma is separated from blood, the invention can be used to verify the effectiveness of red cell removal and the available volume of plasma. An alternative to moving the sample containing tip is to move the camera Such a system can have the following advantages:
1. Quantitative measurement of sample
2. Ability to identify the sample type
3. Creation of an objective, quantitative record of sample volume
4. Enables assays to give results when sample volume is not correct
5. Improves reliability of assay system Example 5

Tips

Figure 18:
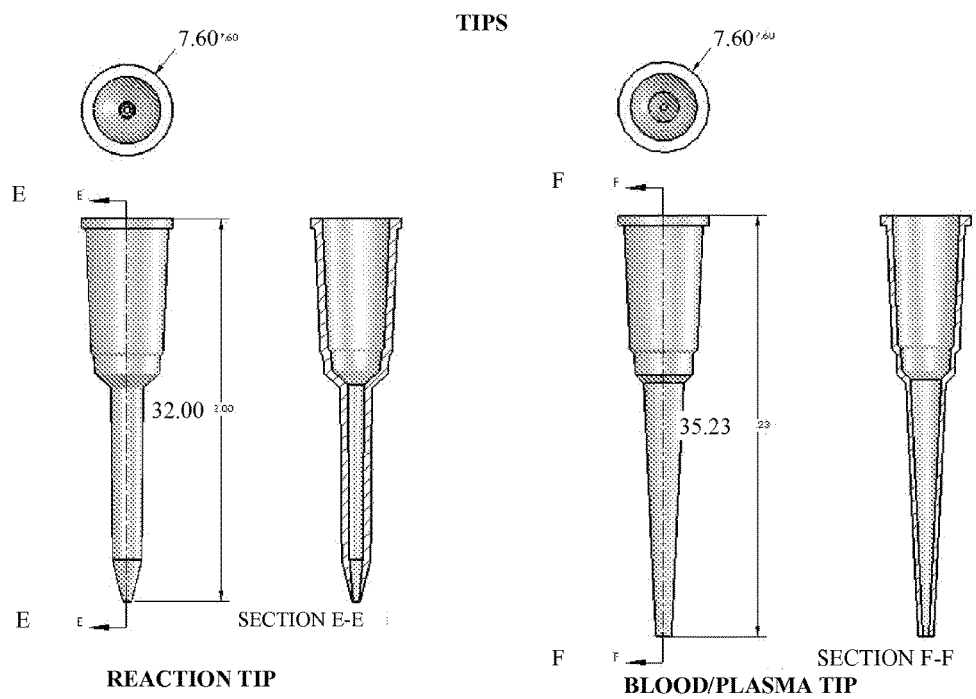
FIG. 18 shows a diagram of a tip used for reactions and a tip used for blood/plasma (dimensions shown in mm).

FIG. 18 shows diagrams of tips used to aspirate samples and reagents (dimensions in mm).

Example 6

Geometry Measurements of a Cylindrical Capillary

Figure 19:
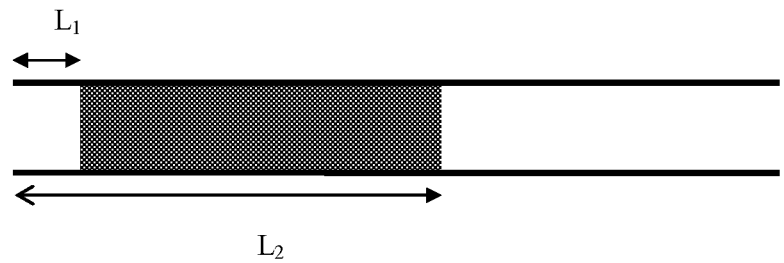
FIG. 19 shows a cylindrical capillary containing a sample.

FIG. 19 shows dimensions of a cylindrical capillary containing a sample.
R=radius
L1=distance from lower end of cylinder to lower sample meniscus
L2=distance from lower end of to lower upper meniscus $$\text{Volume introduced} = \pi*(R^2)*(L2-L1)$$

Example 7

Geometry Measurements of a Conical Capillary

Figure 20:
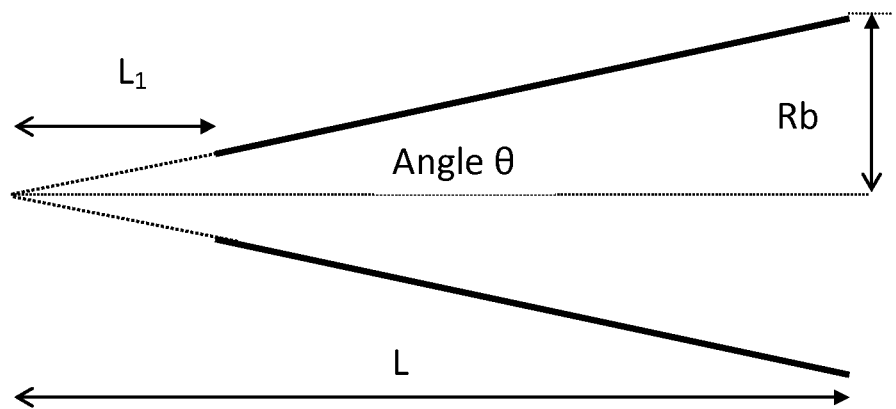
FIG. 20 shows angles and dimensions for calculating volumes within a conical container, e.g. a capillary.
Figure 21:
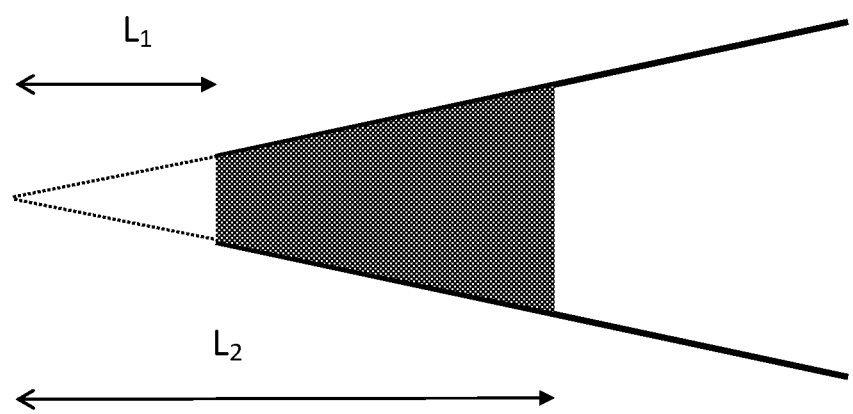
FIG. 21 shows angles and dimensions for calculating volumes within a conical container, e.g., a capillary.

FIG. 20 and FIG. 21 shows dimensions of a conical capillary.
Rb=radius at base of cone
L=length
L1=distance from (projected) top of the cone to lower sample meniscus
L2=distance from (projected) top of the cone to lower upper meniscus $$\text{Volume introduced} = \pi*(Rb/L)^2*[(L_1)^3-(L_2)^3]3$$

$$\text{Tan } \theta = Rb/L$$

Example 8

Effects of Liquid Meniscus

As is well known, liquids in capillaries typically have a curved meniscus. Depending on the contact angle the meniscus may be curved inward or outward relative to the liquid. When no net external pressure is applied, if the capillary surface is hydrophilic (contact angle<$\pi/2$) the meniscus is inward directed or outward directed if the surface is hydrophobic (contact angle>$\pi/2$). When net pressure is applied to the liquid column (capillary oriented vertically or pneumatic pressure applied by the instrument) the lower meniscus can project below the lower end of the capillary. In small diameter capillaries, surface tension forces are strong relative to the small gravitational force across a meniscus. Surface tension pressure across a meniscus in a vertically oriented circular capillary is $2\pi*R*\gamma*\cos\theta$ where $\gamma$ is the surface tension and $\theta$ is the contact angle. Pressure across a meniscus caused by gravity is $\rho g \Delta L/(\pi*R^2)$ where $\rho$ is liquid density and $\Delta L$ is the distance across the meniscus and g is the gravitational constant. Accordingly the meniscus surface is spherical. The volume of liquid in the segment(s) occupied by the meniscus (menisci) can be calculated as follows and used to obtain a more accurate estimate of volume.

Distances defined from the bottom of the sample capillary
L1=distance to the bottom of the lower meniscus
L2=distance to the top of the lower meniscus
L3=distance to the bottom of the upper meniscus
L4=distance to the top of the upper meniscus
Volume of a spherical cap $$\pi h(3a^2+h^2)/6$$

Figure 22:
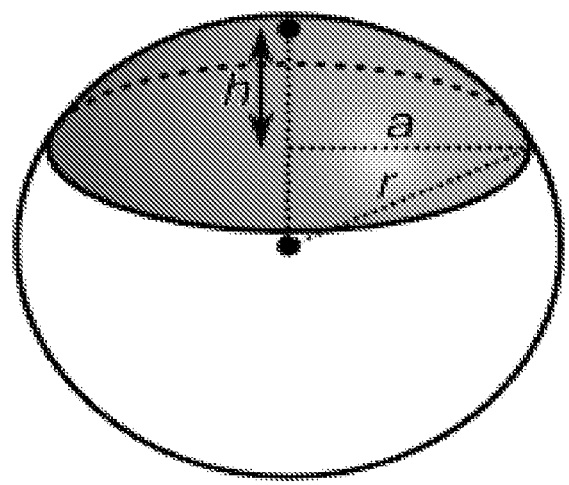
FIG. 22 shows angles and dimensions for calculating volume of a spherical cap.

Dimensions of a spherical cap are shown in FIG. 22.

Several different situations can arise defined by the number and location of the menisci. Note that the formulae given below deal with both inward and outwardly curved menisci.

Figure 23:
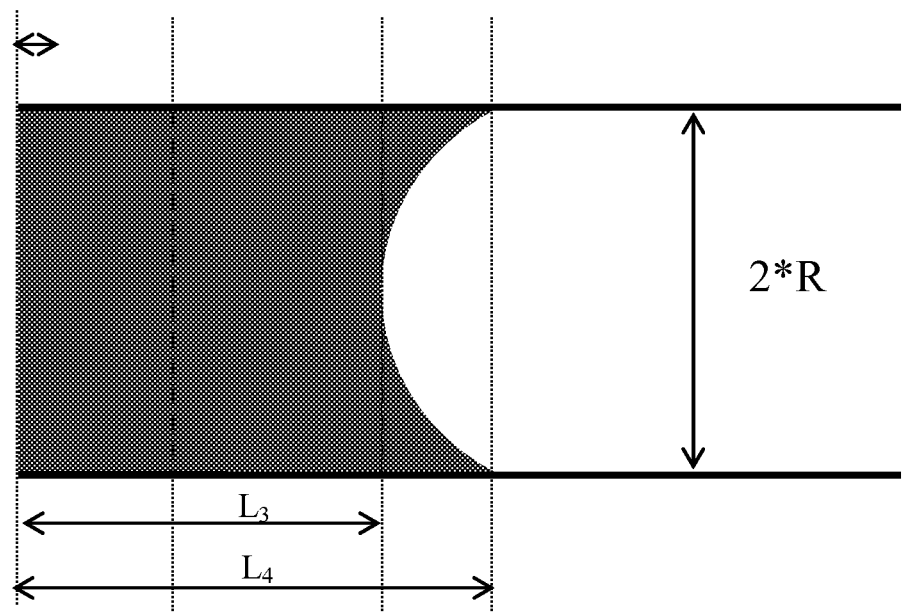
FIG. 23 shows dimensions for calculating the volume of a sample contained within a cylindrical tip, where the sample has a single meniscus.

Case 1: Upper meniscus is curved, lower is horizontal (as shown in FIG. 23)
Substituting: a=R, h=$L_4$−$L_3$
Volume between $L_3$ and $L_4$=$\pi*(L_4-L_3)*(3*(R)^2+(L_4-L_3)^2)/6$ $$\text{Total volume}=\pi*((R^2)*L_3+(L_4-L_3)*(3*(R)^2+(L_4-L_3)^2)/6)$$

Figure 24:
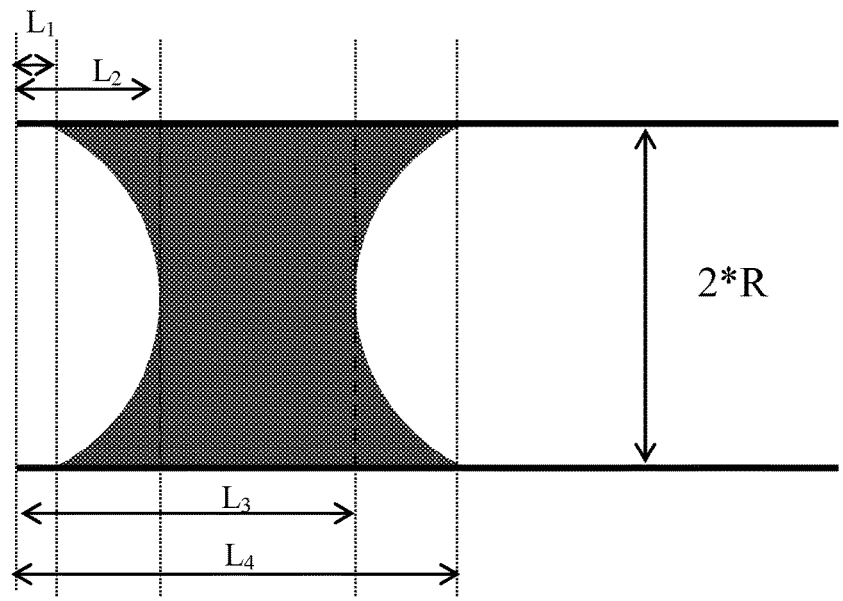
FIG. 24 shows dimensions for calculating the volume of a sample contained within a cylindrical tip, where the sample has two menisci.

Case 2: Both menisci are within the capillary and curved (as shown in FIG. 24)

$$\text{Total volume}=\pi*((R^2)*L_3-(L_2-L_1)*(3*(R)^2+(L_2-L_1)^2)/6+(L_4-L_3)*(3*(R)^2+(L_4-L_3)^2)/6$$

Figure 25:
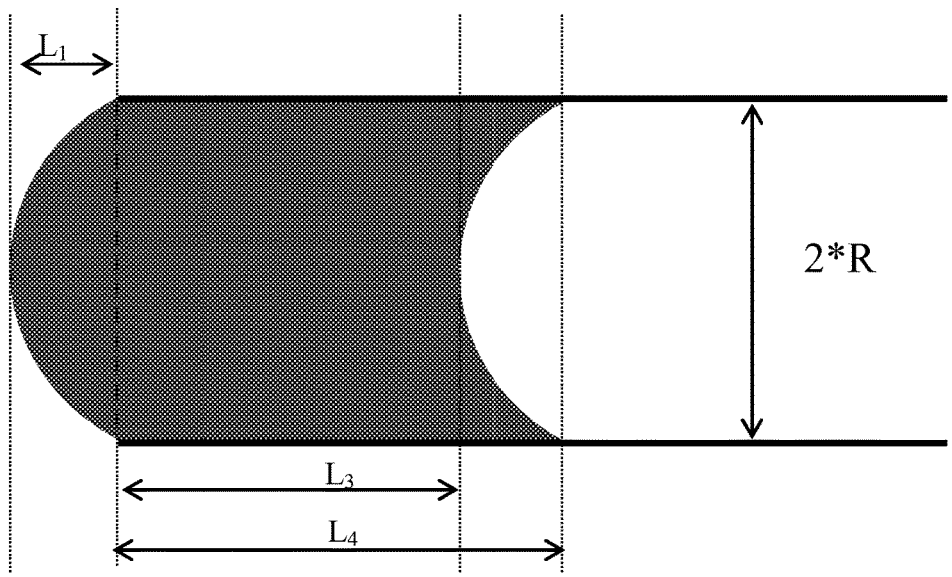
FIG. 25 shows dimensions for calculating the volume of a sample contained within and/or associated with a cylindrical tip, where the sample has two menisci and one of which is external to the cylindrical tip.

Case 3: There are two curved menisci. The lower being curved and below the lower end of the capillary (as shown in FIG. 25)

$$\text{Total volume}=\pi*((R^2)*L_3+(L_1)*(3*(R)^2+(L_1)^2)/6+(L_4-L_3)*(3*(R)^2+(L_4-L_3)^2)/6)$$

Example 9

Bubbles

Bubbles in liquid samples or reagents cause variable reductions in volume of liquid metered. In small capillaries bubbles when smaller than the capillary cross section, are spherical. When they are bigger they occupy a cylindrical space (in a cylindrical capillary) and have hemispherical ends.

Figure 26:
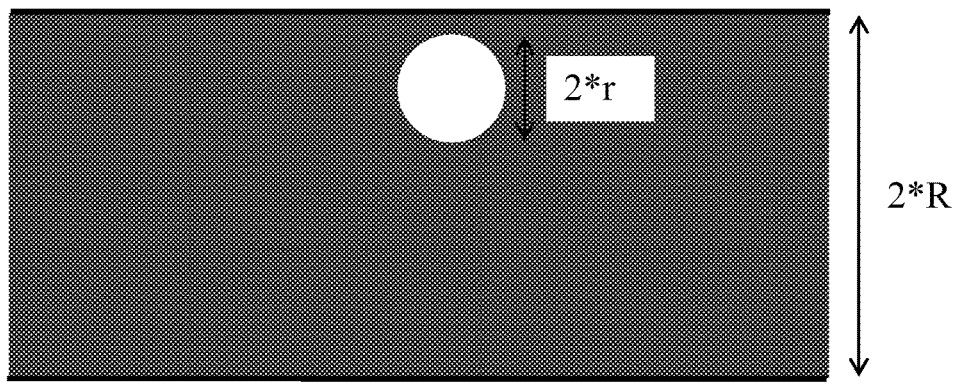
FIG. 26 shows dimensions for calculating the volume of a sample contained within a cylindrical tip, where there is a bubble in the sample.

Case 1: Bubble is not big enough to span the width of the capillary (as shown in FIG. 26)

$$\text{Subtract bubble volume}=(4/3)*\pi*r^3$$

Figure 27:
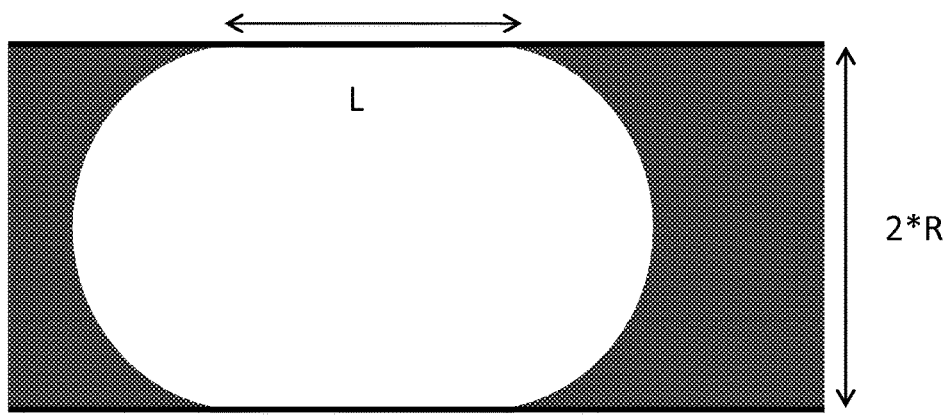
FIG. 27 shows dimensions for calculating the volume of a sample contained within a cylindrical tip, where there is a bubble in the sample that spans the width of the cylindrical tip.

Case 2: Bubble occludes the entire width of the capillary (as shown in FIG. 27)

$$\text{Subtract bubble volume}=4\pi*R^3+\pi*R^2*L$$

Example 10

Blood Outside the Capillary Tip

Figure 28:
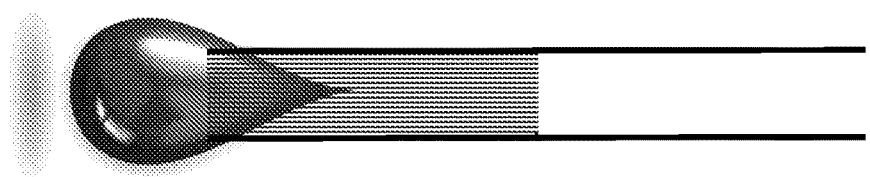
FIG. 28 shows dimensions for calculating the volume of a sample contained within and/or associated with a cylindrical tip, where the sample includes a pendant droplet of sample outside the cylindrical tip.

Case 1: Pendant blood or reagents outside a vertical capillary can cause major problems in assays since it represents an out-of-control situation. As shown in FIG. 28, imaging can easily recognize this situation.

Case 2: Blood outside the capillary other than pendant

Residual blood outside the capillary also is problematic since it is a potential source of contamination of reagents and of extra volume. Again imaging can recognize the situation.

Example 11

Residual Blood Inside the Capillary Once Sample Dispensing has Occurred

Figure 29:
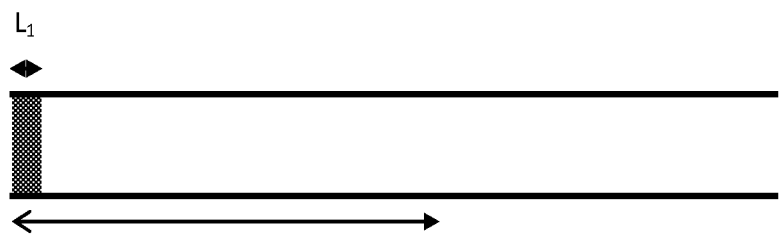
FIG. 29 shows dimensions for calculating the volume of a residual sample contained within a cylindrical tip.

This can be dealt with by estimating the residual volume and subtracting from the total sample volume. FIG. 29 shows an example of a capillary with residual blood.

$$\text{Residual volume}=\pi*R^2*L$$

Example 12

Evaluation of Red Cell Separation from Blood Samples

In many assays it is desirable to remove red cells from the sample thus making plasma. When this is done, it is desirable, especially in POC devices, to know that the separation was effective and to determine that there is sufficient plasma to perform the assay.

Figure 30:
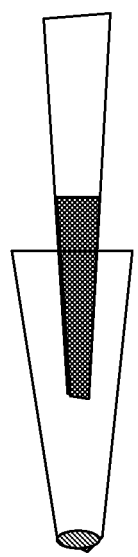
FIG. 30 shows a blood sample within a tip prior to being mixed with a magnetic reagent.
Figure 31:
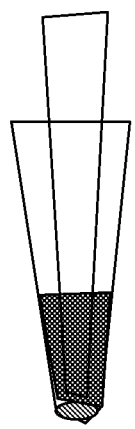
FIG. 31 shows a blood sample being mixed with a magnetic reagent.
Figure 32:
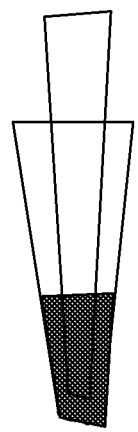
FIG. 32 shows a blood sample mixed with a magnetic reagent.
Figure 33:
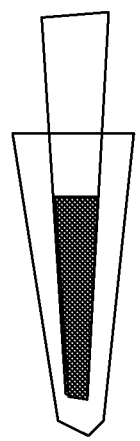
FIG. 33 shows a blood sample mixed with a magnetic reagent contained within a tip.
Figure 34:
FIG. 34 shows a blood sample mixed with a magnetic reagent moved to a selected position within a tip.
Figure 35:
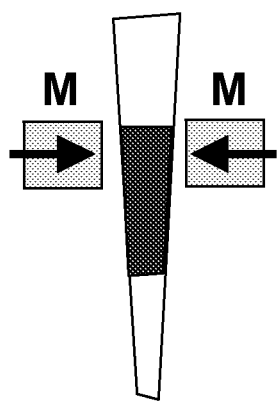
FIG. 35 shows a magnetic force applied by a magnet (M) to a blood sample mixed with a magnetic reagent.
Figure 36:
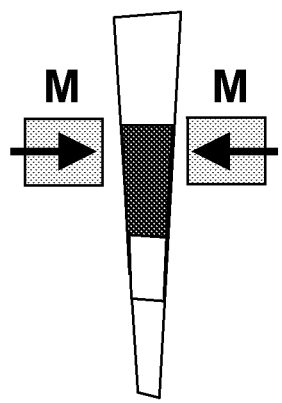
FIG. 36 shows a blood sample that has been separated into a red cell component and a plasma component using magnetic force.
Figure 37:
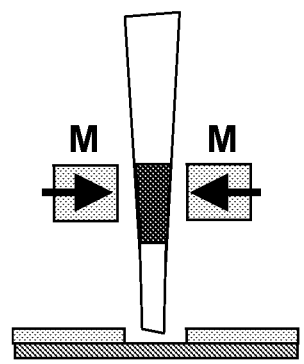
FIG. 37 shows a well positioned beneath a tip containing a blood sample that has been separated into a red cell component and a plasma component.
Figure 38:
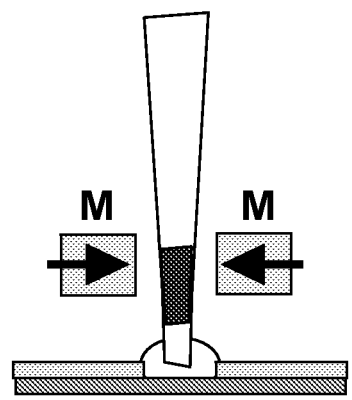
FIG. 38 shows a depiction of blood plasma being transferred from a tip to a well.
Figure 39:
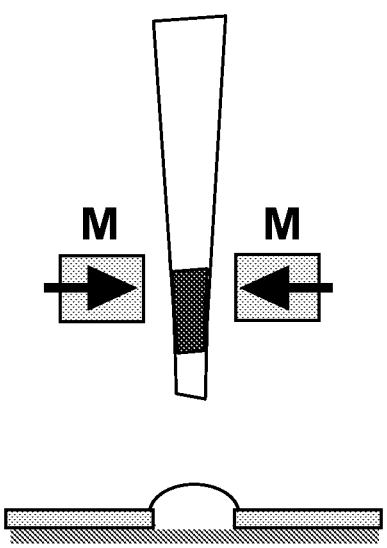
FIG. 39 shows a tip after dispensing of blood plasma to a well.

FIG. 30-FIG. 39 show a schematic of one preferred embodiment of red cell removal suited to POC devices of the present invention. Magnetizable particles have antibody to red cells mixed with free antibody to red cells are provided as a dried preparation in the well that will receive a blood sample, as shown in FIG. 30. When a blood sample is added to the well (shown in FIG. 31) and mixed with the magnetic reagent (shown in FIG. 32, FIG. 33, and FIG. 34), the red cells agglutinate with the magnetic particles and can be removed by placing the blood-containing well in proximity to a strong magnet (shown in FIG. 35). By appropriately moving the well relative to the magnet, the red cells are separated from plasma (shown in FIG. 36) which can then be ejected into a receiving well for use in an assay (shown in FIG. 37, FIG. 38, and FIG. 39). It is evident that the imaging analysis can determine how effectively the separation was effected and estimate the volume of plasma available for assay.

Example 13

Images of Liquid Samples in Capillaries

Figure 40:
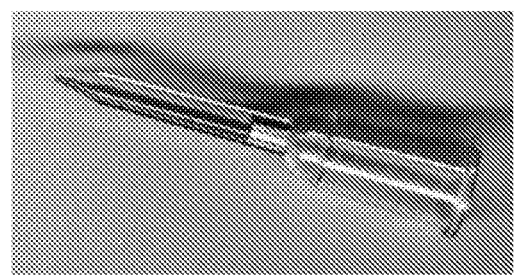
FIG. 40 shows a high contrast image of a cylindrical tip containing a liquid with low absorbance.

FIG. 40 shows a high contrast image of a cylindrical tip containing a liquid with low absorbance.

Figure 41:
FIG. 41 shows an image of a conical tip containing a liquid with high absorbance.

FIG. 41 shows an image of a conical tip containing a liquid with high absorbance.

Figure 42:
FIG. 42 shows a tip with a high absorbance liquid showing two menisci within the tip.

FIG. 42 shows a tip with a high absorbance liquid showing two menisci within the tip.

Figure 43:
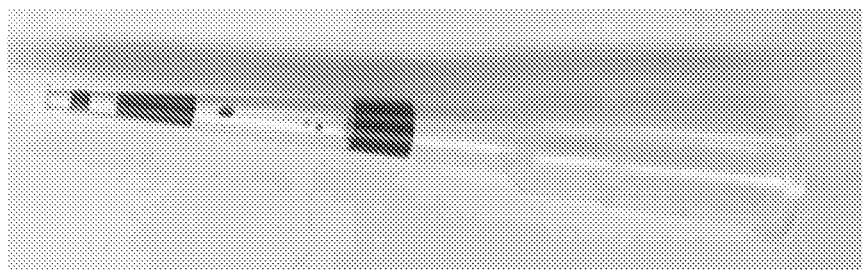
FIG. 43 shows a tip with a sample liquid and large bubbles that span the diameter of the tip.

FIG. 43 shows a tip with a sample liquid and large bubbles that span the diameter of the tip.

Figure 44:
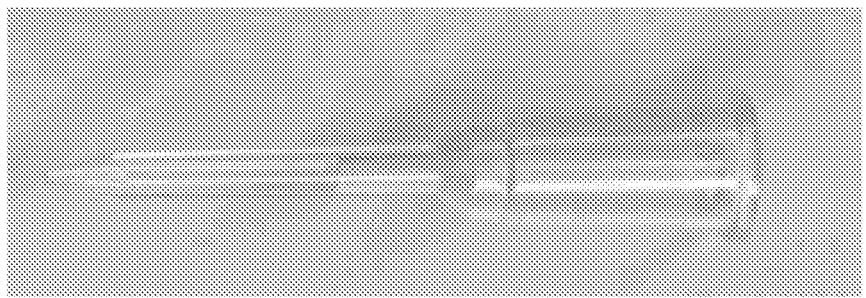
FIG. 44 shows a tip containing water showing a clear upper meniscus in a transparent tip or capillary.

FIG. 44 shows a tip containing water showing a clear upper meniscus in a transparent tip or capillary.

FIG. 41 was analyzed for the length of the liquid column (corresponding to 5 uL) and the resolution of the upper liquid meniscus (Definition of the position of the meniscus with >90% confidence). The precision of the meniscus location corresponded to <1% of the length of the liquid column.

| Dimensions | Pixel widths |
|---|---|
| Length | 276 |
| Resolution of meniscus | 2 |
| Precision | 0.7% |

Example 14

Effect of Insufficient Sample Volume on Assay Result

Figure 45:
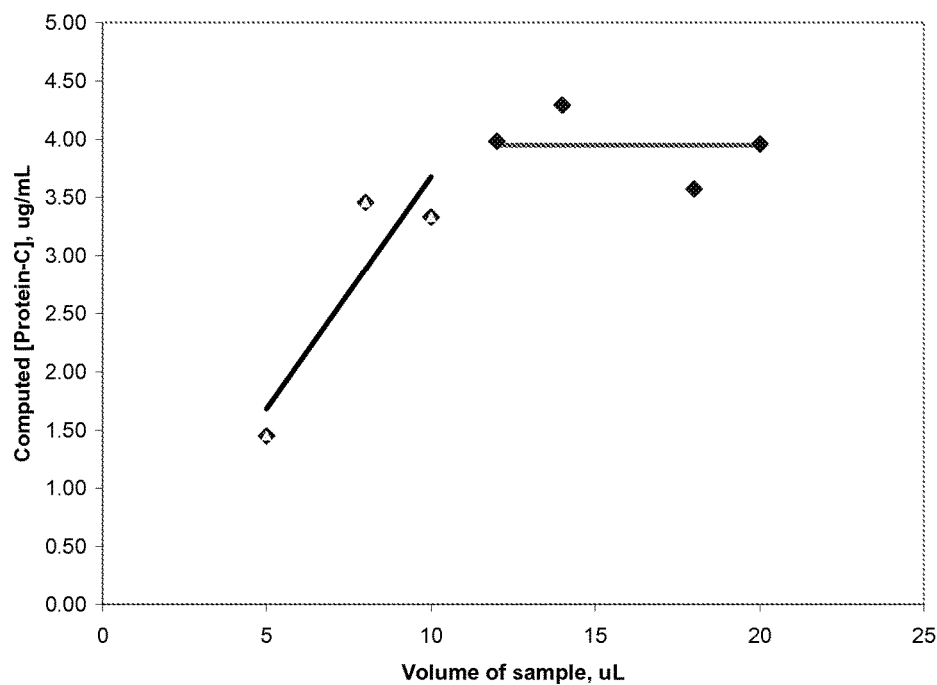
FIG. 45 shows a graph of computed Protein-C concentration as a function of sample volume.

The system was used to measure Protein-C in blood. The sample volume inserted into the system was designed to be 20 uL when the sample transfer device was used properly. The instrument was set up to use 10 uL of blood from this sample. The analyte concentration calculated by the system is shown in FIG. 45 as the sample volume was deliberately decreased from the target level. The result was essentially constant until the sample volume was less than the volume required.

Example 15

Sample Transfer Device

Figure 46:
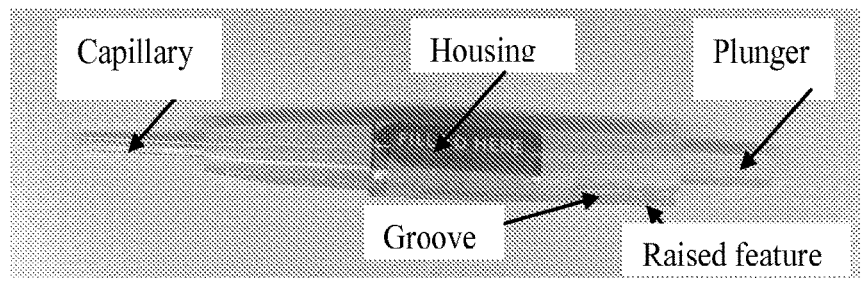
FIG. 46 shows an image of a sample transfer device with a capillary, housing, plunger, groove, and raised feature. The raised feature may help locate the plunger in the housing.

FIG. 46 shows an example of a sample transfer device. The device consists of (a) a capillary (made of glass or plastic) optionally coated with an anticoagulant or other reagent suitable for pre-analytical treatment of samples, (b) a housing which holds the capillary fitted with (c) a plunger (piston) which can slide within the housing and has a raised feature which slides within a groove in the housing, (d) a groove in the housing which engages the piston feature and limits the axial motion of the plunger so that its motion stops once the sample has been displaced and (e) a vent in the housing normally open which is blocked when the plunger is activated (moved towards the distal end of the device) so as to displace any liquid in the capillary.

Figure 47:
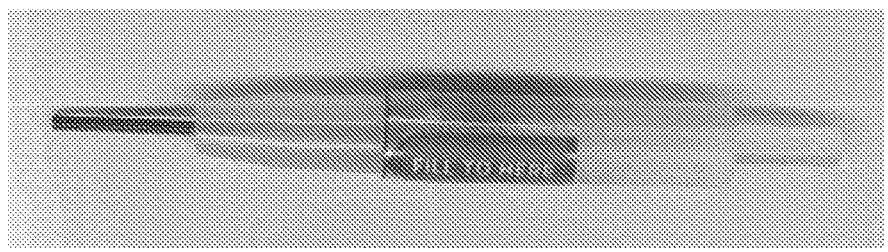
FIG. 47 shows a sample contained with the capillary of a sample transfer device.

FIG. 47 shows a sample transfer device with its capillary filled with sample. The "fill to" location is indicated.

Figure 48:
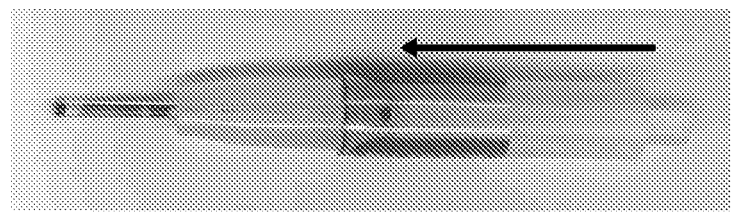
FIG. 48 shows a sample transfer device after a sample has been ejected by a plunger.

FIG. 48 shows a sample transfer device with sample displaced by movement of the plunger.

Figure 49:
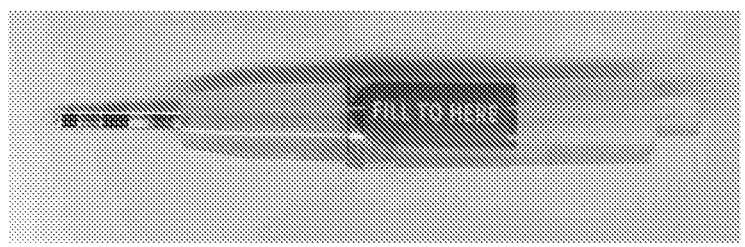
FIG. 49 shows a sample transfer device after a sample has been incompletely ejected.

FIG. 49 shows a sample transfer device after a sample has been incompletely ejected.

Example 16

Measurement of Volume by Image Analysis

Figure 50:
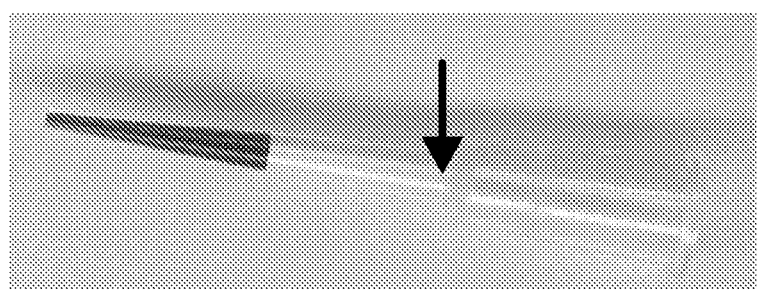
FIG. 50 shows a conical tip containing a sample, with the position L3 indicated by the arrow shown.

Known volumes of a liquid sample were aspirated into sample tips using a pipetting device. Images of the tips were collected using a commercial flatbed scanner (Dell) and the distances (a) from the distal end of the tip to the meniscus and (b) from the distal end of the tip to the feature marked on the image below measured. The orientation of the tip and its position relative to the scanner platen were not controlled since the image was analyzed by measuring the ratio of distance (a) to distance (b) as a measure of sample volume. Locations of the tip, meniscus and feature were measured using commercially imaging software (Jasc). The image was oriented horizontally using the software before the locations were recorded and could be read directly on a scale provided by the software. FIG. 50 shows an exemplary image.

Distance L1 was the location of the tip
Distance L2 was the location of the meniscus
Distance L3 was the location of the arrow indicated in FIG. 50.

| Vol. | Distances in arb units | | | | | | Calc. Vol. |
|---|---|---|---|---|---|---|---|
| uL | L1 | L2 | L3 | ΔL2-1 | ΔL3-1 | Ratio | uL |
| 10.0 | 120 | 374 | 590 | 254.00 | 470 | 0.540426 | 9.7 |
| 12.5 | 112 | 400 | 584 | 288.00 | 472 | 0.610169 | 12.9 |
| 15.0 | 156 | 470 | 636 | 314.00 | 480 | 0.654167 | 15.2 |
| 17.5 | 171 | 505 | 654 | 334.00 | 483 | 0.691511 | 17.3 |
| 20.0 | 114 | 469 | 596 | 355.00 | 482 | 0.736515 | 20.0 |
| 25.0 | 214 | 600 | 694 | 386.00 | 480 | 0.804167 | 24.5 |
| 30.0 | 165 | 585 | 640 | 420.00 | 475 | 0.884211 | 30.3 |

Figure 51:
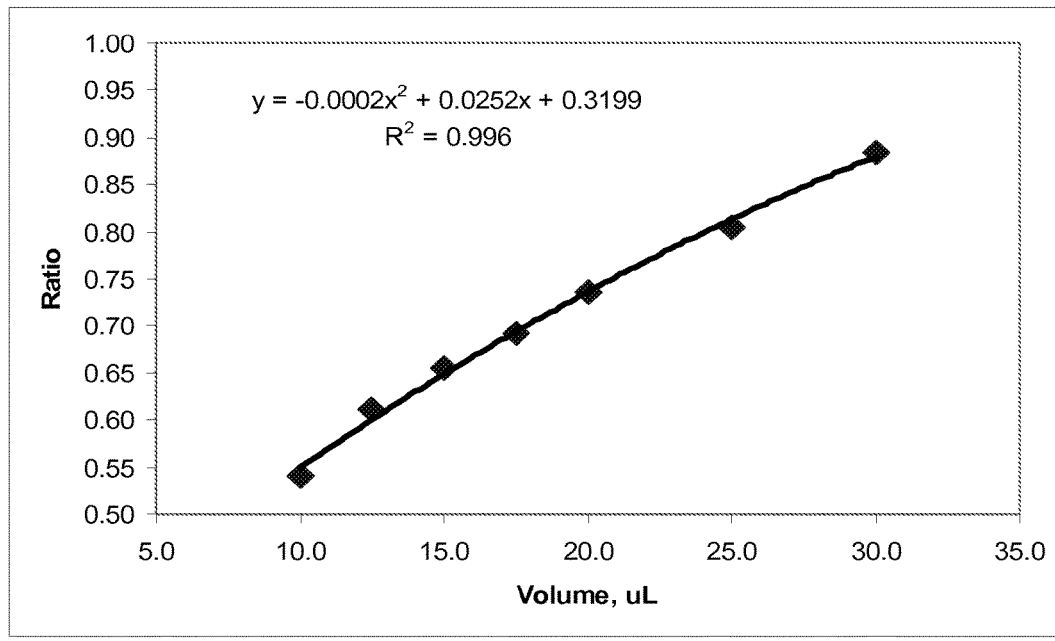
FIG. 51 shows a graph of the ratio of the distance between L2 and L1 and the distance between L3 and L1 as a function of sample volume.

As shown in FIG. 51 the volume was simply related to the ratio of distances and could be calculated. The volume estimate was within less than 2% of the actual volume on average.

Example 17

Images of Blood Centrifuged in a Tip

Hematocrits were determined from digital images by measuring the ratio of length of the column of packed red cells and the total liquid column (tip to meniscus). This is easily achieved by feature recognition software which orients the tip to a known direction and counts pixels between the features. For the tips above, the distances corresponded to several hundred pixels permitting a precise measurement.

Figure 10:
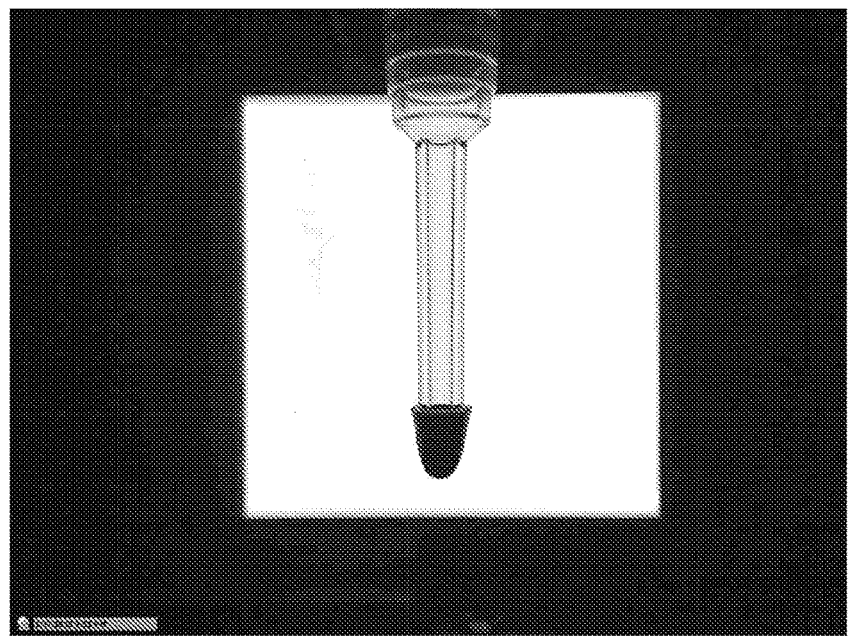
FIG. 10 shows an empty capped sample tip.

FIG. 10 shows an empty capped sample tip.

Figure 11:
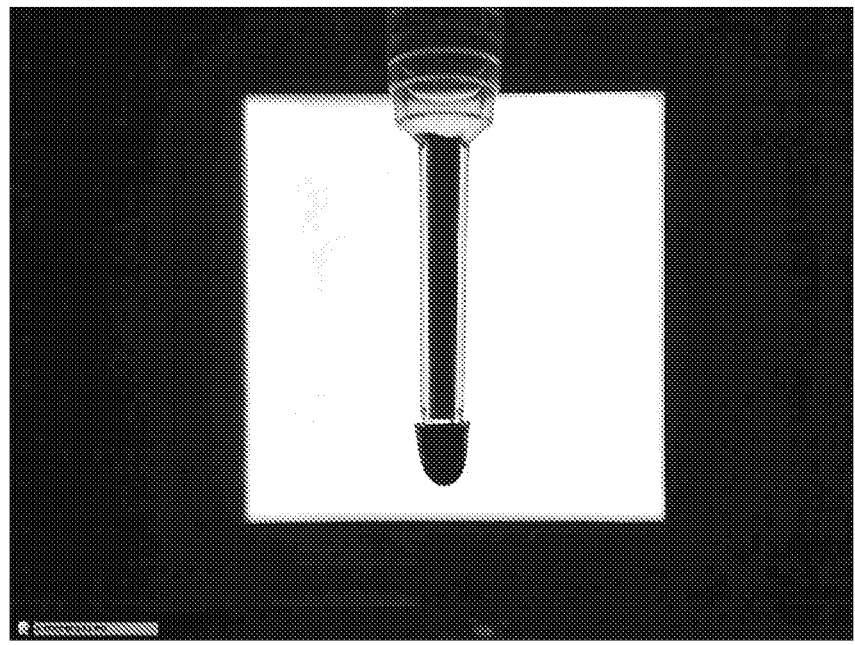
FIG. 11 shows a capped sample tip containing a sample of a bodily fluid, e.g., blood.

FIG. 11 shows a capped sample tip containing a sample of blood.

Figure 12:
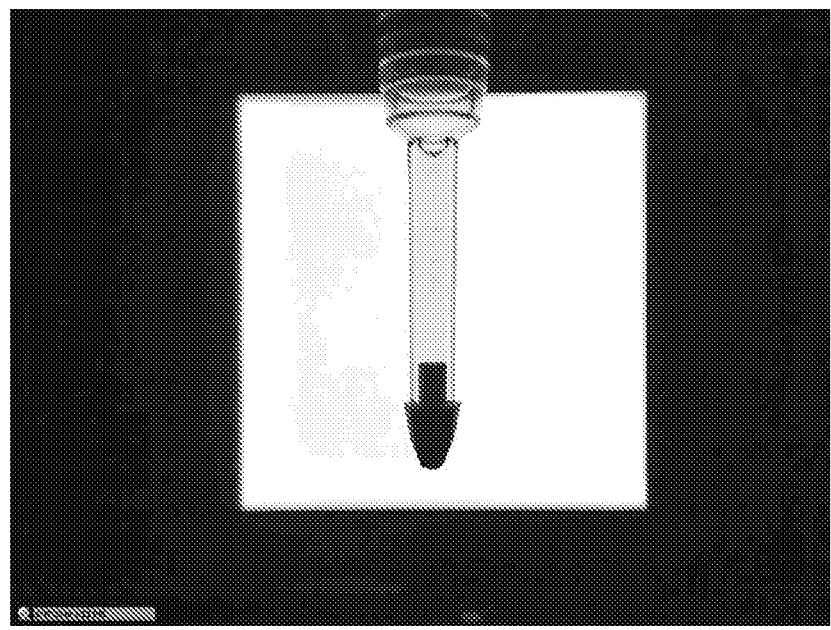
FIG. 12 shows a capped sample tip containing a sample of about 23% hematocrit blood after centrifugation.

FIG. 12 shows a capped sample tip containing a sample of 23% hematocrit blood after centrifugation.

Figure 13:
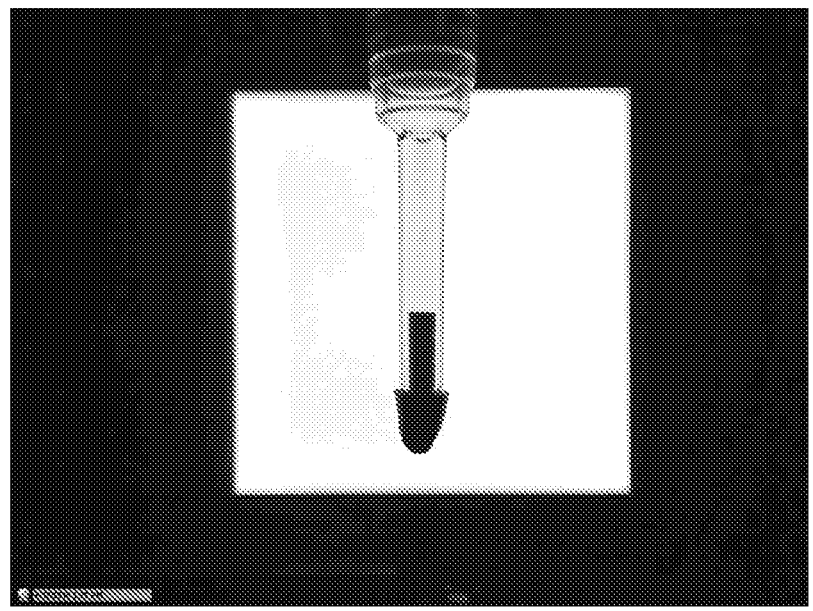
FIG. 13 shows a capped sample tip containing a sample of about 31% hematocrit blood after centrifugation.

FIG. 13 shows a capped sample tip containing a sample of 31% hematocrit blood after centrifugation.

Figure 14:
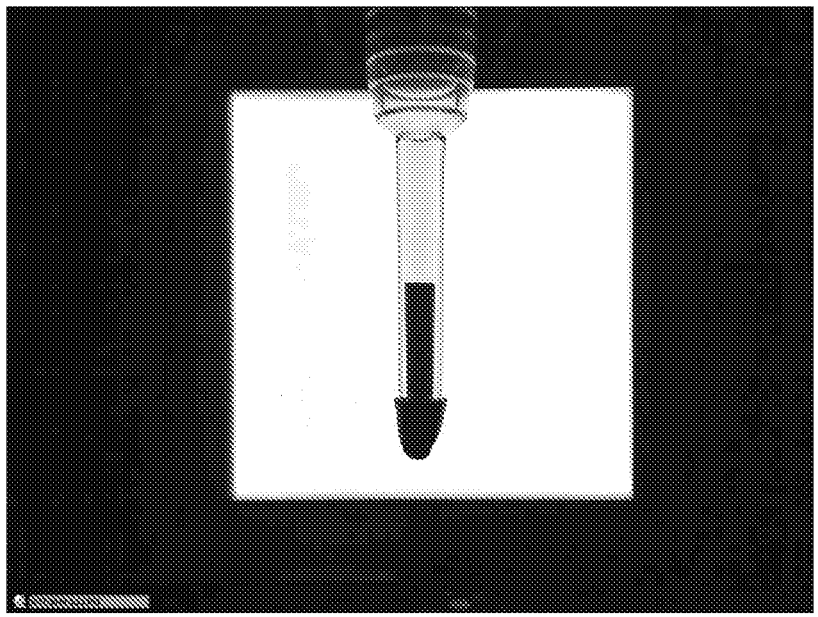
FIG. 14 shows a capped sample tip containing a sample of about 40% hematocrit blood after centrifugation.

FIG. 14 shows a capped sample tip containing a sample of 40% hematocrit blood after centrifugation.

Figure 15:
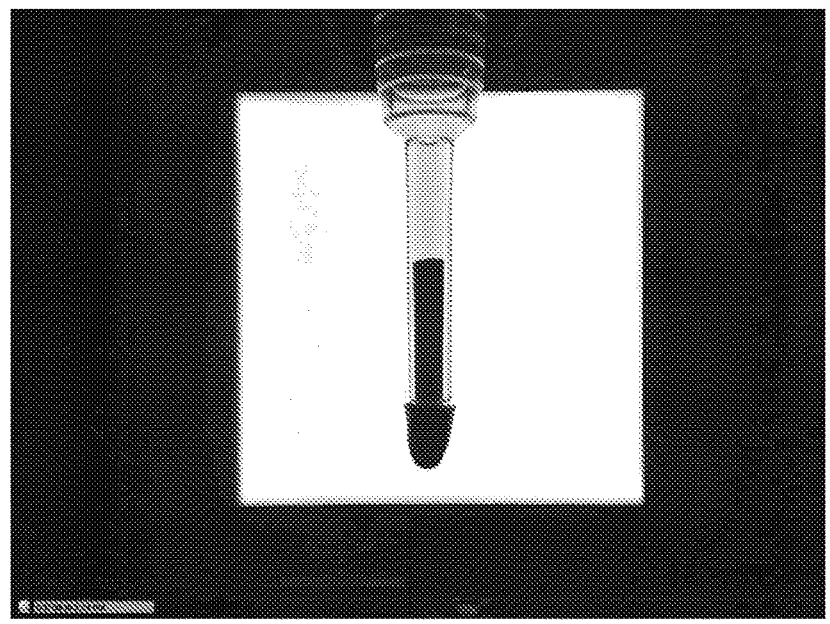
FIG. 15 shows a capped sample tip containing a sample of about 52% hematocrit blood after centrifugation.

FIG. 15 shows a capped sample tip containing a sample of 52% hematocrit blood after centrifugation.

Figure 16:
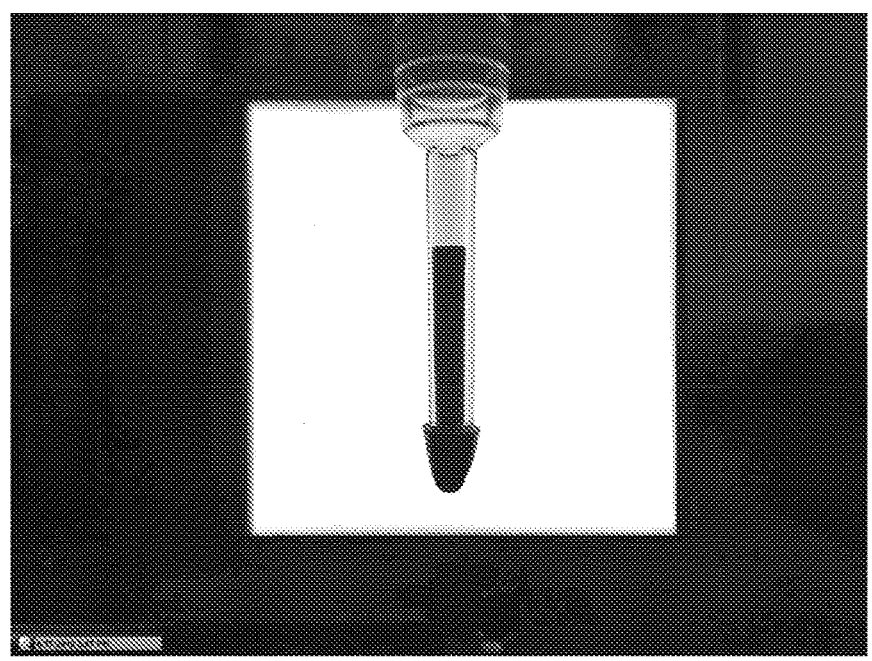
FIG. 16 shows a capped sample tip containing a sample of 68% hematocrit blood after centrifugation.

FIG. 16 shows a capped sample tip containing a sample of 68% hematocrit blood after centrifugation.

Figure 17:
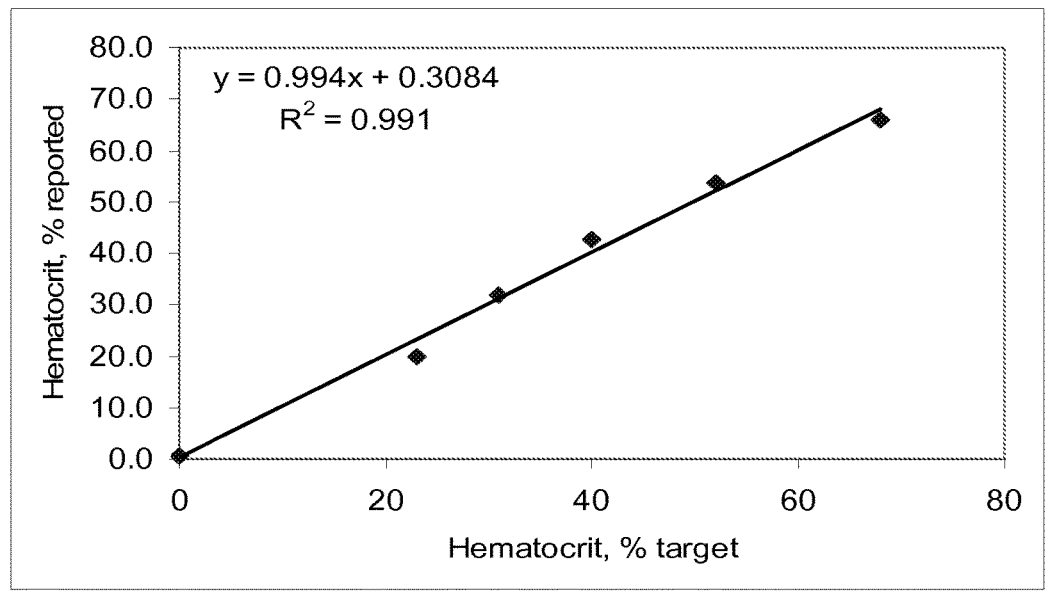
FIG. 17 shows a comparison of hematocrit measured using by digitally imaging system a centrifuged sample ("hematocrit, % reported") and hematocrit measured by standard microhematocrit apparatus ("hematocrit, % target")

FIG. 17 shows a comparison of hematocrit measured using by the digitally imaging system a centrifuged sample (hematocrit, % reported) and hematocrit measured by standard techniques (hematocrit, % target). An example of a standard technique of hematocrit measurement may include microhematocrit measurement in a glass capillary using a standard laboratory centrifuge and measuring the length of the packed red cell bed and the total length of capillary occupied by the sample.

Example 18

System Including Components for Blood Separation

A system designed for separation of blood can include the following features:
1. Design of the tip shape.
  a. Aspect ratio about 20:1 length:diameter provides convenient lengths for measurement of sample, packed cell and plasma volumes
  b. Shaped tips enable tight sealing with a vinyl cap and easy removal of cap if needed.
  c. Slight draft angle conical shape of main part of tip and wider conical upper section of tip are optimal for insertion of the plasma recovery means. Note that the "counter radial" design (tip is narrower at the end distal to the axis of rotation) is unusual.
  d. Wider conical upper section of tip is configured to be accommodated on an automated pipetting and x-y-z movement stage. Connection to form a fluid tight connection and easy removal when needed are facilitated.
2. Use of a very precise and accurate x-y-z stage to move the plasma recovery tip.
3. Use of imaging technology automatically to control the operations of centrifugation and plasma recovery. Movement of the plasma recovery tip to within less than a millimeter of the packed cell-plasma interface.

Example 19

Use of Image Measurement of Liquid Volumes to Improve Assay Calibration

Automatic pipetting devices are generally accurate and precise to about 5% or better in the range (say) 5-50 uL. In many assays, volume accuracy and precision have both to be very good (say <2%) to obtain the required accuracy and precision of analyte measurement. Metering and delivery of (1) liquids at volumes less than 5 uL (highly desirable when maximum use of a small volume sample is required), and (2) liquids having "problematic" physical properties (such as viscous solutions, solutions containing detergents etc.) can often have poor precision and accuracy which compromises the accuracy of assay results. One inventive solution to these issues is to use image analysis of the liquids to measure the volume of liquids (samples, diluents, reagents, calibrators and controls) and then to correct the assay calibration function to allow for deviations (up to [say] 20%) from the intended volume. We have shown that in pipette tips which have very precise dimensions, volumes as small as 5 uL can be measured with very good accuracy and precision (<2%). Below we document (1) volume measurement accuracy and precision and (2) use of known relationships between the volumes of solutions used in assays (samples, reagents etc.) and assay response to correct the calibration of assays.

(1) Accuracy of Volume Measurement by Image Analysis:

In the table below, known volumes of a solution of bromphenol blue were aspirated into conical tips.

The solutions were positioned in the middle portion of the tip and imaged using a scanner. Tip orientation and position were determined by standard methods. The tip orientation was adjusted by an algorithm and the length of the liquid column measured. Using the known internal dimensions of the tip, the liquid volume was calculated. Four replicate images were taken for four aliquots in four tips. The error given below therefore reflects image reproducibility and tip dimensional accuracy and precision.

| Target volume uL | Measured volume uL | Total Error % |
|---|---|---|
| 5 | 5.01 | 1.39 |
| 20 | 19.98 | 1.80 |

Note that the volume measurement does not rely on accurately positioning the liquid in the tip. Image analysis provides information as to the location of the liquid in the tip. Knowing the dimensions of the tip one can always compute the volume from the portion of the tip occupied by the liquid wherever it is.

Figure 105:
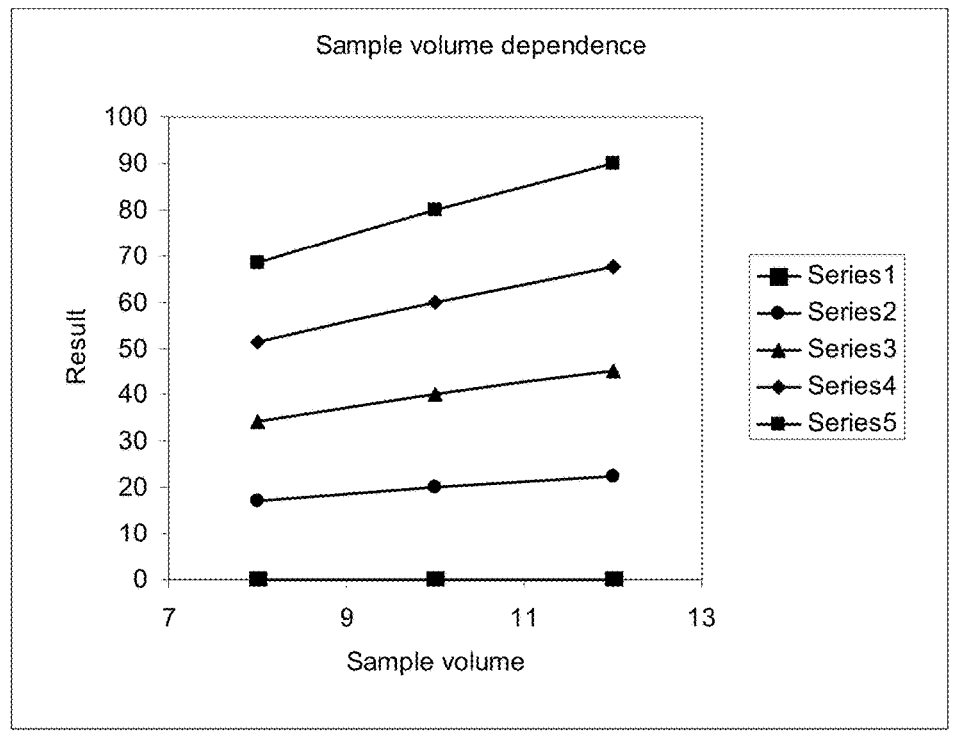
FIG. 105 shows a graph of signal as a function of sample volume. Series 1-5 may correspond to different analyte concentrations, such as 0, 20, 40, 60, and 80 respectively.
Figure 106:
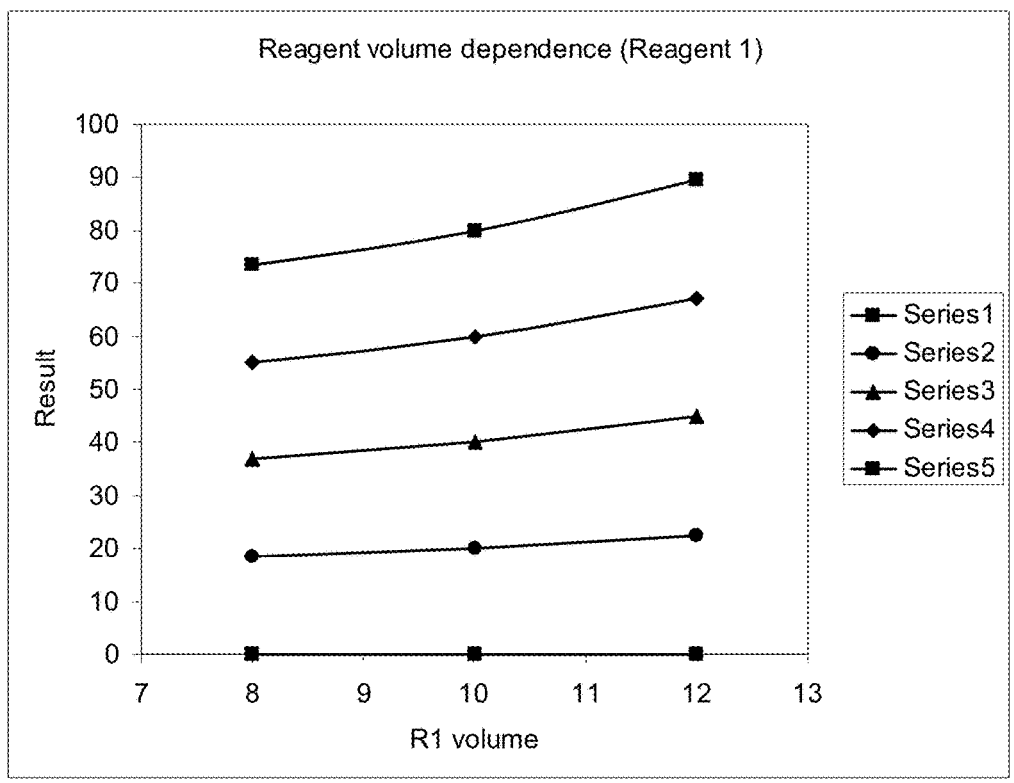
FIG. 106 shows a graph of signal as a function of sample volume. Series 1-5 may correspond to different analyte concentrations, such as 0, 20, 40, 60, and 80 respectively.
Figure 107:
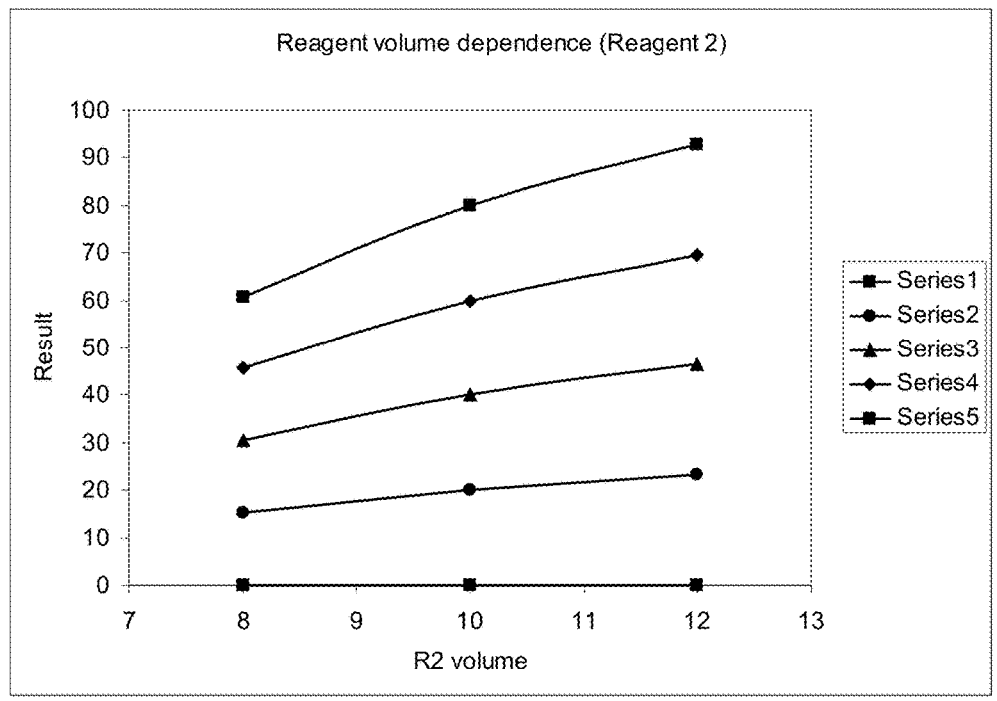
FIG. 107 shows a graph of signal as a function of sample volume. Series 1-5 may correspond to different analyte concentrations, such as 0, 20, 40, 60, and 80 respectively.

(2) Correction of Assay Calibration by Incorporation of Liquid Volume Measurement This is achieved as illustrated in the following simulation. Consider an assay in which a sample is combined with two reagents (called 1 and 2). The target volume for sample, reagent 1 and reagent 2 is 10 uL. The assay result is calculated from a standard curve relating measured signal to analyte concentration. As part of the assay calibration process the experiments can be performed in which volumes used for sample and reagents are changed to 8 and 12 uL in addition to 10 uL and assay results calculated based on the calibration appropriate for 10 uL volumes. In FIG. 105, FIG. 106, and FIG. 107, the results were plotted against actual volumes. For the sample volume, the assay result is essentially directly proportional to the volume used (shown in FIG. 105). For the reagents, somewhat non-rectilinear responses were seen (shown in FIG. 106 and FIG. 107). These responses are based on "typical" assays well-known in the field and the magnitude of the changes with volume are representative.

Figure 108:
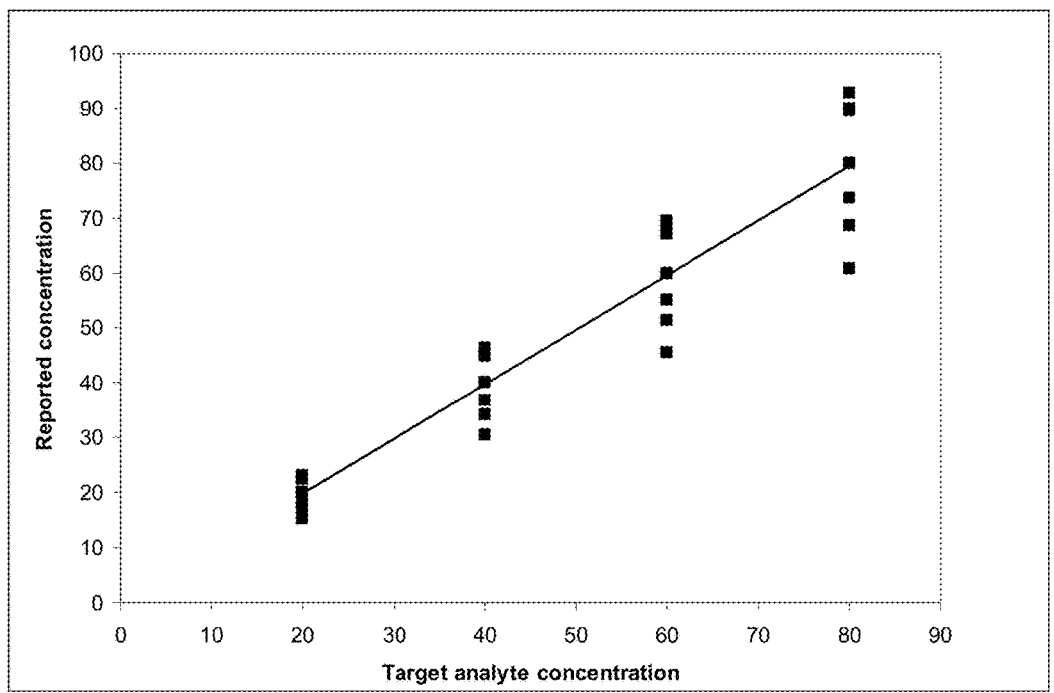
FIG. 108 shows a graph of measured analyte concentration as a function of actual analyte concentration.

We then simulate an evaluation in which we have imposed a degree of random error (about 5%, to reflect a "real world situation") on assay results in addition to the effects of the use of inappropriate volumes. We include results in which sample, reagent 1 and reagent 2 volumes are set at 8, 10 and 12 uL in all combinations. When the results from this exercise are plotted as shown in FIG. 108 without correction for volume errors, as would be expected there is a significant error in the reported result due to ignoring the fact that the actual volumes used were different from those used for assay calibration.

Figure 109:
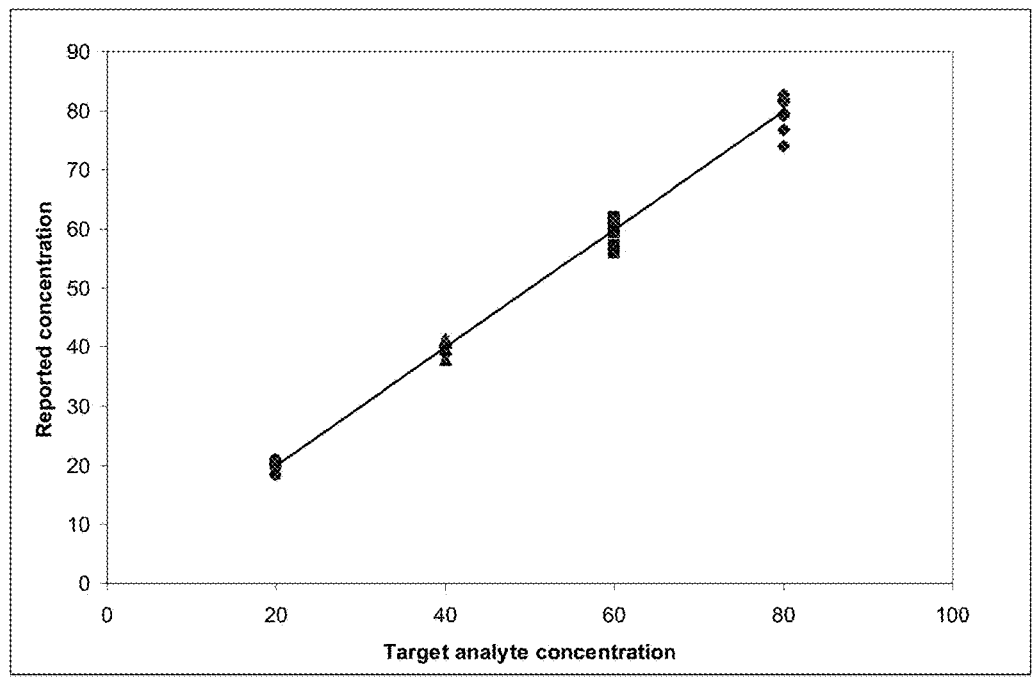
FIG. 109 shows a graph of measured analyte concentration as a function of actual analyte concentration.

When we allow for the volume variances from target values using the known assay response to volumes, and plot corrected analyte values we obtain the much improved result shown in FIG. 109, however. This was achieved by multiple regression analysis of the data.

Summary statistics comparing results calculated with and without volume correction are presented in the table below and reflect a significant improvement in all metrics by the use of volume correction. SEE is the standard error of the estimate.

| Volume correction | Regression slope | Correlation coefficient $R^2$ | Analyte CV % | SEE/Mean % |
|---|---|---|---|---|
| No correction | 0.994 | 0.914 | 13.3 | 16.5 |
| Correction | 0.999 | 0.994 | 3.6 | 7.4 |

Example 20

Hemagglutination Inhibition Assay Read Using Microscopy and Image Analysis

Figure 131:
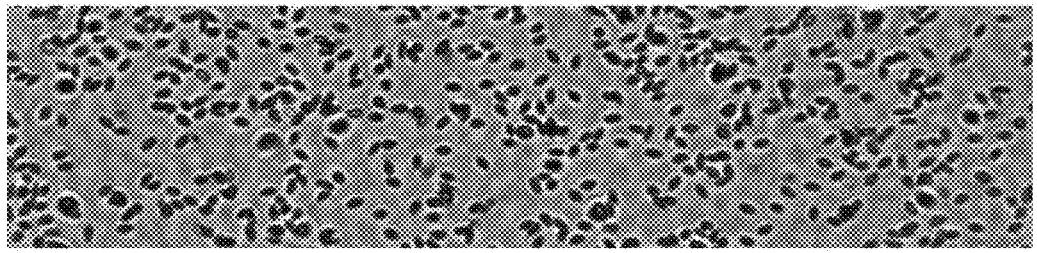
FIG. 131 shows images collected by a digital camera.
Figure 131:
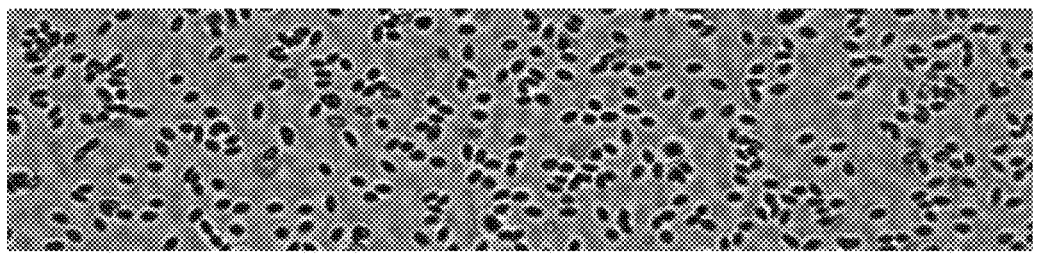
Figure 131:
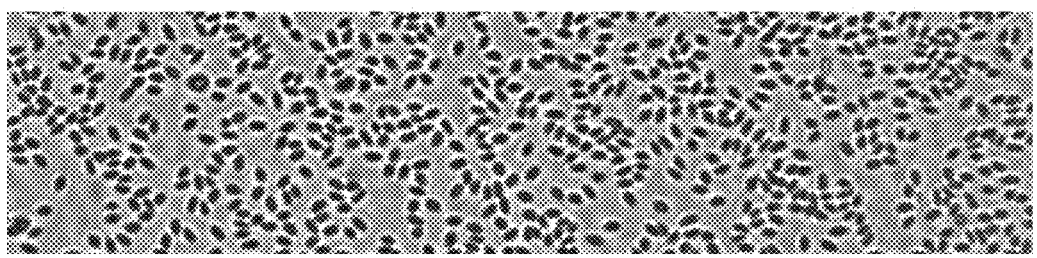

In phosphate buffered saline (100 uL), containing 0.3% w/v glutaraldehyde stabilized turkey red blood cells, and 0.5 mg/mL bovine serum albumin and, where indicated, 2 hemagglutination units of inactivated influenza virus and 15 ug goat polyclonal anti-influenza B antibody were incubated for 15 minutes in a conical bottom PCR tube at RT. The reaction product from the bottom of the tube was transferred to a transparent slide illuminated with white light and imaged with a 4-fold magnification using a digital camera. As may be seen in FIG. 131, agglutination caused by reaction of the red cells with the hemeagglutinin of the virus (FIG. 131 sample 3) is easily observable by comparison with an unagglutinated control (FIG. 131 sample 1). When excess antibody to the virus was also present agglutination was completely inhibited. Two effects of the agglutination reaction are notable: (1) in agglutinated samples, there are more red cells due to the more rapid sedimentation of the agglutinates compared with the control and (2) each red cell is on average more clustered with other red cells. The agglutination reaction can be quantified following image recognition software to identify, locate and count red cells and agglutinates.

FIG. 131 sample 1 shows a non-agglutinated control (no virus, no antibody). FIG. 131 sample 2 shows non agglutinated sample (virus plus antibody). FIG. 131 sample 3 shows an agglutinated (virus, no antibody).

Example 21

Figure 132:
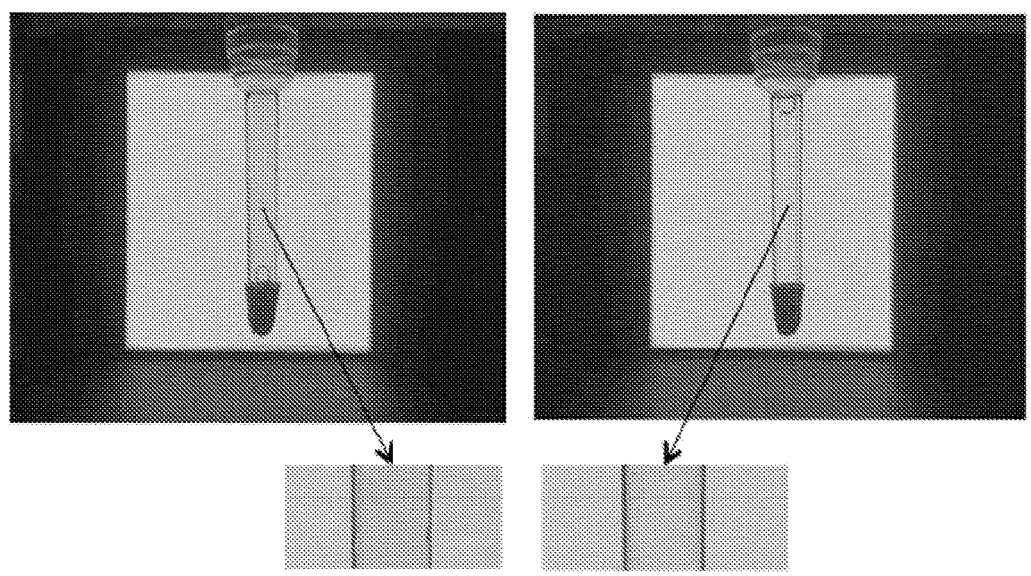
FIG. 132 illustrates examples of images taken of reaction product.
Figure 134:
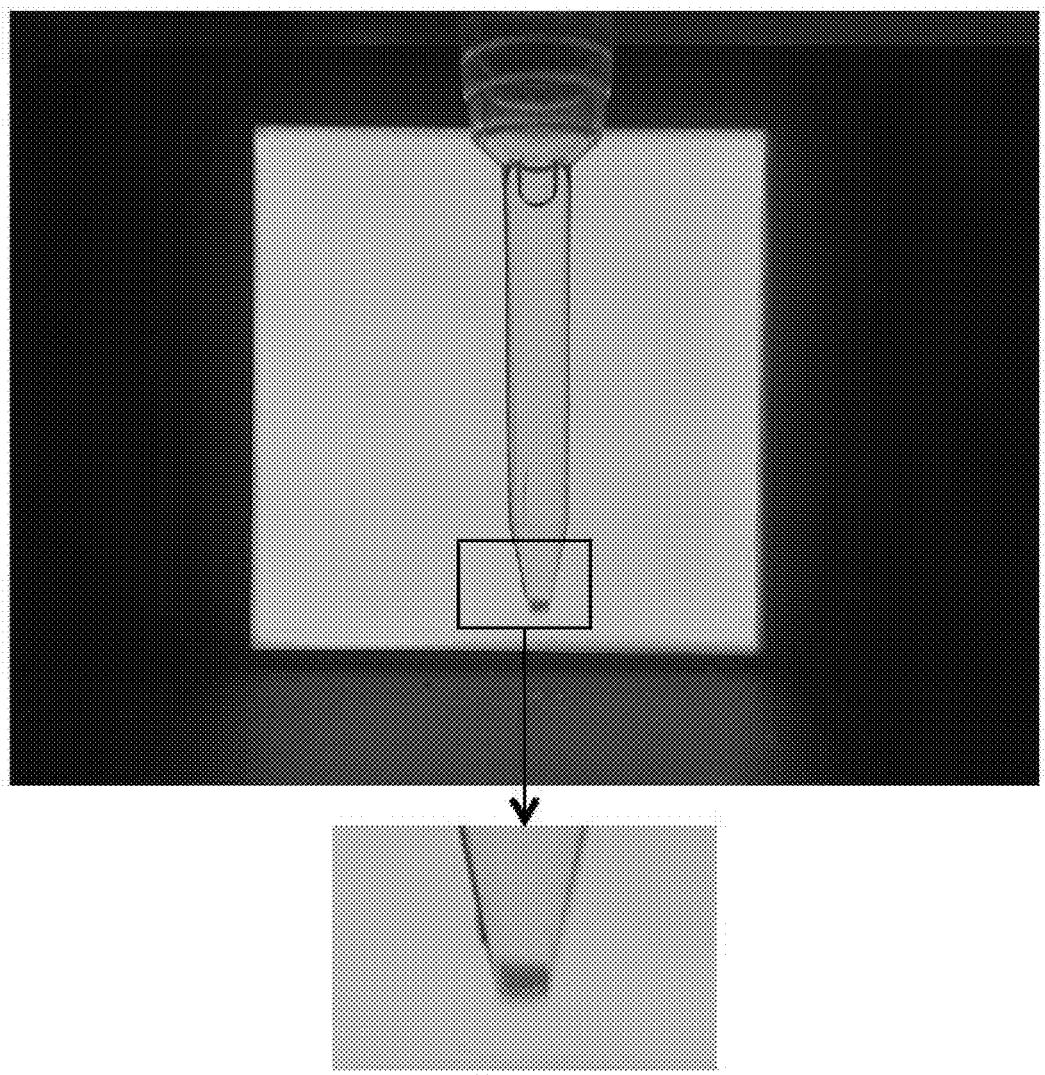
FIG. 134 illustrates examples of images taken of reaction product.

Sample Preparation, Examination of Supernatant Quality and Estimation of the Quality of the LDL Precipitate Plasma was diluted (1:10) into a mixture of dextran sulfate (25 mg/dL) and magnesium sulfate (100 mM) then incubated for 1 minute to precipitate LDL-cholesterol. The reaction product was aspirated into the tube of a centrifuge, capped then and spun at 3000 rpm for three minutes. Images were taken of the original reaction mixture prior to centrifugation (showing the white precipitate), following centrifugation (showing a clear supernatant) and of the LDL-cholesterol pellet (after removal of the cap). For example, FIGS. 132, 134 illustrate examples of images taken of reaction product.

Figure 133:
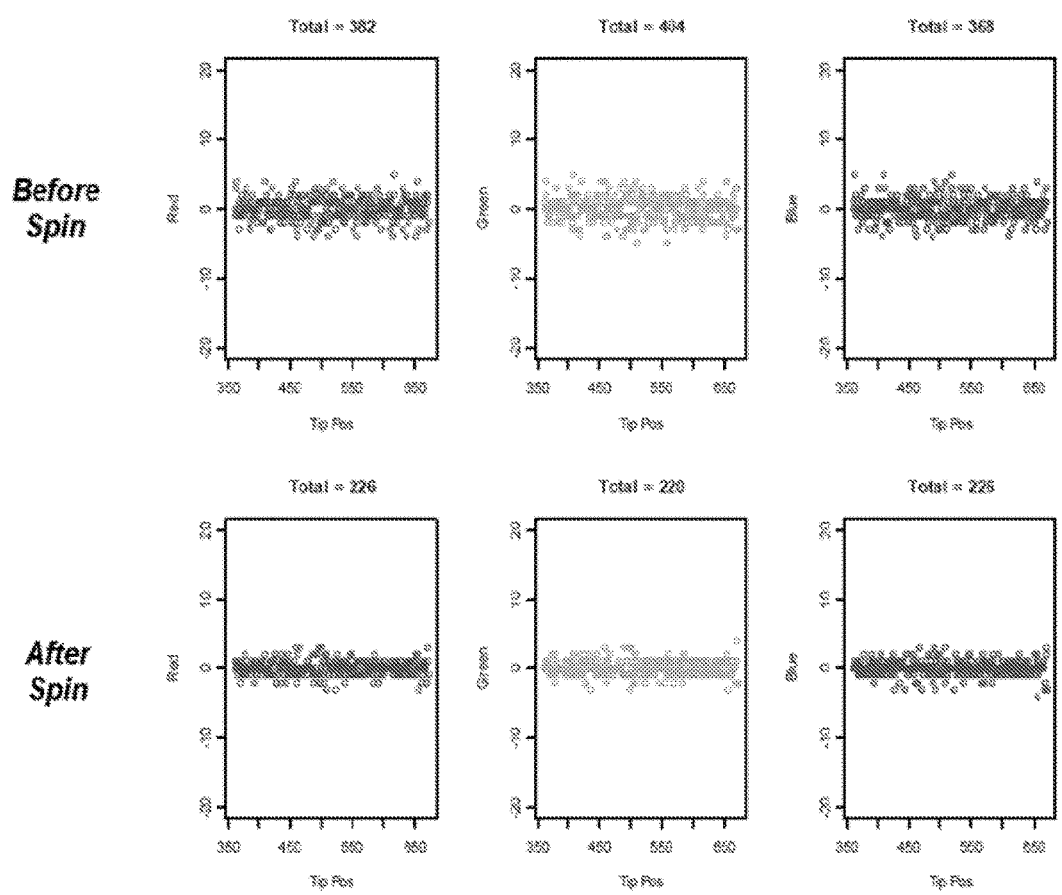
FIG. 133 provides examples of images that were analyzed before spinning in the centrifuge, and after spinning in the centrifuge.

Images of the LDL-precipitation reaction product were analyzed as follows. The pixel color levels were plotted as a function of their vertical position. The variance of the values was measured and values for the three colors summed. Because of the particles of precipitated LDL, which strongly scatter light, the precipitate value (1154) was much greater than (672) of the clear supernatant. Comparison of the supernatant value with that of a control no exposed to the precipitation reagent allows the quality of the centrifugation to be evaluated (data not shown). FIG. 133 provides examples of images that were analyzed before spinning in the centrifuge, and after spinning in the centrifuge.

After removal of the black vinyl cap, an image of the LDL precipitate was taken. Its volume can be measured quite accurately, knowing the geometry of the tip and the size of a pixel in the image. In this experiment, the volume of the precipitate was estimated as 0.155+/−0.015 uL.

Example 22

Improving the Performance of an Assay for Alanine Aminotransferase (ALT) by use of 3-Color Image Blanking of Optical Signals Due to the Sample ALT in serum can be measured in an assay in which the enzyme converts alanine to pyruvate which is in turn used to make hydrogen peroxide with oxygen and pyruvate oxidase. The peroxide is then used to make a colored product by the enzyme horseradish peroxidase, aminoantipyrene and N-Ethyl-N-(3sulfopropyl)aniline. The colored product absorbs maximally at 560 nm.

Figure 135:
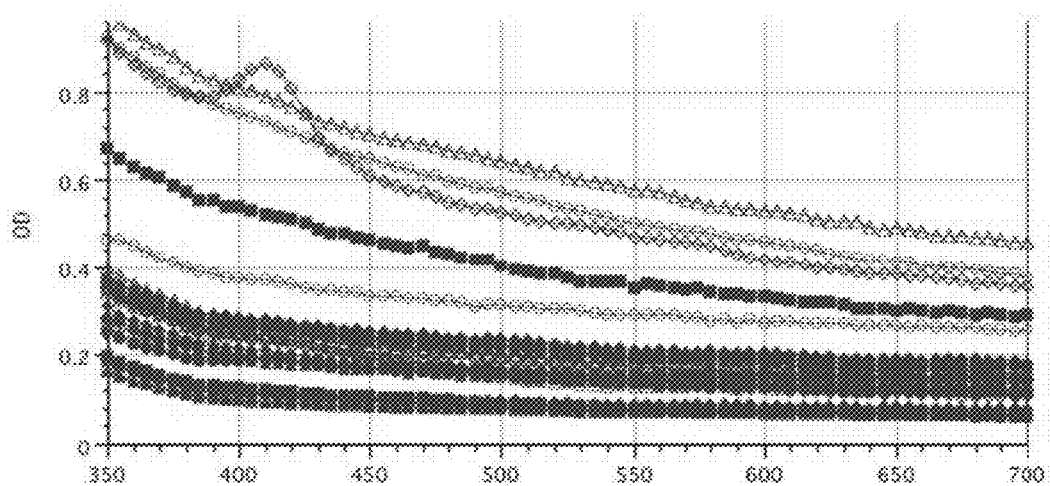
FIG. 135 illustrates spectra of several serum samples.

It was found that some serum samples have significant absorbance at this wavelength as shown in FIG. 135 and accordingly interfered with the assay. In particular when using relatively high sample concentrations (such as a final dilution in the assay of 1:10), 3-color image analysis of the ALT assay gave poor results with clinical samples.

FIG. 135 illustrates spectra of several serum samples diluted 1:10 into buffer; OD is plotted against wavelength (nm). Great variation of OD is illustrated in FIG. 135.

In conventional spectroscopy, this issue is dealt with by taking a blank reading of the sample without the assay ingredients added and subtracting the blank from the signal generated by the assay. In 3-color image analysis as in the present invention, it has been found that an analogous method can be used. The diluted sample may be imaged and three-color values extracted. The assay calibration algorithm may then be changed to include the signals from the unreacted sample. Specifically in this case, the original algorithm (not including sample blank signal) was ALT concentration=$a+b*R+c*G+d*B+e*R^2$ where a, b, c, d and e are empirically derived constants and R, G, B are the signal values in red, green and blue channels respectively. The improved algorithm was: ALT concentration=$a+b*R+c*G+d*B+e*Rs,+f*Rs^2$ where Rs is the signal from the sample blank in the red channel (note that the empirically derived values of a, b, c, d and e were different from those of the original algorithm).

When 21 serum samples ranging in ALT activity from 0 to 250 U/L were measured in triplicate and results of 3-color image analysis compared with those provided by a clinical laboratory method (Teco) the following regression statistics were obtained indicating much-improved results.

| Calibration method | $R^2$ | Slope | Intercept (U/L) | SEE |
|---|---|---|---|---|
| Original | 0.922 | 0.922 | 4.5 | 18.9 |
| Improved | 0.972 | 0.972 | 1.6 | 10.0 |

Example 23

Speeding-Up and Providing Objective Analysis of a Hemagglutination Inhibition Assay for Anti-Influenza Antibodies Reaction mixtures prepared as described in Example 20, were incubated for only one minute then introduced into three separate micro channels (as described for the cytometry examples above) and imaged. About 5-10 images are taken for each sample, in order to get adequate statistics. On average, each image consists of around 800-900 cells. The agglutination process can be objectively evaluated by measuring the radial distribution of cells around a representative selection of individual cells using the function.

The images were processed to obtain centroid positions of the individual cells in 2D space. The 2D positions were used to compute a radial distribution function (RDF), also known as a pair correlation function. The radial distribution function, g(r) quantifies the probability of finding a cell at a distance r from the selected cell. Mathematically, $$g(r)=\rho(r)/\rho_o$$

where $\rho(r)2\pi r dr$ is the number of cells found at a distance of r from a particular cell and $\rho_o$ is the average cell density over the entire image window. The value g(r) is calculated as an average over all particles in the image and over multiple images, to ensure a statistically meaningful result.

Results

The value of the first peak of g(r) quantifies the number of doublets in the sample. Hence, the g(r) for the agglutinated sample should be higher in magnitude compared to the other two samples. The value of g rises quickly from 0 to a maximum over a distance of about 20 pixels (corresponding to about 12 um about twice the diameter of a red cell) then declines to about 1.0. As shown below, the agglutination due to virus was distinguishable from no agglutination when virus is absent or antibody inhibits the virus-induced agglutination.

| Virus | Antibody | Agglutination | gmax |
|---|---|---|---|
| None | None | No | 1.44 |
| Present | None | Yes | 1.67 |
| Present | Present | No | 1.47 |

Example 24

Preparation of Analyte Detection Systems using Aptamers

Two oligo DNA aptamers were designed to selectively capture proteins (thrombin and insulin). The oligo DNA aptamer was composed of a binding site having a sequence selected from published data, an inert portion to extend the binding site from the surface of the bead or microarray, and a reactive group to chemically immobilize the aptamer to the surface. Aptamer 1 (specific for thrombin) had the following sequence: 5'-Am-(T)$_{45}$GGTTGGTGTGGTTGG-3' (SEQ ID NO:1). Aptamer 2 (specific for insulin) had the following sequence: 5'-Am-(T)$_{32}$ACAGGGGTGTGGGGACA-GGGGTGTGGGG-3' (SEQ ID NO:2). The "Am" at the beginning of each sequence represents an amino group.

Figure 139:
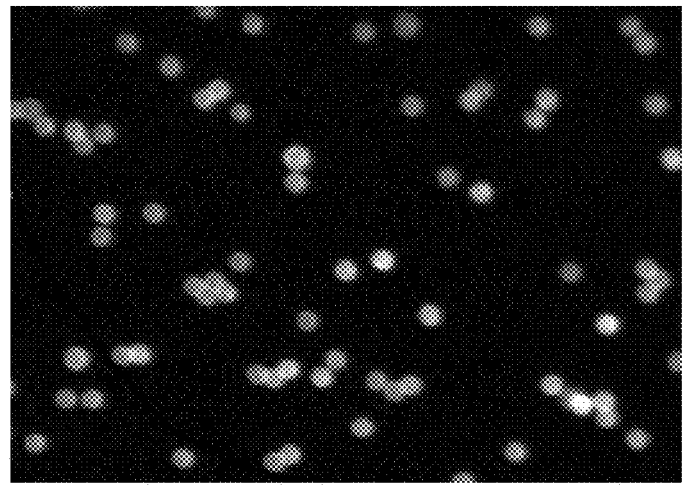
FIG. 139 illustrates detection of aptamer binding to a complementary probe.
Figure 140:
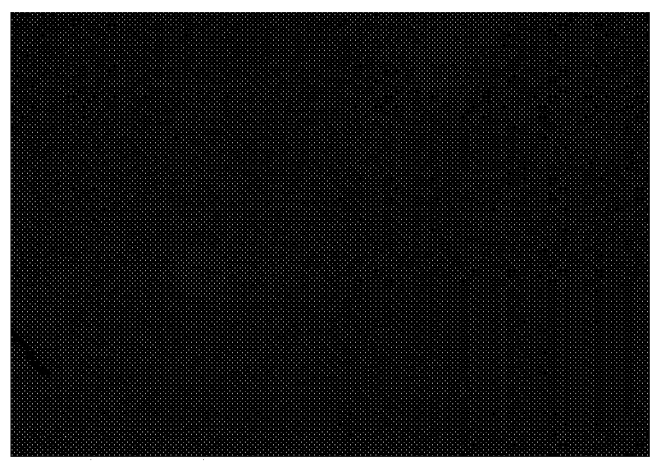
FIG. 140 illustrates absence of binding between aptamer and a non-complementary probe.
Figure 141:
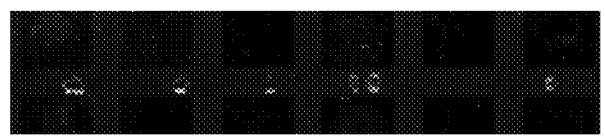
FIG. 141 illustrates binding specificity of aptamers on an array.
Figure 142:
FIG. 142 shows a more detailed view of analyte detection on an array.
Figure 143:
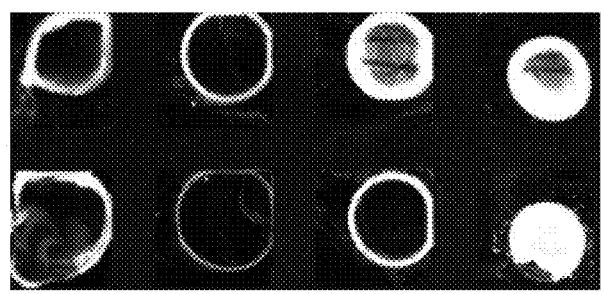
FIG. 143 shows an example array.

The two aptamers were immobilized on polystyrene beads (5 um) functionalized with carboxyl groups. The beads were then washed and the excess reagent removed. The beads were then mixed with oligo DNA probes fluorescently labeled and complementary to the binding sites of the aptamers. Hybridization of the probes with the aptamers was detected by fluorescence emission. Only the complementary probe showed a positive hybridization event, as measured by mean fluorescence emission. Hybridization specificity is illustrated by comparison of FIG. 139, which shows beads after hybridization with complementary probe, to FIG. 140, which shows beads after hybridization with non-complementary probe. Detection was performed with a laser excitation at 635 nm, and emission filtered at 650 nm (±10 nm) on a CCD camera, after deposition of the beads on the analysis substrate. A similar procedure was used on a glass surface coated with epoxysilane to immobilize Aptamers 1 and 2. The array was hybridzed with the fluorescent probe and the specific recognition of the aptamer binding site measured by fluorescence emission detection with a CCD camera set-up and an Array Scanner (Inopsys). FIG. 141 illustrates the binding specificity of the aptamers on the array, with more detail illustrated in FIG. 142. FIG. 143 shows an example array scan.

Example 25

Detection of Analyte Using Aptamers

An array comprising Aptamer 1 hybridized with fluorescently labeled, complementary probe was prepared as in Example 24. Thrombin was introduced to the array at a concentration of about 100 nM and allowed to react with the Aptamer 1-probe complex. The fluorescent emission signal from Aptamer 1 on the array was reduced by 2.5 fold, indicating displacement of the probe by binding of Aptamer 1 and thrombin.

Example 26

Binders

Two types of binder are biotinylated and used to create capture surfaces on an assay unit solid-phase coated with avidin. Assay reagent production and luminescence-readout assay results are obtained using (1) aptamers and (2) single-chain Fv antibody fragments (SCFVs) on microtiter plates. Aptamer and SCFVs as binders for luminescence-based assays are adaptable to tips and imaging systems and devices provided herein. Analytes can be assayed and read using cameras to measure color by changing the signal-generating reagent from alkaline phosphatase to, e.g., horse-radish peroxidase with a chromogenic substrate or using alkaline phosphatase with a chromogenic substrate. Tips in microtiter plate (or other formats) can be read in any cartridge (assay unit) format.

Example 27

Vitamin D Assay Using DNA Aptamers on Microtiter Plate

In this example, an assay for vitamin D is performed using single-stranded DNA aptamers. Biotinylated DNA aptamers are coated on a ultravidin coated polystyrene surface of a microtiter plate having a plurality of wells. Before coating, the aptamers are quickly denatured and renatured by heating at about 95 degrees Celsius, then immediately cooled on ice. About 15 microliters of the refolded biotinylated vitamin D DNA aptamers in 25 mM Tris, containing NaCl, MgCl2, 10% Ethanol, pH 7.5, are then added into each well to form the capture surface. After coating, the wells are washed and blocked with about 100 uL of a blocking reagent to reduce nonspecific binding.

Figure 144:
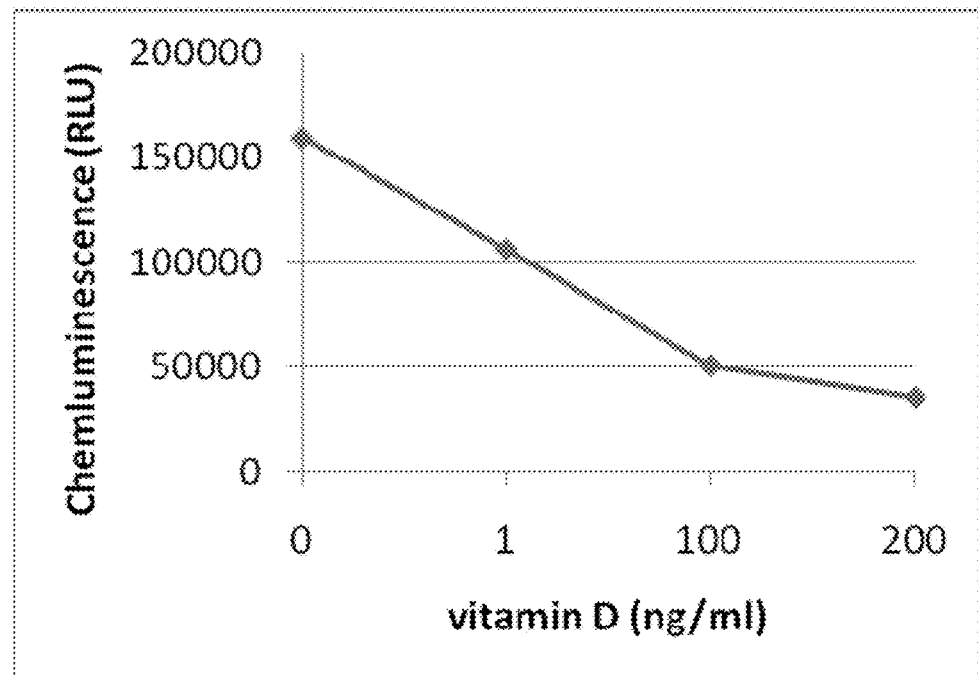
FIG. 144 shows a plot of chemiluminescence against concentration for a vitamin D assay.

The analyte for the assay (vitamin D) is diluted in Tris, NaCl, MgCl2, 10% Ethanol, pH 7.5, and is mixed with a solution of vitamin D-Alkaline Phosphatase conjugate at different concentrations in the desired assay range, and provided to the assay unit for 10 minutes incubation at room temperature. The assay unit is then washed three times with 100 uL of wash buffer. About 40 uL of substrate for Alkaline phosphatase is added to each assay well and chemiluminescence data (table below) is collected after about 10 minutes. FIG. 144 is a plot of chemiluminescence against the concentration (ng/ml) of vitamin D.

|  | Vitamin D (ng/ml) | | | |
| --- | --- | --- | --- | --- |
|  | 0 | 1 | 100 | 200 |
| Chemluminescence (RLU) | 155674.1 | 113824.3 | 49346.13 | 33824.27 |
|  | 159471 | 110794.2 | 49699.04 | 35794.18 |
|  | 162650.3 | 101655.7 | 53158.25 | 36655.66 |
|  | 159920.8 | 99266.41 | 50195.63 | 35166.41 |
| Avg | 159429.1 | 106385.1 | 50599.76 | 35360.13 |
| cv % | 1.80 | 6.60 | 3.44 | 3.37 |
| B/B0 | 100% | 67% | 32% | 22% |

Example 28

Estradiol Assay on Microtiter Plate

In this example, an assay is performed for a steroid hormone (estradiol) using single-chain variable fragments (scfv). In this assay, the inner surface of the assay unit is coated with biotinylated scFv on ultravidin coated polystyrene surface of a microtiter plate having a plurality of wells. About 15 microliters of 1 ug/ml biotinylated scFv in Tris buffered Saline, pH 8, 0.03% BSA, 0.05% Thimerasol were added to each assay unit. After washing, each assay unit is fixed with 100 uL Fixative reagent followed by an overnight dry with dry air and stored dessicated.

The analyte for the assay (free estradiol) is diluted in Tris buffered Saline, pH 8, BSA, Thimerasol, mixed with an estradiol-Alkaline Phosphatase conjugate, in stabilizer from Biostab, and is provided to the assay unit coated with the scfv for about 10 minutes at room temperature.

Figure 145:
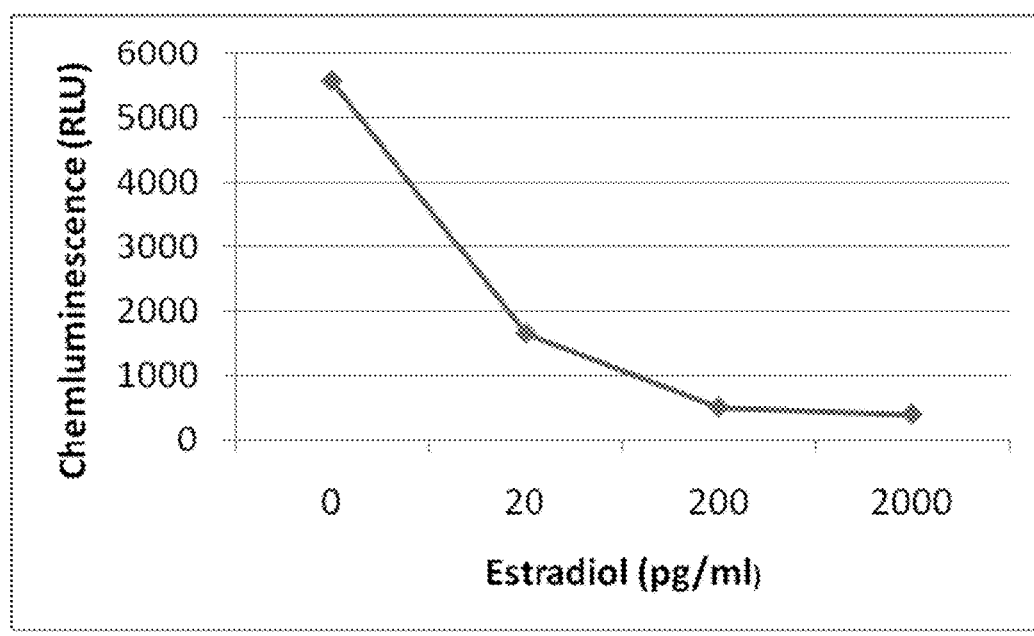
FIG. 145 shows a plot of chemiluminescence against concentration for an estradiol assay.

The assay wells are then washed 5 times with 100 uL of wash buffer. After the washes, 40 uL of luminogenic substrate for Alkaline phosphatase (KPL PhosphaGlo) is added to each assay unit and chemiluminescence data (table below) is collected after about 10 minutes. FIG. 145 is a plot of chemiluminescence against the concentration (pg/ml) of estradiol.

|  | Estradiol (pg/ml) | | | |
| --- | --- | --- | --- | --- |
|  | 0 | 20 | 200 | 2000 |
| Chemluminescence (RLU) | 5505.454 | 1997.885 | 493.864 | 389.863 |
|  | 5505.454 | 2005.112 | 496.932 | 374.317 |
|  | 5659.613 | 1739.771 | 503.25 | 417.021 |
| avg | 5557 | 1914 | 498 | 394 |
| % cv | 1.6 | 7.9 | 1.0 | 5.5 |
| b/bo | 100% | 34% | 9% | 7% |

Example 29

White Blood Cell Count and Differential Assay

The concentration of white blood cells (WBCs) in the peripheral blood of human subjects can range from about 1000 cells/ul to 100,000 cells/ul. However, in some cases the range of the imaging system is more limited, such as from about 4000 cells/ul to 7000 cells/ul. If the cell concentration is less than 4000 cells/ul, the system may not be able to enumerate a target of 10,000 cells, as may be required by the assay. If the cell concentration in the sample is more than 7000 cells/ul, each field of view may be too crowded to perform accurate image segmentation and cell enumeration. An exemplary approach for imaging WBCs is provided below.

In an example, an imaging system (e.g., cytometer) is provided configured for fluorescence spectrophotometry. The system uses fluorescence spectrophotometry to measure the cell concentration in the sample. The sample is labeled with fluorescently conjugated antibodies for imaging (e.g., AF647-CD45) and also with a fluorescent nucleic acid marker (e.g., DRAQ5). A quantitative fluorescence readout on the spectrophotometer module provides a measurement of the concentration of WBCs at low sensitivity (LLOQ of about 5000 cells/ul) but high dynamic range (e.g., 5000-100,000 cells/ul). A concentration measured on the spectrophotometer allows the calculation of the optimal dilution ratio such that the final concentration of the cell suspension is between 4000-7000 cells/ul.

Figure 146:
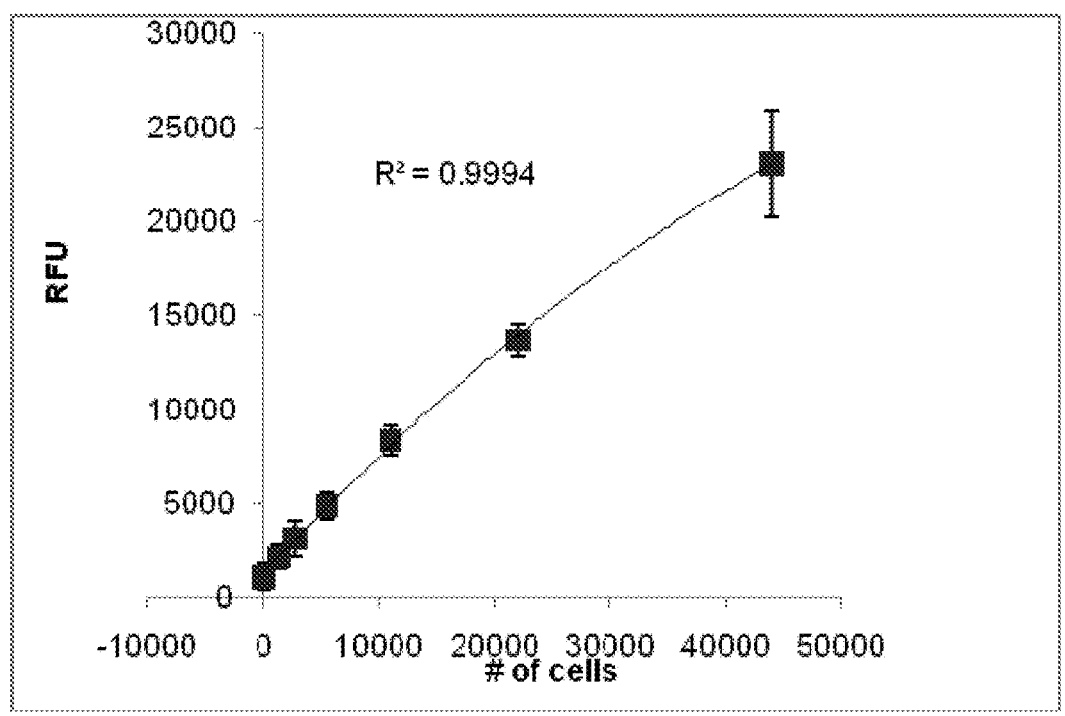
FIG. 146 shows a spectrophotometric measurement of WBC concentration.

FIG. 146 shows the high dynamic range of fluorescence in the spectrophotometric measurement of WBC concentration. WBCs tagged with fluorescently labeled anti-CD45 and other antibodies were excited with red light having a wavelength of about 640 nm and the quantitative fluorescence emission spectrum was collected. Integrated fluorescence is plotted on the y-axis.

Example 30

Streptococcus Group A Detection by Isothermal Amplification

Figure 147:
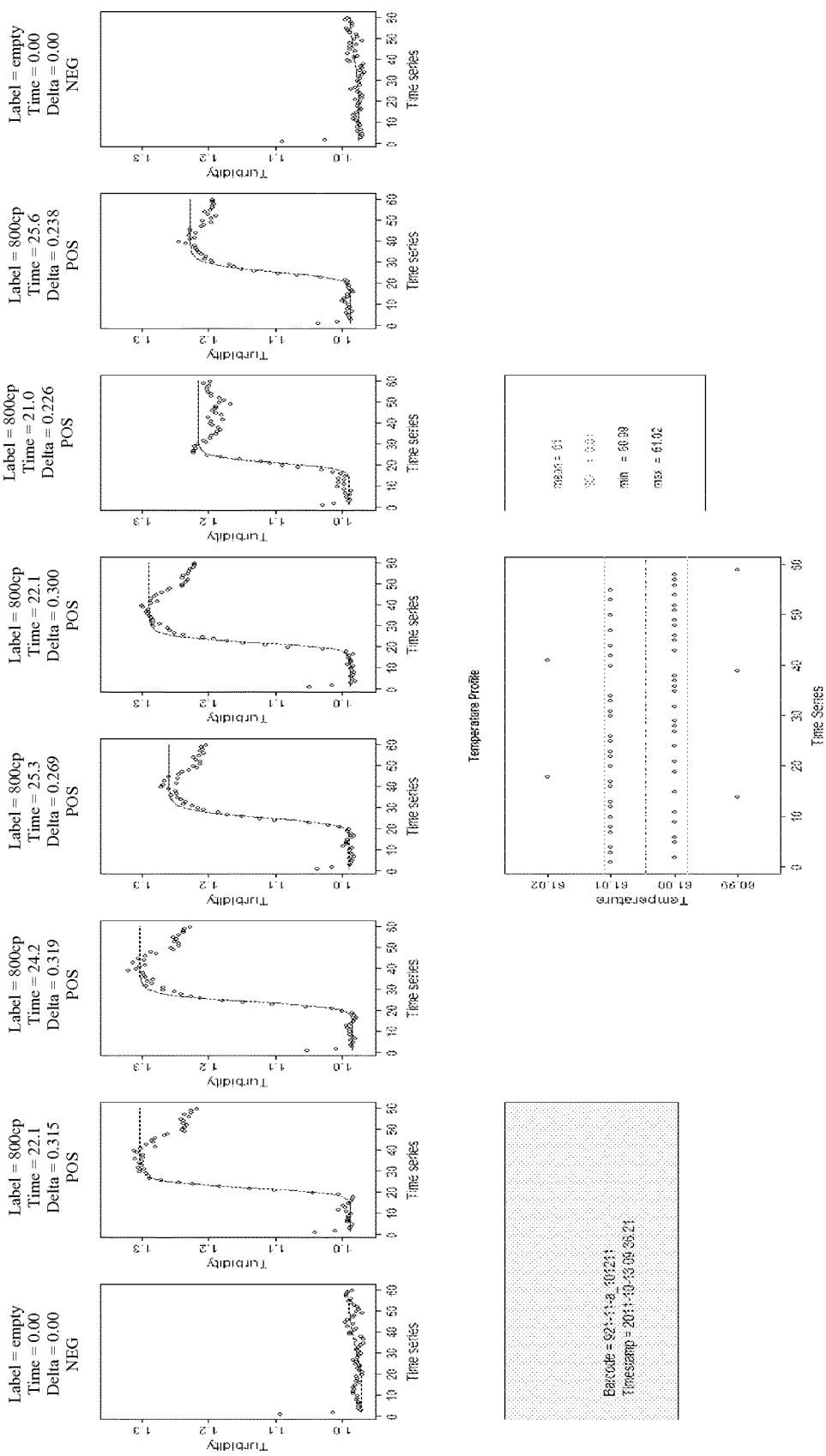
FIG. 147 shows plots of turbidity as a function of time.

Isothermal amplification of specific genomic samples can be detected by turbidity. In this example, a genomic sample extracted from Streptococcus group A (StrepA) cells (stock concentration=$2 \times 10^8$ org/ml from My biosource) was amplified by isothermal amplification and the progress of the reaction measured by Turbidity. About 5 ul of stock bacterial cells and 45 ul RT PCR grade Water (10× dilution of stock) were heat treated at about 95 degrees Celsius from about 8 to 10 minutes (Cell ruptures and releases the DNA). The genomic sample was diluted and introduced in a sample volume of about 25 ul in a PCR tube containing reagents for amplification (e.g., DNA Polymerase, Primers, Buffer). The PCR tube was incubated at about 61 degrees Celsius for about 60 minutes while the progress of the reaction was recorded by turbidity. The results are as follows, and FIG. 147 shows plots of turbidity as a function of time:

| Conc. (copies/uL) | T (min) | St. dev (min) |
| --- | --- | --- |
| 800 | 24.0 | 1.6 |
| 80 | 28.3 | 2.9 |
| 0 | n/a | n/a |

Figure 148:
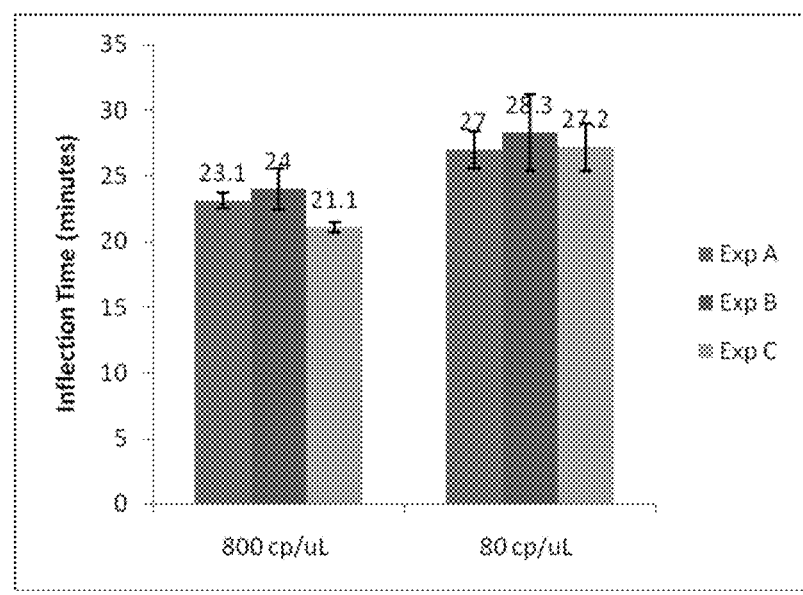
FIG. 148 is a plot of inflection points for three experiments at 800 copies/uL and 80 copies/uL.

Three separate experiments were conducted at 800 copies/uL and 80 copies/uL. Experiment A was performed using StrepA having a synthetic genomic DNA template (from Genescript). Experiment B was performed by diluting stock StrepA 10-fold followed by heat inactivation at 95 degrees Celsius from about 8 to 10 min, and followed by serial dilution of heat inactivated ten-fold diluted stock StrepA. Experiment C was performed using a variable concentration of stock StrepA (inactivated bacterial cells) followed by heat inactivation at 95 degrees Celsius for about 10 min. The inflections points for each experiment are shown in FIG. 148. For each of 800 copies/uL and 80 copies/uL, a grouping of three plots includes Experiment A at the left, Experiment B in the middle and Experiment C at the right. The average inflections points are provided in the following table:

|          | Experiment A | | Experiment B | | Experiment C | |
|----------|------|-------|------|-------|------|-------|
|          | AVG  | STDEV | AVG  | STDEV | AVG  | STDEV |
| 800 cp/uL | 23.1 | 0.6   | 24   | 1.6   | 21.1 | 0.4   |
| 80 cp/uL  | 27   | 1.4   | 28.3 | 2.9   | 27.2 | 1.8   |

Example 31

Use of Magnetic Beads

Figure 110:
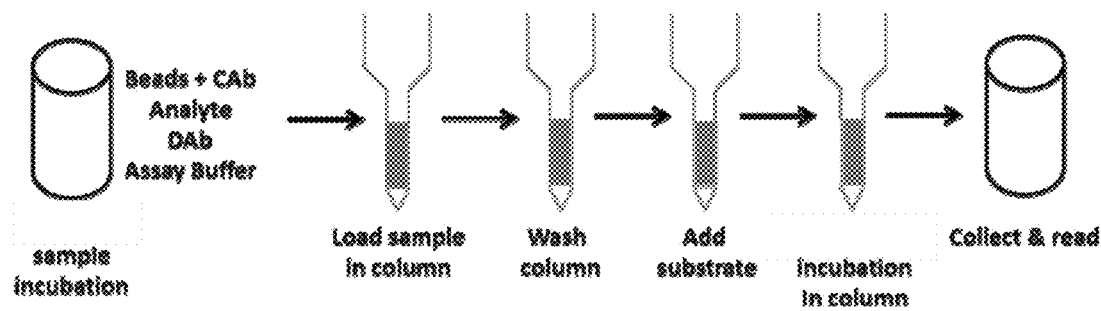
FIG. 110 schematically illustrates an exemplary method for an ELISA assay.
Figure 149:
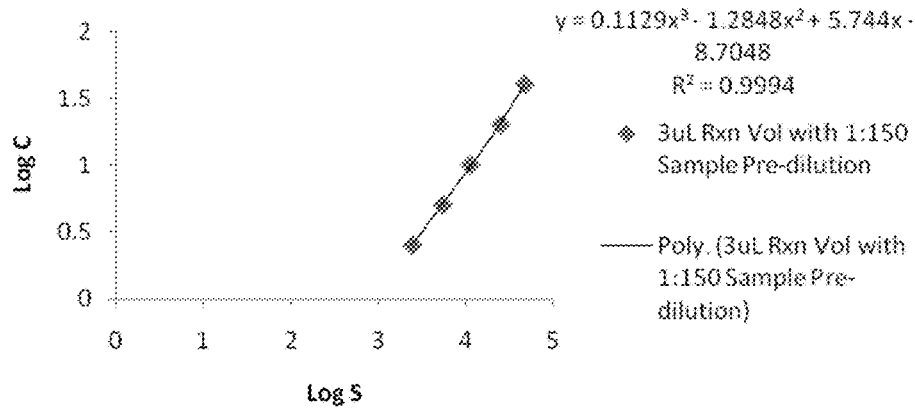
FIG. 149 is a plot of an example in which magnetic beads are used for the analysis of proteins and small molecules via ELISA assays.

In this example, magnetic beads are used for the analysis of proteins and small molecules via ELISA assays. FIG. 110 schematically illustrates an exemplary method for the ELISA assay. The assays include two proteins, Protein 1 and Protein 2. Protein 1 has a sample dilution of about 150-fold (tip protocol=30-fold), a sample volume of about 0.007 uL, a diluted sample volume of about 1 uL, a reaction volume of about 3 uL, and a reaction time of about 10 minutes (min) (sample incubation and substrate incubation). Results for Protein 1 are shown in the following table. The results of Test 2 for Protein 1 are shown in FIG. 149.

| Conc. (ng/mL) | Test 1 | Test 2 | Test 3 | Cal 1 | Cal 2 | Cal 3 | Recov 1 | Recov 2 | Recov 3 | % CV |
|------|-------|-------|-------|-----|-----|-----|-----|-----|-----|-----|
| 40   | 59316 | 46862 | 57396 | 40  | 40  | 40  | 99  | 99  | 99  | 0.3 |
| 20   | 25120 | 25225 | 25099 | 21  | 20  | 20  | 104 | 102 | 102 | 1.2 |
| 10   | 10551 | 11360 | 11463 | 9   | 10  | 10  | 92  | 96  | 97  | 2.6 |
| 5    | 5940  | 5607  | 5825  | 5   | 5   | 5   | 106 | 102 | 102 | 2.2 |
| 2.5  | 2476  | 2588  | 2497  | 2.5 | 2.5 | 2.5 | 99  | 99  | 100 | 0.3 |
| 0    | 190   | 166   | 166   |     |     |     |     |     |     |     |

Figure 150:
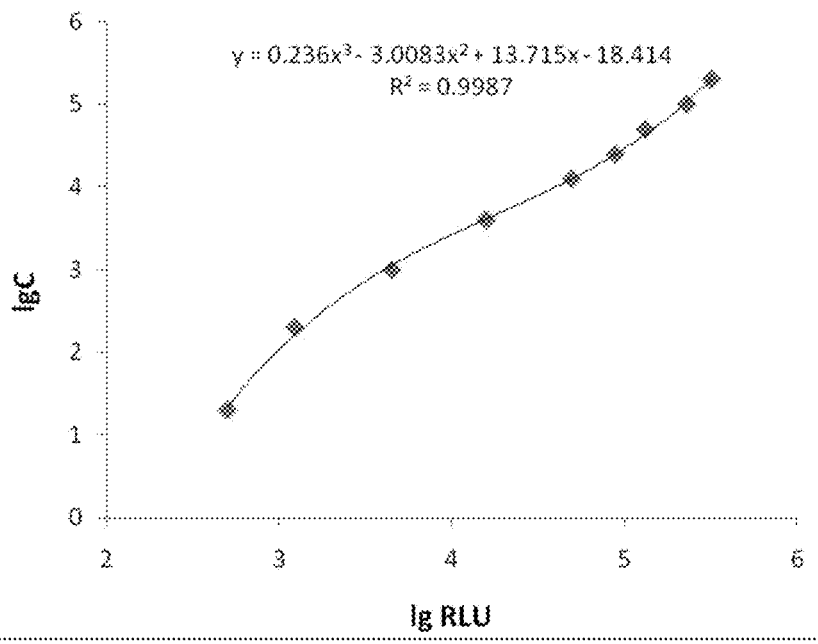
FIG. 150 is a plot of an example in which magnetic beads are used for the analysis of proteins and small molecules via ELISA assays.

Protein 2 has a sample dilution of about 667-fold, a sample volume of about 0.0015 uL, a diluted sample volume of about 1 uL, a reaction volume of about 3 uL, and a reaction time of about 10 min (sample incubation and substrate incubation). Results for Protein 2 are shown in the following table. The results of Test 1 for Protein 2 are shown in FIG. 150.

| Conc (ng/ml) | Test 1 | Test 2 | Cal 1 | Cal 2 | Recov 1 | Recov 2 | % CV |
|--------|--------|--------|--------|--------|------|------|----|
| 200000 | 322161 | 381202 | 203030 | 172490 | 102  | 86   | 12 |
| 100000 | 232455 | 310876 | 107910 | 117056 | 108  | 117  | 6  |
| 50000  | 133290 | 192460 | 43286  | 52415  | 87   | 105  | 13 |
| 25000  | 89282  | 101643 | 24919  | 21908  | 100  | 88   | 9  |
| 12500  | 49856  | 59574  | 12576  | 12041  | 101  | 96   | 3  |
| 4000   | 15926  | 18350  | 4117   | 4059   | 103  | 101  | 1  |
| 1000   | 4547   | 4722   | 1140   | 1124   | 114  | 112  | 1  |
| 200    | 1238   | 1229   | 163    | 172    | 82   | 86   | 4  |
| 20     | 504    | 458    | 22     | 21     | 109  | 106  | 2  |
| 0      | 302    | 292    |        |        |      |      |    |

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense.

Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method for handling a bodily fluid sample, the method comprising:
   receiving in an instrument a cartridge, wherein the cartridge contains the bodily fluid sample, wherein:
      the bodily fluid sample has a volume of 250 microliters or less;
      the instrument comprises: i) a centrifuge comprising at least a first bucket, and ii) a pipette comprising a nozzle, and
      the cartridge further contains: i) a first tip, ii) a second tip, and iii) a tip seal,
      wherein the first tip and second tip each have a first open end and a second open end, wherein the first open end of each tip is configured to engage with the nozzle of the pipette and the second open end of each tip is configured to permit the movement of fluid into or out of the tip;
   engaging the first open end of the first tip with the nozzle of the pipette;
   aspirating at least a portion of the bodily fluid sample into the engaged first tip through the second open end of the first tip;
   pressing with the pipette the second open end of the engaged first tip containing the at least a portion of the bodily fluid sample into the tip seal such that the second open end of the first tip is capped with and sealed by the tip seal;
   inserting with the pipette the sealed first tip into the bucket of the centrifuge and disconnecting the sealed first tip from the pipette nozzle; and
   centrifuging the sealed first tip in the bucket of the centrifuge.

2. The method of claim 1, wherein the bodily fluid sample is a blood sample obtained from a fingerstick.

3. The method of claim 1, wherein upon centrifuging the sealed first tip, the sample in the sealed first tip is separated into a supernatant and a pellet.

4. The method of claim 3, wherein the method further comprises:
   engaging the first open end of the second tip with the nozzle of the pipette; and
   aspirating at least a portion of the supernatant from the sealed first tip into the second tip.

5. The method of claim 4, wherein the supernatant comprises blood plasma or blood serum.

6. The method of claim 5, further comprising using at least a portion of the supernatant to perform at least one assay for an analyte.

7. The method of claim 3, wherein the pellet contains red blood cells and white blood cells.

8. The method of claim 7, further comprising:
   imaging at least a portion of the sealed first tip, wherein the imaged portion of the sealed first tip contains the pellet; and
   determining the hematocrit of the sample.

9. The method of claim 7, further comprising:
   removing the supernatant from the sample in the sealed first tip; and
   resuspending the pellet in a reagent which acts as a lysing agent for the red blood cells.

10. The method of claim 9, further comprising:
    centrifuging the sealed first tip comprising the resuspended pellet, such that upon centrifuging the sealed first tip, the resuspended pellet is separated into a supernatant comprising lysed red blood cells and a pellet comprising white blood cells.

11. A method for handling a bodily fluid sample, the method comprising:
    receiving in an instrument a cartridge, wherein the cartridge contains the bodily fluid sample, wherein:
       the bodily fluid sample has a volume of 250 microliters or less;
       the instrument comprises: i) a centrifuge comprising at least a first bucket, and ii) a pipette comprising a nozzle, and
       the cartridge further contains: i) a first tip, ii) a second tip, and iii) a tube having an open end and an opposing closed end, wherein the first tip and second tip each have a first open end and a second open end, wherein the first open end of each tip is configured to engage with the nozzle of the pipette and the second open end of each tip is configured to permit the movement of fluid into or out of the tip, and wherein the open end of the tube is configured to engage with the nozzle of the pipette;
    engaging the first open end of the first tip with the nozzle of the pipette;
    aspirating at least a portion of the bodily fluid sample into the engaged first tip through the second open end of the first tip;
    dispensing the at least a portion of the fluid sample from the engaged first tip into the tube;
    disengaging the engaged first tip from the pipette nozzle;
    engaging the open end of the tube comprising the at least a portion of the fluid sample with the pipette nozzle;
    inserting with the pipette the tube comprising the at least a portion of the fluid sample into the first bucket of the centrifuge and disconnecting the tube from the pipette nozzle; and
    centrifuging the tube in the bucket of the centrifuge.

12. The method of claim 11, wherein the bodily fluid sample is a blood sample obtained from a fingerstick.

13. The method of claim 11, wherein upon centrifuging the tube, the sample in the tube is separated into a supernatant and a pellet.

14. The method of claim 13, wherein the method further comprises:
    engaging the first open end of the second tip with the nozzle of the pipette; and
    aspirating at least a portion of the supernatant from the tube into the second tip.

15. The method of claim 14, wherein the supernatant comprises blood plasma or blood serum.

16. The method of claim 15, further comprising using at least a portion of the supernatant to perform at least one assay for an analyte.

17. The method of claim 13, wherein the pellet contains red blood cells and white blood cells.

18. The method of claim 17, further comprising:
imaging at least a portion of the tube, wherein the imaged portion of the tube contains the pellet; and
determining the hematocrit of the sample.

19. The method of claim 17, further comprising:
removing the supernatant from the sample in the tube; and
resuspending the pellet in a reagent which acts as a lysing agent for the red blood cells.

20. The method of claim 19, further comprising:
centrifuging the tube comprising the resuspended pellet, such that upon centrifuging the tube, the resuspended pellet is separated into a supernatant comprising lysed red blood cells and a pellet comprising white blood cells.

21. An instrument comprising:
i) a centrifuge comprising at least a first bucket, ii) a pipette comprising a nozzle, and iii) a housing, wherein:
the centrifuge and pipette are within the housing,
the housing comprises a door through which a cartridge containing a tip or tube may be inserted, the pipette is configured to, upon the insertion of a cartridge containing a tip or tube into the housing of the instrument: i) engage with its nozzle a tip or tube in the cartridge, ii) move the engaged tip or tube from the cartridge to the centrifuge, iii) insert the engaged tip or tube into the bucket of the centrifuge, and iv) disconnect the engaged tip or tube from the nozzle into the bucket of the centrifuge, such that the tip or tube is parked in the bucket of the centrifuge.

22. The instrument of claim 21, the instrument further comprising:
iv) the cartridge, wherein the cartridge contains: A) a first tip, B) a second tip, and C) a tip seal,
wherein the first tip and second tip each have a first open end and a second open end, wherein the first open end of each tip is configured to engage with the nozzle of the pipette and the second open end of each tip is configured to permit the movement of fluid into or out of the tip.

23. The instrument of claim 21, the instrument further comprising:
iv) the cartridge, wherein the cartridge contains: A) a first tip, B) a second tip, and C) a tube having an open end and an opposing closed end, wherein the first tip and second tip each have a first open end and a second open end, wherein the first open end of each tip is configured to engage with the nozzle of the pipette and the second open end of each tip is configured to permit the movement of fluid into or out of the tip, and wherein the open end of the tube is configured to engage with the nozzle of the pipette.

\* \* \* \* \*